US011117879B2

(12) United States Patent
Zhu et al.

(10) Patent No.: US 11,117,879 B2
(45) Date of Patent: Sep. 14, 2021

(54) PHOTO-CROSSLINKED HYDROGEL MATERIAL AND PREPARATION, COMPOSITION, AND APPLICATION THEREOF PHOTO-CROSSLINKED HYDROGEL

(71) Applicant: Zhongshan Guanghe Medical Technology Co., Ltd., Guangdong (CN)

(72) Inventors: Linyong Zhu, Shanghai (CN); Yujie Hua, Shanghai (CN); Qiuning Lin, Shanghai (CN); Yiqing Zhang, Shanghai (CN); Chunyan Bao, Shanghai (CN); Xuepeng Zhong, Shanghai (CN)

(73) Assignee: Zhongshan Guanghe Medical Technology Co., Ltd., Guangdong (CN)

( * ) Notice: Subject to any disclaimer, the term of this patent is extended or adjusted under 35 U.S.C. 154(b) by 0 days.

(21) Appl. No.: 16/848,372

(22) Filed: Apr. 14, 2020

(65) Prior Publication Data

US 2020/0262802 A1 Aug. 20, 2020

Related U.S. Application Data

(63) Continuation of application No. PCT/CN2018/080170, filed on Mar. 23, 2018.

(30) Foreign Application Priority Data

Nov. 15, 2017 (CN) .......................... 201711132472.2

(51) Int. Cl.
| | |
|---|---|
| *C08F 2/46* | (2006.01) |
| *C08F 2/50* | (2006.01) |
| *C08G 61/04* | (2006.01) |
| *C07D 291/08* | (2006.01) |
| *A61L 24/00* | (2006.01) |
| *A61L 24/04* | (2006.01) |

(Continued)

(52) U.S. Cl.
CPC ........ *C07D 291/08* (2013.01); *A61L 24/0031* (2013.01); *A61L 24/046* (2013.01); *A61L 24/06* (2013.01); *A61L 24/08* (2013.01); *A61L 26/008* (2013.01); *A61L 26/0014* (2013.01); *A61L 26/0019* (2013.01); *A61L 26/0023* (2013.01); *A61L 27/16* (2013.01); *A61L 27/18* (2013.01); *A61L 27/20* (2013.01); *A61L 27/52* (2013.01); *A61L 31/042* (2013.01); *A61L 31/048* (2013.01); *A61L 31/06* (2013.01); *A61L 31/145* (2013.01); *C07C 235/12* (2013.01); *C08B 37/0072* (2013.01); *C08F 220/68* (2013.01); *C08G 69/10* (2013.01); *C08G 73/06* (2013.01); *C08J 3/075* (2013.01); *C08J 3/28* (2013.01); *C08J 2305/08* (2013.01); *C08J 2333/14* (2013.01); *C08J 2377/04* (2013.01); *C08J 2379/04* (2013.01)

(58) Field of Classification Search
CPC ...... A61L 24/00; A61L 24/06; A61L 24/0031; A61L 24/08; A61L 24/046; A61L 24/10; A61L 24/04; A61L 31/06; A61L 31/45; A61L 31/042; A61L 31/048; A61L 27/16; A61L 27/18; A61L 27/54; A61L 27/52; A61L 27/20; A61L 26/008; A61L 26/0023; A61L 26/00; A61L 26/0019; C08G 69/10; C08G 73/06; C07C 235/12; C08J 3/075; C08J 3/28; C08J 2379/04; C08J 2333/01; C08J 2377/04; C08J 2305/08; C08B 37/0072; C08F 220/68; C07D 291/08

USPC ........... 522/40, 33, 6, 189, 184, 1, 71; 520/1
See application file for complete search history.

(56) References Cited

U.S. PATENT DOCUMENTS

| | | |
|---|---|---|
| 6,020,480 A | 2/2000 | Cohen et al. |
| 2016/0108172 A1 | 4/2016 | Sivaguru et al. |

FOREIGN PATENT DOCUMENTS

| | | |
|---|---|---|
| CA | 2941395 A1 | 9/2015 |
| CN | 102531910 A | 7/2012 |

(Continued)

OTHER PUBLICATIONS

Zhu et al, CN 105131315 Machine Translation, Dec. 9, 2015 (Year: 2015).*

(Continued)

*Primary Examiner* — Jessica Whiteley
(74) *Attorney, Agent, or Firm* — Hamre, Schumann, Mueller & Larson, P.C.

(57) ABSTRACT

This invention provides preparations, compositions, products, and applications of photo-crosslinked hydrogels. Component A—a photosensitive polymer derivative, component B—the photoinitiator, and auxiliary component C—other biocompatible polymer derivative each are respectively dissolved in a biocompatible medium to obtain solution A, solution B, and solution C. The solution A, the solution B, and the optional solution C are mixed homogenously to obtain a hydrogel precursor solution. The hydrogel precursor solution is subject to irradiation of the UV light for photocoupled crosslinking to form a photo-crosslinked hydrogel. The photo-crosslinked hydrogel exhibit rapid speed of photo-curing, strong tissue adhesion, excellent mechanical properties, good biocompatibility, and excellent clinical operability. In addition, this invention also provides a kit for making the photo-crosslinked hydrogel, and applications thereof in tissue engineering, regenerative medicine, 3D printing, and as a carrier of cell, protein, or drug.

14 Claims, 4 Drawing Sheets

(51) Int. Cl.

| | | |
|---|---|---|
| A61L 24/06 | (2006.01) | |
| A61L 24/08 | (2006.01) | |
| A61L 26/00 | (2006.01) | |
| A61L 27/16 | (2006.01) | |
| A61L 27/18 | (2006.01) | |
| A61L 27/20 | (2006.01) | |
| A61L 27/52 | (2006.01) | |
| A61L 31/04 | (2006.01) | |
| A61L 31/06 | (2006.01) | |
| A61L 31/14 | (2006.01) | |
| C07C 235/12 | (2006.01) | |
| C08B 37/08 | (2006.01) | |
| C08F 220/68 | (2006.01) | |
| C08G 69/10 | (2006.01) | |
| C08G 73/06 | (2006.01) | |
| C08J 3/075 | (2006.01) | |
| C08J 3/28 | (2006.01) | |

(56) References Cited

FOREIGN PATENT DOCUMENTS

| | | | |
|---|---|---|---|
| CN | 105131315 | * | 12/2015 |
| CN | 105131315 | A | 12/2015 |
| CN | 105153362 | A | 12/2015 |
| CN | 106349465 | A | 1/2017 |
| CN | 106822183 | A | 6/2017 |
| WO | 2016082725 | A1 | 6/2016 |

OTHER PUBLICATIONS

STN Registry 842150-25-8 (Mar. 4, 2005), 107573-91-1 (Apr. 11, 1987) and 59945-42-5 (Nov. 16, 1984).
Peng et al.,"Dextran based photodegradable hydrogels formed via a Michael addition", Soft Matter, Issue 10, 2011, pp. 4881-4887.
Ye et al., "Photo-responsive shell cross-linked micelles based on carboxymethyl chitosan and their application in controlled release of pesticide", Carbohydrate Polymers 132, 2015, pp. 520-528.
Office Action issued in corresponding Chinese Application No. 201711132472.2, dated Apr. 27, 2020, with English machine translation, 16 pages provided.
Search Report issued in corresponding Chinese Application No. 201711132472.2, with English machine translation, 4 pages provided.
International Search Report (in English and Chinese) published in PCT/CN2018/080170, dated Aug. 8, 2018, 7 pages provided.
Yang et al., "Tissue-Integratable and Biocompatible Photogelation by the Imine Crosslinking Reaction", published in Advanced Materials, vol. 28, No. 14, Feb. 3, 2016, pp. 2724-2730; cited in International Search Report.
Oommen et al., "Smart Design of Stable Extracellular Matrix Mimetic Hydrogel: Synthesis, Characterization, and in Vitro and in Vivo Evaluation for Tissue Engineering", Advanced Functional Materials, first published Oct. 12, 2012, pp. 1273-1280, discussed in Specification.
Peng et al., "Cyclodextrin-Dextran Based in Situ Hydrogel Formation: A Carrier for Hydrophobic Drugs", Soft Matter, first published Oct. 23, 2009, pp. 85-87, discussed in Specification.
Li et al., "Biodegradable and Injectable in situ Cross-linking Chitosan-Hyaluronic Acid Based Hydrogels for Postoperative Adhesion Prevention", Biomaterials, first published Feb. 4, 2014, pp. 3903-3917, discussed in Specification.
Delaittre et al., "Acrylamide-Based Copolymers Bearing Photoreleasable Thiols for Subsequent Thiol-Ene Functionalization", Macromolecules, first published Feb. 8, 2012, pp. 1792-1802, discussed in Specification.
Fu et al., "Visible-Light-Initiated Thiol-Acrylate Photopolymerization of Heparin-Based Hydrogels", BioMacromolecules, first published Dec. 23, 2014, pp. 497-506, discussed in Specification.
Ozdemir et al., "Tuning Hydrogel Properties to Promote the Assembly of Salivary Gland Spheroids in 3D", ACS Biomaterials Science & Engineering, first published Oct. 18, 2016, pp. 2217-2230, discussed in Specification.
Choi et al., "Thiolated Dextran-Coated Gold Nanorods for Photothermal Ablation of Inflammatory Macrophages", Langmuir Article, first published Oct. 7, 2010, pp. 17520-17527, discussed in Specification.
Zhang et al., "In Situ Gelable Interpenetrating Double Network Hydrogel Formulated from Binary Components: Thiolated Chitosan and Oxidized Dextran", BioMacromolecules, first published Mar. 16, 2011, pp. 1428-1437, discussed in Specification.
Cameron et al., "Photogeneration of Organic Bases from o-Nitrobenzyl-Derived Carbamates", J. Am. Chem. Soc., first published in 1991, pp. 4303-4313, discussed in Specification.
Pirrung et al., "Pentadienylnitrobenzyl and Pentadienylnitropiperonyl Photochemically Removable Protecting Groups", J. Org. Chem., first published Jun. 17, 1999, pp. 5042-5047, discussed in Specification.
Aujard et al., "o-Nitrobenzyl Photolabile Protecting Groups with Red-Shifted Absorption: Syntheses and Uncaging Cross-Sections for One- and Two-Photon Excitation", Chemistry a European Journal, first published Jun. 8, 2006, pp. 6865-6879, discussed in Specification.
Russell et al., "alpha-Carboxy-6-nitroveratryl: A Photolabile Protecting Group for Carboxylic Acids", J. Org. Chem., first published Jun. 10, 2010, pp. 4648-4651, discussed in Specification.
Specht et al., "1-(o-Nitrophenyl)-2,2,2-trifluoroethyl Ether Derivatives as Stable and Efficient Photoremovable Alcohol-Protecting Groups", Angew. Chem. Int. Ed., first published 2004, pp. 2008-2012, discussed in Specification.
Baldwin et al., "New Photolabile Phosphate Protecting Groups", Tetrahedron, first published 1990, pp. 6879-6884, discussed in Specification.
Pauloehrl et al., "(Bio)Molecular Surface Patterning by Phototriggered Oxime Ligation", Angewandte Chem. Int. Ed., first published 2012, pp. 9181-9184, discussed in Specification.
Patchornik et al., "Photosensitive Protecting Groups", Journal of the American Chemical Society, first published Oct. 21, 1970, pp. 6333-6335, discussed in Specification.
Kalbag et al., "A Photolabile Protecting Group for Histidine", Journal of the American Chemical Society, first published Jan. 22, 1975, pp. 440-441, discussed in Specification.
Engels et al., "Synthesis, Structure, and Reactivity of Adenosine Cyclic 3', 5' Phosphate Benzyl Triesters", Journal of Medicinal Chemistry, first published 1977, pp. 907-911, discussed in Specification.
Riguet et al., "New Safety-Catch Photolabile Protecting Group", Organic Letters, first published Nov. 30, 2007, pp. 5453-5456, discussed in Specification.
Bley et al., "Photoprocesses of Molecules with 2-Nitrobenzyl Protecting Groups and Caged Organic Acids", Photochemistry and Photobiology, first published in 2008, pp. 162-171, discussed in Specification.
Singh et al., "3-Nitro-2-naphthalenemethanol: a photocleavable protecting group for carboxylic acids", Tetrahedron, first published in 2005, pp. 10007-10012, discussed in Specification.
Friedrich et al., "A two-photon activatable amino acid linker for the induction of fluorescence", Chem. Commun., first published in 2015, pp. 15382-15385, discussed in Specification.
Groszek et al., "Synthesis and adrenolytic activity of 1-(1H-indol-4-yloxy)-3-(2-(2-methoxyphenoxy)ethylamino)propan-2-ol analogs and its enantiomers. Part 2", European Journal of Medicinal Chemistry, first published Jul. 21, 2009, pp. 5103-5111, discussed in Specification.
Greene et al., "Synthesis and Biochemical Evaluation of 3-Phenoxy-1,4-diarylazetidin-2-ones as Tubulin-Targeting Antitumor Agents", Journal of Medicinal Chemistry, first published Dec. 3, 2015, pp. 90-113, discussed in Specification.
Wu et al., "Synthesis and Evaluation of 3-Aroylindoles as Anticancer Agents: Metabolite Approach", Journal of Medicinal Chemistry, first published Jul. 8, 2009, pp. 4941-4945, discussed in Specification.
Agasti et al., "Photoregulated Release of Caged Anticancer Drugs from Gold Nanoparticles", J. Am. Chem. Soc. first published in 2009, pp. 5728-5729, discussed in Specification.

(56) References Cited

OTHER PUBLICATIONS

Subramani et al., "Direct photopatterning of light-activated gold nanoparticles", Journal of Materials Chemistry, first published in 2011, pp. 14156-14158, discussed in Specification.
Muraoka et al., "Quadruple Helix Formation of a Photoresponsive Peptide Amphiphile and Its Light-Triggered Dissociation into Single Fibers", J. Am. Chem. Soc., first published in 2008, pp. 2946-2947, discussed in Specification.
Morihiro et al., "Photoinduced changes in hydrogen bonding patterns of 8-thiopurine nucleobase analogues in a DNA strand", Organic & Biomolecular Chemistry, first published in 2014, pp. 2946-2952, discussed in Specification.
Bao et al., "Long conjugated 2-nitrobenzyl derivative caged anticancer prodrugs with visible light regulated release: preparation and functionalizations", Organic & Biomolecular Chemistry, Dec. 31, 2012, Royal Society of Chemistry, vol. 10, pp. 5238-5244.
Lin et al., "Phototriggers: Work mechanisms and applications", Imaging science and photochemistry, vol. 32 No. 1, Jan. 31, 2014, with English Abstract, 25 pages provided.
Office Action issued in Chinese Application No. 201711132436.6, dated Apr. 15, 2020, with English machine translation, 15 pages provided.
Search Report issued in Chinese Application No. 201711132436.6 dated Apr. 7, 2020, with English translation; 3 pages provided.

\* cited by examiner

*in situ* photogelation

Hepatic hemorrhage     Light hemostasis     Completion of hemostasis

Experimental group     Control group

PHOTO-CROSSLINKED HYDROGEL MATERIAL AND PREPARATION, COMPOSITION, AND APPLICATION THEREOF PHOTO-CROSSLINKED HYDROGEL

FIELD OF THE INVENTION

The invention belongs to the field of biological materials, and relates to the preparation, compositions, products, and applications of photo-crosslinked hydrogel material.

BACKGROUND OF THE INVENTION

A hydrogel is designed as highly hydrated and crosslinked 3D polymeric networks. Due to its excellent biocompatibility and certain mechanical strength, it can highly fit the micro-environment of biological tissues and is widely used in tissue engineering and regenerative medicine. In clinical applications, in-situ forming hydrogels have excellent tissue integration ability. Currently, in-situ forming hydrogels are mainly classified into temperature-sensitive hydrogels, two-component injectable hydrogels, and photosensitive hydrogels according to their gelation mechanisms. A mechanism of the temperature-sensitive hydrogels is that a gel precursor, which is a liquid phase at a low temperature, undergoes phase-change gelation under body temperature after reaching the body to realize in-situ forming (such as LeGoo, hydroxybutyl chitosan, etc.). This kind of hydrogels generally has problems such as weak gel strength, slow temperature response, and slow degradation in the body. The two-component injectable hydrogel mainly implements in-situ forming by injecting while mixing gel precursor containing reactive functional group by a two-component syringe (for example, Fibrin Glue, Adherus AutoSpray, etc.). Thus there is a high requirement for the crosslinking speed of the reactive functional groups. If the gelation rate is too slow, the gel precursor will be diluted or washed away by the blood or exudate in the body. If the gelation rate is too fast, it is unfavorable to clinical operation and the gel precursor is easy to block needles. And the two-component syringe is relatively expensive, which greatly increase application cost. The above drawbacks limit the wide application of these materials.

Compared to the temperature-sensitive hydrogel and two-component injectable hydrogel, the photosensitive hydrogel is more practical in clinical operation due to its precisely controllable ability in time and space. For the current method of preparing a hydrogel via photo-crosslinking, unsaturated biomacromolecule polymerization crosslinking via free-radical crosslinking is the most common method. Although the photo-initiated radical polymerization crosslinking method has a fast cure rate (about 2 s), free radicals inevitably cause damage to cells or biological tissues, and the intrinsic oxygen inhibition of free radicals makes it difficult to construct a thin layer of a hydrogel in situ by this method. Meanwhile, the lack of adhesion ability of such hydrogel to a tissue has also been a barrier of the clinical application of this technique. So far, the FDA has approved only one case of photosensitive hydrogel named FocalSeal for preventing hernia formation after pneumonectomy. Recently, Biomet has acquired the in situ hydrogel construction technology from John Hopkins University for cartilage repair. Although the above techniques have achieved excellent clinical effects, they must be used for combining with an additional primer coat to promote the integration between the photosensitive hydrogel and a tissue, which complicates their clinical use(s).

In view of the deficiencies of the photoinitiating free-radical crosslinking technology in preparing a hydrogel, Linyong Zhu et al. proposed a non-free radical photocoupling crosslinking technology in 2014 (Yunlong Yang; Jieyuan Zhang; Zhenzhen Liu; Qiuning Lin; Xiaolin Liu; Chunyan Bao; Yang Wang; Linyong Zhu. Adv. Mater. 2016, 28, 2724; Linyong Zhu et. al. PCT. No. WO2016082725 A1, issued Jun. 2, 2016), this technology is based on the imine crosslinking reaction between aldehyde group produced by o-nitrolbenzyl alcohol under irradiation of ultraviolet light and amine group in a polymer derivative containing amine(s). This completely avoids generation of free radicals and effectively solve the problem of the toxicity of free radicals and oxygen inhibition, and the thickness of the gel layer can be adjusted. Meantime, the aldehyde group produced by o-nitrobenzyl alcohol under irradiation of light can further react with the amine group of a protein in a surface of a tissue. Thereby, this can realize the chemical bond linking between the gel layer and the tissue and solve the problem of tissue adhesion and integration in the above conventional photosensitive hydrogel. However, the slow gelation rate limits its clinical application.

CONTENT OF THE INVENTION

The first objective this invention is to provide a cyclic o-nitrobenzyl phototrigger as shown in Formula I-2:

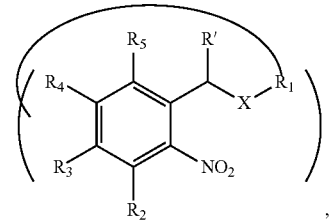

where,

X=O, S or N; when X=O, it is a cyclic o-nitrobenzyl alcohol phototrigger; when X=S, it is a cyclic o-nitrobenzyl sulfide phototrigger; when X=N, it is a cyclic o-nitrobenzyl amine phototrigger.

One end of $R_1$ is connected with X, and the other end is connected optionally with groups of $R_2$, $R_3$, $R_4$ or $R_5$ to form a cyclic structure.

R' is selected from the group consisting of the group consisting of a hydrogen atom, a halogen atom, a hydroxyl group, a sulphydryl group, an amine group, a nitro group, a cyano group, an aldehyde group, a ketone group, an ester group, an amide group, a phosphonic acid group, a phosphonate group, a sulfonate group, a sulfonic acid ester group, a sulfoxide group, an aryl group, a heteroaryl group, an alkyl group, an alkylene group, a modified alkyl group and a modified alkylene group.

$R_1$ is selected from the group consisting of a hydrogen group, an ether group, an ester group, a carbonate group, an amino formate ester group, a mercaptoformic ester group and phosphoric acid ester group.

$R_2$, $R_3$, $R_4$ and $R_5$ are freely selected from the group consisting of a hydrogen atom, a halogen atom, a hydroxyl group, a mercapto group, an amine group, a nitro group, a cyano group, an aldehyde group, a ketone group, a carboxyl group, an ester group, an amide group, a phosphonic acid group, a phosphonate group, a sulfonic acid group, a sulfonate group, a sulfone group, a sulfoxide group, an aryl group, a heteroaryl group, an alkyl group, an alkylene group, a modified alkyl group and a modified alkylene group.

Preferably, $R_2$, $R_3$, $R_4$ and $R_5$ are interconnected to each other and connected together with a carbon atom to form a saturated or unsaturated alicyclic or heteroalicyclic ring, or an aromatic ring or an aromatic heterocyclic ring.

Further, the alkyl group is a saturated or unsaturated aliphatic linear or branched alkyl group having 1 to 30 carbon atoms.

The alkylene group is a saturated or unsaturated aliphatic linear chain or branched alkylene group with 1-30 carbon atoms.

Modified alkyl group is an alkyl group whose any carbon atom is at least substituted by one of the groups consisting of a halogen atom, —OH, —SH, —NO$_2$, —CN, —CHO, —COOH, ester, amide, aromatic, arylidene, —CO—, —O—, —S—, —SO—, —SO$_2$—, amino, secondary amine, tertiary amine, quaternary ammonium salt, saturated or unsaturated single or double cyclic alkylene, bridged aliphatic heterocyclic. And the modified alkyl group has 1~30 carbon atoms whose carbon-carbon single bond is replaced optionally and independently by a carbon-carbon double bond or a carbon-carbon triple bond.

Modified alkylene group is an alkylene group whose any carbon atom is at least substituted by one of the groups consisting of a halogen atom, —OH, —SH, —NO$_2$, —CN, —CHO, —COOH, ester, amide, aromatic, arylidene, —CO—, —O—, —S—, —SO—, —SO$_2$—, amino, secondary amine, tertiary amine, quaternary ammonium salt, saturated or unsaturated single or double cyclic alkylene, bridged aliphatic heterocyclic. And the modified alkyl group has 1~30 carbon atoms whose carbon-carbon single bond is replaced optionally and independently by a carbon-carbon double bond or a carbon-carbon triple bond.

The ether group is selected from the following structures:
—(CH$_2$)$_x$CH$_3$, —(CH$_2$CH$_2$O)$_x$CH$_3$, —(CH$_2$)$_x$(CH$_2$CH$_2$O)$_y$CH$_3$, or

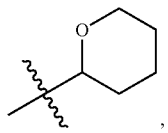

wherein x and y≥0 and are integers.

The ester group is selected from the following structures:
—CO(CH$_2$)$_x$CH$_3$, —CO(CH$_2$CH$_2$O)$_x$CH$_3$, —CO(CH$_2$)$_x$(CH$_2$CH$_2$O)$_y$CH$_3$, wherein x and y≥0 and are integers.

The carbonate group is selected from the following structures:
—COO(CH$_2$)$_x$CH$_3$, —COO(CH$_2$CH$_2$O)$_x$CH$_3$, —COO(CH$_2$)$_x$(CH$_2$CH$_2$O)$_y$CH$_3$, wherein x and y≥0 and are integers.

The amino formate ester group is selected from the following structures:
—CONH(CH$_2$)$_x$CH$_3$, —CONH(CH$_2$CH$_2$O)$_x$CH$_3$, —CONH(CH$_2$)$_x$(CH$_2$CH$_2$O)$_y$CH$_3$, wherein x and y≥0 and are integers.

The mercapto formate ester group is selected from the following structures:
—COS(CH$_2$)$_x$CH$_3$, —COS(CH$_2$CH$_2$O)$_x$CH$_3$, —COS(CH$_2$)$_x$(CH$_2$CH$_2$O)$_y$CH$_3$, wherein x and y≥0 and are integers.

The phosphate ester group is selected from the following structures:
—POOO(CH$_2$)$_x$CH$_3$, —POOO(CH$_2$CH$_2$O)$_x$CH$_3$, —POOO(CH$_2$)$_x$(CH$_2$CH$_2$O)$_y$CH$_3$, wherein x and y≥0 and are integers.

The aryl ring is a monocyclic or fused bicyclic ring of 5-10 atoms.

The heteroaryl is a monocyclic or fused bicyclic ring containing 5 to 10 atoms, the ring contains at least one hetero atom selected from N, O, S or Si.

The halogen atom is independently selected from F, Cl, Br or I.

The alicyclic ring is a saturated or unsaturated monocyclic or polycyclic alicyclic ring of 3 to 10 atoms.

The alicyclic ring is a saturated or unsaturated monocyclic or polycyclic alicyclic ring of 3 to 10 atoms, and the ring contains at least one hetero atom selected from N, O, S or Si. When the heteroalicyclic ring contains an S atom, it is selected optionally from —S—, —SO— or —SO$_2$—; H on the alicyclic or alicyclic ring may be optionally substituted by a halogen atom, a nitro group, an aryl group or an alkyl group or a modified alkyl group.

The aromatic ring is a monocyclic or fused bicyclic ring of 5-10 atoms.

The aromatic heterocycle is a monocyclic or fused bicyclic ring containing 5 to 10 atoms, the ring contains at least one hetero atom selected from N, O, S or Si; H on the aromatic ring or the aromatic heterocyclic ring may also be optionally substituted by a halogen atom, a nitro group, an aryl group, an alkyl group or a modified alkyl group.

The above cyclic o-nitrobenzyl phototrigger is preferably selected from the following cyclic structures:

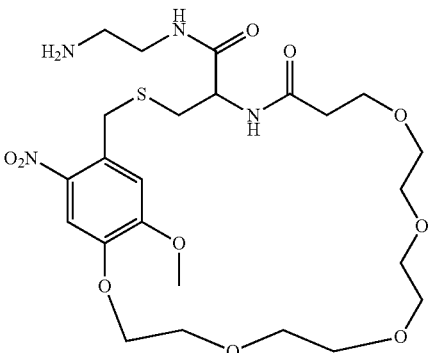

Compound 93

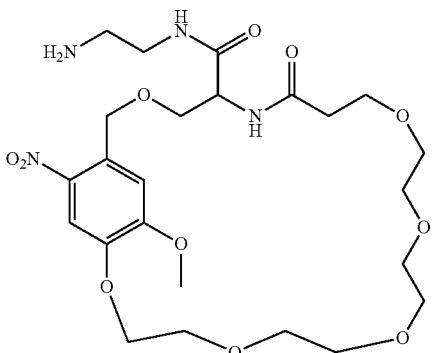

Compound 94

Compound 95
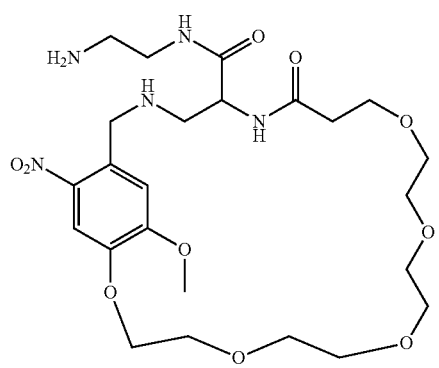
Compound 96
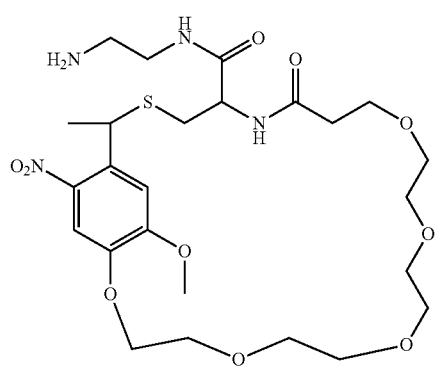
Compound 97
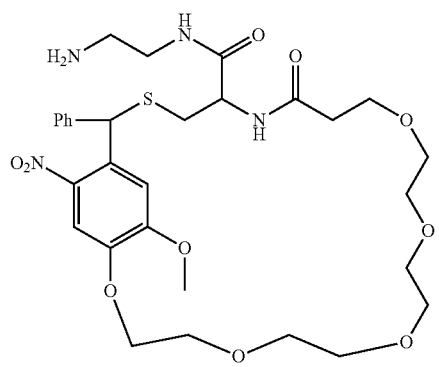
Compound 98
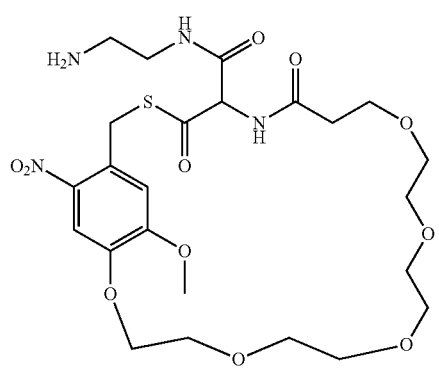
Compound 99
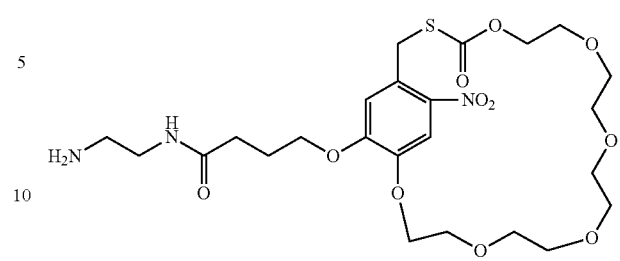
Compound 100
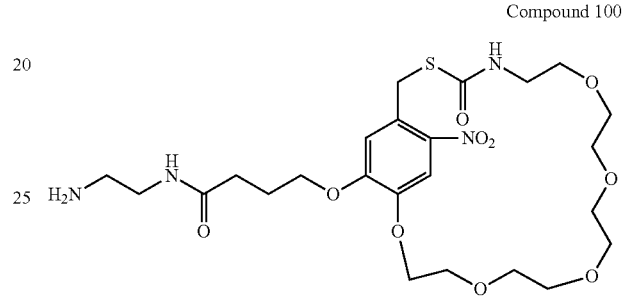
Compound 103
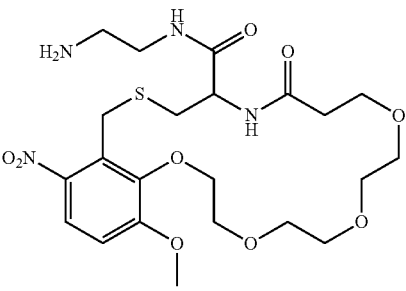
Compound 104
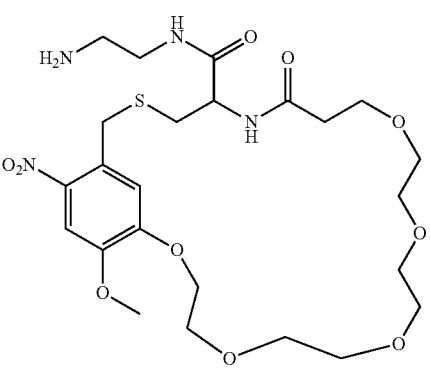

Compound 105

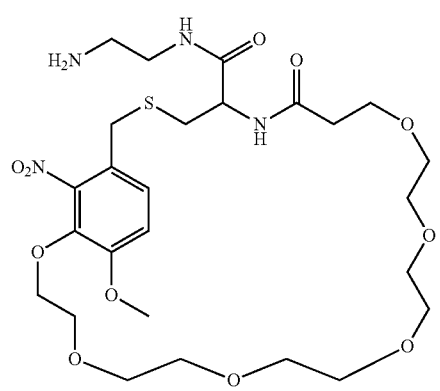

Compound 106

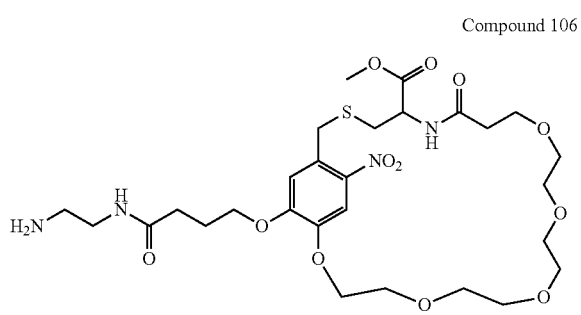

Compound 107

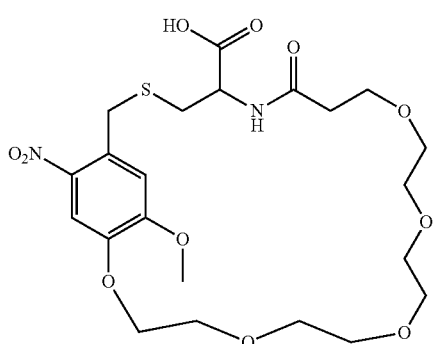

Compound 108

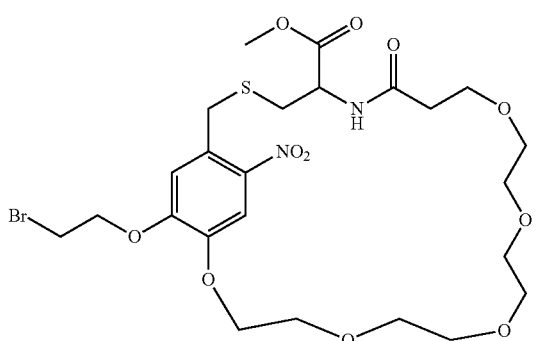

Compound 109

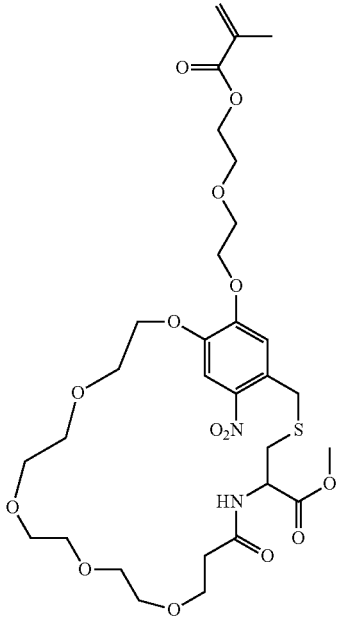

The second objective of this invention is to provide a series of photosensitive polymer derivatives.

The photosensitive polymer derivatives provided by this invention are comprised of three structures:

1. Photosensitive polymer derivatives modified by o-nitrobenzyl phototriggers, referred to $A_1$, have the structure of Formula A-I;

2. Photosensitive polymer derivatives modified by double bond functional group, referred to $A_2$, have the structure of Formula A-II;

3. Photosensitive polymer derivatives modified by both o-nitrobenzyl group phototriggers and double bond functional group, referred to $A_3$, have the structure of Formula A-III.

Formula A-I

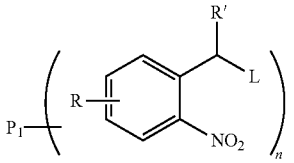

Formula A-II

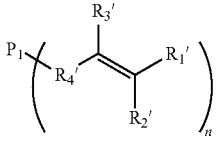

Formula A-III

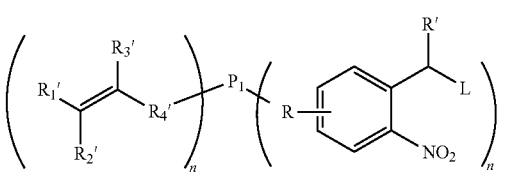

Among them, o-nitrobenzyl group phototriggers as shown in Formula I has two structures such as Formula I-1 and Formula I-2. Formula I-1 represents an o-nitrobenzyl phototrigger that does not contain a cyclic structure. Formula I-2 represents a cyclic o-nitrobenzyl based phototriggers named cNB.

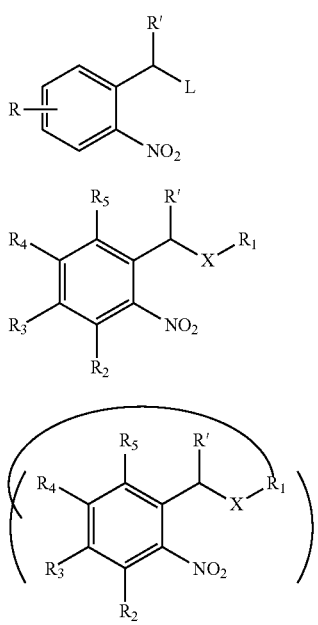

Formula I

Formula I-1

Formula I-2

In Formula I-1 and Formula I-2, when X=O, it is an o-nitrobenzyl alcohol phototrigger named NB; when X=S, it is an o-nitrobenzyl sulfide phototrigger named sNB; when X=N, it is an o-nitrobenzylamine phototrigger named nNB.

In Formula A-I, Formula A-III, Formula I, Formula I-1 and Formula I-2, R' is selected from the group consisting of a hydrogen atom, a halogen atom, a hydroxyl group, a sulphydryl group, an amine group, a nitro group, a cyano group, an aldehyde group, a ketone group, an ester group, an amide group, a phosphonic acid group, a phosphonate group, a sulfonate group, a sulfonic acid ester group, a sulfoxide group, an aryl group, a heteroaryl group, an alkyl group, an alkylene group, a modified alkyl group and a modified alkylene group.

In Formula I-1 and Formula I-2, $R_1$ is selected from the group consisting of a hydrogen atom, an ether group, an ester group, a carbonate group, an amino formate ester group, a mercaptoformic ester group and phosphoric acid ester group.

In Formula I-1 and Formula I-2, $R_2$, $R_3$, $R_4$ and $R_5$ are freely selected from the group consisting of a hydrogen atom, a halogen atom, a hydroxyl group, a mercapto group, an amine group, a nitro group, a cyano group, an aldehyde group, a ketone group, a carboxyl group, an ester group, an amide group, a phosphonic acid group, a phosphonate group, a sulfonic acid group, a sulfonate group, a sulfone group, a sulfoxide group, an aryl group, a heteroaryl group, an alkyl group, an alkylene group, a modified alkyl group and a modified alkylene group.

In Formula I-1 and Formula I-2, preferably, $R_2$, $R_3$, $R_4$ and $R_5$ are interconnected to each other and connected together with a carbon atom to form a saturated or unsaturated alicyclic or heteroalicyclic ring, or an aromatic ring or an aromatic heterocyclic ring.

In the Formula I-2, X is O, S, or NH. And one end of $R_1$ is connected to X, the other end is connected to any one of $R_2$, $R_3$, $R_4$ and $R_5$ to form a cyclic structure.

In the Formula A-I and Formula A-III, n≥2. This means the average number of o-nitrobenzyl phototriggers on a single molecule of the photosensitive polymer derivative is more than or equal to 2.

In the Formula A-I and Formula A-III, $P_1$ is a hydrophilic or water-soluble natural polymer or synthetic polymer, or independently selected from a various of hydrophilic or water-soluble natural polymers or synthetic polymers.

For the photosensitive polymer derivatives containing double bond groups or both o-nitrobenzyl phototriggers and double bond groups in Formula A-II and Formula A-III, $R'_1$, $R'_2$ and $R'_3$ are selected from the group consisting of a hydrogen atom, alkyl, modified alkyl or aryl; $R_4'$ is selected from the group consisting of an alkyl group, an ether group, an ester group, an amide group.

Alternatively, in Formula A-II and Formula A-III, $R_1'$, $R_2'$ and $R_3'$ can connect with each other together with carbon atoms to form a saturated or unsaturated alicyclic ring, or alicyclic heterocycle.

In Formula A-II and Formula A-III, n≥2. This means the average number of o-nitrobenzyl phototriggers on a single molecule of the photosensitive polymer derivative is more than or equal to 2. $P_1$ is a hydrophilic or water-soluble natural polymer or synthetic polymer, or independently selected from a variety of hydrophilic or water-soluble natural polymers or synthetic polymers.

The polymer $P_1$ in the above three kinds of photosensitive polymer derivatives can be a hydrophilic or water-soluble natural high polymer, or a hydrophilic or water-soluble synthetic polymer.

Hydrophilic or water-soluble natural polymers include natural polysaccharides and their decorations or degradations, proteins and their decorations, modifiers and degradable peptides, etc.

The natural polysaccharides include hyaluronic acid, carboxymethyl cellulose, methyl cellulose, hydroxyethyl cellulose, hydroxypropyl cellulose, alginate, dextran, agarose, heparin, chondroitin sulfate, glycol chitosan, propylene glycol chitosan, chitosan lactate, carboxymethyl chitosan or quaternary ammonium salt of chitosan.

The protein includes various hydrophilic or water-soluble animal and plant proteins, collagen, serum proteins, silk fibroin proteins and elastin, and the protein degradations include gelatin or polypeptides.

Hydrophilic or water-soluble synthetic polymers include two-arm or multi-arm poly (ethylene glycol), poly (ethylene imine), dendrites, synthetic peptides, polylysine, poly (glutamic acid), poly (acrylic acid), poly (methacrylic acid), polyacrylate, poly (methacrylate), poly (acrylamide), poly (methacrylamide), poly (vinyl alcohol), poly (vinyl pyrrolidone).

The above three photosensitive polymer derivatives may be hydrophilic or water-soluble polymers containing one or more different groups at the same time, or a mixture of hydrophilic or water-soluble polymers containing one or more different groups.

When component A is a photosensitive polymer derivative modified by o-nitrobenzyl phototriggers with a structure of Formula A-I, When o-nitrobenzyl phototriggers are selected from the structure of Formula I-1, $P_1$ is connected to any one or more groups of $R_2$, $R_3$, $R_4$ and $R_5$, or connected to a saturated or unsaturated alicyclic or heteroalicyclic ring formed by $R_2$, $R_3$, $R_4$ and $R_5$, or connected to an aromatic ring or aromatic heterocyclic ring formed by $R_2$, $R_3$, $R_4$ and $R_5$, via a linkage bond.

When the o-nitrobenzyl phototriggers are selected from Formula I-2, $P_1$ is connected to any one or more groups of $R_2$, $R_3$, $R_4$ and $R_5$, or connected to a saturated or unsaturated alicyclic or heteroalicyclic ring formed by $R_2$, $R_3$, $R_4$ and $R_5$, or connected to an aromatic ring or aromatic heterocyclic ring formed by $R_2$, $R_3$, $R_4$ and $R_5$, or connected to a cyclic chain formed by connecting $R_1$ with any one group of $R_2$, $R_3$, $R_4$ or $R_5$, via a linkage bond.

The linkage bond includes at least one selected from the group consisting of —O—, —S—, —NH—, -alkyl group-, —COO— and —CONH—.

When component A is a photosensitive polymer derivative modified by both o-nitrobenzyl phototriggers and double bond groups with a structure of Formula A-III, When o-nitrobenzyl phototriggers is selected from the structure of Formula I-1, One end of $P_1$ is connected to any one or more groups of $R_2$, $R_3$, $R_4$ and $R_5$, or connected to a saturated or unsaturated alicyclic or heteroalicyclic ring formed by $R_2$, $R_3$, $R_4$ and $R_5$, or connected to an aromatic ring or aromatic heterocyclic ring formed by $R_2$, $R_3$, $R_4$ and $R_5$, via a linkage bond. And the other end of $P_1$ is connected to $R'_4$, via a linkage bond.

When the o-nitrobenzyl phototriggers is selected from Formula I-2,

One end of $P_1$ is connected to any one or more groups of $R_2$, $R_3$, $R_4$ and $R_5$, or connected to a saturated or unsaturated alicyclic or heteroalicyclic ring formed by $R_2$, $R_3$, $R_4$ and $R_5$, or connected to an aromatic ring or aromatic heterocyclic ring formed by $R_2$, $R_3$, $R_4$ and $R_5$, or connected to a cyclic chain formed by connecting $R_1$ with any one group of $R_2$, $R_3$, $R_4$ or $R_5$, via a linkage bond. And the other end of $P_1$ is connected to $R'_4$, via a linkage bond.

The linkage bond includes at least one selected from the group consisting of —O—, —S—, —NH—, -alkyl group-, —COO— and —CONH—.

Among them, Formula A-I is photosensitive polymer derivative modified by o-nitrobenzyl phototriggers, Formula A-II is photosensitive polymer derivative containing double bond groups, Formula A-III is photosensitive polymer derivative containing both o-nitrobenzyl phototriggers and double bond groups, and the structure design of Formula A-III is in the foundation of the structure of Formula A-I and Formula A-II. The o-nitrobenzyl phototriggers and the double bond groups simultaneously grafted in one polymer chain can simultaneously achieve two kinds of crosslinking, which make the hydrogel have the advantage of the fast speed of free radical polymerization crosslinking and the advantage of strong adhesive force of photo-coupling reaction crosslinking. And double crosslinking way can improve the mechanical properties of the hydrogel. Therefore, the optimization of the molecular structure make it as a photosensitive groups modification of polymer derivatives to exhibit more excellent material performance, such as the crosslinking speed increases from 30 s in the aldehyde-amine photocoupling crosslinking to less than 2 s, the tissue adhesion strength increases to about 80-100 KPa, the mechanical properties increases to about 1-2 MPa, specific data are shown in implementation example of one hundred and sixty-seven, one hundred and sixty-eight and one hundred and sixty-nine.

Further, the alkyl group is a saturated or unsaturated aliphatic linear or branched alkyl group having 1 to 30 carbon atoms.

The alkylene group is a saturated or unsaturated aliphatic linear chain or branched alkylene group with 1-30 carbon atoms.

Modified alkyl group is an alkyl group whose any carbon atom is at least substituted by one of the groups consisting of a halogen atom, —OH, —SH, —NO$_2$, —CN, —CHO, —COOH, ester, amide, aromatic, arylidene, —CO—, —O—, —S—, —SO—, —SO$_2$—, amino, secondary amine, tertiary amine, quaternary ammonium salt, saturated or unsaturated single or double cyclic alkylene, bridged aliphatic heterocyclic. And the modified alkyl group has 1~30 carbon atoms whose carbon-carbon single bond is replaced optionally and independently by a carbon-carbon double bond or a carbon-carbon triple bond.

Modified alkylene group is an alkylene group whose any carbon atom is at least substituted by one of the groups consisting of a halogen atom, —OH, —SH, —NO$_2$, —CN, —CHO, —COOH, ester, amide, aromatic, arylidene, —CO—, —O—, —S—, —SO—, —SO$_2$—, amino, secondary amine, tertiary amine, quaternary ammonium salt, saturated or unsaturated single or double cyclic alkylene, bridged aliphatic heterocyclic. And the modified alkyl group has 1~30 carbon atoms whose carbon-carbon single bond is replaced optionally and independently by a carbon-carbon double bond or a carbon-carbon triple bond.

The ether group is selected from the following structures:
—(CH$_2$)$_x$CH$_3$, —(CH$_2$CH$_2$O)$_x$CH$_3$, —(CH$_2$)$_x$(CH$_2$CH$_2$O)$_y$CH$_3$, or

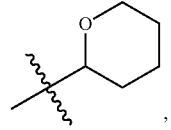

wherein x and y≥0 and are integers.

The ester group is selected from the following structures:
—CO(CH$_2$)$_x$CH$_3$, —CO(CH$_2$CH$_2$O)$_x$CH$_3$, —CO(CH$_2$)$_x$(CH$_2$CH$_2$O)$_y$CH$_3$, wherein x and y≥0 and are integers.

The carbonate group is selected from the following structures:
—COO(CH$_2$)$_x$CH$_3$, —COO(CH$_2$CH$_2$O)$_x$CH$_3$, —COO(CH$_2$)$_x$(CH$_2$CH$_2$O)$_y$CH$_3$, wherein x and y≥0 and are integers.

The amino formate ester group is selected from the following structures:
—CONH(CH$_2$)$_x$CH$_3$, —CONH(CH$_2$CH$_2$O)$_x$CH$_3$, —CONH(CH$_2$)$_x$(CH$_2$CH$_2$O)$_y$CH$_3$, wherein x and y≥0 and are integers.

The mercapto formate ester group is selected from the following structures:
—COS(CH$_2$)$_x$CH$_3$, —COS(CH$_2$CH$_2$O)$_x$CH$_3$, —COS(CH$_2$)$_x$(CH$_2$CH$_2$O)$_y$CH$_3$, wherein x and y≥0 and are integers.

The phosphate ester group is selected from the following structures:
—POOO(CH$_2$)$_x$CH$_3$, —POOO(CH$_2$CH$_2$O)$_x$CH$_3$, —POOO(CH$_2$)$_x$(CH$_2$CH$_2$O)$_y$CH$_3$, wherein x and y≥0 and are integers.

The aryl ring is a monocyclic or fused bicyclic ring of 5-10 atoms.

The heteroaryl is a monocyclic or fused bicyclic ring containing 5 to 10 atoms, the ring contains at least one hetero atom selected from N, O, S or Si.

The halogen atom is independently selected from F, Cl, Br or I.

The alicyclic ring is a saturated or unsaturated monocyclic or polycyclic alicyclic ring of 3 to 10 atoms.

The heteroalicyclic ring is a saturated or unsaturated monocyclic or polycyclic alicyclic ring of 3 to 10 atoms, and the ring contains at least one hetero atom selected from N, O, S or Si. When the heteroalicyclic ring contains an S atom, it is selected optionally from —S—, —SO— or —SO$_2$—; H on the alicyclic or alicyclic ring may be optionally substituted by a halogen atom, a nitro group, an aryl group or an alkyl group or a modified alkyl group.

The aromatic ring is a monocyclic or fused bicyclic ring of 5-10 atoms.

The aromatic heterocycle is a monocyclic or fused bicyclic ring containing 5 to 10 atoms, the ring contains at least one hetero atom selected from N, O, S or Si; H on the aromatic ring or the aromatic heterocyclic ring may also be optionally substituted by a halogen atom, a nitro group, an aryl group, an alkyl group or a modified alkyl group.

Further, the alicyclic or heteroalicyclic ring are preferably selected from:

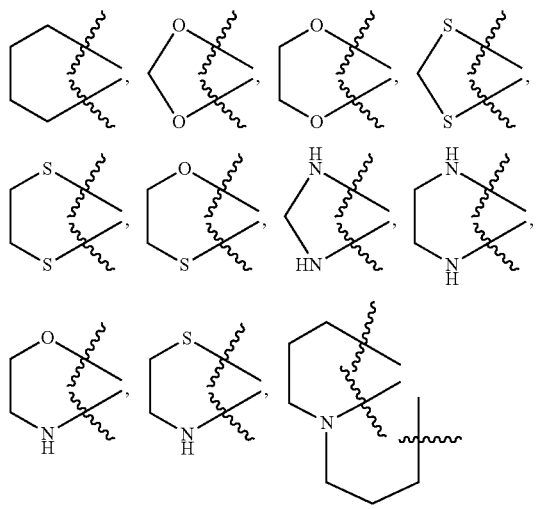

etc;

Further, the aromatic ring or the aromatic heterocyclic ring are preferably selected from:

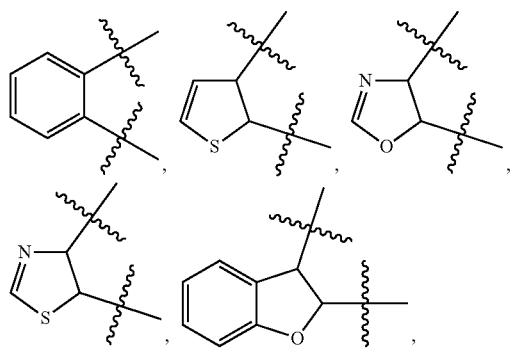

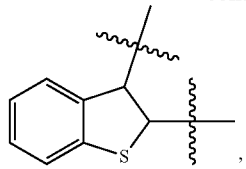

etc;

R' is preferably selected from:
—H, —CH$_3$, —CH$_2$CH$_3$, —CH═CH—CH═CH—CH$_3$, —F, —Cl, —Br, —I, —CF$_3$, —CCl$_3$, —CBr$_3$, —CI$_3$, —CN, —COOH, -Ph,

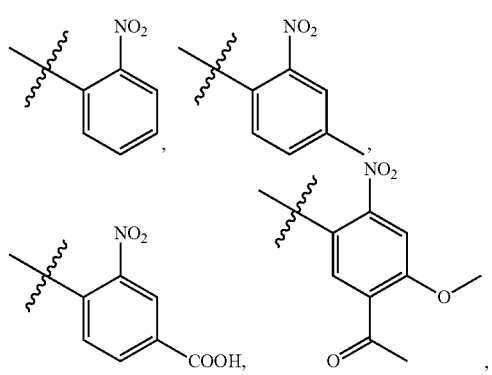

etc;

R$_2$, R$_3$, R$_4$ and R$_5$ are preferably selected from:
—H, —OH, —SH, —NH$_2$, —F, —Cl, —Br, —I, —CF$_3$, —CCl$_3$, —CBr$_3$, —CI$_3$, —NO$_2$, —CN, —CHO, —COOH, —COONH$_2$, —SO$_3$H, etc;

Alkyl substituent is preferably selected from linear alkyl as —(CH$_2$)$_x$CH$_3$, branched alkyl as —(CH$_2$)$_x$ (CY'Y")$_y$CH$_3$ (Y', Y" is hydrogen, alkyl or modified Alkyl), etc., wherein x and y≥0, x and y are integers;

The ether substituent is preferably selected from —O(CH$_2$)$_x$CH$_3$, —O(CH$_2$CH$_2$O)$_x$CH$_3$, —O(CH$_2$)$_x$(CH$_2$CH$_2$O)$_y$CH$_3$, etc., wherein x and y≥0, x and y are integers;

The thioether substituent is preferably selected from —S(CH$_2$)$_x$CH$_3$, —S(CH$_2$CH$_2$O)$_x$CH$_3$, —S(CH$_2$)$_x$(CH$_2$CH$_2$O)$_y$CH$_3$, etc., wherein x and y≥0, x and y are integers; Amino substituent is preferably selected from —NH(CH$_2$)$_x$CH$_3$, —NH(CH$_2$)$_x$(CY'Y")$_y$CH$_3$, —N(CY'Y")$_x$ (CY'Y")$_y$,

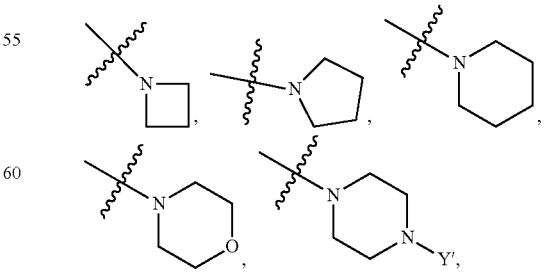

(Y, Y' is hydrogen, alkyl or modified alkyl), etc., wherein x and y≥0, x and y are integers;

The ester substituent is preferably selected from —COO(CH$_2$)$_x$CH$_3$, —COO(CH$_2$CH$_2$O)$_x$CH$_3$, —COO(CH$_2$)$_x$(CH$_2$CH$_2$O)$_y$CH$_3$ or the like, wherein x and y≥0, x and y are integers;

The amide substituent is preferably selected from —CONH(CH$_2$)$_x$CH$_3$, —CONH(CH$_2$CH$_2$O)$_x$CH$_3$, —CONH(CH$_2$)$_x$(CH$_2$CH$_2$O)$_y$CH$_3$ or the like, wherein x and y≥0, x and y are integers;

The aromatic substituent is preferably selected from -Ph,

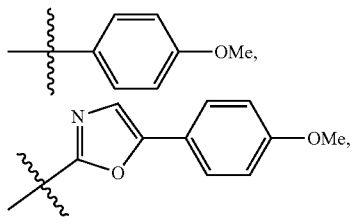

etc.

The polymer P$_1$ in the polymer derivatives modified by the o-nitrobenzyl phototriggers may be a hydrophilic or water-soluble natural polymer including natural polysaccharides and their modifications or degradants, proteins and their modifications or degradants and etc. The natural polysaccharides include hyaluronic acid, carboxymethyl cellulose, methyl cellulose, hydroxyethyl cellulose, hydroxypropyl cellulose, alginate, dextran, agarose, heparin, chondroitin sulfate, glycol chitosan, propylene glycol chitosan, chitosan lactate, carboxymethyl chitosan or quaternary ammonium salt of chitosan. The protein includes various hydrophilic or water-soluble animal and plant proteins, collagen, serum proteins, silk fibroin proteins and elastin, and the protein degradations include gelatin or polypeptides. Hydrophilic or water-soluble synthetic polymers include two-arm or multi-arm poly (ethylene glycol), poly (ethylene imine), dendrites, synthetic peptides, polylysine, poly (glutamic acid), poly (acrylic acid), poly (methacrylic acid), polyacrylate, poly (methacrylate), poly (acrylamide), poly (methacrylamide), poly (vinyl alcohol), poly (vinyl pyrrolidone).

In the above grafted or polymerized water-soluble or hydrophilic polymer derivative, the average number of o-nitrobenzyl phototriggers on a single polymer chain is greater than or equal to 2 (n≥2).

The polymer derivative modified by the o-nitrobenzyl phototriggers may be a hydrophilic or water-soluble polymer simultaneously containing one or more different groups, or a mixture of hydrophilic or water-soluble polymers with one or more different groups. The hydrophilic or water-soluble polymer refers to a hydrophilic or water-soluble natural polymer, or a hydrophilic or water-soluble synthetic polymer.

Alternatively, the polymer derivative modified by o-nitrobenzyl phototriggers in Formula A-I may be selected from the following structures of Component A-1 to A-50:

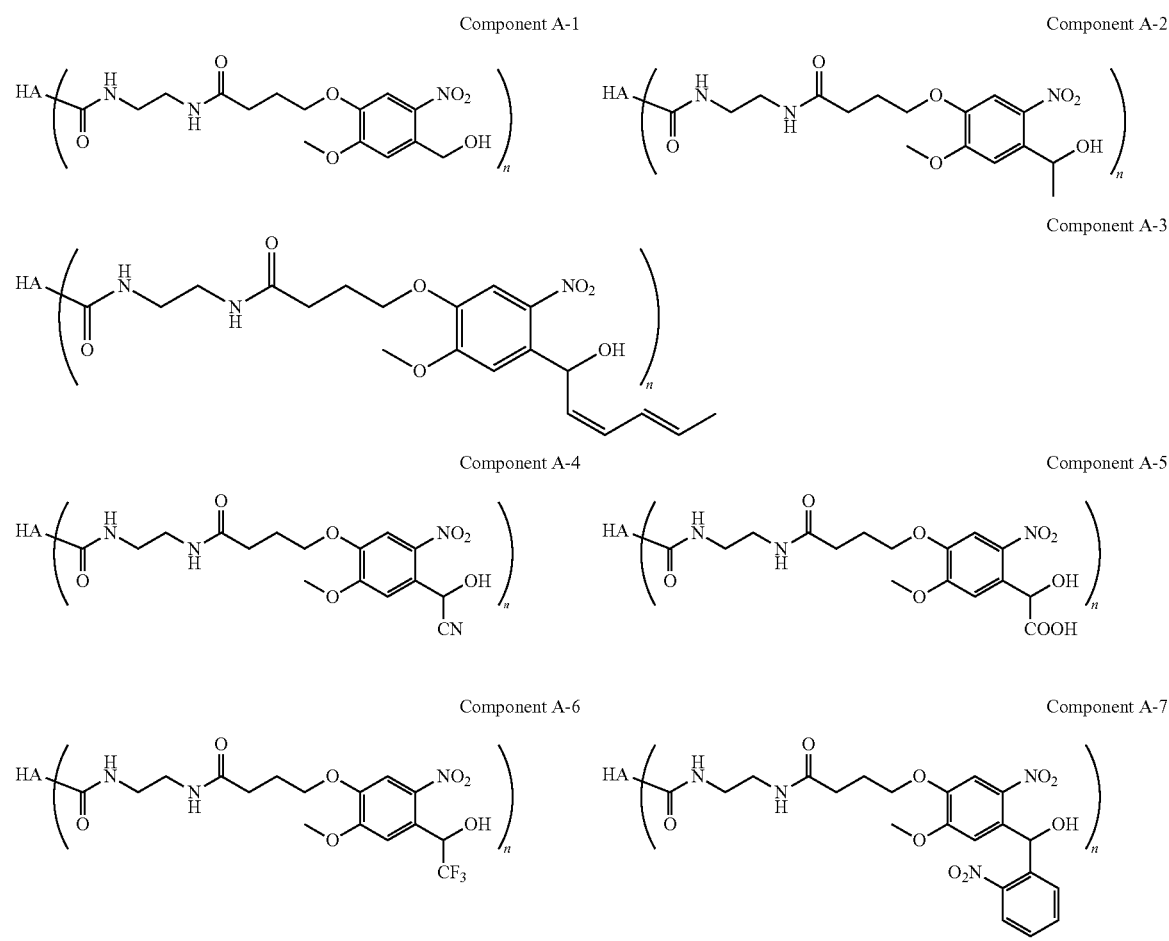

Component A-8
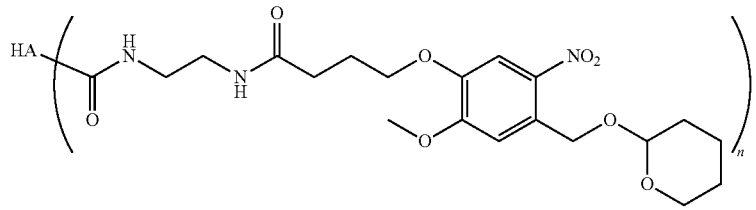
Component A-9
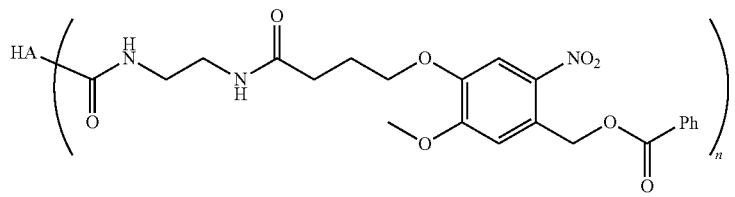
Component A-10
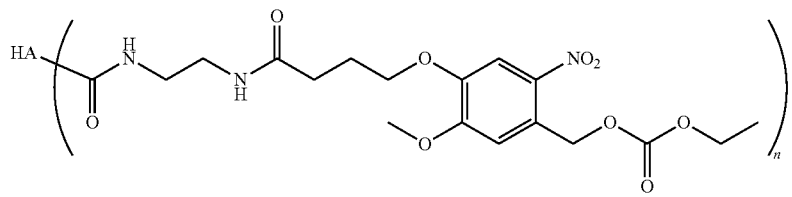
Component A-11
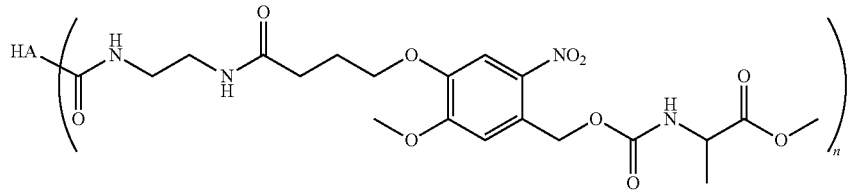
Component A-12
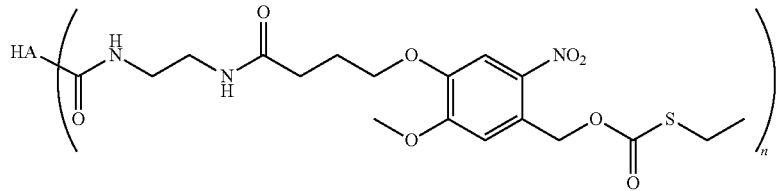
Component A-13
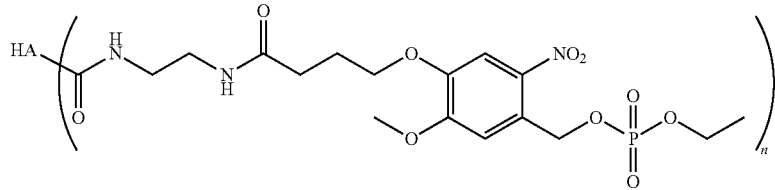
Component A-21
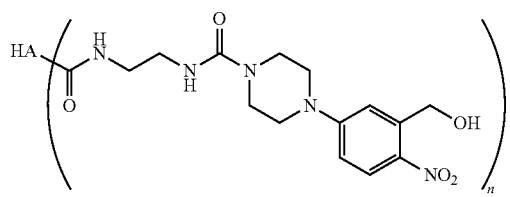
Component A-22
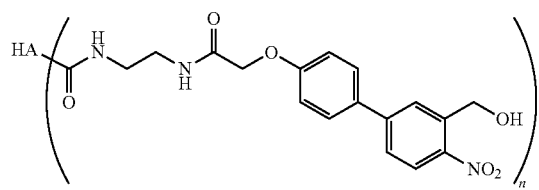

-continued
Component A-25
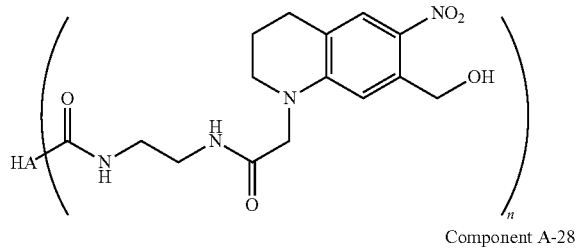
Component A-26
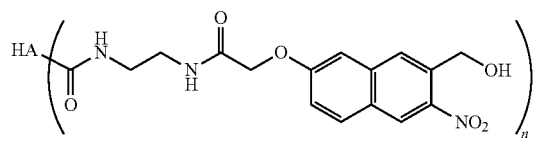
Component A-28
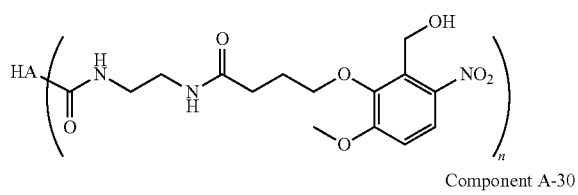
Component A-29
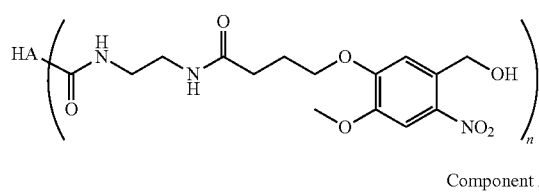
Component A-30
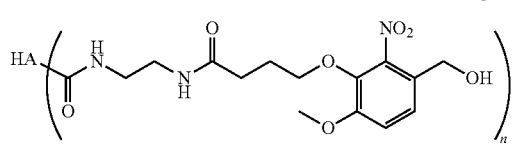
Component A-31
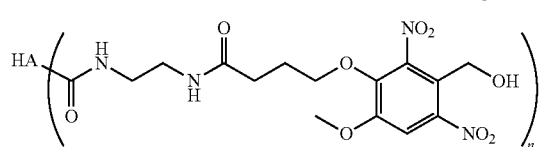
Component A-32
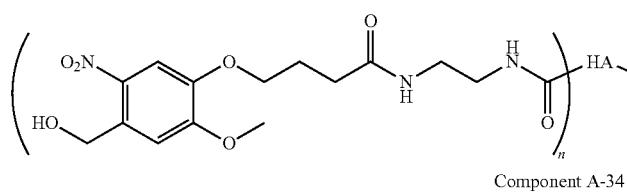
Component A-33
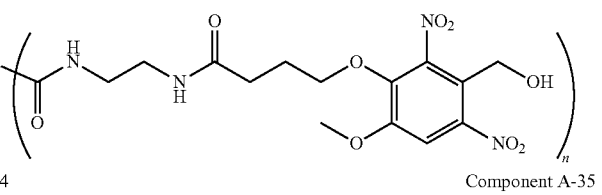
Component A-34
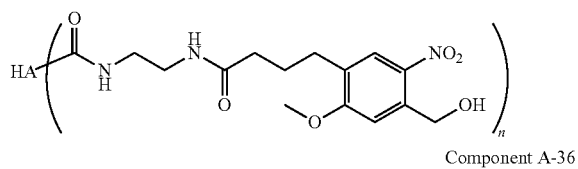
Component A-35
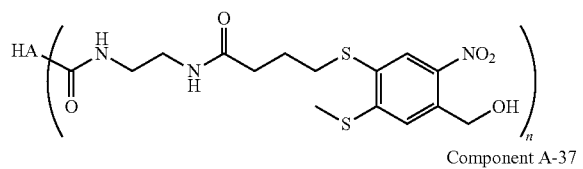
Component A-36
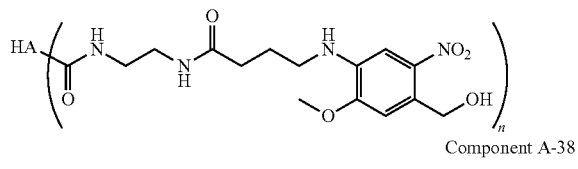
Component A-37
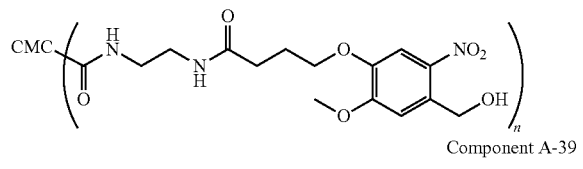
Component A-38
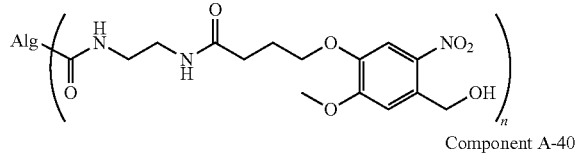
Component A-39
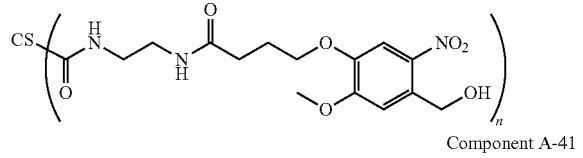
Component A-40
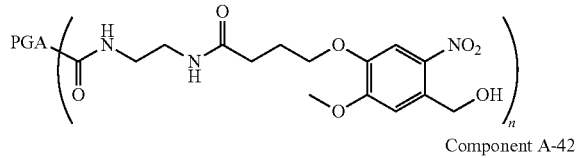
Component A-41
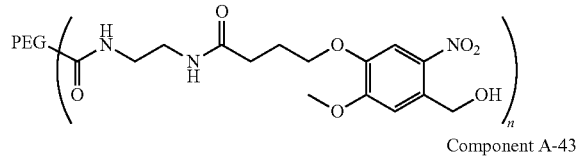
Component A-42
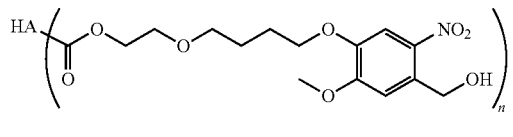
Component A-43
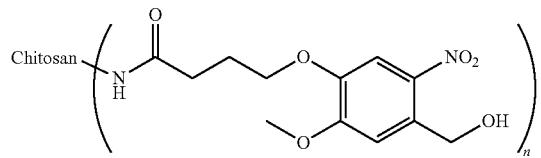

Component A-44
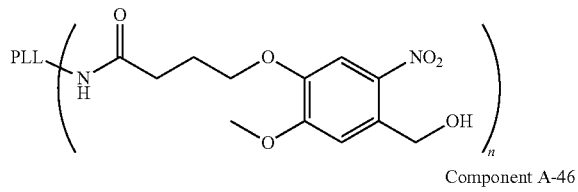
Component A-45
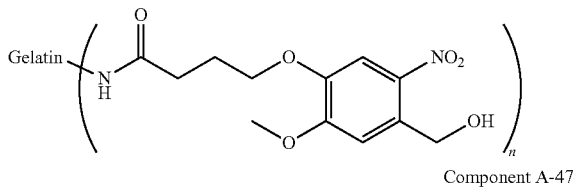
Component A-46
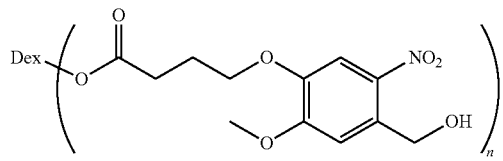
Component A-47
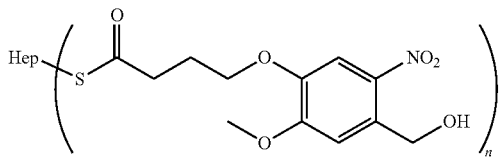
Component A-48
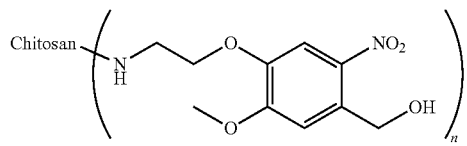
Component A-49
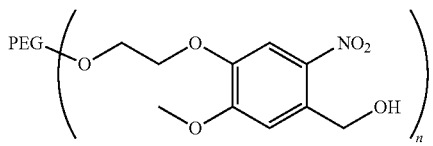
Component A-50
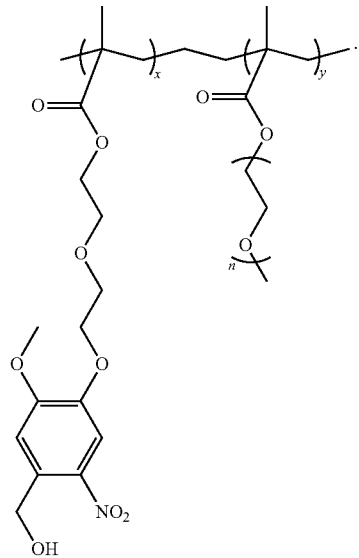
Alternatively, the polymer derivative modified by o-nitrobenzyl sulfide phototriggers in the Formula A-I may be selected from the following structures of Component A-51 to A-69:
Component A-51
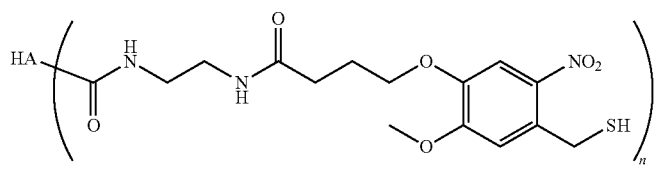

-continued
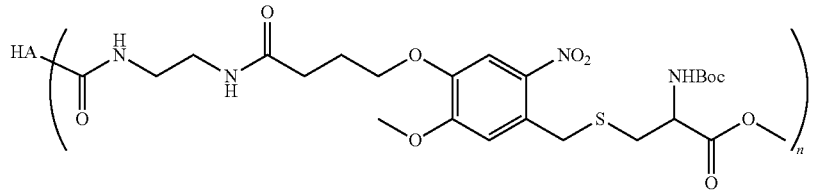
Component A-52
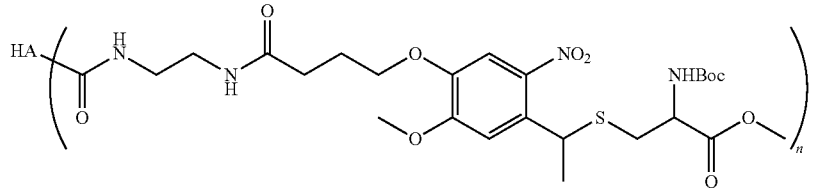
Component A-53
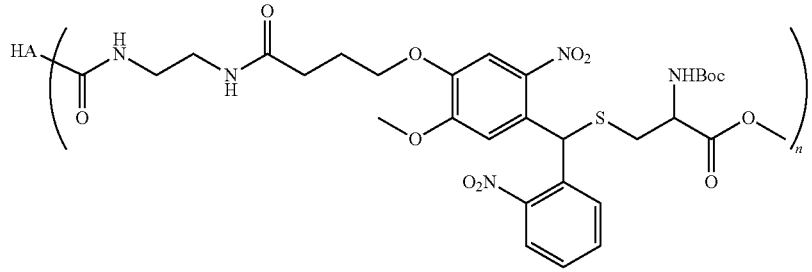
Component A-54
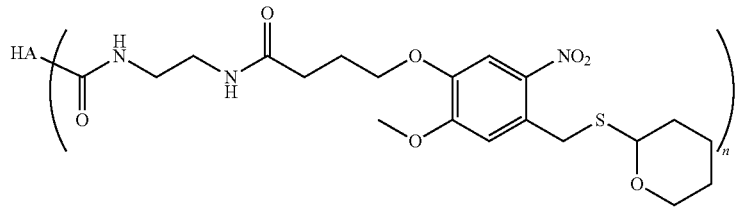
Component A-55
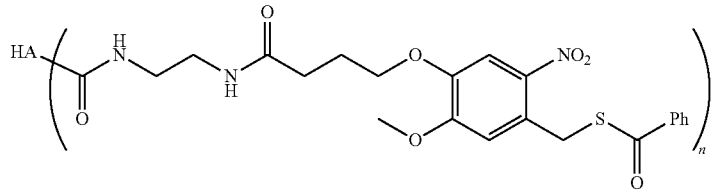
Component A-56
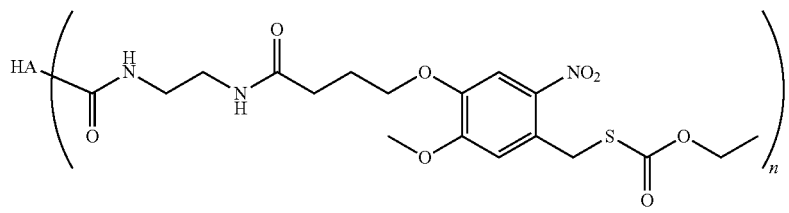
Component A-57
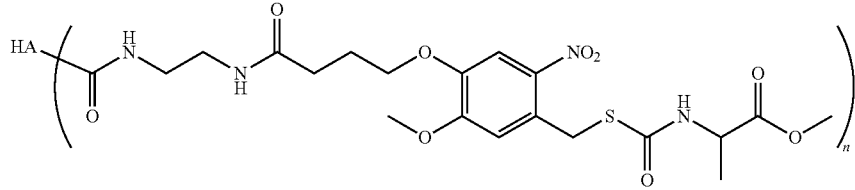
Component A-58

-continued
Component A-59
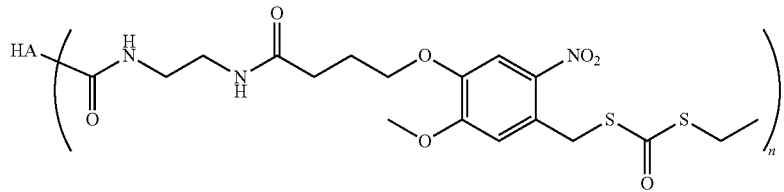
Component A-60
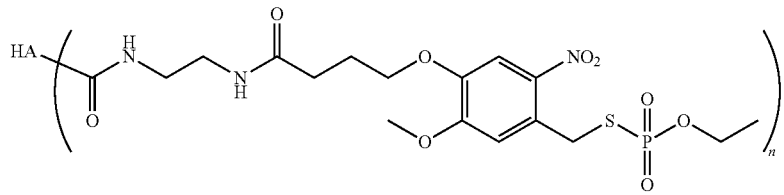
Component A-62
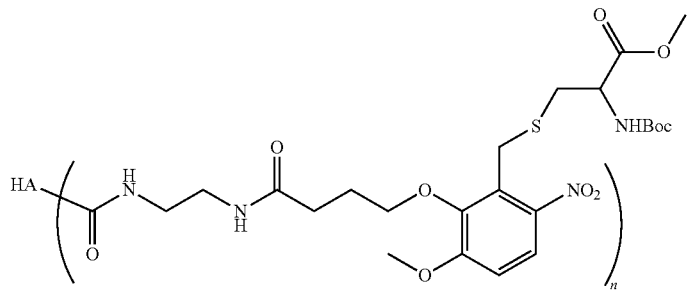
Component A-63
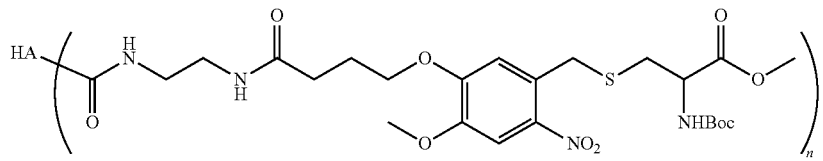
Component A-64
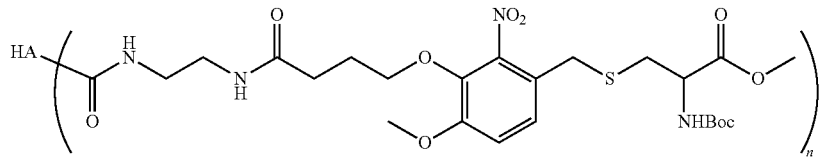
Component A-65
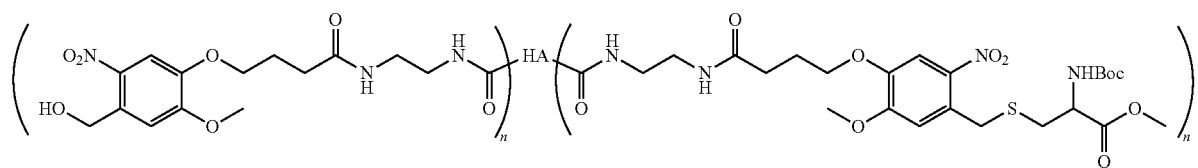
Component A-66
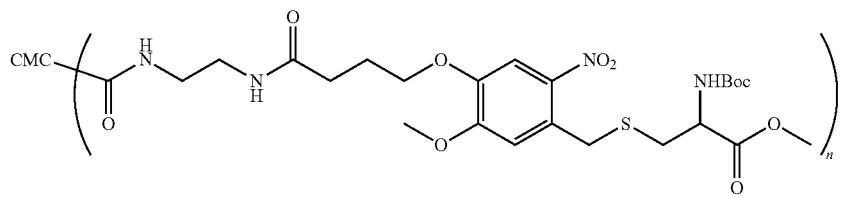
Component A-67
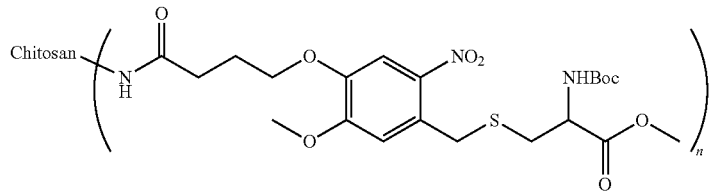

-continued
Component A-68
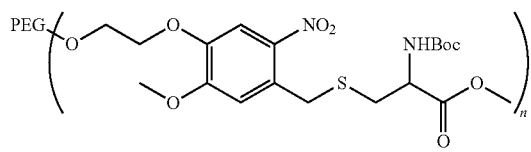
Component A-69
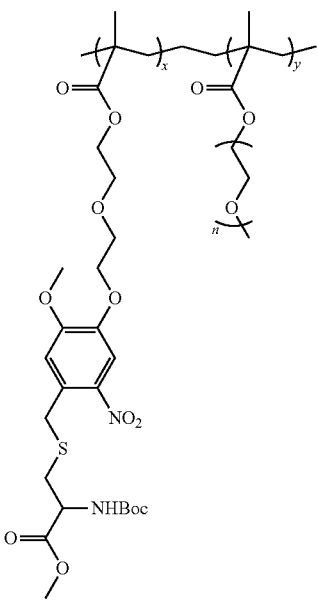
Alternatively, the polymer derivative modified by o-nitrobenzylamine phototriggers in the Formula A-I may be selected from the following structures of Component A-70 to A-87:
Component A-70
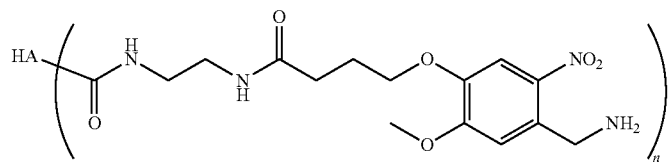
Component A-71
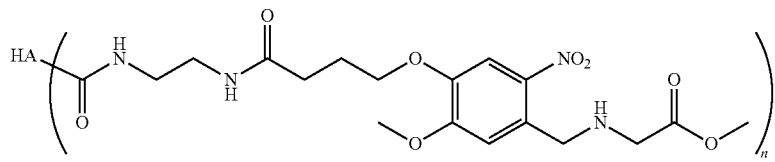
Component A-72
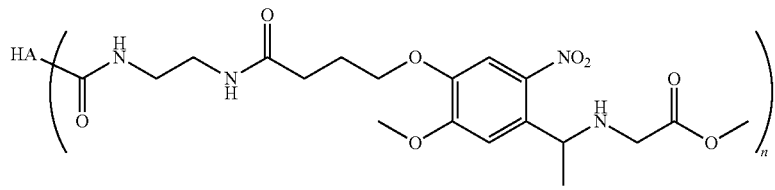
Component A-74
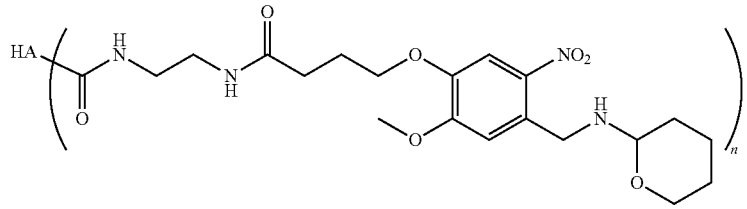

Component A-75
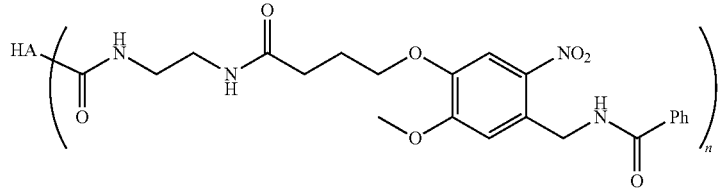
Component A-76
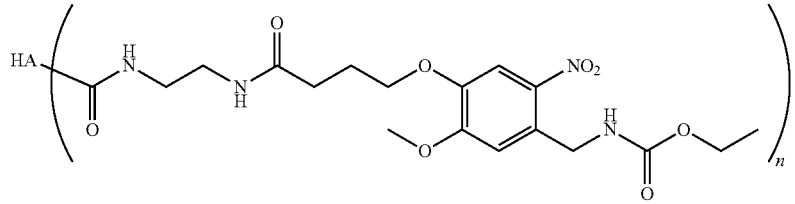
Component A-77
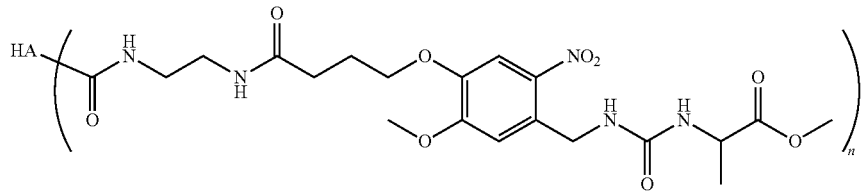
Component A-80
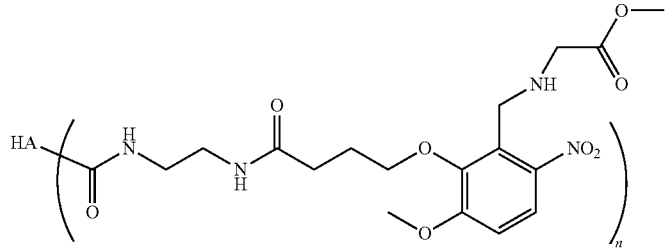
Component A-81
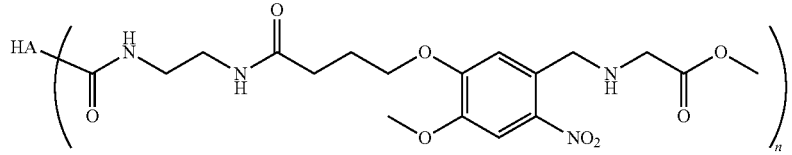
Component A-82
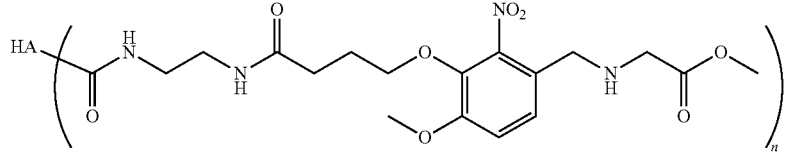
Component A-83
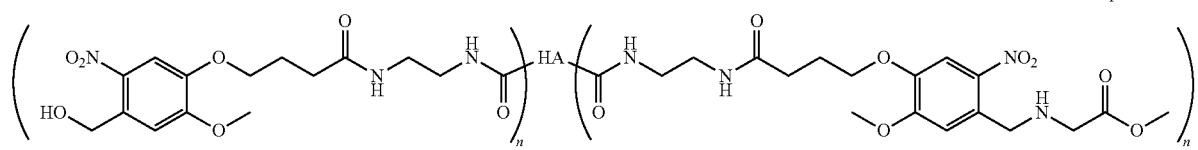
Component A-84
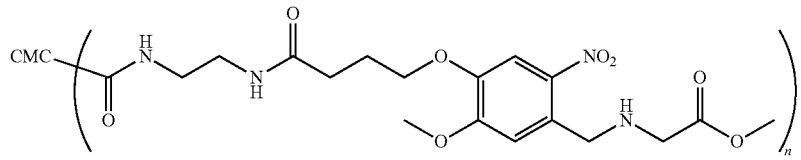

Component A-85
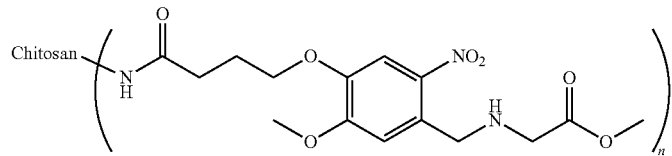
Component A-85
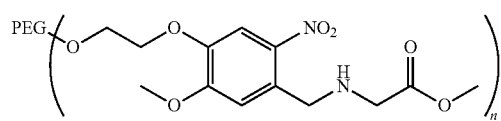
Component A-86
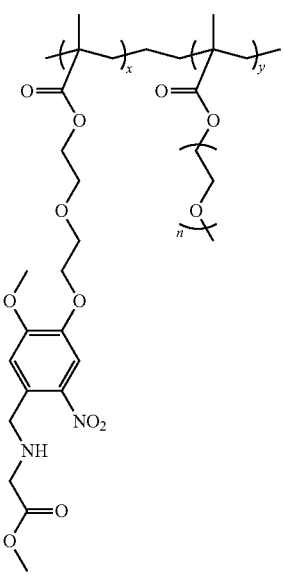
Alternatively, the polymer derivative modified by cyclic o-nitrobenzyl phototriggers in the Formula A-I may be selected from the following structures of Component A-88 to A-106:
Component A-88
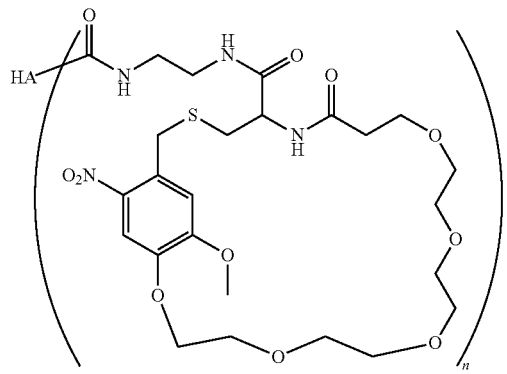
Component A-89
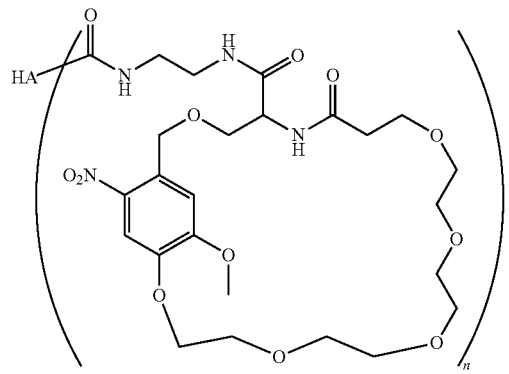

-continued
Component A-90
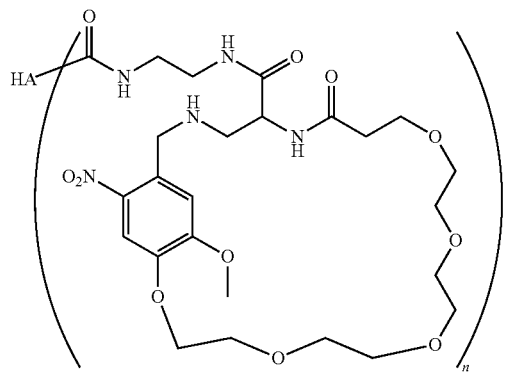
Component A-91
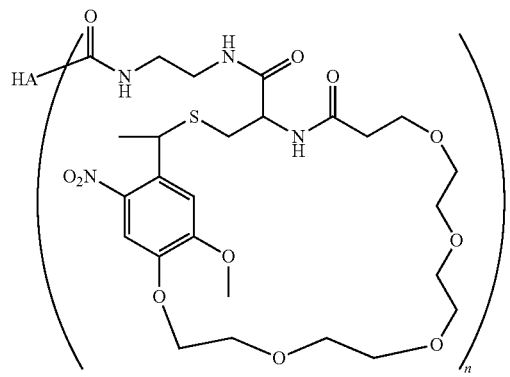
Component A-93
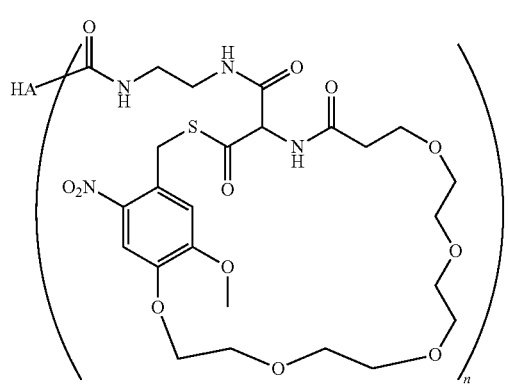
Component A-94
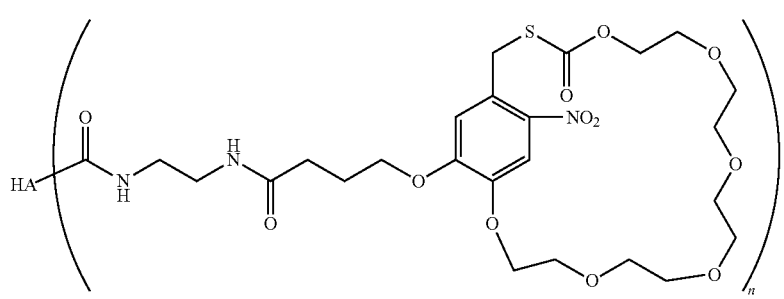
Component A-95
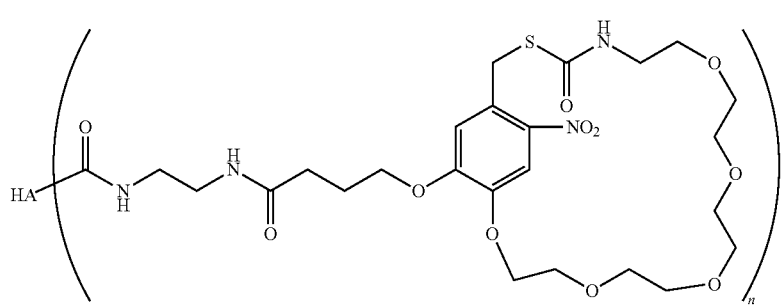

-continued
Component A-98
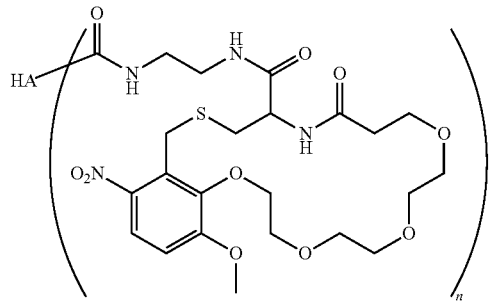
Component A-99
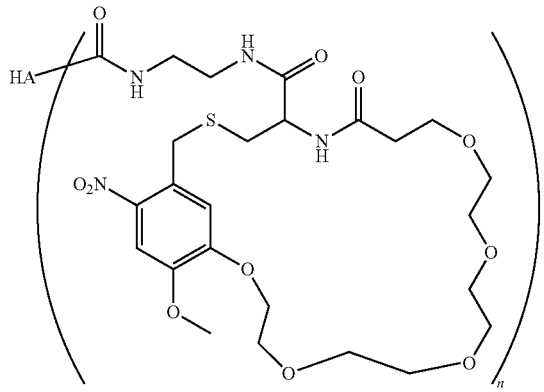
Component A-100
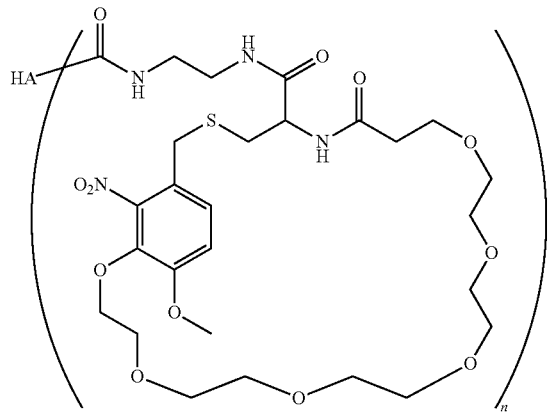
Component A-101
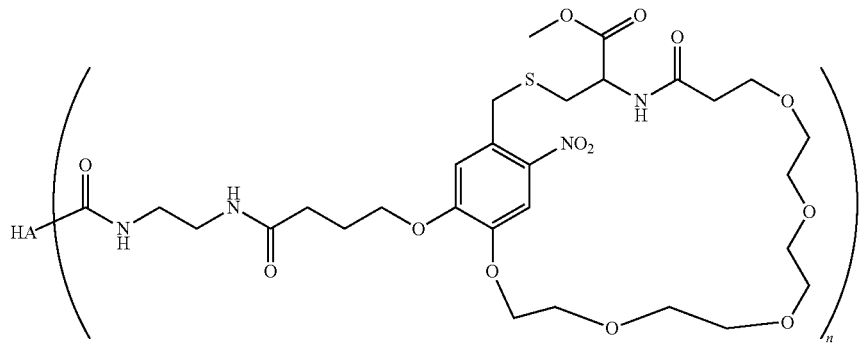
Component A-102
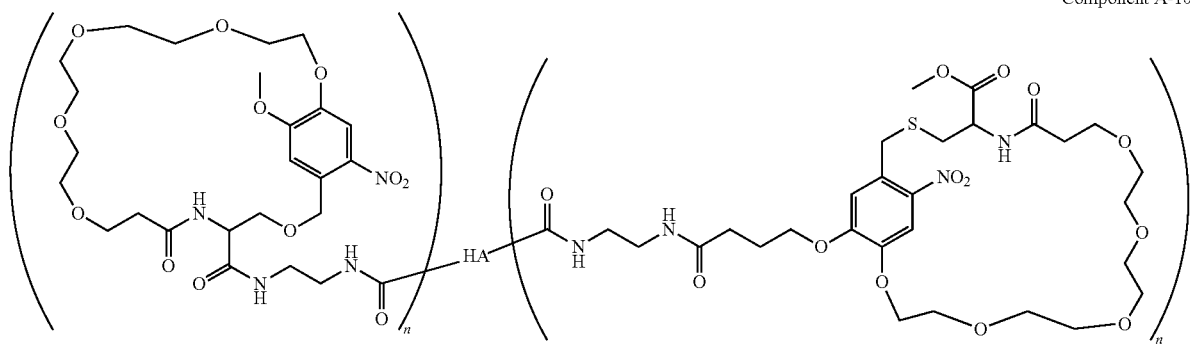

Component A-103
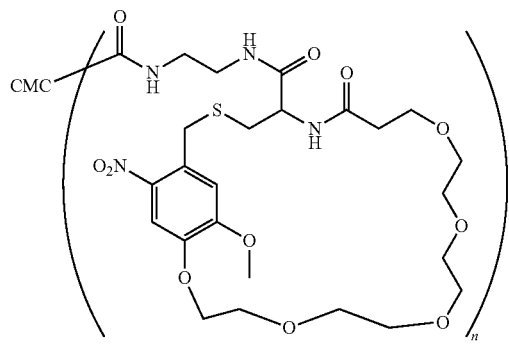
Component A-104
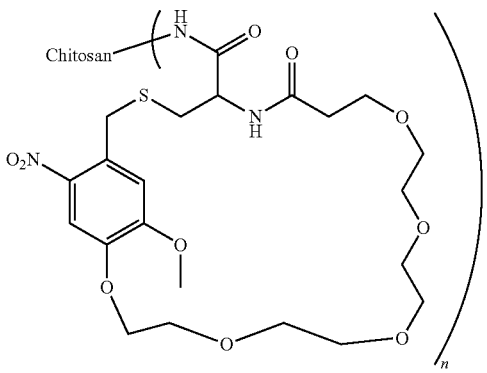
Component A-105
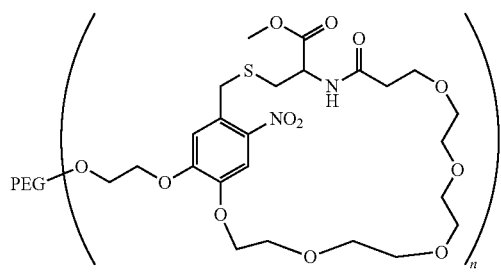
Component A-106
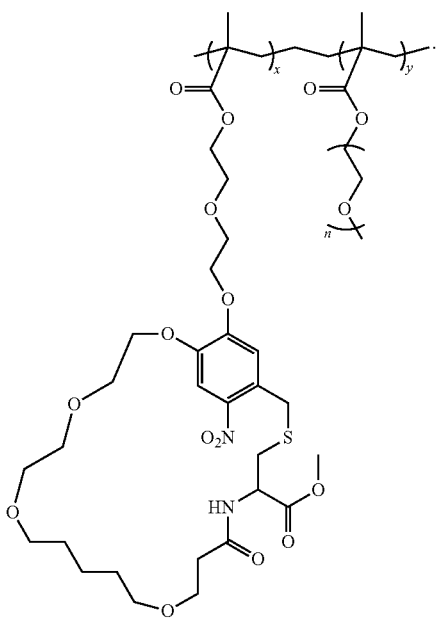
In Component A-1 to Component A-106, n≥2.
Alternatively, the polymer derivative modified by the double bond groups in the Formula A-II may be selected from the followings structures of Component A-107 to A-115:
Component A-107
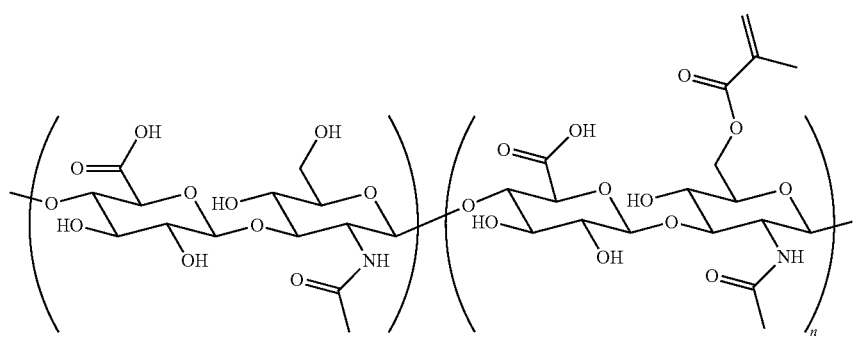

-continued
Component A-108
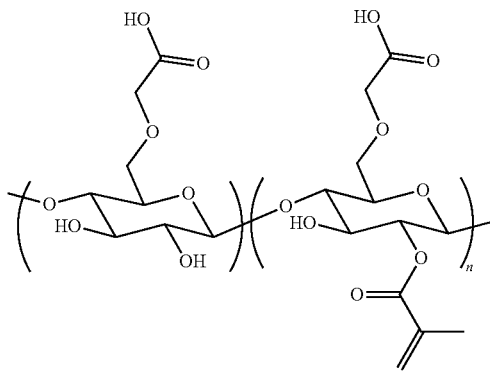
Component A-109
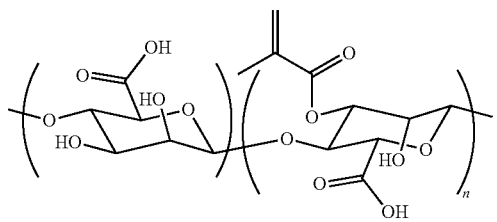
Component A-110
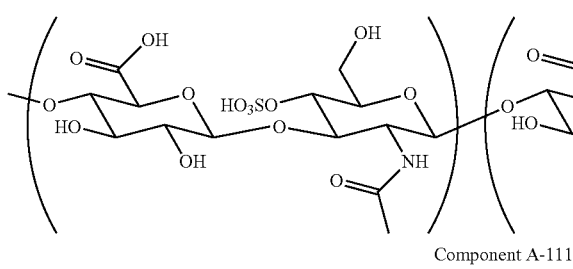
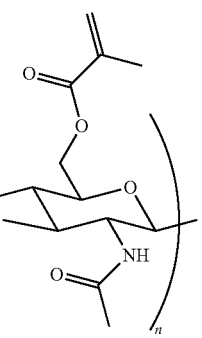
Component A-111
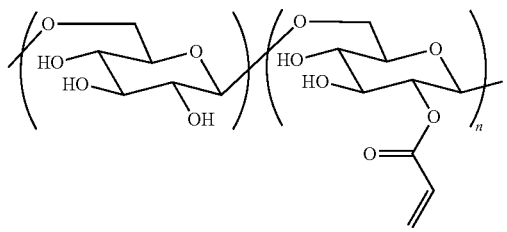
Component A-112
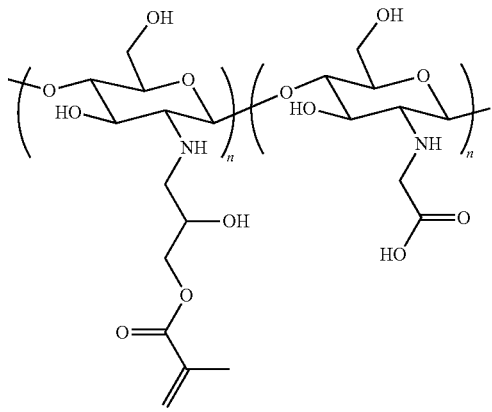
Component A-113
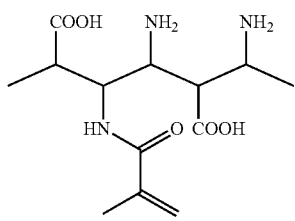
Component A-114
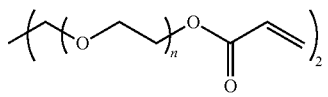
Component A-115
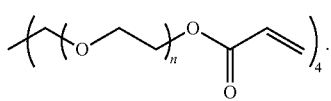

In Component A-107 to Component A-115, n≥2.
Alternatively, the polymer derivative modified by both o-nitrobenzyl group phototriggers and double bond groups in the Formula A-III may be selected from the following structures of Component A-116 to A-154:
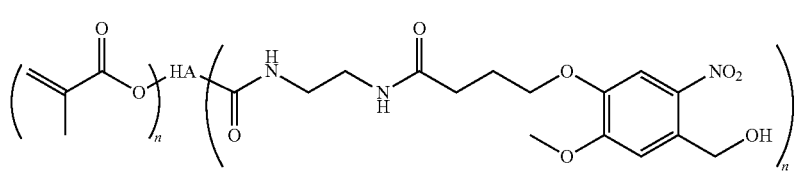
Component A-116

Component A-117
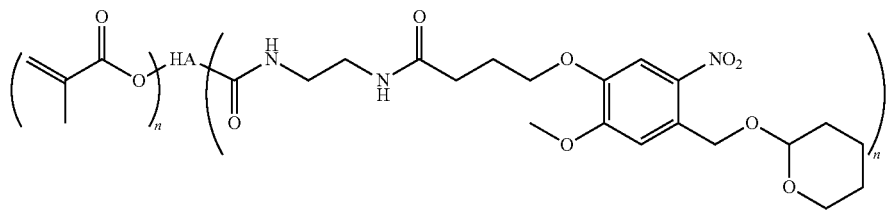
Component A-118
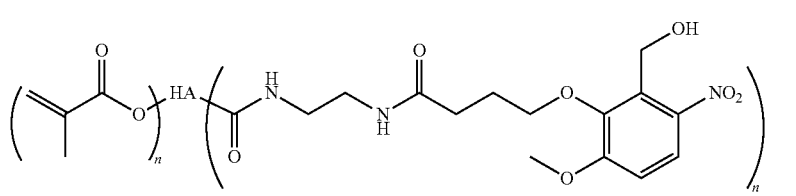
Component A-119
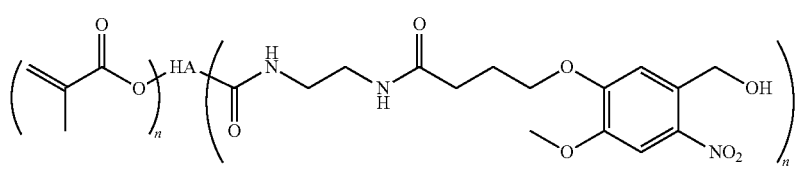
Component A-120
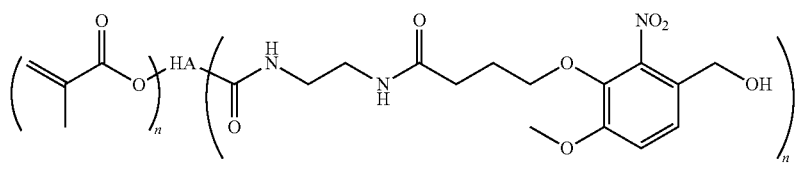
Component A-121
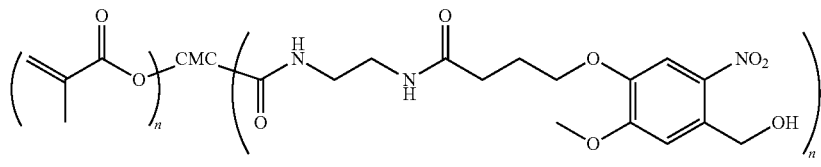
Component A-122
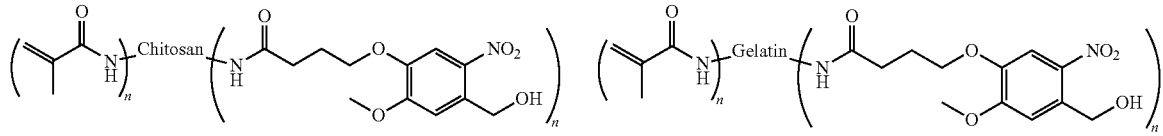
Component A-123    Component A-124

Component A-125
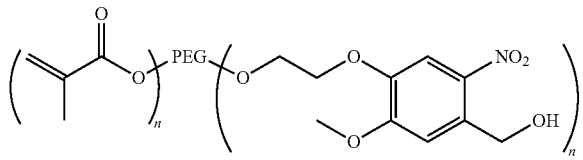
Component A-126
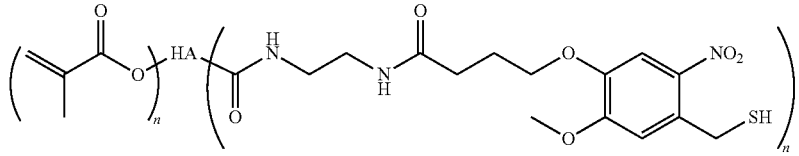
Component A-127
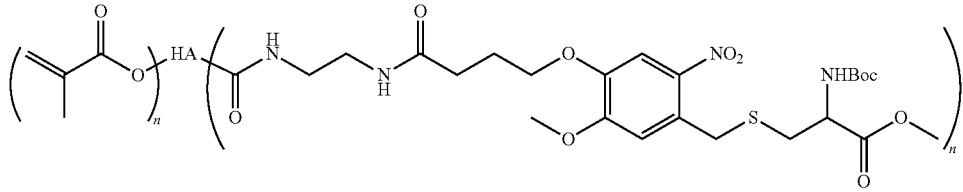
Component A-128
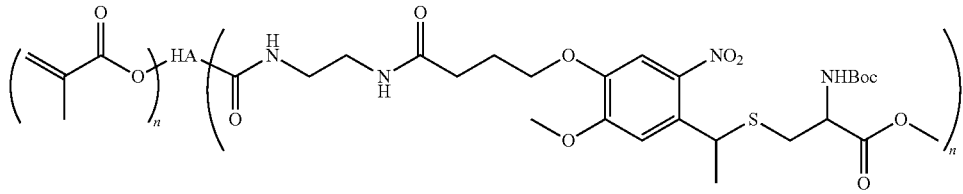
Component A-129
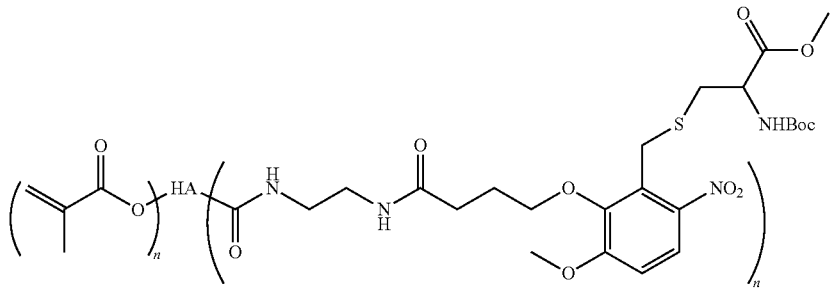
Component A-130
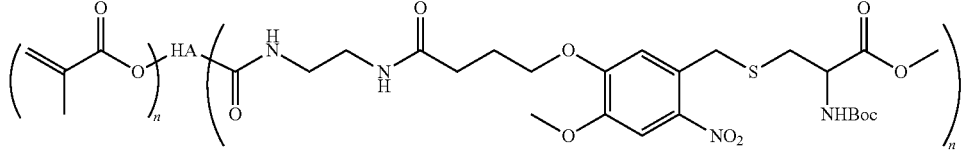
Component A-131
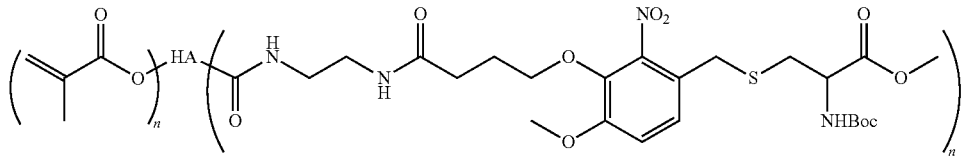
Component A-132
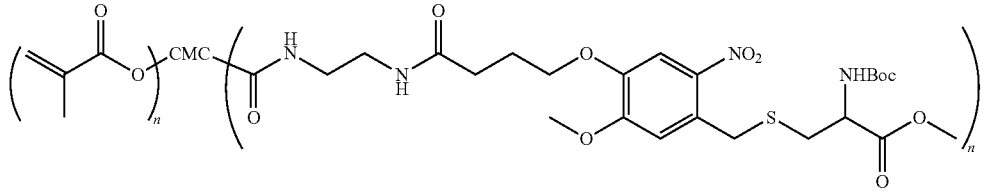

-continued
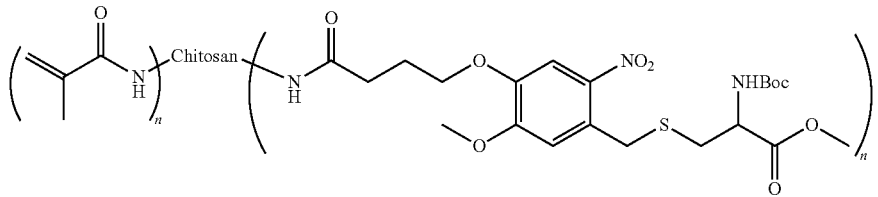
Component A-133
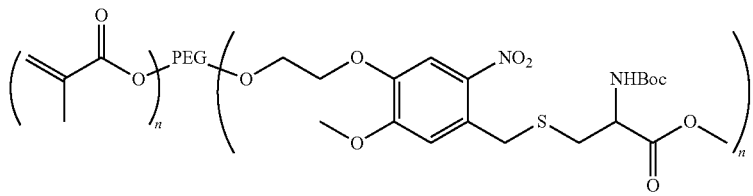
Component A-134
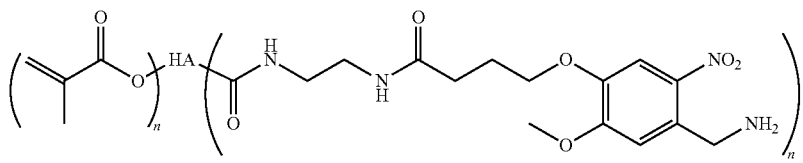
Component A-135
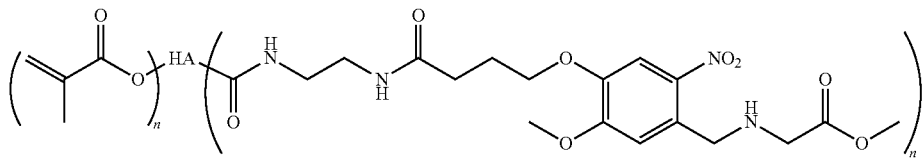
Component A-136
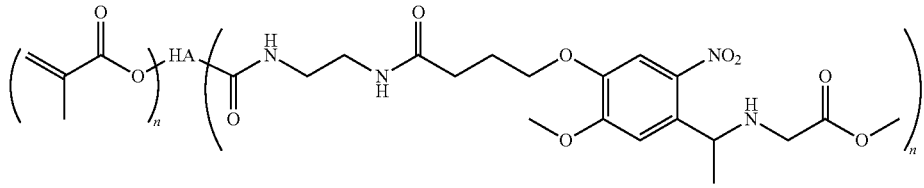
Component A-137
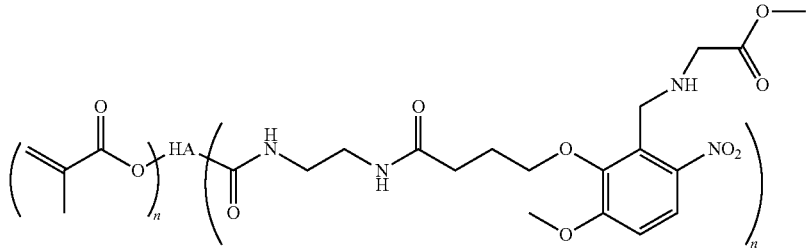
Component A-138
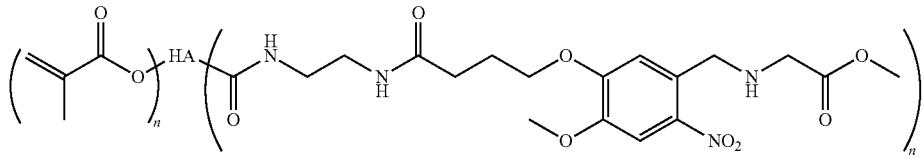
Component A-139
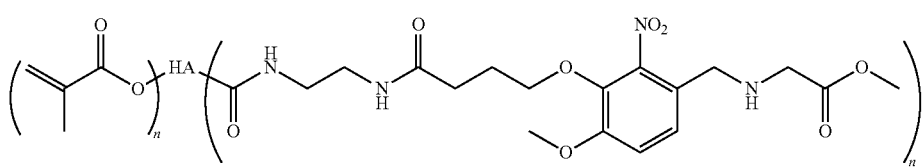
Component A-140

-continued
Component A-141
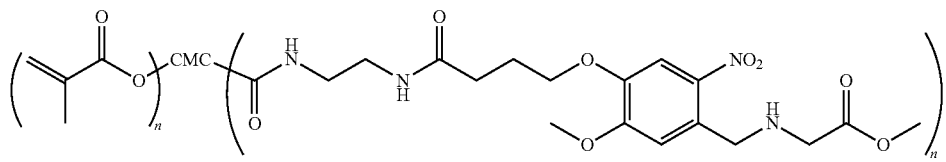
Component A-142
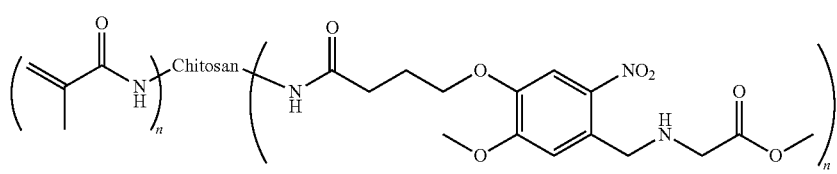
Component A-143
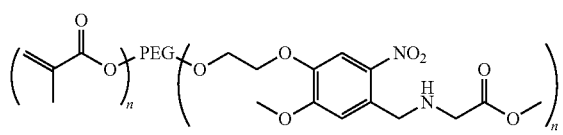
Component A-144
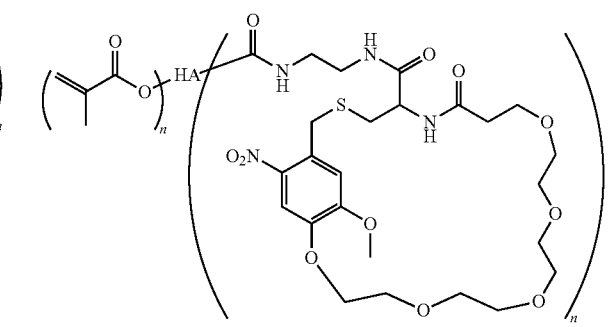
Component A-145
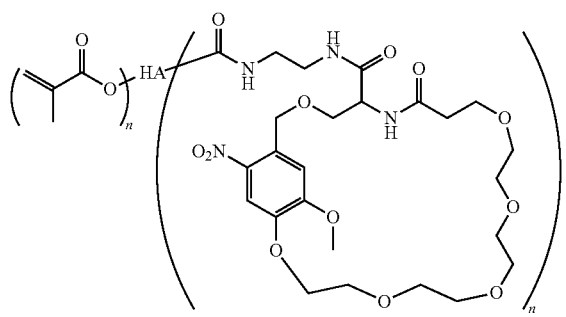
Component A-146
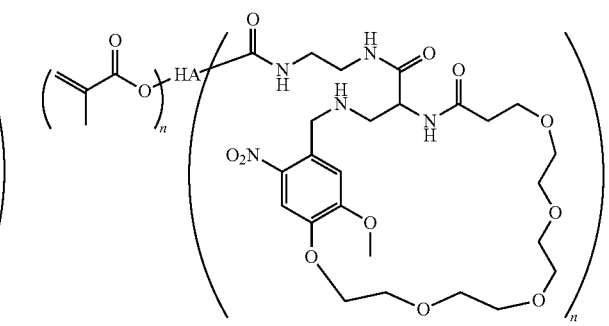
Component A-147
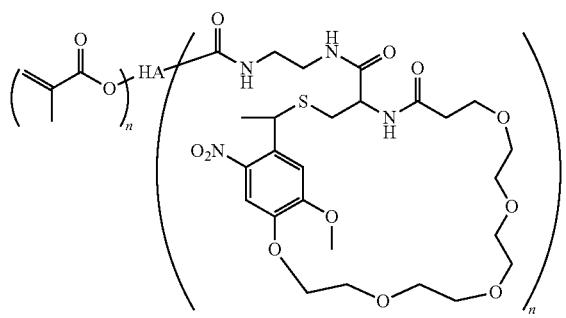
Component A-148
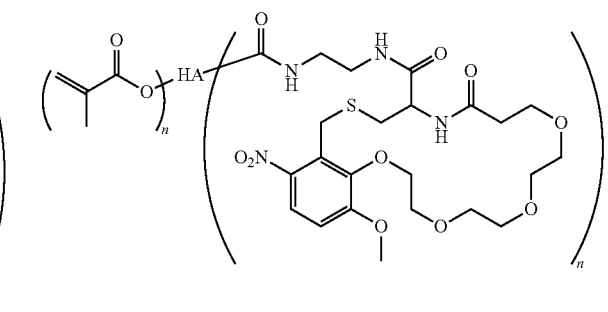

-continued

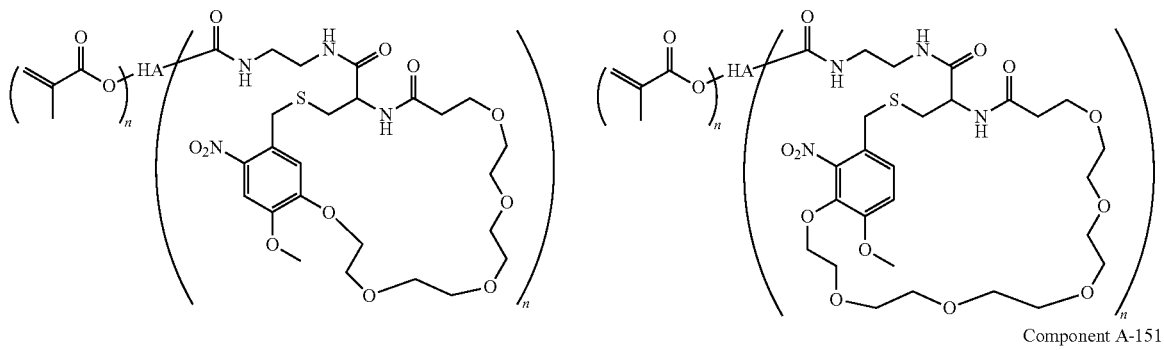

Component A-149   Component A-150

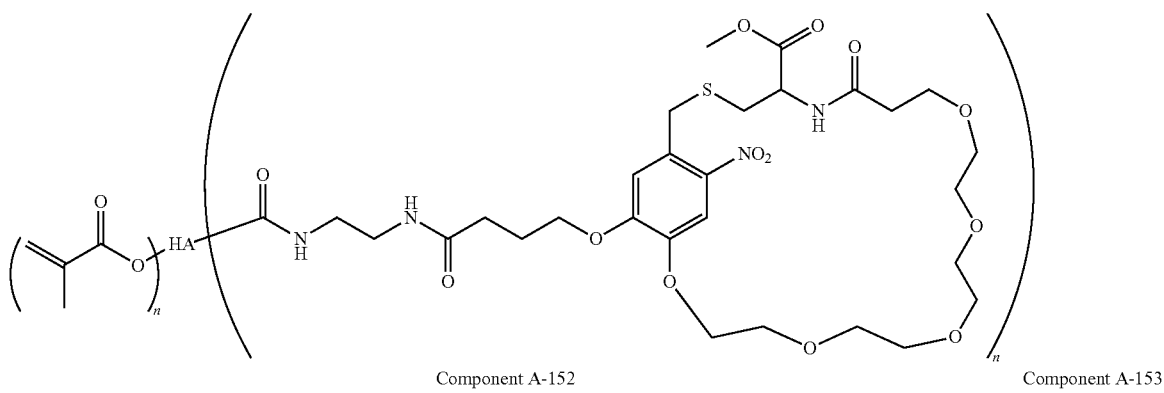

Component A-151

Component A-152   Component A-153

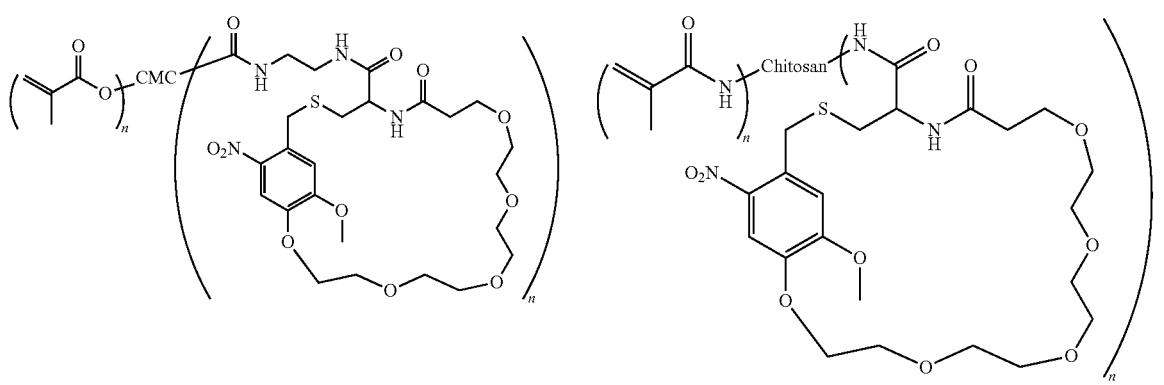

Component A-154

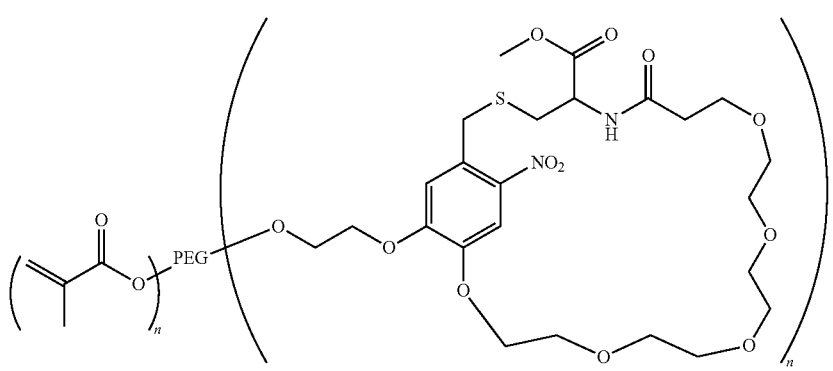

In the molecules of Component A-116 to Component A-154, n≥2, HA stands for hyaluronic acid; CMC stands for carboxymethyl cellulose; Alg stands for alginic acid; CS stands for chondroitin sulfate; PGA stands for polyglutamic acid; PEG sands for polyethylene glycol; Chitosan is chitosan; Gelatin is gelatin; PLL stands for polylysine; Dex stands for dextran; Hep stands for heparin.

In Formula I-1 and Formula I-2, when X=S, it is an o-nitrobenzyl sulfide phototrigger. In the polymer derivatives modified by o-nitrobenzyl sulfide phototriggers, the oxygen atom (O) is replaced by a sulfur atom (S). Because the 3d empty orbit of the sulfur atom could facilitate intramolecular charge transfer to speed up the photolysis rate and photolysis efficiency of the phototriggers. That is, the aldehyde group/keto group or nitroso group can be released more rapidly and more completely under irradiation which accelerates its crosslinking speed as crosslinking sites. And the released aldehyde/ketone group or nitroso can be connected to the active group on the surface of the tissue, which can greatly improve the adhesion strength between the material and the tissue. In addition, the simultaneous release and crosslinking of various reactive functional groups (single aldehyde-amine photocoupled crosslinking is only the release and crosslinking of a single reactive functional group) greatly improve the crosslinking efficiency and crosslinking density, which further improve the mechanical properties of the material. Therefore, the optimization of the molecular structure makes it as a photosensitive group modification of polymer derivatives to exhibit more excellent material performance, such as the crosslinking speed increases from 30 s in the aldehyde-amine photocoupling crosslinking to less than 2 s, the tissue adhesion strength increases to about 80-100 KPa, the mechanical properties increases to about 1-2 MPa, specific data are shown in Example 167, Example 168 and Example 169.

In Formula I-1 and Formula I-2, when X=N, it is an o-nitrobenzylamine phototrigger.

In the polymer derivatives modified by o-nitrobenzylamine phototriggers, the oxygen atom (O) is replaced by a nitrogen atom (N). Because nitrogen being a strong electron donor could facilitate intramolecular charge transfer, which speeds up the photolysis rate and photolysis efficiency of the phototriggers. That is, the aldehyde group/keto group or nitroso group can be released more rapidly and more completely under irradiation which accelerates its crosslinking speed as crosslinking sites. And the released aldehyde/ketone group or nitroso can be connected to the active group on the surface of the tissue, which can greatly improve the adhesion strength between the material and the tissue. In addition, the simultaneous release and crosslinking of various reactive functional groups (single aldehyde-amine photocoupled crosslinking is only the release and crosslinking of a single reactive functional group) greatly improve the crosslinking efficiency and crosslinking density, which further improve the mechanical properties of the material. Therefore, the optimization of the molecular structure makes it as a photosensitive group modification of polymer derivatives to exhibit more excellent material performance, such as the crosslinking speed increases from 30 s in the aldehyde-amine photocoupling crosslinking to less than 2 s, the tissue adhesion strength increases to about 80-100 KPa, the mechanical properties increases to about 1-2 MPa, specific data are shown in Example 167, Example 168 and Example 169.

In Formula I-2, it is a cyclic o-nitrobenzyl phototrigger having an intramolecular ring structure, including cyclic o-nitrobenzyl phototriggers or cyclic o-nitrobenzyl sulfide phototriggers or cyclic o-nitrobenzylamine phototriggers. The phototriggers are designed to release another reactive functional group (such as a sulphydryl group) under irradiation which can be retained on the precursor of o-nitrobenzyl (another reactive functional group released from simple aldehyde-amine photocoupling crosslinking will be removed from the precursor of o-nitrobenzyl), thereby the additional release of the sulphydryl group on the basis of simultaneously release of the aldehyde group/keto group or nitroso group could further increase the effective crosslinking. In addition, in the cyclic o-nitrobenzyl sulfide phototriggers, the 3d empty orbital of the sulfur atom (S) facilitates intramolecular charge transfer; in the cyclic o-nitrobenzylamine phototriggers, nitrogen atom (N) is a strong electron donor, which is conducive to intramolecular charge transfer and accelerates the photolysis rate and photolysis efficiency of the phototriggers. That is, the aldehyde group/keto group or nitroso group can be released more rapidly and more completely under irradiation which accelerates its crosslinking speed as crosslinking sites. And the released aldehyde/ketone group or nitroso can be connected to the active group on the surface of the tissue, which can greatly improve the adhesion strength between the material and the tissue. In addition, the simultaneous release and crosslinking of various reactive functional groups (single aldehyde-amine photocoupled crosslinking is only the release and crosslinking of a single reactive functional group) greatly improve the crosslinking efficiency and crosslinking density, which further improve the mechanical properties of the material. Therefore, the optimization of the molecular structure makes it as a photosensitive group modification of polymer derivatives to exhibit more excellent material performance, such as the crosslinking speed increases from 30 s in the aldehyde-amine photocoupling crosslinking to less than 2 s, the tissue adhesion strength increases to about 80-100 KPa, the mechanical properties increases to about 1-2 MPa, specific data are shown in Example 167, Example 168 and Example 169.

The third objective of the invention is to provide the preparation methods of photosensitive polymer derivatives. 2.1 The preparation method of photosensitive polymer derivative (abbreviated as $A_1$) modified by an o-nitrobenzyl phototriggers is provided.

The o-nitrobenzyl phototriggers can have two structures including an o-nitrobenzyl phototriggers without a cyclic structure and a cyclic o-nitrobenzyl phototriggers symboled as cNB.

In addition, the o-nitrobenzyl phototriggers include o-nitrobenzyl alcohol phototriggers symboled as NB, o-nitrobenzyl sulfide phototriggers symboled as sNB, o-nitrobenzylamine phototriggers symboled as nNB.

The photopolymer derivative (abbreviated as $A_1$) modified by o-nitrobenzyl phototriggers is prepared by a chemical labeling method and a manual polymerization method.

Among them, the chemical labeling method is a chemical reaction between a polymer and a chemical group in an o-nitrobenzyl phototriggers, including labeling method between a polymer containing carboxyl group and an o-nitrobenzyl molecule containing hydroxyl group, mercapto group or amino group (O. P. Oommen, S. Wang, M. Kisiel, M. Sloff, J. Hilbom, O. P. Varghese, Adv. Funct. Mater. 2013, 23, 1273.); labeling method between a polymer containing hydroxyl group and an o-nitrobenzyl molecule containing carboxyl group or bromine group (Reference K. Peng, I. Tomatsu, A V Korobko, A. Kros, Soft Matter 2010, 6, 85; L. Li, N. Wang, X. Jin, R. Deng, S. Nie, L. Sun, Q. Wu, Y Wei, C. Gong, Biomaterials 2014, 35, 3903.); labeling method between a polymer containing amine group and an o-nitrobenzyl molecule containing carboxyl group or bromine group (reference L. Li, N. Wang, X. Jin, R. Deng, S. Nie, L. Sun, Q. Wu, Y Wei, C. Gong, Biomaterials 2014, 35, 3903.) and so on.

The method of artificial polymerization is copolymerization of a functional monomer of o-nitrobenzyl derivative with a comonomer, and the method can be random free radical polymerization or controlled free radical polymerization (such as ATRP and RAFT polymerization) and so on.

In the invention, some of implementable preparation methods of the polymer derivative modified by o-nitrobenzyl phototriggers are as follows:

The first implementable preparation method is: The solution of a water-soluble polymer or a polymer containing a carboxyl group in distilled water is added o-nitrobenzyl molecule containing reactive functional group hydroxyl group or mercapto group or amine group, and then added condensing agent 1-ethyl-(3-dimethyl amine propyl) carbodiimine hydrochloride (EDC-HCl) and the activator hydroxybenzotriazole (HOBt), then the mixture is stirred at room temperature for 24-48 h. After the reaction is completed, the reaction solution is added to a dialysis bag and dialyzed against a dilute hydrochloric acid solution for 2-3 d, and then freeze-dried to obtain the o-nitrobenzyl modified photosensitive polymer derivative.

The second implementable preparation method is: The solution of a water-soluble polymer or a polymer containing a carboxyl group in 0.01 mol/L 2-(N-morpholine) ethylsulfonic acid (MES) buffer solution (pH=5.2) is added in o-nitrobenzyl molecule dissolved in dimethyl sulfoxide. Then, 4-(4, 6-dimethoxytriazin-2-yl)-4-methylmorpholine hydrochloride (DMTMM) dissolved in MES buffer solution is added in the above reaction solution in three times (every 1 h), and the mixture is reacted at 35° C. for 24 h. Then, the reaction solution is poured into a dialysis bag, dialyzed against deionized water for 2-3 d, and then freeze-dried to obtain the o-nitrobenzyl modified photopolymer derivative.

In the first implementable preparation method and the second implementable preparation method, the above water-soluble polymer or polymer containing carboxyl group may be polyethylene glycol, polysaccharide containing carboxyl group (eg, hyaluronic acid, carboxymethyl cellulose, alginic acid, etc.), protein or polypeptide containing carboxyl group (eg., gelatin, etc.), preferably be multi-arm carboxy polyethylene glycol, hyaluronic acid, carboxymethyl cellulose and gelatin. More preferably, it is hyaluronic acid.

The third implementable preparation method is: The solution of water-soluble polymer containing hydroxyl group or amine group dissolved in distilled water is added o-nitrobenzyl molecule containing a reactive functional group of carboxyl group. And the mixture is added a condensing agent of 1-ethyl-(3-dimethylaminopropyl) carbodiimide hydrochloride (EDC-HCl) and a catalyst of toluene pyridinium p-toluenesulfonate (DPTS) and stirred at room temperature for 24-48 h. Then the reaction solution is poured into an insoluble solvent to reprecipitate (for example, the modified polyethylene glycol derivative can be poured into diethyl ether to reprecipitate, the polysaccharide polymer derivative can be poured into ethanol to reprecipitate). The obtained sediment is dissolved in water and dialyzed for 2-3 days in a dialysis bag, and freeze-dried to obtain o-nitrobenzyl modified photosensitive polymer derivative.

The fourth implementable preparation method is: The solution of water-soluble polymer containing hydroxyl group or amine group dissolved in distilled water is added o-nitrobenzyl molecule containing a reactive functional group of bromine and potassium carbonate as a base, and the mixture is stirred at room temperature for 24-48 hours. Then the reaction solution is poured into an insoluble solvent to reprecipitate (for example, the modified polyethylene glycol derivative can be poured into diethyl ether to re-precipitate, the polysaccharide polymer derivative can be poured into ethanol to re-precipitate). The obtained sediment is dissolved in water and dialyzed for 2-3 days in a dialysis bag, and freeze-dried to obtain o-nitrobenzyl modified photosensitive polymer derivative.

In the third implementable preparation method and the fourth implementable preparation method, the above water-soluble polymer or polymer containing hydroxyl group or amine group may be polyethylene glycol or natural polysaccharide or protein/polypeptide containing hydroxyl group or amine group, preferably multi-arm hydroxy polyethylene glycol, multi-arm amine polyethylene glycol, ethylene glycol chitosan, propylene glycol chitosan, carboxymethyl chitosan, chitosan lactate, natural polysaccharide, polylysine or gelatin, etc., further preferably ethylene glycol chitosan, multi-arm hydroxy polyethylene glycol.

In the above reaction, the molar ratio of the carboxyl group, the hydroxyl group or the amine group in the water-soluble polymer to the molecule of o-nitrobenzyl derivative is preferably 1:0.1-2; the molar ratio of amine-modified o-nitrobenzyl molecule to 1-ethyl-(3-dimethylamine-propyl) carbodiimide hydrochloride (EDC-HCl) and the activator of hydroxybenzotriazole (HOBt) is 1:2:1; the molar ratio of amine-modified o-nitrobenzyl molecule to 4-(4, 6-dimethoxytriazine-2-group)-4-methyl morpholine hydrochloride (DMTMM) is 1:7.5; the molar ratio of carboxyl-modified o-nitrobenzyl molecule to 1-ethyl-(3-dimethylamine-propyl) carbodiimine hydrochloride (EDC-HCl) and the catalyst of DPTS is 1:2:1; the molar ratio of o-nitrobenzyl bromide molecule to potassium carbonate is 1:2.

The fifth implementable preparation method is: The o-nitrobenzyl modified synthetic copolymer can be obtained by polymerization between an o-nitrobenzyl polymerizable monomer derivative and one or more polymerizable co-monomers. It is purified by multiple dissolution-re-precipitation methods.

The above o-nitrobenzyl polymerizable monomer derivative may be acrylate ester, methacrylate, acrylamide or methacrylamide, preferably methacrylate and acrylamide, more preferably methacrylate.

At least one of the above polymerizable comonomers must be water-soluble comonomer selected from the water-soluble polymerizable comonomer of polyethylene glycol methacrylate (PEG-MA), polyethylene glycol acrylate, methacrylic acid (MAA), acrylic acid (AA), hydroxyethyl acrylate, acrylamide (AM), etc. The polymerizable monomer is preferably polyethylene glycol methacrylate (PEG-MA). Other co-monomers are selected for different applications.

The polymerization molar ratio of the above o-nitrobenzyl polymerizable monomer derivative to the water-soluble comonomer may be from 1:20 to 1:2, preferably from 1:9 to 1:3, further preferably 1:4.

The above polymerization method may be random radical polymerization or controlled radical polymerization (such as RAFT polymerization, ATRP polymerization, etc.). It is preferably a random radical polymerization. That is, the o-nitrobenzyl polymerizable monomer derivative and the comonomer are co-dissolved in a certain solvent, and the solution is added a radical initiator. After three freeze-vacuum cycle operations, the mixture is reacted under heating overnight. Then, the reaction solution is poured into dry diethyl ether to precipitate, and after several times of dissolution-re-precipitation purification process, the o-nitrobenzyl group-containing copolymer is obtained by vacuum drying. (G. Delaittre, T. Pauloehrl, M. Bastmeyer, C. Barner-Kowollik, Macromolecules 2012, 45, 1792-1802.) 2.2 The invention provides a preparation method of a photosensitive polymer derivative (abbreviated as $A_2$) containing double bond functional group.

In the invention, the preparation methods of the double bond modified photosensitive polymer derivative include the following:

The first implementable preparation method is: The solution of water-soluble polymer containing hydroxyl group or amine group dissolved in deionized water is added anhydride or methacrylate anhydride at 0-4° C. and then slowly added 5M NaOH, the mixture is stirred for 24 h. Then, the reaction solution is poured into a dialysis bag, dialyzed against deionized water for 2-3 d, and then freeze-dried to obtain the double bond-modified photosensitive polymer derivative.

The above water-soluble polymer or polymer containing hydroxyl group or amine group may be polyethylene glycol, hydroxyl group or amine group-containing polysaccharide (e.g., hyaluronic acid, alginic acid, carboxymethyl cellulose, carboxymethyl chitosan, dextran, chondroitin sulfate, etc.), protein or polypeptide containing hydroxyl group or amine group (e.g., gelatin, etc.), preferably be hyaluronic acid, gelatin, alginic acid, carboxymethylcellulose, chondroitin sulfate, and more preferably be hyaluronic acid.

The second implementable preparation method is: The solution of water-soluble polymer containing hydroxyl or amine group dissolved in deionized water is added glycidyl acrylate or glycidyl methacrylate at 40° C. and then added 5M NaOH, and the mixture is reacted for 2-3 h. Then the reaction solution is poured into a dialysis bag, dialyzed against deionized water for 2-3 d, and then freeze-dried to obtain the double bond-modified photosensitive polymer derivative.

The above water-soluble polymer or polymer containing hydroxyl group or amine group may be polyethylene glycol, hydroxyl group or amine group-containing polysaccharide (e.g., hyaluronic acid, alginic acid, carboxymethyl cellulose, carboxymethyl chitosan, dextran, chondroitin sulfate, etc.), protein or polypeptide containing hydroxyl group or amine group (e.g., gelatin, etc.), preferably be hyaluronic acid, gelatin or carboxymethyl chitosan, and more preferably be carboxymethyl chitosan.

The third implementable preparation method is: The solution of water-soluble polymer containing hydroxyl or amine groups dissolved in dry dimethyl sulfoxide is added triethylamine and then acryloyl chloride or methacryloyl chloride dissolved in dichloromethane, and the reaction is carried out for 10 hours. Then, the reaction solution is poured into ethyl alcohol to re-precipitate. The crude product obtained by filtration is re-dissolved in deionized water, dialyzed for 2-3 d, and then freeze-dried to obtain the double-bond modified photopolymer derivative.

The water-soluble polymers or polymers containing hydroxyl or amine group mentioned above may be polyethylene glycol, polysaccharides containing hydroxyl or amine groups (such as: glucan, etc.), preferably be multi-arm polyethylene glycol and glucan, and further preferably be glucan.

2.3 The prepatation method of photosensitive polymer derivative (abbreviated as $A_3$) containing both o-nitrobenzyl phototriggers and double bond functional group.

The o-nitrobenzyl phototriggers have two structures, such as an o-nitrobenzyl phototriggers without a ring structure and cyclic o-nitrobenzyl phototriggers symboled as cNB.

In addition, the o-nitrobenzyl phototriggers include o-nitrobenzyl alcohol phototriggers symboled as NB, o-nitrobenzyl sulfide phototriggers symboled as sNB, o-nitrobenzylamine phototriggers symboled as nNB.

In the invention, the photosensitive polymer derivative (abbreviated as $A_3$) containing both o-nitrobenzyl phototriggers and a double bond functional group is prepared by labeling o-nitrobenzyl phototriggers and then double bond functional group or labeling double bond functional group and then o-nitrobenzyl phototriggers. The specific labeling method is according to the above mentioned labeling method of o-nitrobenzyl phototriggers or double bond functional group. The o-nitrobenzyl phototriggers labeling method is a chemical reaction between the functional group in polymer and o-nitrobenzyl phototriggers. It may be labeled through carboxyl group-containing polymer and hydroxyl group/sulfhydryl group/amino-containing o-nitrobenzyl molecule; or labeled through hydroxyl group-containing polymer and carboxyl group or bromine-containing o-nitrobenzyl molecule; or labeled through amine group-containing polymer and carboxyl group or bromine-containing o-nitrobenzyl molecule. It may also be a small molecular marker of o-nitrobenzylidene and carboxyl group or bromine. It may also be a method for the labeling of amine-containing polymers with o-nitrobenzyl-like molecule containing carboxyl or bromine. The double bond functional group labeling method is to use acrylic anhydride, methacrylic acid, glycidyl acrylate, glycidyl methacrylate, acryloyl chloride, methacryloyl chloride and so on.

In the invention, the preparation method of the photosensitive polymer derivative (abbreviated as $A_3$) containing both the o-nitrobenzyl phototriggers and the double bond functional group is shown as follows:

The first implementable preparation method is: The solution of water-soluble polymer containing o-nitrobenzyl phototriggers dissolved in deionized water is added anhydride or methacrylate anhydride at 0-4° C. and then slowly added 5M NaOH, the mixture is stirred for 24 h. Then, the reaction solution is poured into a dialysis bag, dialyzed against deionized water for 2-3 d, and then freeze-dried to obtain the above photosensitive polymer derivative containing both o-nitrobenzyl phototriggers and double bond groups.

The second implementable preparation method is: The solution of water-soluble polymer containing o-nitrobenzyl phototriggers dissolved in deionized water is added glycidyl acrylate or glycidyl methacrylate at 40° C. and then added 5M NaOH, and the mixture is reacted for 2-3 h. Then the reaction solution is poured into a dialysis bag, dialyzed against deionized water for 2-3 d, and then freeze-dried to obtain the above photosensitive polymer derivative containing both o-nitrobenzyl phototriggers and double bond groups.

The third implementable preparation method is: The solution of water-soluble polymer containing o-nitrobenzyl phototriggers dissolved in dry dimethyl sulfoxide is added triethylamine and then acryloyl chloride or methacryloyl chloride dissolved in dichloromethane, and the reaction is carried out for 10 hours. Then, the reaction solution is poured into ethyl alcohol to re-precipitate. The crude product obtained by filtration is re-dissolved in deionized water, dialyzed for 2-3 d, and then freeze-dried to obtain the above photosensitive polymer derivative containing both o-nitrobenzyl phototriggers and double bond groups.

The fourth implementable preparation method is: The solution of a water-soluble polymer or a polymer containing double bond groups in distilled water is added o-nitrobenzyl molecule containing reactive functional group hydroxyl group or mercapto group or amine group, and then added condensing agent 1-ethyl-(3-dimethyl amine propyl) carbodiimine hydrochloride (EDC-HCl) and the activator hydroxybenzotriazole (HOBt), then the mixture is stirred at room temperature for 24-48 h. After the reaction is completed, the reaction solution is added to a dialysis bag and dialyzed against a dilute hydrochloric acid solution for 2-3 d, and then freeze-dried to obtain the above photosensitive polymer derivative containing both o-nitrobenzyl phototriggers and double bond groups.

The fifth implementable preparation method is: The solution of a water-soluble polymer or a polymer containing double bond groups in 0.01 mol/L 2-(N-morpholine) ethylsulfonic acid (MES) buffer solution (pH=5.2) is added in o-nitrobenzyl molecule dissolved in dimethyl sulfoxide. Then, 4-(4, 6-dimethoxytriazin-2-yl)-4-methylmorpholine hydrochloride (DMTMM) dissolved in MES buffer solution is added in the above reaction solution in three times (every 1 h), and the mixture is reacted at 35° C. for 24 h. Then, the reaction solution is poured into a dialysis bag, dialyzed against deionized water for 2-3 d, and then freeze-dried to obtain the above photosensitive polymer derivative containing both o-nitrobenzyl phototriggers and double bond groups.

The sixth implementable preparation method is: The solution of water-soluble polymer containing double bond groups dissolved in distilled water is added o-nitrobenzyl molecule containing a reactive functional group of carboxyl group. And the mixture is added a condensing agent of 1-ethyl-(3-dimethylaminopropyl) carbodiimide hydrochloride (EDC-HCl) and a catalyst of toluene pyridinium p-toluenesulfonate (DPTS) and stirred at room temperature for 24-48 h. Then the reaction solution is poured into an insoluble solvent to reprecipitate (for example, the modified polyethylene glycol derivative can be poured into diethyl ether to re-precipitate, the polysaccharide polymer derivative can be poured into ethanol to re-precipitate). The obtained sediment is dissolved in water and dialyzed for 2-3 days in a dialysis bag, and freeze-dried to obtain the above photosensitive polymer derivative containing both o-nitrobenzyl phototriggers and double bond groups.

The seventh implementable preparation method is: The solution of water-soluble polymer containing double bond groups dissolved in distilled water is added o-nitrobenzyl molecule containing a reactive functional group of bromine and potassium carbonate as a base, and the mixture is stirred at room temperature for 24-48 hours. Then the reaction solution is poured into an insoluble solvent to re-precipitate (for example, the modified polyethylene glycol derivative can be poured into diethyl ether to re-precipitate, the polysaccharide polymer derivative can be poured into ethanol to re-precipitate). The obtained sediment is dissolved in water and dialyzed for 2-3 days in a dialysis bag, and freeze-dried to obtain the above photosensitive polymer derivative containing both o-nitrobenzyl phototriggers and double bond groups.

The fourth objective of the invention is to provide a preparation method of photo-crosslinked hydrogel material. The photo-crosslinked hydrogel material is prepared from the photosensitive polymer derivative described in second objective.

The Component A—photosensitive polymer derivatives is dissolved in a biocompatible medium to obtain photosensitive polymer solution A;

The component B—photoinitiator is dissolved in a biocompatible medium to obtain photoinitiator solution B.

Solution A and solution B are mixed evenly to obtain a hydrogel precursor solution. Under the irradiation of the light, the o-nitrobenzyl phototriggers and/or double bond functional groups in component A and photoinitiator in component B are respectively cross-linked via free radical crosslinking to form the hydrogel (free radical crosslinking of o-nitrobenzyl phototriggers and free radical crosslinking of double bond functional group).

Further, the method of preparing another photo-crosslinked hydrogel material is shown as follows:

The Component A—photosensitive polymer derivative is dissolved in a biocompatible medium to obtain photosensitive polymer solution A;

The component B—photoinitiator is dissolved in a biocompatible medium to obtain photoinitiator solution B.

The auxiliary component C—other biocompatible polymer derivative is dissolved in a biocompatible medium to obtain polymer solution C. The auxiliary component C—other biocompatible polymer derivative is a polymer derivative containing amine, hydrazine, hydrazide or hydroxylamine functional groups, or a polymer derivative containing mercapto groups.

The solution A, the solution B, and the solution C are mixed homogeneously to obtain a hydrogel precursor solution which can form hydrogel under the irradiation of the light via a crosslinking mode. The crosslinking mode is as follows: the o-nitrobenzyl phototriggers and/or double bond functional groups in component A and photoinitiator in component B are respectively cross-linked by free radical crosslinking. And aldehyde or ketone group produced by irradiation of o-nitrobenzyl phototriggers in component A can react with the amines, hydrazine, hydrazide, or hydroxylamine functional groups in component C through photocoupling crosslinking. And nitroso group produced by irradiation of o-nitrobenzyl phototriggers in component A can react with the sulphydryl group in component C through photoinduced nitroso crosslinking. This is a complex form of photo-crosslinking.

In the invention, the configuration of the hydrogel precursor solution according to different requirements can be selected from the component A, component B and component C, wherein component A and component B are essential components, and component C is auxiliary. Thus, the hydrogel precursor solution can be component A/component B or component A/component B/component C. The configuration of the component A may be selected from the photosensitive polymer derivatives $A_1$, $A_2$, and $A_3$ according to various needs, or a mixture of one or more photosensitive polymer derivatives, but cannot be a single component of $A_2$. Therefore, all possible component combinations are $A_1$/B; $A_3$/B; $A_1$, $A_2$/B; $A_1$, $A_3$/B; $A_2$, $A_3$/B; $A_1$, $A_2$, $A_3$/B; $A_1$/B/C; $A_3$/B/C; $A_1$, $A_2$/B/C; $A_1$, $A_3$/B/C; $A_2$, $A_3$/B/C; $A_1$, $A_2$, $A_3$/B/C.

In the preparation method of the invention, the biocompatible medium is selected from the group consisting of distilled water, physiological saline, buffer solution, and cell culture medium solution. Different media can be selected according to different applications.

In the preparation method of the invention, in the uniformly formed hydrogel precursor solution, if it is component A/component B, the concentration of component A may be 0.1% wt-60% wt, preferably 1% wt-10% wt, the concentration of component B may be 0.01% wt-10% wt, preferably 0.05% wt-1.0% wt, and the total polymer concentration may be 0.1% wt-60% wt, preferably 1% wt-10% wt; if it is component A/component B/component C, the mass ratio of component A to component C may be 1:0.02-50, preferably 1:0.1-10, the concentration of component B may be 0.01% wt-10% wt, preferably 0.05% wt-1.0% wt, the total polymer concentration may be 0.1% wt-60% wt, preferably 1% wt-10% wt.

In the preparation method of the invention, the wavelength of the light source is determined according to the absorption wavelength of the o-nitrobenzyl phototriggers and the photoinitiator, and may be 250-500 nm, preferably 300-450 nm, and more preferably 365, 375, 385, 395, or 405 nm.

The technical principle adopted in the preparation method of the photo-crosslinked hydrogel of this invention is as follows: the o-nitrobenzyl phototriggers and/or double bond functional groups in component A and photoinitiator in component B are respectively cross-linked by free radical crosslinking. And aldehyde or ketone group produced by irradiation of o-nitrobenzyl phototriggers in component A can react with the amines, hydrazine, hydrazide, or hydroxylamine functional groups in component C through photocoupling crosslinking. And nitroso group produced by irradiation of o-nitrobenzyl phototriggers in component A can react with the sulphydryl group in component C through photoinduced nitroso crosslinking. This can achieve multiple crosslinks under one illumination and results in a complex form of photo-crosslinking.

For the preparation method of the photo-crosslinked hydrogel material,

Component B—photoinitiator which can generate radical under illumination is preferably selected from water-soluble photoinitiator or photoinitiator dispersible in water, further preferably selected from I 2959 (Component B-1), LAP (Component B-2), Eosin-Y (Component B-3) and its derivatives.

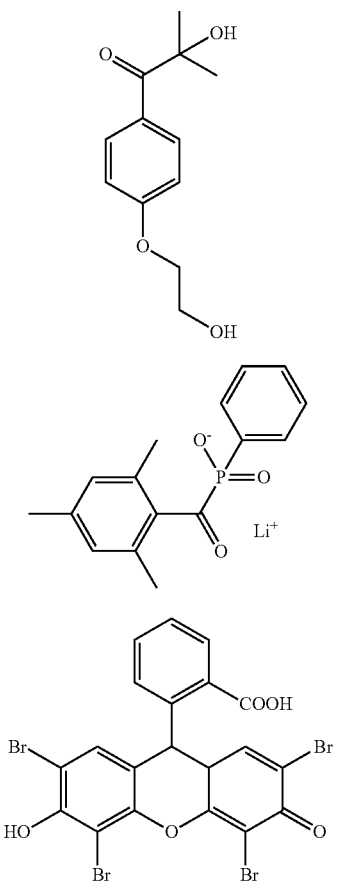

Component B-1

Component B-2

Component B-3

Component C—a polymer derivative containing an amine group, a hydrazine, a hydrazide or a hydroxylamine functional group has the structure of Formula C-I, C-II, C-III, or C-IV; a polymer derivative containing a sulphydryl functional group has the structure of Formula C-V:

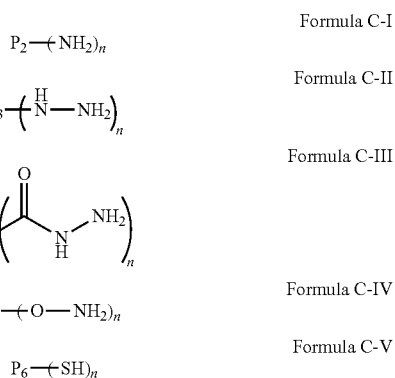

In the structures of Formula C-I, C-II, C-III, C-IV, and C-V, $n \geq 2$; $P_2$, $P_3$, $P_4$, $P_5$ and $P_6$ each independently are hydrophilic or water-soluble natural polymers, hydrophilic or water-soluble synthetic polymers, etc.

Hydrophilic or water-soluble natural polymers include natural polysaccharides and their decorations or degradations, proteins and their decorations, modifiers and degradable peptides, etc.

The natural polysaccharides include hyaluronic acid, carboxymethyl cellulose, methyl cellulose, hydroxyethyl cellulose, hydroxypropyl cellulose, alginate, dextran, agarose, heparin, chondroitin sulfate, glycol chitosan, propylene glycol chitosan, chitosan lactate, carboxymethyl chitosan or quaternary ammonium salt of chitosan.

The protein includes various hydrophilic or water-soluble animal and plant proteins, collagen, serum proteins, silk fibroin proteins and elastin, and the protein degradations include gelatin or polypeptides.

Hydrophilic or water-soluble synthetic polymers include two-arm or multi-arm poly (ethylene glycol), poly (ethylene imine), dendrites, synthetic peptides, polylysine, poly (glutamic acid), poly (acrylic acid), poly (methacrylic acid), polyacrylate, poly (methacrylate), poly (acrylamide), poly (methacrylamide), poly (vinyl alcohol), poly (vinyl pyrrolidone).

The polymer derivative containing amine group, hydrazine, hydrazide, hydroxylamine or mercapto group may be hydrophilic or water-soluble natural polymer or synthetic polymer containing one or more different groups at the same time, or a hydrophilic or water soluble natural polymer or synthetic polymer containing one or more different groups.

For polymer derivative containing amine group, hydrazine, hydrazide or hydroxylamine, the structure in the Formula C-I represents a water-soluble or hydrophilic polymer having amine groups of size n. The structure in the Formula C-II represents a water-soluble or hydrophilic polymer containing hydrazino groups of size n. The structure in the Formula C-III represents a water-soluble or hydrophilic polymer containing n hydrazide groups. The structure in the Formula C-IV represents a water-soluble or hydrophilic polymer containing n hydroxylamine groups. The structure in the Formula C-V represents a water-soluble or hydrophilic polymer containing n mercapto groups.

Alternatively, the Formula C-I may be selected from the following structures of Component C-1 to C-9; the Formula C-II may be selected from the following structures of Component C-10; Formula C-III may be selected from the following structures of Component C-11 to C-13; the Formula C-IV may be selected from the following structures of Component C-14 to C-15; The Formula C-V may be selected from the following structures of Component C-16 to C-21:

Component C-1

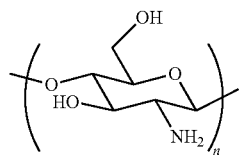

Component C-2

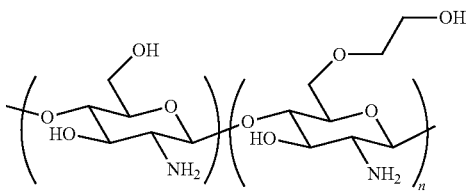

Component C-3

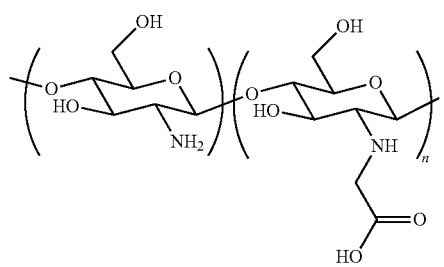

Component C-4

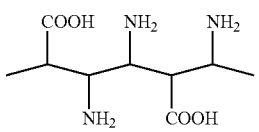

Component C-5

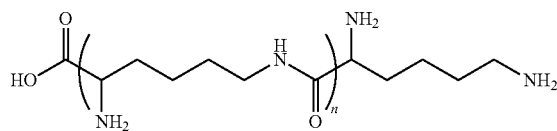

Component C-6

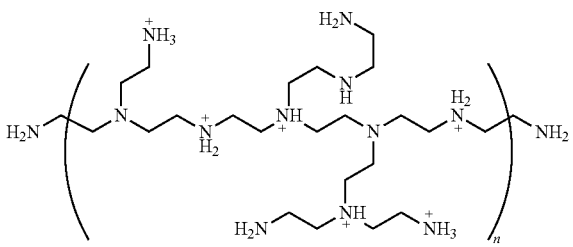

Component C-7

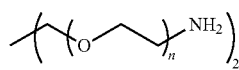

Component C-8

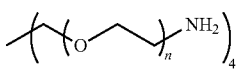

Component C-9

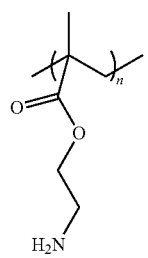

Component C-10

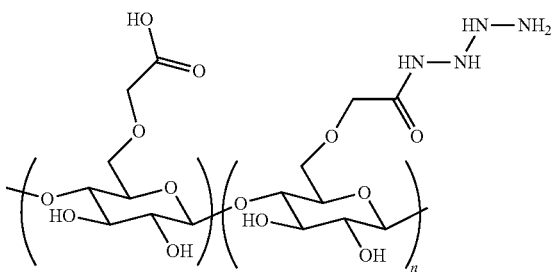

Component C-11

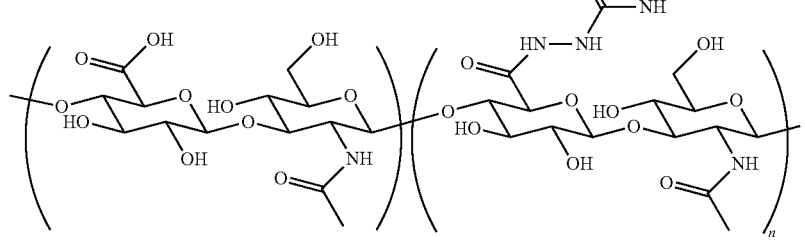

-continued
Component C-12
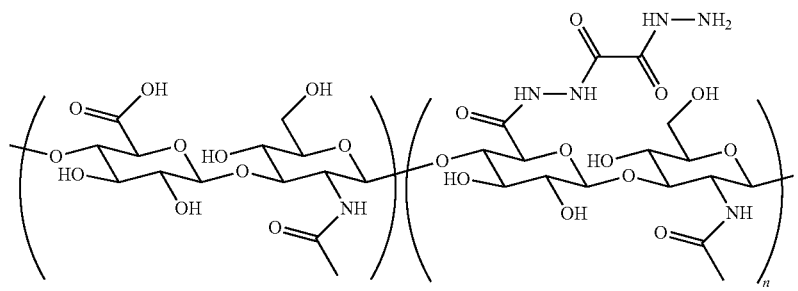
Component C-13
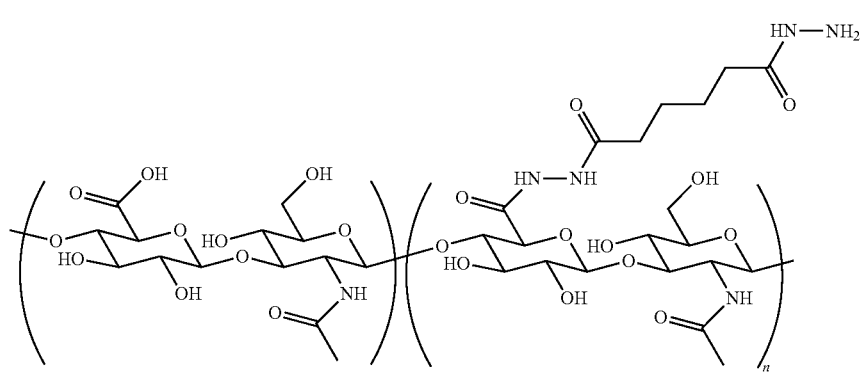
Component C-14
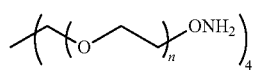
Component C-15
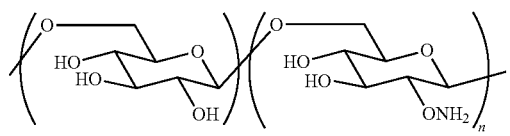
Component C-16
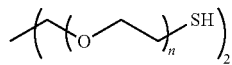
Component C-17
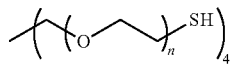
Component C-18
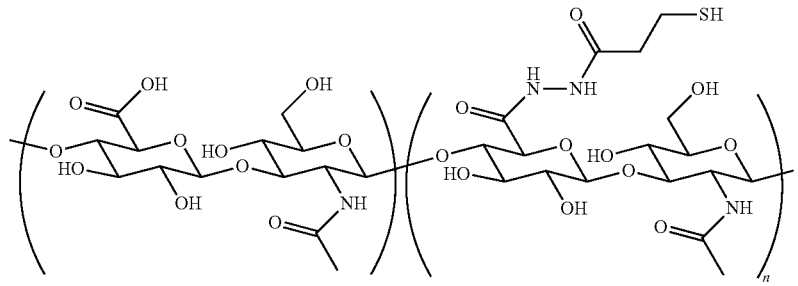
Component C-19
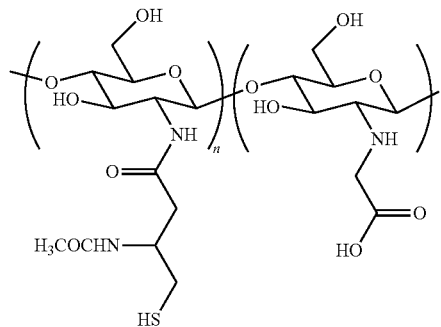
Component C-20

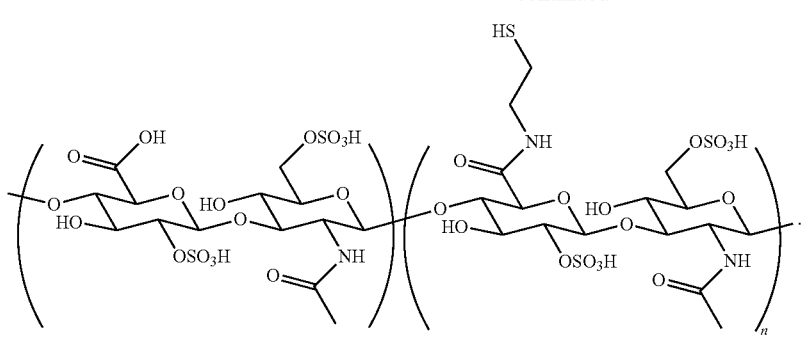

Component C-21

In Component C-1 to Component C-21, n≥2, Component C-1 is chitosan; Component C-2 is glycol chitosan; Component C-3 is carboxymethyl chitosan; Component C-4 is gelatin; Component C-5 is polylysine; Component C-6 is polyethyleneimine; Component C-7 is two-arm amine-based polyglycol; Component C-8 is tetra-arm amine-based polyethylene glycol; Component C-9 is amine-based polymer; Component C-10 is hydrazine-modified carboxymethyl cellulose; Component C-11 to Component C-13 are hydrazide-modified hyaluronic acid; Component C-14 is tetra-arm hydroxyamine polyethylene glycol; Component C-15 is hydroxylamine-modified dextran; Component C-16 is two-arm mercapto-based polyethylene glycol; Component C-17 is tetra-arm mercapto-based polyethylene glycol; Component C-18 is sulphydryl-modified hyaluronic acid; Component C-19 is sulphydryl-modified chitosan; Component C-20 is sulphydryl-modified Glucan; Component C-21 is sulphydryl-modified heparin.

The invention also provides preparation methods of component C—polymer derivatives containing amine, hydrazine, hydrazide or hydroxylamine group.

In the invention, the amine-modified water-soluble polymer may be synthetic polyamine polymer and its decorations (such as polyethyleneimine PEI, dendrimer PAMAM, two-arm or multi-arm amine-based polyethylene glycol), or natural amino-containing polysaccharide hydrophilic or water-soluble polymer and its modifications or degradation products (such as ethylene glycol chitosan, propylene glycol chitosan, chitosan lactate, carboxymethyl chitosan, chitooligosaccharides, etc.). It may also be protein extracted by biological or microbial expression and its modifications or degradants (such as collagen, serum protein and gelatin, etc.). It can also be synthesized artificially or expressed and extracted by microorganisms or hydrophilic or water-soluble polypeptide (such as polylysine, etc.) containing two or more amino groups, or acrylates or methacrylates or acrylamide or methacrylamide polymers and their modifiers. Preferred is gelatin or ethylene glycol chitosan.

In the invention, the preparation method of the hydrazine-modified polymer derivative is: The solution of water-soluble polymer containing carboxyl group and diamine dissolved in distilled water is added 1-ethyl-(3-dimethylamine propyl) carbodiimine hydrochloride (EDC-HCl) and the activator hydroxybenzotriazole (HOBt). The mixture is stirred at room temperature for 24-48 h. After the reaction is completed, the reaction solution is poured into a dialysis bag and dialyzed against dilute hydrochloric acid solution for 2-3 d, and then freeze-dried to obtain the hydrazine-modified polymer derivative.

The above carboxyl group-containing water-soluble polymer may be carboxylic polyethylene glycol or carboxyl group-containing polysaccharide (such as chitosan lactate, carboxymethyl chitosan, hyaluronic acid, alginic acid, carboxymethyl fiber). Preferably, it is multi-arm carboxy polyethylene glycol or hyaluronic acid, and further preferably is hyaluronic acid.

In the above reaction, the molar ratio of the carboxyl group in the water-soluble polymer to the molecule diamine is preferably 1:0.1-2. The molar ratio of the diamine molecule to 1-ethyl-(3-dimethylaminopropyl) carbodiimide hydrochloride (EDC-HCl) and the activator hydroxybenzotriazole (HOBt) is preferably 1:2:1.5.

In the invention, the preparation method of the hydrazide-modified polymer derivative is: The solution of water-soluble polymer containing carboxyl group and dihydrazide dissolved in distilled water is added 1-ethyl-(3-dimethyl aminopropyl) carbodiimine hydrochloride (EDC-HCl) and the activator hydroxybenzotriazole (HOBt). The mixture is stirred at room temperature for 24-48 h. Then, the reaction solution is poured into a dialysis bag and dialyzed against dilute hydrochloric acid solution for 2-3 d, freezed-drying to obtain the hydrazide-modified polymer derivative.

The above carboxyl group-containing water-soluble polymer may be a carboxypolyethylene glycol, carboxyl-containing polysaccharide (such as chitosan lactate, carboxymethyl chitosan, hyaluronic acid, alginic acid, carboxymethyl fiber, etc.). Preferably, it is multi-arm carboxy polyethylene glycol or hyaluronic acid, and more preferably hyaluronic acid.

In the invention, the hydroxylamine-modified polymer derivative is prepared in accordance with the following method. A hydroxyl group-containing polymer and N-hydroxyl phthalaimide are dissolved in dichloromethane to obtain a solution. triphenylphosphine is then added into the solution, followed by slowly adding diisopropyl azo dicarboxylate and then reacting for 16-24 h to obtain a polymer. The polymer is precipitated in diethyl ether, and then re-dissolved in dichloromethane solution, followed by adding hydrazine hydrate to react for 1-3 h to obtain a hydroxylamine-modified polymer derivative.

The above hydroxyl group-containing polymer may be polyethylene glycol, polysaccharide (such as dextran or chitosan), or preferably multi-arm hydroxy polyethylene glycol.

In the above reaction, a molar ratio of the hydroxyl group in the polymer to N-hydroxyphthalimide, triphenylphosphine, diisopropylazodicarboxylate, and hydrazine hydrate is preferably 1:10:10:10:10.

The invention also provides a preparation method of component C—mercapto group-containing polymer derivative.

The mercapto-containing polymer derivative, i.e., a polymer derivative modified by sulphydryl, is prepared by a chemical labeling method. Specifically, the polymer and the chemical groups contained in the mercapto-containing derivative are linked by chemical reaction therebetween. They may be carboxyl-containing polymers and small molecular markers containing amines or hydrazides or hydroxylamines. (Amy Fu, Kihak Gwon, Julia A. Kornfield, Biomacromolecules. 2015, 16, 497; Tugba Ozdemir, Swati Pradhan-Bhatt, Xinqiao Jia, ACS Biomater. Sci. Eng. 2016, 2, 2217.); polymer containing hydroxyl group and molecule containing carboxyl or bromine (Reference Rayun Choi, Yong-Min Huh, Seungjoo Haam, Langmuir. 2010, 26, 17520.); polymer containing amine group and molecule containing carboxyl or bromine (Reference Hanwei Zhang, Aisha Qadeer, Weiliam Chen, Biomacromolecules. 2011, 12, 1428.).

The preparation method of the sulphydryl-modified polymer derivative includes the following:

The first implementable preparation method is as follows. a water-soluble polymer or a polymer containing a carboxyl group in dissolved distilled water. A mall mercapto-containing molecule containing active functional group such as amine or hydrazide or hydroxylamine is added. thereafter, and the condensing agent 1-ethyl-(3-dimethyl amine propyl) carbodiimine hydrochloride (EDC-HCl) and the activator hydroxybenzotriazole (HOBt) are added, followed by stirring at room temperature for 24-48 h to react. After the reaction is completed, the reaction solution is added to a dialysis bag and dialyzed against a dilute hydrochloric acid solution for 2-3 d, and then freeze-dried to obtain the sulfhydryl-modified polymer derivative.

The above water-soluble polymers or polymers containing carboxyl groups can be polyethylene glycol, polysaccharides containing carboxyl groups (such as: hyaluronic acid, carboxymethyl cellulose, alginate, heparin, etc.), preferably polyethylene glycol, hyaluronic acid, heparin, and further be hyaluronic acid and heparin.

The second implementable preparation method is as follows. A water-soluble polymer or a polymer containing hydroxyl or amine group is dissolved in distilled water. A molecule containing sulphydryl and carboxyl functional groups is then added. Thereafter, the condensing agent 1-ethyl-(3-dimethyl amine propyl) carbodiimine hydrochloride (EDC-HCl) and the activator 4-(dimethylamine) pyridine are added to obtain a mixture. The mixture is stirred at room temperature for 24-48 h. After the reaction is completed, the reaction solution is poured into an insoluble solvent to re-precipitate (for example, the modified polyethylene glycol derivative can be poured into diethyl ether to re-precipitate, the polysaccharide polymer derivative can be poured into ethanol to re-precipitate). The obtained sediment is dissolved in water and dialyzed for 2-3 days in a dialysis bag, and freeze-dried to obtain sulphydryl modified photosensitive polymer derivative.

The water-soluble polymer or polymer containing hydroxyl group may be polyethylene glycol or natural polysaccharide, preferably be multi-arm polyethylene glycol or dextran, and more preferably be dextran. The above mentioned amino-containing water-soluble polymer or polymer may be polyethylene glycol, natural polysaccharide, protein or polypeptide, preferably be poly-arm amine-contained polyethylene glycol, ethylene glycol chitosan, propylene glycol chitosan, carboxymethyl chitosan, chitosan lactates or proteins and peptides, more preferably be carboxymethyl chitosan.

The third implementable preparation method is as follow. A water-soluble polymer containing hydroxyl group or amine group is dissolved in distilled water. A small molecule containing mercapto protective group and the active functional group bromine is added. Potassium carbonate is then added as a base to obtain a mixture. The mixture is stirred at room temperature for 24-48 h. Then the obtained reaction solution is poured into an insoluble solvent to reprecipitate (for example, the modified polyethylene glycol derivative can be poured into diethyl ether to re-precipitate, the polysaccharide polymer derivative can be poured into ethanol to re-precipitate). The obtained sediment is dissolved in water and added DTT for deprotection. After reaction for a period of time, the solution is poured into a dialysis bag to dialyze for 2-3 days and freeze-dried to obtain polymer derivative modified by sulphydryl.

The above water-soluble polymer or polymer containing hydroxyl group may be polyethylene glycol or natural polysaccharide, preferably be multi-arm polyethylene glycol or dextran, and more preferably be dextran. The above water-soluble polymer or polymer containing amino group may be polyethylene glycol or natural polysaccharide or protein and polypeptide, preferably be poly-arm amine-based polyethylene glycol, ethylene glycol chitosan, propylene glycol chitosan, carboxymethyl chitosan, chitosan lactates or proteins and peptides, more preferably be carboxymethyl chitosan.

In the above reaction, the molar ratio of the carboxyl group, the hydroxyl group or the amine group in the water-soluble polymer to the molecule mercapto derivative is preferably 1:0.1-2; the molar ratio of small mercapto molecules modified by amines or hydrazides or hydroxylamines to 1-ethyl-(3-dimethylamine propyl) carbodiimine hydrochloride (EDC-HCl) and the activator hydroxybenzotriazole (HOBt) is optimized to be 1:1.5:1.5; the molar ratio of carboxyl-modified mercapto molecule to 1-ethyl-(3-dimethylamine propyl) carbodiimine hydrochloride (EDC-HCl) and catalyst 4-(dimethylamine) pyridine is optimized to be 1:1.5:1.5, and the molar ratio of bromide mercapto molecule to potassium carbonate is optimized to be 1:2.

The fifth object of the invention is to provide a product obtained by the preparation method of photo-crosslinked hydrogel material in the fourth object of the invention. The product is named a photo-crosslinked hydrogel material or a composite photo-crosslinked hydrogel material.

The sixth objective of the invention is to provide a kit for preparing hydrogel used in this invention.

The first kit comprises: Component A—photosensitive polymer derivative; Component B—photoinitiator, and instructions for preparation and application of the hydrogel.

Here, the Component A—photosensitive polymer derivative includes two structures:

1. The photosensitive polymer derivative modified by o-nitrobenzyl phototriggers, referred to as $A_1$, has the structure of the above Formula A-I;
2. The photosensitive polymer derivative containing both o-nitrobenzyl phototriggers and double bond functional group, referred to as $A_3$, has the structure of the above Formula A-III.

Among them, o-nitrobenzyl phototriggers as shown in Formula I has two structures as shown in Formula I-1 and structural Formula I-2. Formula I-1 represents an o-nitrobenzyl phototriggers which does not contain a cyclic structure. Formula I-2 represents a cyclic o-nitrobenzyl phototriggers symbolized as cNB. In Formula I-1 or Formula I-2, when X=O, it is an o-nitrobenzyl alcohol phototrigger symbolized as NB; when X=S, it is an o-nitrobenzyl sulfide phototrigger symbolized as sNB; when X=N, it is an o-nitrobenzylamine phototrigger symbolized as nNB.

Component B—a photoinitiator which can generate a radical under irradiation, preferably is a water-soluble photoinitiator or a photoinitiator dispersible in water, further preferably is I2959 (Component B-1), LAP (Component B-2), Eosin-Y (Component B-3) and their derivatives.

The second kit, except for the content of the first kit, also includes the photosensitive polymer derivative containing double bond functional groups added in the Component A—photosensitive polymer derivative in the first kit. The photosensitive polymer derivative containing double bond functional groups, referred to as $A_2$, has the structure of Formula A-II.

The fourth kit, based on the second kit, further comprises an auxiliary component C, The auxiliary component C is another biocompatible polymer derivative, and includes a polymer derivative containing an amine group, a hydrazine, a hydrazide, a hydroxylamine or a sulphydryl group. The definition of the auxiliary component C is the same as the definition of the auxiliary component C in the method for preparing the photo-crosslinked hydrogel material of the fourth object of the invention.

The above four kits can also include a biocompatible media such as distilled water, physiological saline, buffer, and cell culture media.

The instructions in the above four kits describe the application of hydrogels, including postoperative wound closure, tissue fluid leakage sealing, hemostasis material, tissue engineering scaffold material, 3D printed bio-ink and its application as a cell, protein or drug carrier.

The seventh purpose of the invention is to provide application of a product prepared by the preparation method of photo-crosslinked hydrogel material.

The invention provides the use of the above-mentioned photo-crosslinked hydrogel to prepare postoperative wound closure-skin repair material or medicament.

The invention also provides the above-mentioned photo-crosslinked hydrogel to prepare postoperative wound closure-postoperative anti-adhesion material or medicine.

The invention also provides the use of the above photo-crosslinked to prepare a postoperative wound closure-oral ulcer material or medicament.

The invention also provides the above photo-crosslinked hydrogel to prepare tissue fluid leakage sealing-enteric leakage sealing material or medicine.

The invention also provides the use of the above photo-crosslinked hydrogel to prepare tissue fluid leakage sealing-surgical suture material or medicament.

The invention also provides the use of the above photo-crosslinked hydrogel to prepare hemostatic material-hepatic hemostatic material or medicament.

The invention also provides the use of the above photo-crosslinked hydrogel to prepare hemostatic material-bone section hemostatic material or medicament.

The invention also provides the use of the above photo-crosslinked hydrogel to prepare hemostatic material-arterial hemostatic material or drug.

The invention also provides the use of the above photo-crosslinked hydrogel to prepare hemostatic material-cardiac hemostatic material or medicament.

The invention also provides the use of the above photo-crosslinked hydrogel to prepare tissue engineering scaffold material-cartilage repair material or drug.

The invention also provides the use of the above photo-crosslinked hydrogel to prepare tissue engineering scaffold materials-bone repair materials or drugs.

The invention also provides the use of the above photo-crosslinked hydrogel to prepare tissue engineering scaffold materials-bone/cartilage composite defect repair materials or drugs.

The invention also provides the use of the above photo-crosslinked hydrogel in 3D printing (FDM) material-bio-ink.

The invention also provides the use of the above photo-crosslinked hydrogel in 3D printing (DLP) material-bio-ink.

The invention also provides the use of the above photo-crosslinked hydrogel as a carrier for preparing cells, proteins, and drugs.

In the invention, the Formula A-I is photosensitive polymer derivative modified by o-nitrobenzyl group phototriggers, and the Formula A-II is photosensitive polymer derivative containing double bond functional group, wherein the Formula A-III is photosensitive polymer derivative containing both o-nitrobenzyl group phototriggers and double bond functional group. The component A is composed of one or more photosensitive polymer derivatives in the Formula A-I, the Formula A-II, and the Formula A-III; The derivative of a photosensitive polymer named component A, the photoinitiator named component B and other biocompatible polymer derivative named auxiliary component C are dissolved in biocompatible medium to obtain photosensitive polymer solution A, photoinitiator solution B and auxiliary polymer solution C respectively. Solution A and solution B (or auxiliary solution C) are mixed evenly to obtain the hydrogel precursor solution which is crosslinked under the irradiation of the UV light to form the hydrogel. The crosslinking methods can be divided into the following two Formulas:

Method one: The solution A and the solution B are uniformly mixed to obtain hydrogel precursor solution which is photo-crosslinking to form a hydrogel under irradiation of a light source. The crosslinking method is as follows: the o-nitrobenzyl phototriggers and/or double bond functional groups in component A and photoinitiator in component B are respectively cross-linked by free radical crosslinking (free radical crosslinking of o-nitrobenzyl phototriggers and free radical crosslinking of double-bond functional group). The free radical crosslinking method of o-nitrobenzyl phototriggers is the nitroso produced by o-nitrobenzyl phototriggers under the illumination can capture the free radical generated by the photoinitiator under light to form the highly active nitroso free radical which can undergo dimerization crosslinking by its own and addition crosslinking with other active groups in component A (such as mercapto, hydroxyl, amine, carboxyl, sulfonate, carbonyl, double bond, etc.) to form hydrogel. Since the reactivity of the nitroso radical is higher than that of the simple nitroso group, the crosslinking speed and crosslinking efficiency of the hydrogel can be further improved. Free radical crosslinking of functional double bonds is the transfer of free radicals generated by photoinitiator under light to the double bonds, which then leads to polymerization crosslinking of double bonds. The above two kinds of radical crosslinking methods may be carried out only one Formula of crosslinking, that is, the component A alone is selected from the photosensitive polymer derivative represented by the Formula A-I or the Formula A-II; or may be simultaneously carried out the two Formulas of crosslinking under illumination, that is, component A is alone selected from the photosensitive polymer derivative described in Formula A-III, or simultaneously is selected from two or more photosensitive polymer derivatives of Formula A-I, Formula A-II, and Formula A-III. This kind of photo-crosslinking method has the advantage of fast crosslinking speed of photoinduced radical polymerization and the advantage of strong tissue adhesion of o-nitrobenzyl phototriggers crosslinking, and the multiple crosslinking method can further improve the mechanical properties of hydrogels. Therefore, the crosslinking speed increases from 30 s in the aldehyde-amine photo-coupled crosslinking to less than 2 s, the tissue adhesion strength increases to about 80-100 KPa, the mechanical properties increases to about 1-2 MPa, specific data are shown in implementation example of one hundred and sixty-seven, one hundred and sixty-eight and one hundred and sixty-nine.

Method 2: The solution A, the solution B and the solution C are uniformly mixed to obtain hydrogel precursor solution, and the hydrogel precursor solution is photo-crosslinking to form a hydrogel under irradiation of a light source. Its crosslinking method is: The o-nitrobenzyl phototriggers and/or double bond functional groups in component A and component B—photoinitiators are crosslinked by free radicals under light respectively (that is, the free radical crosslinking of o-nitrobenzyl phototriggers and the free radical crosslinking of double-bond functional groups). The free radical crosslinking method of o-nitrobenzyl phototriggers is the nitroso produced by o-nitrobenzyl phototriggers under the illumination can capture the free radical generated by the photoinitiator under light to form the highly active nitroso free radical which can undergo dimerization crosslinking by its own and addition crosslinking with other active groups in component A (such as mercapto, hydroxyl, amine, carboxyl, sulfonate, carbonyl, double bond, etc.) to form hydrogel. Since the reactivity of the nitroso radical is higher than that of the simple nitroso group, the crosslinking speed and crosslinking efficiency of the hydrogel can be further improved. Free radical crosslinking of functional double bonds is the transfer of free radicals generated by photoinitiator under light to the double bonds, which then leads to polymerization crosslinking of double bonds. At the same time, the aldehyde/ketone group produced by the o-nitrobenzyl phototriggers in component A under light crosslinks with the amino, hydrazine, hydrazide or hydroxylamine functional groups in component C by schiff base crosslinking, and the resulting nitroso group can crosslink with the mercapto functional group in component C through photoinduced imine crosslinking. The above two kinds of free radical crosslinking methods may be carried out with only one formula of crosslinking, that is, the component A is alone selected from the photosensitive polymer derivative represented in the Formula A-I or the Formula A-II; It can also be simultaneously carried out with two formulae of crosslinking under illumination, that is the component A is alone selected from the photosensitive polymer derivatives represented in the Formula A-III, or simultaneously selected from two or more photosensitive polymer derivatives represented in the Formula A-I, Formula A-II, Formula A-III. This kind of photo-crosslinking method has the advantage of fast crosslinking speed of photoinduced radical polymerization and the advantage of strong tissue adhesion of o-nitrobenzyl phototriggers crosslinking, and the multiple crosslinking method can further improve the mechanical properties of hydrogels. Therefore, the crosslinking speed increases from 30 s in the aldehyde-amine photocoupling crosslinking to less than 2 s, the tissue adhesion strength increases to about 80-100 KPa, the mechanical properties increases to about 1-2 MPa, specific data are shown in implementation example of one hundred and sixty-seven, one hundred and sixty-eight and one hundred and sixty-nine.

The following is schematic diagram of the preparation of this photo-crosslinked hydrogel:

1. The free radical crosslinking of o-nitrobenzyl

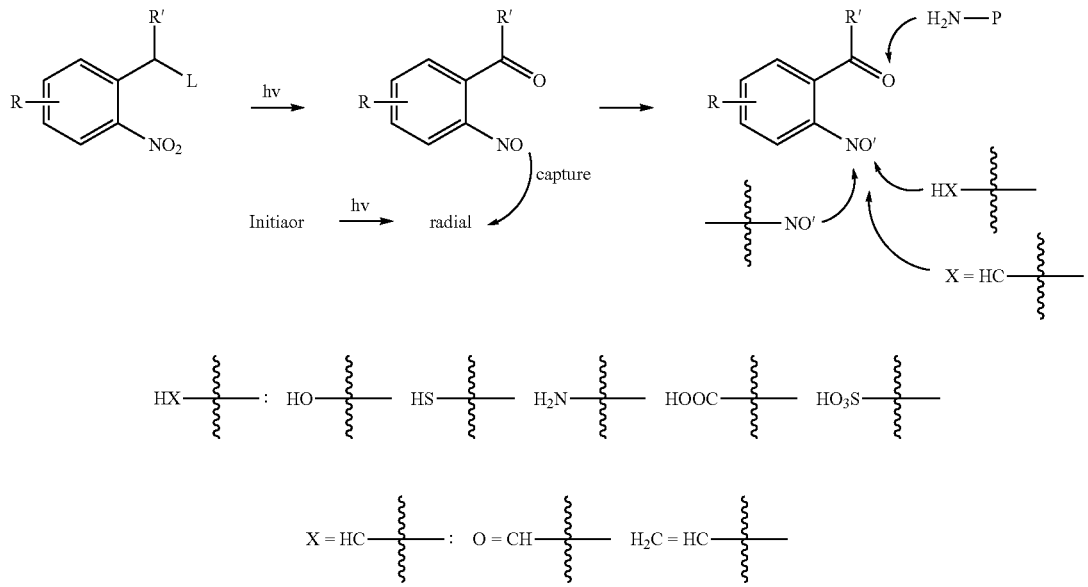

2. The free radical crosslinking of double bond group

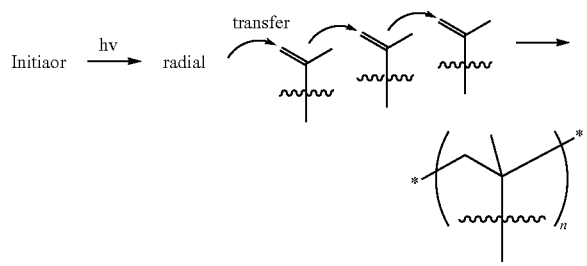

In the invention, the photo-crosslinked hydrogel is a novel photo-crosslinking gel technology proposed on the basis of the existing photo-crosslinking mode (i.e., simple aldehyde-amine based photocoupled crosslinks or photoinitiated free radical polymerization crosslinks). The introduction of component B—photoinitiator not only improves the crosslinking speed and crosslinking efficiency of the original o-nitrobenzyl phototriggers (crosslinking by generating a very reactive nitroso radical), but also can mix the polymer derivatives participated in photo-initiate free radical polymerization crosslinking and the polymer derivatives participated in photo coupled reaction to form composite photosensitive polymer solution. Under illumination, the initiator can be activated to generate free radicals, and the composite solution can perform free radical cross-linking respectively (i.e., free radical crosslinking of o-nitrobenzyl phototriggers and free radical crosslinking of double bond functional group), or photocoupled crosslinking (i.e., Schiff base crosslinking between the aldehyde/ketone group produced by the o-nitrobenzyl phototriggers under illumination and the amino, hydrazine, hydrazide or hydroxylamine functional groups in component C) and photo-induced nitroso crosslinking (i.e., photo-induced nitroso crosslinking between the nitroso group produced by the nitroso generated by o-nitrobenzyl phototriggers under illumination and the sulfhydryl functional group in component C). Thus, a multiple photo-crosslinking is achieved to prepare a composite hydrogel.

The invention has the following innovations compared to the prior art:

(1) The light curing speed is fast. The gelation point can be reached in 1-2 s, and the final modulus is reached in 10-20 s. Since multiple photo-crosslinking is realized at one time, the photocuring speed is better than simple photoinduced radical polymerization crosslinking and photocoupled crosslinking.

(2) Tissue adhesion is strong. It can gel in situ on the surface of tissue. Meanwhile, the aldehyde/ketone group and nitroso group generated by illumination can react with the mercapto group, amine group and carboxyl group on the surface of tissue so as to realize the integration of the hydrogel and the chemical bond of surrounding tissues and overcome the problem of requirement of additional primer in free radical polymerization crosslinking.

(3) Excellent mechanical properties. It has good ductility and strength, and overcome the problems of poor mechanical properties, weak and brittle of most hydrogels;

(4) Good biocompatibility. The raw materials are mainly derived from natural polymer materials, and the formed hydrogel can be degraded;

(5) Convenient clinical operation. Due to the excellent spatiotemporal controllability of photo-crosslinking, hydrogel precursor solution can be painted or sprayed on the wound tissue during use and quickly form hydroegl to integrate with tissue synchronously under light without the need of base coating, thereby, wound closure can be achieved in one step;

(6) The chemical structure, composition and degradability as well as the strength and thickness of the gel are adjustable. The composition and properties of the gel material can be flexibly adjusted according to different applications. Especially the thin hydrogel formed in the wound in situ is especially suitable for the sealing and repair of postoperative wounds. It is also suitable for tissue leakage and sealing. It can also be used as a hemostatic material or as a tissue engineering scaffold. It can also be used for 3D printed bio-ink, and can also provide an in situ carrier for cells, proteins or drugs, which is effectively applied to regenerative medicine.

Therefore, the technical breakthrough of the photo-crosslinked hydrogel system is expected to substantially promote the clinical application of photo in situ gel technology.

DESCRIPTION OF DRAWINGS

Note: NB is o-nitrobenzyl phototriggers in Component A-1 of the invention; cNB is cyclic o-nitrobenzyl phototriggers in Component A-88 of the invention; cNB-MA is cyclic o-nitrobenzyl phototriggers and double bond functional group in Component A-144 of invention. Among them, HA-NB is Component A-1; HA-cNB is Component A-88; HA-cNB-MA is Component A-144.

EXAMPLES

Figure 1:
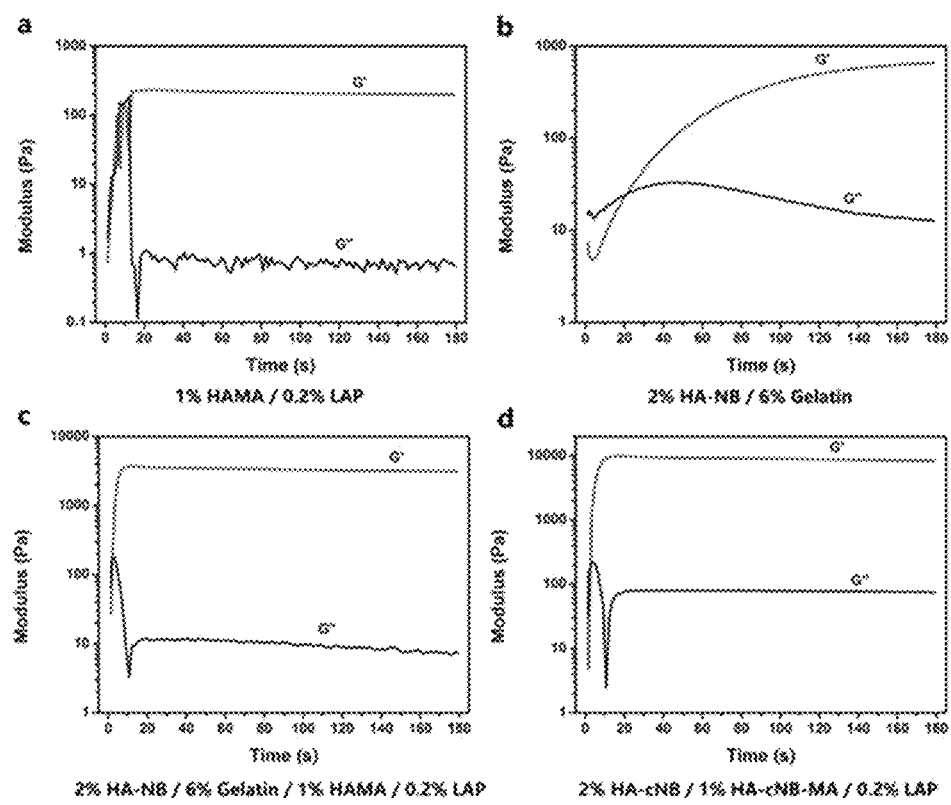
FIG. 1 is a dynamic time sweep rheological diagram of a hydrogel precursor solution (2% HA-NB/6% Gelatin/1% HAMA/0.2% LAP 或 2% HA-cNB/1% HA-cNB-MA/0.2% LAP) which is illuminated to form a gel.

The following use example s to describe the present invention in more detail. The invention will be further described in conjunction with the accompanying drawings and example s as following. However, the examples are merely illustrative of the preferred example s of the invention, but not intended to limit the scope of the invention. Any Example 1: Synthesis of Component A-1

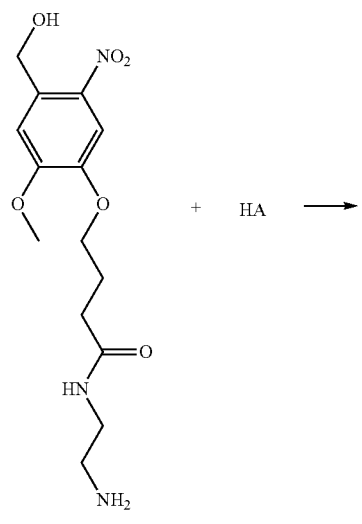

Compound 1

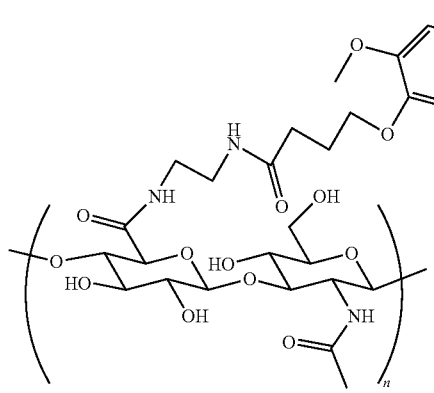

Component A-1

(1) Synthesis of Compound 1. The synthesis was carried out according to the method disclosed in the reference (Yunlong Yang; Jieyuan Zhang; Zhenzhen Liu; Qiuning Lin; Xiaolin Liu; Chunyan Bao; Yang Wang; Linyong Zhu. Adv. Mater. 2016, 28, 2724). $^1$H NMR (400 MHz, CDCl$_3$): δ=7.71 (s, 1H), 7.22 (s, 1H), 4.96 (s, 2H), 4.13 (t, J=6.1 Hz, 2H), 3.99 (s, 3H), 3.32 (dd, J=11.6, 5.7 Hz, 2H), 2.82 (t, J=5.9 Hz, 2H), 2.44 (t, J=7.2 Hz, 2H), 2.26-2.17 (m, 2H). MS (ESI): [M+H] 328.1507.

(2) Synthesis of Component A-1. To a solution of hyaluronic acid (2 g, 340 kDa) in 100 mL 0.01 mol/L 2-(N-morpholine) mesylate (MES) buffer solution (pH=5.2) was added Compound 1 (65 mg, 0.2 mmol) dissolved in 10 mL dimethyl sulfoxide (DMSO). 4-(4, 6-Dimethoxytriazin-2-yl)-4-methylmorpholine hydrochloride (DMTMM, 0.4 g, 1.5 mmol) dissolved in 3 mL MES buffer was added to the above reaction solution by three times (every 1 h), and the mixture was reacted at 35° C. for 24 h. Then, the reaction solution was poured into a dialysis bag (MWCO 7000), dialyzed against deionized water for 2-3 d, and lyophilized to obtain the photosensitive hyaluronic acid derivative Compound A-1 (1.85 g). According to the nuclear magnetic resonance spectrum, the grafting degree of Compound 1 could be calculated to be about 3.42%.

Example 2: Synthesis of Component A-2

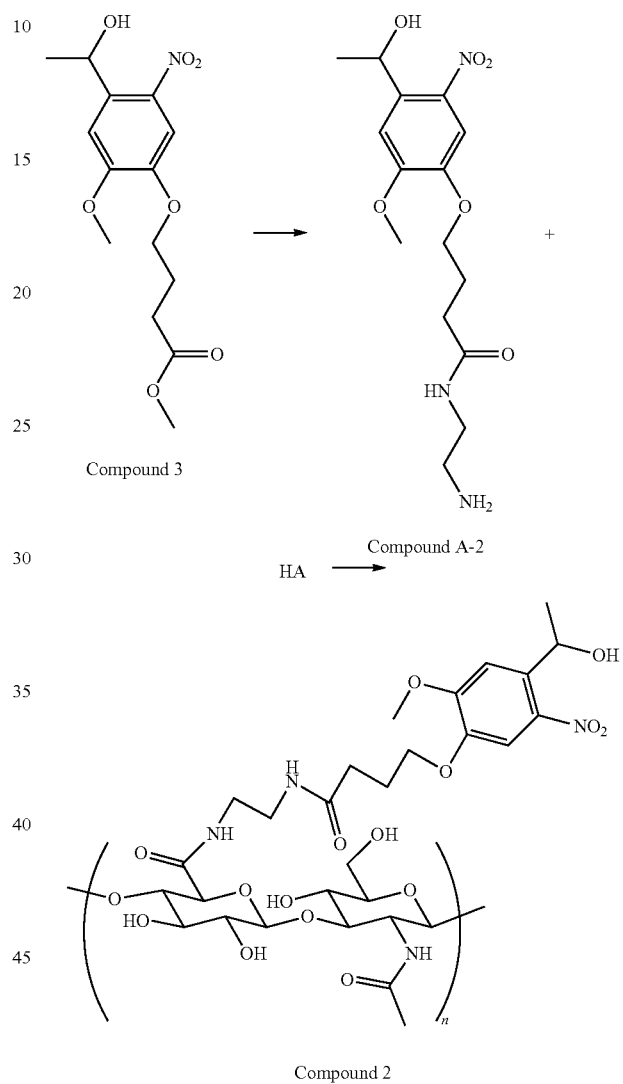

(1) Synthesis of Compound 2. The synthesis was carried out according to the method disclosed in the reference (James F. Cameron; Jean M. J. Frechet. J. Am. Chem. Soc. 1991, 113, 4303).

(2) Synthesis of Compound 3. The solution of Compound 2 (1 g, 3.2 mmol) and ethylenediamine (1.1 mL) dissolved in methanol (50 mL) were reluxed overnight. The solvents were removed by rotary evaporation under reduced pressure, and then the residue was re-dissolved in ethyl acetate and washed with a saturated solution of NaCl. After removing the solvent by rotary evaporation under reduced pressure, the crude product was dissolved in methanol and re-precipitated from ethyl acetate. Compound 3 (0.89 g, 82%) was obtained by filtration and vacuum drying after repeated dissolution and heavy precipitation. $^1$H NMR (400 MHz, CDCl$_3$): δ=7.71 (s, 1H), 7.22 (s, 1H), 4.96 (m, 1H), 4.13 (t, J=6.1 Hz, 2H), 3.99 (s, 3H), 3.32 (dd, J=11.6, 5.7 Hz, 2H), 2.82 (t, J=5.9 Hz, 2H), 2.44 (t, J=7.2 Hz, 2H), 2.26-2.17 (m, 2H), 1.33 (d, J=6.9 Hz, 3H). MS (ESI): [M+H] 342.1624.

(3) Synthesis of Component A-2. To a solution of hyaluronic acid sodium (2 g, 340 kDa) in 100 mL 0.01 M 2-(N-morpholine) mesylate (MES) buffer solution (pH=5.3) was added Compound 1 (68 mg, 0.2 mmol) dissolved in 10 mL dimethyl sulfoxide (DMSO). Then, DMTMM (0.6 g, 2 mmol) dissolved in 9 mL water was added into the above solution three times with an interval of 30 min, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-1 (1.92 g). According to the nuclear magnetic resonance spectrum, the grafting degree of Compound 1 could be calculated to be about 3.29%.

Example 3: Synthesis of Component A-3

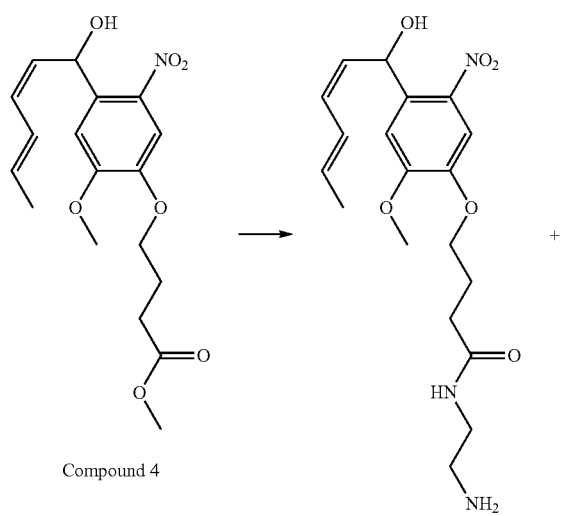

(1) Synthesis of Compound 4. The synthesis was carried out according to the method disclosed in the reference (Michael C. Pirrung; Yong Rok Lee; Kaapjoo; James B. Springer. J. Org. Chem. 1999, 64, 5042).

(2) Synthesis of Compound 5. The solution of Compound 4 (1 g, 2.7 mmol) and ethylenediamine (1.1 mL) dissolved in methanol (50 mL) were refluxed overnight. The solvents were removed by rotary evaporation under reduced pressure, and then the residue was re-dissolved in methanol and re-precipitated in ethyl acetate. Compound 5 (0.80 g, 74%) was obtained by filtration and vacuum drying after several times of dissolution-reprecipitation. $^1$H NMR (400 MHz, CDCl$_3$): δ=7.71 (s, 1H), 7.22 (s, 1H), 6.35 (dd, J=10.0, 15.0 Hz, 1H), 6.04 (m, 1H), 5.8 (m, 1H), 5.4 (m, 1H), 4.96 (m, 1H), 4.13 (t, J=6.1 Hz, 2H), 3.99 (s, 3H), 3.32 (dd, J=11.6, 5.7 Hz, 2H), 2.82 (t, J=5.9 Hz, 2H), 2.44 (t, J=7.2 Hz, 2H), 2.26-2.17 (m, 2H), 1.75 (d, J=6.5 Hz, 3H). MS (ESI): [M+H] 394.1908.

(3) Synthesis of Component A-3. To a solution of hyaluronic acid sodium (2 g, 340 kDa) in 100 mL 0.01 M 2-(N-morpholine) mesylate (MES) buffer solution (pH=5.2) was added Compound 5 (79 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-3 (1.73 g). According to the nuclear magnetic resonance spectrum, the grafting degree of Compound 5 can be calculated to be about 2.97%.

Example 4: Synthesis of Component A-4

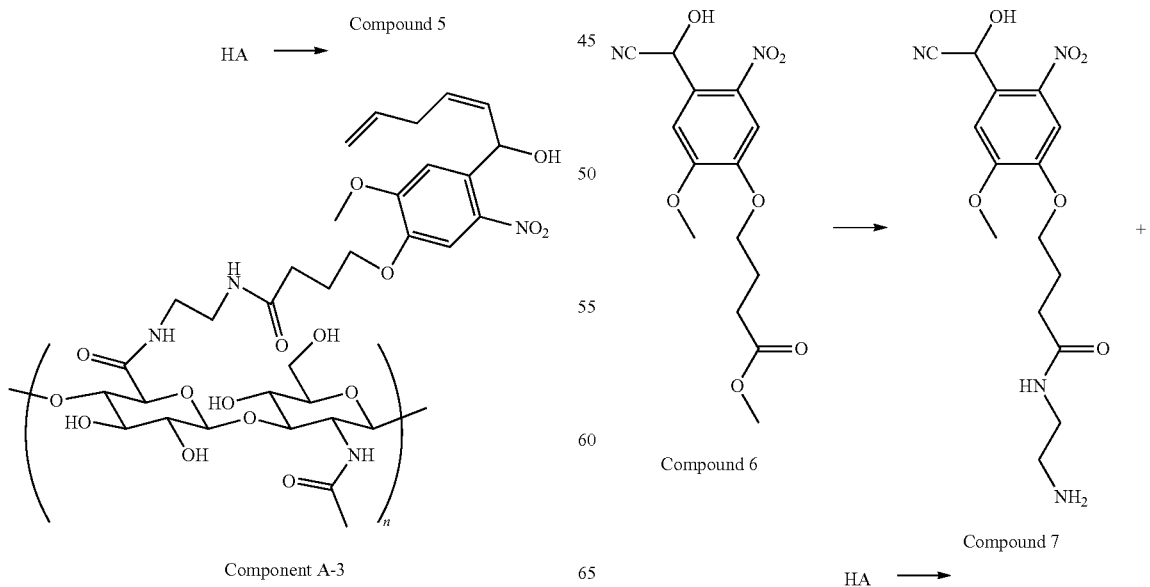

Example 5: Synthesis of Component A-5

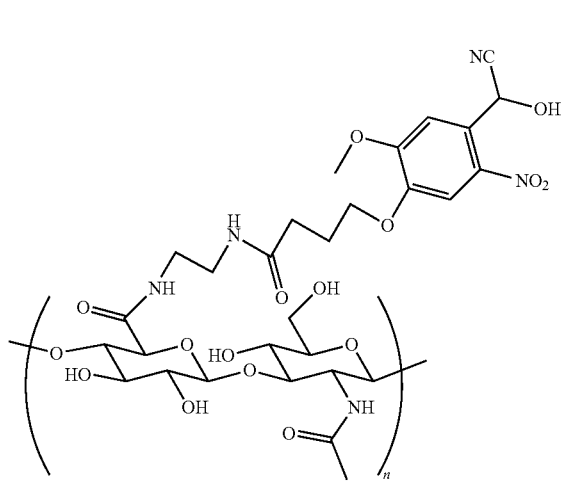

Component A-4

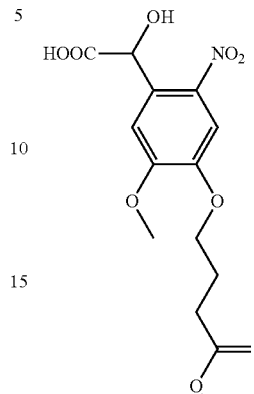

Compound 8

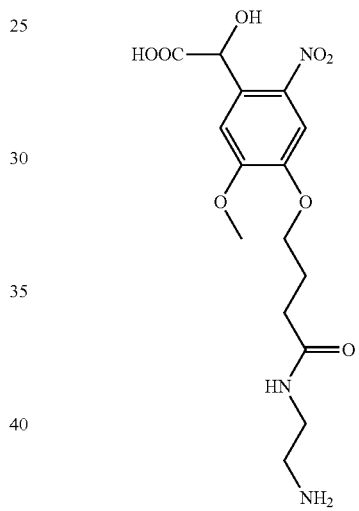

Compound 9

(1) Synthesis of Compound 6. The synthesis was carried out according to the method disclosed in the reference (Isabelle Aujard; Chouaha Benbrahim; Ludovic Jullien. Chem. Eur. J. 2006, 12, 6865).

(2) Synthesis of Compound 7. The solution of Compound 6 (1 g, 3.1 mmol) and ethylenediamine (1.1 mL) dissolved in methanol (50 mL) were refluxed overnight. The solvents were removed by rotary evaporation under reduced pressure, and then the residue was re-dissolved in methanol and re-precipitated in ethyl acetate. Compound 7 (0.85 g, 78%) was obtained by filtration and vacuum drying after several times of dissolution-reprecipitation. $^1$H NMR (400 MHz, CDCl$_3$): δ=7.71 (s, 1H), 7.22 (s, 1H), 4.96 (s, 1H), 4.13 (t, J=6.1 Hz, 2H), 3.99 (s, 3H), 3.32 (dd, J=11.6, 5.7 Hz, 2H), 2.82 (t, J=5.9 Hz, 2H), 2.44 (t, J=7.2 Hz, 2H), 2.26-2.17 (m, 2H). MS (ESI): [M+H] 353.1426.

(3) Synthesis of Component A-4. To a solution of hyaluronic acid sodium (2 g, 340 kDa) in 100 mL 0.01 M 2-(N-morpholine) mesylate (MES) buffer solution (pH=5.2) was added compound 7 (70 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-3 (1.78 g). According to the nuclear magnetic resonance spectrum, the grafting degree of Compound 7 can be calculated to be about 2.49%.

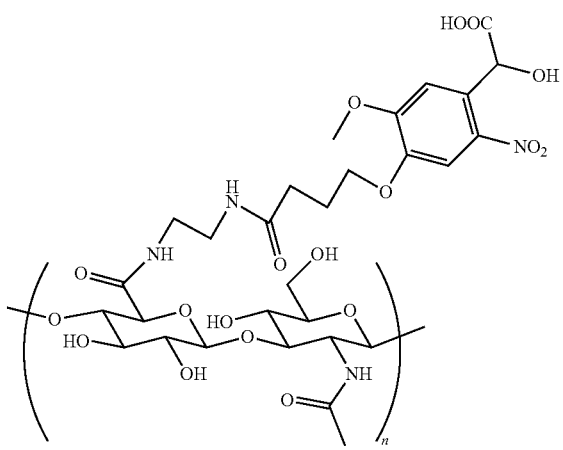

Component A-5

(1) Synthesis of Compound 8. The synthesis was carried out according to the method disclosed in the reference (Alexander G. Russell; Dario M. Bassani; John S. Snaith. J. Org. Chem. 2010, 75, 4648).

(2) Synthesis of Compound 9. The solution of Compound 8 (1 g, 2.9 mmol) and ethylenediamine (1.1 mL) dissolved in methanol (50 mL) were refluxed overnight. The solvents were removed by rotary evaporation under reduced pressure, and then the residue was redissolved in methanol and reprecipitated in ethyl acetate. Compound 9 (0.78 g, 72%) was obtained by filtration and vacuum drying after several times of dissolution-reprecipitation. $^1$H NMR (400 MHz, CDCl$_3$): δ=7.71 (s, 1H), 7.22 (s, 1H), 4.96 (s, 1H), 4.13 (t, J=6.1 Hz, 2H), 3.99 (s, 3H), 3.32 (dd, J=11.6, 5.7 Hz, 2H), 2.82 (t, J=5.9 Hz, 2H), 2.44 (t, J=7.2 Hz, 2H), 2.26-2.17 (m, 2H). MS (ESI): [M+H] 372.1424.

(3) Synthesis of Component A-5. To a solution of hyaluronic acid sodium (2 g, 340 kDa) in 100 mL 0.01 M 2-(N-morpholine) mesylate (MES) buffer solution (pH=5.2) was added compound 9 (74 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-5 (1.76 g). According to the nuclear magnetic resonance spectrum, the grafting degree of Compound 9 can be calculated to be about 3.08%.

Example 6: Synthesis of Component A-6

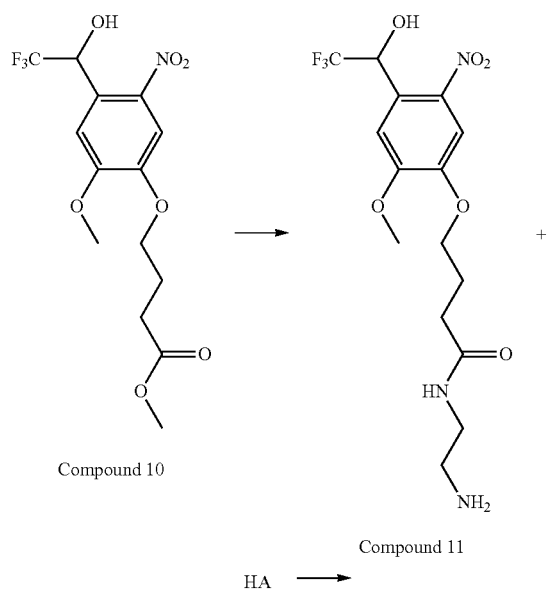

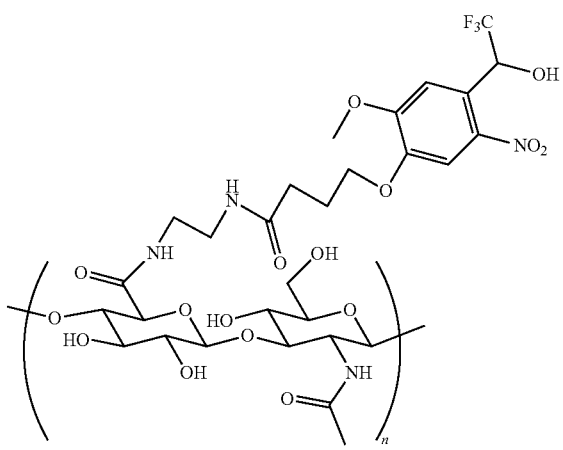

Component A-6

(1) Synthesis of Compound 10. The synthesis was carried out according to the method disclosed in the reference (Alexandre Specht; Maurice Goeldner. Angew. Chem. Int. Ed. 2004, 43, 2008.).

(2) Synthesis of Compound 11. The solution of Compound 10 (1 g, 2.7 mmol) and ethylenediamine (1.1 mL) dissolved in methanol (50 mL) were refluxed overnight. The solvents were removed by rotary evaporation under reduced pressure, and then the residue was re-dissolved in methanol and re-precipitated in ethyl acetate. Compound 11 (0.68 g, 63%) was obtained by filtration and vacuum drying after several times of dissolution-reprecipitation. $^1$H NMR (400 MHz, CDCl$_3$): δ=7.71 (s, 1H), 7.22 (s, 1H), 4.96 (s, 1H), 4.13 (t, J=6.1 Hz, 2H), 3.99 (s, 3H), 3.32 (dd, J=11.6, 5.7 Hz, 2H), 2.82 (t, J=5.9 Hz, 2H), 2.44 (t, J=7.2 Hz, 2H), 2.26-2.17 (m, 2H). MS (ESI): [M+H] 396.1374.

(3) Synthesis of Component A-6. To a solution of hyaluronic acid sodium (2 g, 340 kDa) in 100 mL 0.01 M 2-(N-morpholine) mesylate (MES) buffer solution (pH=5.2) was added Compound 11 (79 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-6 (1.79 g). According to the nuclear magnetic resonance spectrum, the grafting degree of Compound 11 can be calculated to be about 2.34%.

Example 7: Synthesis of Component A-7

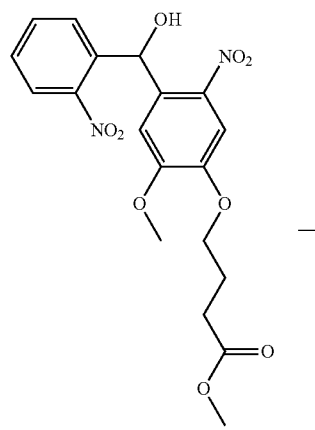

Compound 12

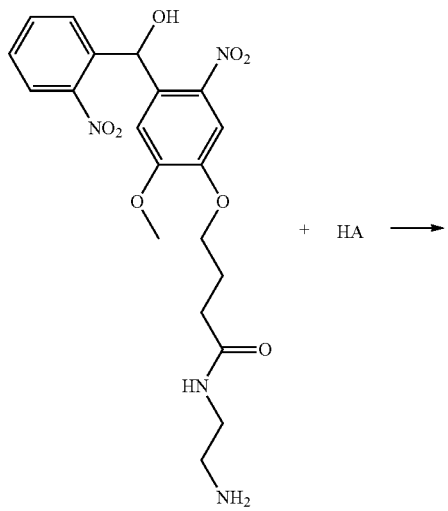

Compound 13

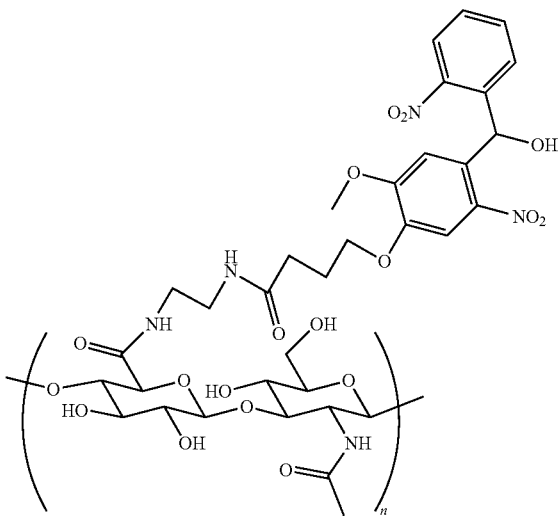

Component A-7

(1) Synthesis of Compound 12. The synthesis was carried out according to the method disclosed in the reference (Jack F. Baldwin; Adrian W. McConnaughie; Sung Bo Shin. Tetrahedron. 1990, 46, 6879.).

(2) Synthesis of Compound 13. The solution of Compound 12 (1 g, 2.4 mmol) and ethylenediamine (1.1 mL) dissolved in methanol (50 mL) were refluxed overnight. The solvents were removed by rotary evaporation under reduced pressure, and then the residue was re-dissolved in methanol and re-precipitated in ethyl acetate. Compound 13 (0.61 g, 57%) was obtained by filtration and vacuum drying after several times of dissolution-reprecipitation. $^1$H NMR (400 MHz, CDCl$_3$): δ=7.71 (s, 1H), 7.75 (ddd, J=8.2, 1.4, 0.4 Hz, 1H), 7.22 (s, 1H), 7.57 (tdd, J=7.3, 1.4, 0.7 Hz, 1H), 7.49 (dd, J=7.9, 1.4 Hz, 1H), 7.36 (ddd, J=8.1, 7.3, 1.4 Hz, 1H), 4.96 (s, 1H), 4.13 (t, J=6.1 Hz, 2H), 3.99 (s, 3H), 3.32 (dd, J=11.6, 5.7 Hz, 2H), 2.82 (t, J=5.9 Hz, 2H), 2.44 (t, J=7.2 Hz, 2H), 2.26-2.17 (m, 2H). MS (ESI): [M+H] 449.1618.

(3) Synthesis of Component A-7. To a solution of hyaluronic acid sodium (2 g, 340 kDa) in 100 mL 0.01 M 2-(N-morpholine) mesylate (MES) buffer solution (pH=5.2) was added Compound 13 (90 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-7 (1.72 g). According to the nuclear magnetic resonance spectrum, the grafting degree of Compound 13 can be calculated to be about 2.38%.

Example 8: Synthesis of Component A-8

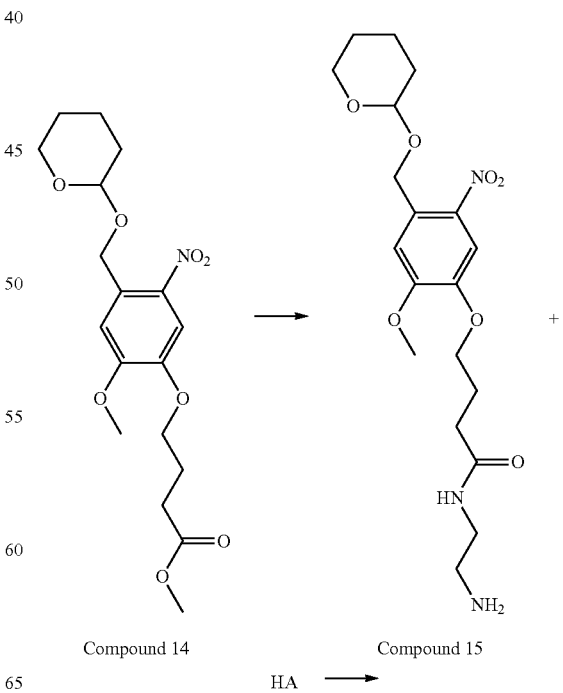

Compound 14                Compound 15

HA →

Example 9: Synthesis of Component A-9

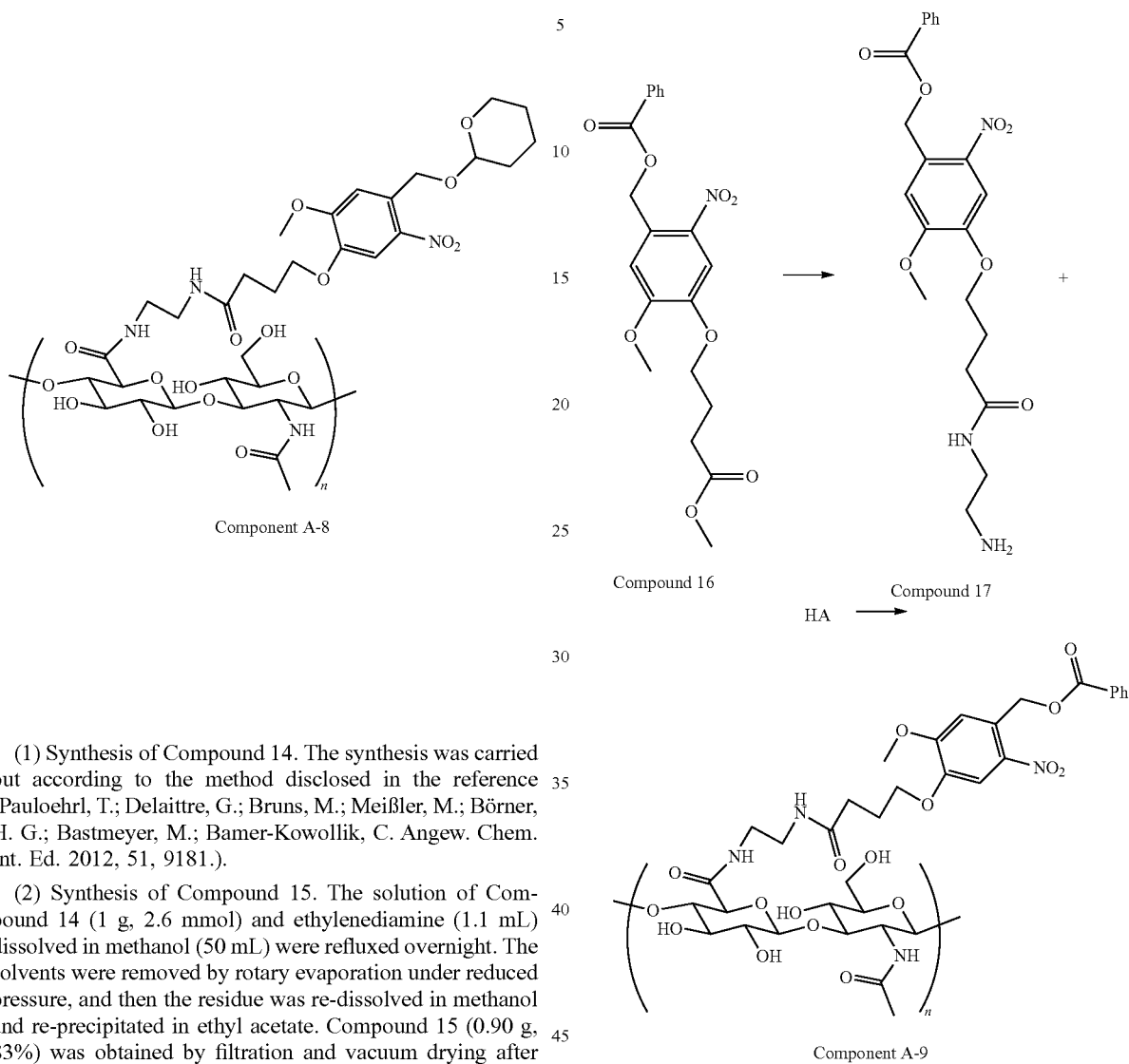

Component A-8

Compound 16

Compound 17

HA →

Component A-9

(1) Synthesis of Compound 14. The synthesis was carried out according to the method disclosed in the reference (Pauloehrl, T.; Delaittre, G.; Bruns, M.; Meißler, M.; Börner, H. G.; Bastmeyer, M.; Bamer-Kowollik, C. Angew. Chem. Int. Ed. 2012, 51, 9181.).

(2) Synthesis of Compound 15. The solution of Compound 14 (1 g, 2.6 mmol) and ethylenediamine (1.1 mL) dissolved in methanol (50 mL) were refluxed overnight. The solvents were removed by rotary evaporation under reduced pressure, and then the residue was re-dissolved in methanol and re-precipitated in ethyl acetate. Compound 15 (0.90 g, 83%) was obtained by filtration and vacuum drying after several times of dissolution-reprecipitation. $^1$H NMR (400 MHz, CDCl$_3$): δ=7.71 (s, 1H), 7.22 (s, 1H), 4.96 (s, 2H), 4.13 (t, J=6.1 Hz, 2H), 3.99 (s, 3H), 3.90-3.80 (m, 1H), 3.63-3.52 (m, 1H), 3.32 (dd, J=11.6, 5.7 Hz, 2H), 2.82 (t, J=5.9 Hz, 2H), 2.44 (t, J=7.2 Hz, 2H), 2.26-2.17 (m, 2H), 2.00-1.34 (m, 6H). MS (ESI): [M+H] 412.2027.

(3) Synthesis of Component A-8. To a solution of hyaluronic acid sodium (2 g, 340 kDa) in 100 mL 0.01 M 2-(N-morpholine) mesylate (MES) buffer solution (pH=5.2) was added compound 15 (82 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-8 (1.86 g). According to the nuclear magnetic resonance spectrum, the grafting degree of Compound 15 can be calculated to be about 3.43%.

(1) Synthesis of Compound 16. The synthesis was carried out according to the method disclosed in the reference (Patchornik Abraham; Amit B.; Woodward R. B. J. Am. Chem. Soc. 1970, 92, 6333.).

(2) Synthesis of Compound 17. The solution of Compound 16 (1 g, 2.5 mmol) and ethylenediamine (1.1 mL) dissolved in methanol (50 mL) were refluxed overnight. The solvents were removed by rotary evaporation under reduced pressure, and then the residue was re-dissolved in methanol and re-precipitated in ethyl acetate. Compound 17 (0.80 g, 75%) was obtained by filtration and vacuum drying after several times of dissolution-reprecipitation. $^1$H NMR (400 MHz, CDCl$_3$): δ=7.71 (s, 1H), 7.22 (s, 1H), 4.96 (s, 2H), 4.13 (t, J=6.1 Hz, 2H), 3.99 (s, 3H), 3.90-3.80 (m, 1H), 3.63-3.52 (m, 1H), 3.32 (dd, J=11.6, 5.7 Hz, 2H), 2.82 (t, J=5.9 Hz, 2H), 2.44 (t, J=7.2 Hz, 2H), 2.26-2.17 (m, 2H), 2.00-1.34 (m, 6H). MS (ESI): [M+H] 412.2027.

(3) Synthesis of Component A-9. To a solution of hyaluronic acid sodium (2 g, 340 kDa) in 100 mL 0.01 M 2-(N-morpholine) mesylate (MES) buffer solution (pH=5.2) was added Compound 17 (86 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid Compound derivative Compound A-9 (1.82 g). According to the nuclear magnetic resonance spectrum, the grafting degree of Compound 17 can be calculated to be about 3.24%.

Example 10: Synthesis of Component A-10

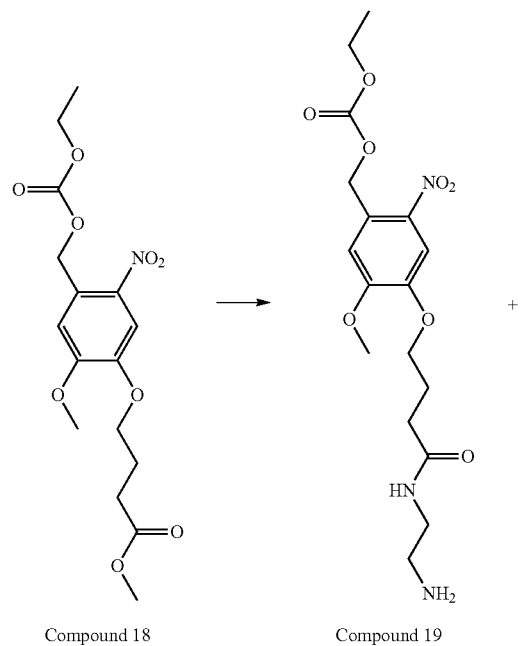

Compound 18                Compound 19

HA  →

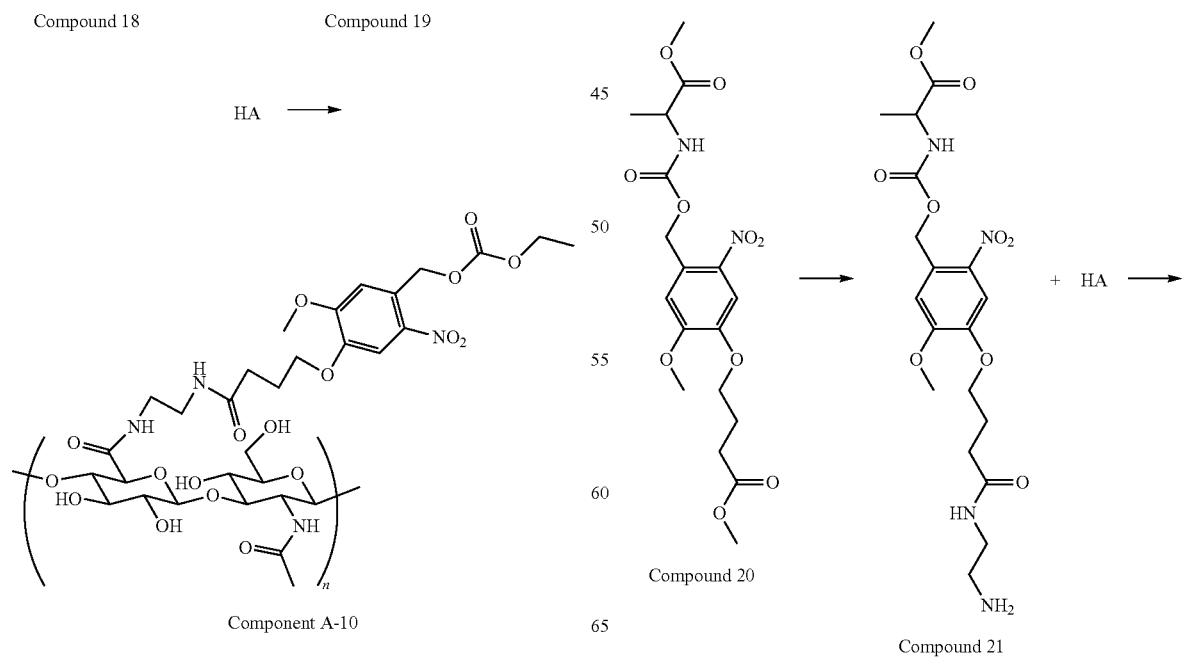

Component A-10

(1) Synthesis of Compound 18. The synthesis was carried out according to the method disclosed in the reference (Patchornik Abraham; Amit B.; Woodward R. B. J. Am. Chem. Soc. 1970, 92, 6333.).

(2) Synthesis of Compound 19. The solution of Compound 18 (1 g, 2.7 mmol) and ethylenediamine (1.1 mL) dissolved in methanol (50 mL) were refluxed overnight. The solvents were removed by rotary evaporation under reduced pressure, and then the residue was re-dissolved in methanol and re-precipitated in ethyl acetate. Compound 19 (0.76 g, 71%) was obtained by filtration and vacuum drying after several times of dissolution-reprecipitation. $^1$H NMR (400 MHz, CDCl$_3$): δ=7.71 (s, 1H), 7.22 (s, 1H), 4.96 (s, 2H), 4.25 (q, J=6.5 Hz, 2H), 4.13 (t, J=6.1 Hz, 2H), 3.99 (s, 3H), 3.32 (dd, J=11.6, 5.7 Hz, 2H), 2.82 (t, J=5.9 Hz, 2H), 2.44 (t, J=7.2 Hz, 2H), 2.26-2.17 (m, 2H), 1.32 (t, J=6.5 Hz, 3H). MS (ESI): [M+H] 400.1742.

(3) Synthesis of Component A-10. To a solution of hyaluronic acid sodium (2 g, 340 kDa) in 100 mL 0.01 M 2-(N-morpholine) mesylate (MES) buffer solution (pH=5.2) was added Compound 19 (80 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-10 (1.88 g). According to the nuclear magnetic resonance spectrum, the grafting degree of Compound 19 can be calculated to be about 3.01%.

Example 11: Synthesis of Component A-11

Compound 20                Compound 21

89
-continued

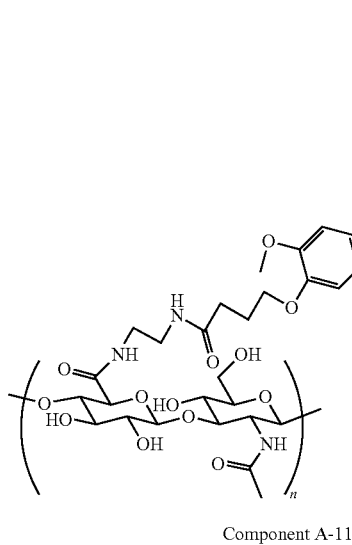

Component A-11

90
Example 12: Synthesis of Component A-12

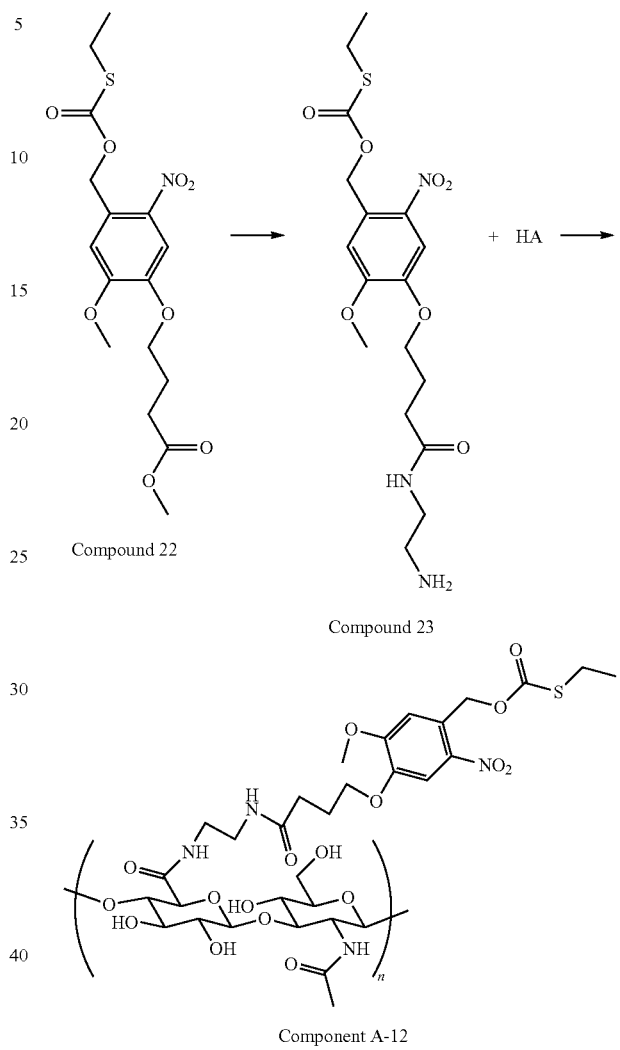

Compound 22

Compound 23

Component A-12

(1) Synthesis of Compound 20. The synthesis was carried out according to the method disclosed in the reference (Kalbag, S. M.; Roeske, R. W. J. Am. Chem. Soc. 1975, 97, 440.).

(2) Synthesis of Compound 21. The solution of Compound 20 (1 g, 2.3 mmol) and ethylenediamine (1.1 mL) dissolved in methanol (50 mL) were refluxed overnight. The solvents were removed by rotary evaporation under reduced pressure, and then the residue was re-dissolved in methanol and re-precipitated in ethyl acetate. Compound 21 (0.84 g, 79%) was obtained by filtration and vacuum drying after several times of dissolution-reprecipitation. $^1$H NMR (400 MHz, CDCl$_3$): δ=7.71 (s, 1H), 7.22 (s, 1H), 4.96 (s, 2H), 4.63 (q, J=6.9 Hz, 1H), 4.13 (t, J=6.1 Hz, 2H), 3.99 (s, 3H), 3.67 (s, 3H), 3.32 (dd, J=11.6, 5.7 Hz, 2H), 2.82 (t, J=5.9 Hz, 2H), 2.44 (t, J=7.2 Hz, 2H), 2.26-2.17 (m, 2H), 1.48 (d, J=6.9 Hz, 3H). MS (ESI): [M+H] 457.1976.

(3) Synthesis of Component A-11. To a solution of hyaluronic acid sodium (2 g, 340 kDa) in 100 mL 0.01 M 2-(N-morpholine) mesylate (MES) buffer solution (pH=5.2) was added Compound 21 (91 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-11 (1.76 g). According to the nuclear magnetic resonance spectrum, the grafting degree of Compound 21 can be calculated to be about 3.15%.

(1) Synthesis of Compound 22. The synthesis was carried out according to the method disclosed in the reference (Patchomik Abraham; Amit B.; Woodward R. B. J. Am. Chem. Soc. 1970, 92, 6333.).

(2) Synthesis of Compound 23. The solution of Compound 22 (1 g, 2.7 mmol) and ethylenediamine (1.1 mL) dissolved in methanol (50 mL) were refluxed overnight. The solvents were removed by rotary evaporation under reduced pressure, and then the residue was re-dissolved in methanol and re-precipitated in ethyl acetate. Compound 23 (0.76 g, 71%) was obtained by filtration and vacuum drying after several times of dissolution-reprecipitation. $^1$H NMR (400 MHz, CDCl$_3$): δ=7.71 (s, 1H), 7.22 (s, 1H), 4.96 (s, 2H), 4.25 (q, J=6.5 Hz, 2H), 4.13 (t, J=6.1 Hz, 2H), 3.99 (s, 3H), 3.32 (dd, J=11.6, 5.7 Hz, 2H), 2.82 (t, J=5.9 Hz, 2H), 2.44 (t, J=7.2 Hz, 2H), 2.26-2.17 (m, 2H), 1.32 (t, J=6.5 Hz, 3H). MS (ESI): [M+H] 416.1422.

(3) Synthesis of Component A-12. To a solution of hyaluronic acid sodium (2 g, 340 kDa) in 100 mL 0.01 M 2-(N-morpholine) mesylate (MES) buffer solution (pH=5.2) was added Compound 23 (80 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-12 (1.88 g). According to the nuclear magnetic resonance spectrum, the grafting degree of Compound 23 can be calculated to be about 3.01%.

Example 13: Synthesis of Component A-13

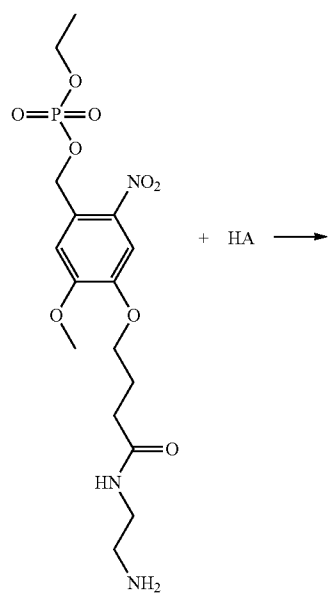

Compound 24

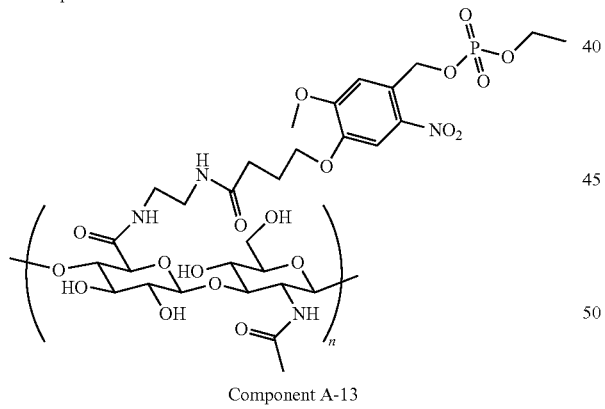

Component A-13

(1) Synthesis of Compound 24. The synthesis was carried out according to the method disclosed in the reference (Engels, J.; Schlaeger, E. J. J. Med. Chem. 1977, 20, 907.). $^1$H NMR (400 MHz, CDCl$_3$): δ=7.71 (s, 1H), 7.22 (s, 1H), 4.96 (s, 2H), 4.25 (q, J=6.5 Hz, 2H), 4.13 (t, J=6.1 Hz, 2H), 3.99 (s, 3H), 3.32 (dd, J=11.6, 5.7 Hz, 2H), 2.82 (t, J=5.9 Hz, 2H), 2.44 (t, J=7.2 Hz, 2H), 2.26-2.17 (m, 2H), 1.32 (t, J=6.5 Hz, 3H). MS (ESI): [M+H]435.1432.

(2) Synthesis of Component A-13. To a solution of hyaluronic acid sodium (2 g, 340 kDa) in 100 mL 0.01 M 2-(N-morpholine) mesylate (MES) buffer solution (pH=5.2) was added Compound 24 (87 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-13 (1.73 g). According to the nuclear magnetic resonance spectrum, the grafting degree of Compound 24 can be calculated to be about 3.08%.

Example 21: Synthesis of Component A-21

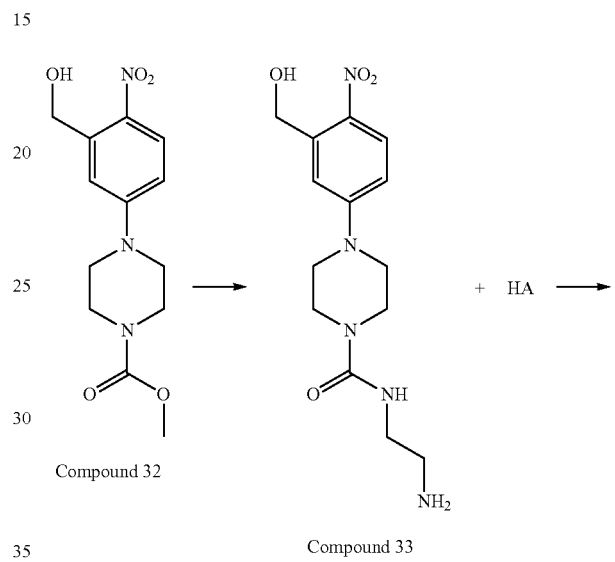

Compound 32     Compound 33

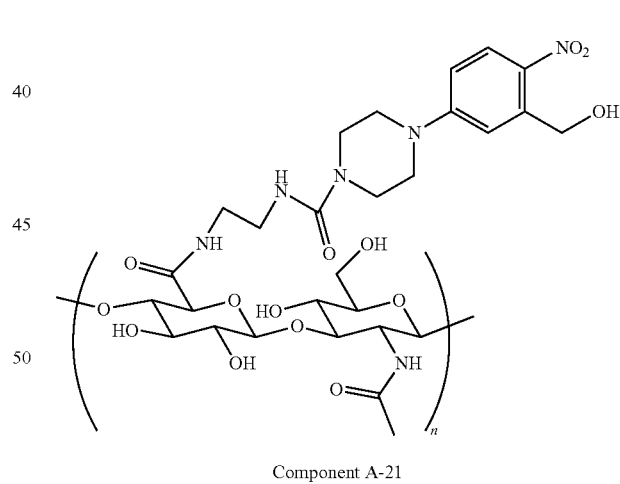

Component A-21

(1) Synthesis of Compound 32. The synthesis was carried out according to the method disclosed in the reference (Emmanuel Riguet; Christian G. Bochet. Org. Lett. 2007, 26, 5453.).

(2) Synthesis of Compound 33. The solution of Compound 32 (1 g, 3.4 mmol) and ethylenediamine (1.1 mL) dissolved in methanol (50 mL) were reluxed overnight. The solvents were removed by rotary evaporation under reduced pressure, then the residue was re-dissolved in methanol and re-precipitated in ethyl acetate. Compound 33 (0.85 g, 78%)

was obtained by filtration and vacuum drying after several times of dissolution-reprecipitation. $^1$H NMR (400 MHz, CDCl$_3$): δ=8.05 (d, J=9.54 Hz, 1H), 7.24 (d, J=2.72 Hz, 1H), 6.92 (dd, J=9.54, 2.72 Hz, 1H), 4.85 (s, 2H), 3.56-3.68 (m, 4H), 3.49-3.56 (m, 2H), 3.42-3.49 (m, 2H), 3.32 (t, J=5.9 Hz, 2H), 2.82 (t, J=5.9 Hz, 2H). MS (ESI): [M+H] 346.1454.

(3) Synthesis of Component A-21. To a solution of hyaluronic acid sodium (2 g, 340 kDa) in 100 mL 0.01 M 2-(N-morpholine) mesylate (MES) buffer solution (pH=5.2) was added Compound 33 (65 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-21 (1.76 g). According to the nuclear magnetic resonance spectrum, the grafting degree of Compound 33 can be calculated to be about 2.84%.

Example 22: Synthesis of Component A-22

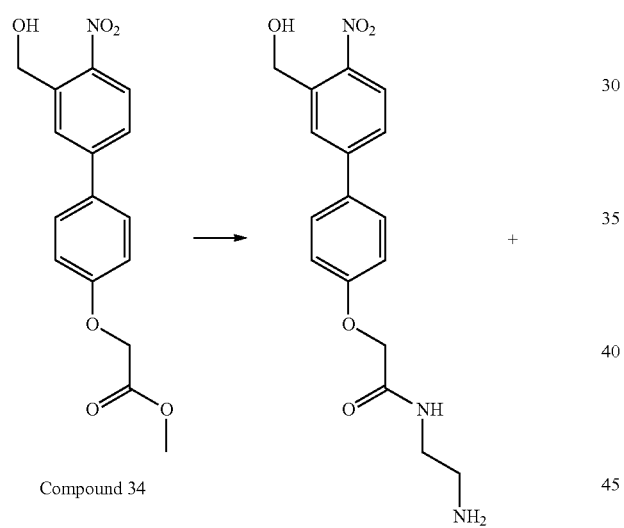

(1) Synthesis of Compound 34. The synthesis was carried out according to the method disclosed in the reference (Isabelle Aujard; Chouaha Benbrahim; Ludovic Jullien. Chem. Eur. J. 2006, 12, 6865.).

(2) Synthesis of Compound 35. The solution of Compound 34 (1 g, 3.2 mmol) and ethylenediamine (1.1 mL) dissolved in methanol (50 mL) were refluxed overnight. The solvents were removed by rotary evaporation under reduced pressure, and then the residue was re-dissolved in methanol and re-precipitated in ethyl acetate. Compound 35 (0.96 g, 88%) was obtained by filtration and vacuum drying after several times of dissolution-reprecipitation. $^1$H NMR (400 MHz, CDCl$_3$): δ=8.05 (d, J=9.54 Hz, 1H), 7.28 (d, J=8.00 Hz, 2H), 7.24 (d, J=2.72 Hz, 1H), 6.92 (dd, J=9.54, 2.72 Hz, 1H), 6.78 (d, 8.00 Hz, 2H), 4.96 (s, 2H), 4.83 (s, 2H), 3.32 (t, J=5.9 Hz, 2H), 2.82 (t, J=5.9 Hz, 2H). MS (ESI): [M+H]346.1454.

(3) Synthesis of Component A-22. To a solution of hyaluronic acid sodium (2 g, 340 kDa) in 100 mL 0.01 M 2-(N-morpholine) mesylate (MES) buffer solution (pH=5.2) was added Compound 35 (69 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-22 (1.83 g). According to the nuclear magnetic resonance spectrum, the grafting degree of Compound 35 can be calculated to be about 3.12%.

Example 25: Synthesis of Component A-25

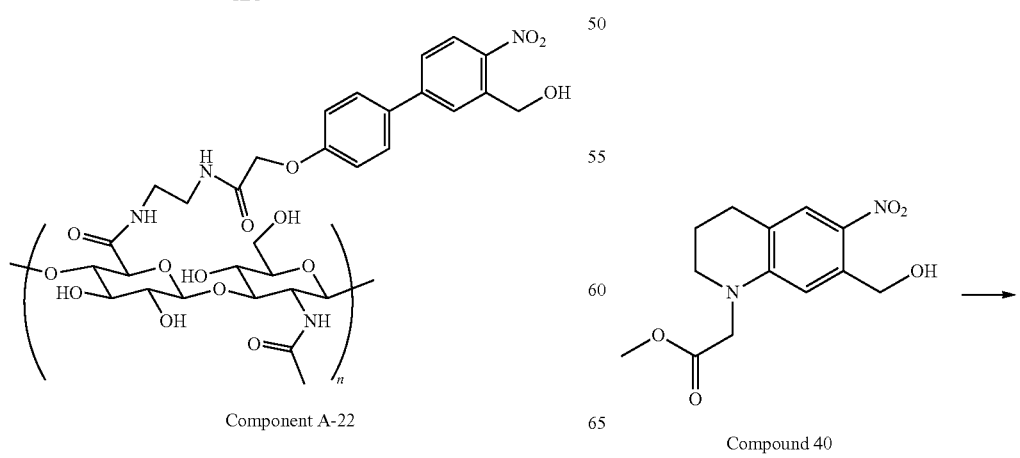

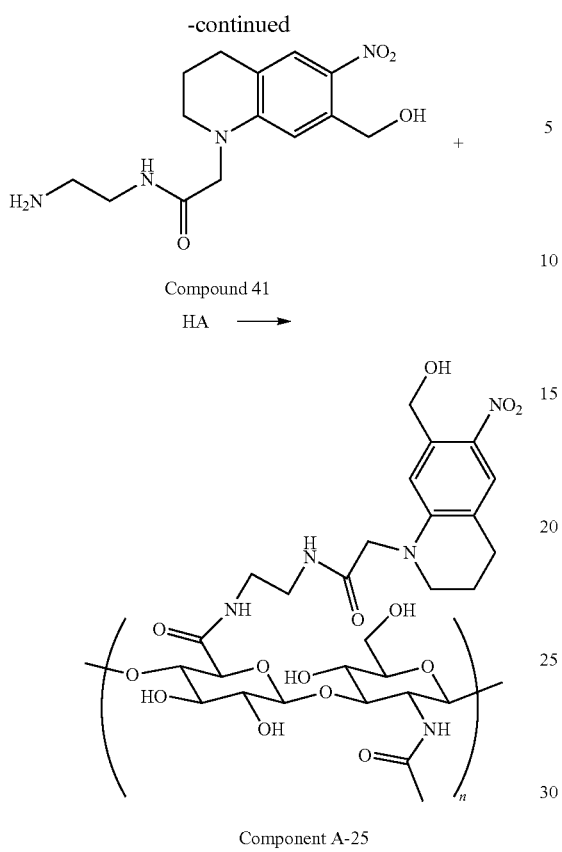

Compound 41

Component A-25

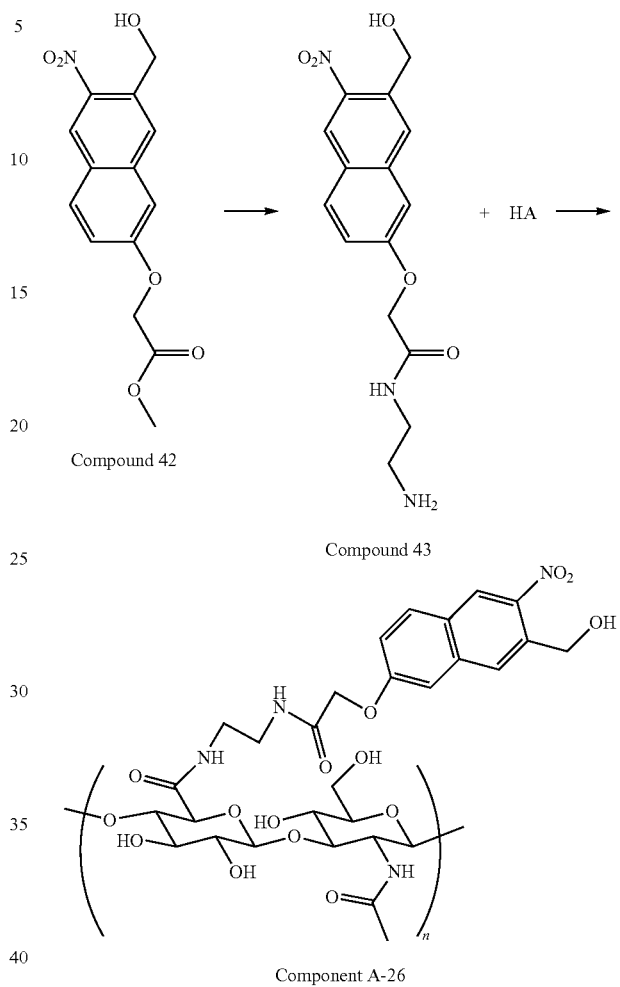

Compound 42

Compound 43

Component A-26

(1) Synthesis of Compound 40. The synthesis was carried out according to the method disclosed in the reference (Emmanuel Riguet; Christian G. Bochet. Org. Lett. 2007, 26, 5453.).

(2) Synthesis of Compound 41. The solution of Compound 10 (1 g, 3.6 mmol) and ethylenediamine (1.1 mL) dissolved in methanol (50 mL) were refluxed overnight. The solvents were removed by rotary evaporation under reduced pressure, and then the residue was re-dissolved in methanol and re-precipitated in ethyl acetate. Compound 41 (0.93 g, 85%) was obtained by filtration and vacuum drying after several times of dissolution-reprecipitation. $^1$H NMR (400 MHz, CDCl$_3$): δ=7.71 (s, 1H), 7.22 (s, 1H), 4.96 (s, 2H), 4.24 (s, 2H), 3.32 (t, J=5.9 Hz, 2H), 3.27-3.21 (m, 2H), 2.82 (t, J=5.9 Hz, 2H), 2.75 (t, J=6.3 Hz, 2H), 2.00-1.91 (m, 2H). MS (ESI): [M+H] 309.1522.

(3) Synthesis of Component A-25: To a solution of hyaluronic acid sodium (2 g, 340 kDa) in 100 mL 0.01 M 2-(N-morpholine) mesylate (MES) buffer solution (pH=5.2) was added Compound 41 (62 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-25 (1.82 g). According to the nuclear magnetic resonance spectrum, the grafting degree of Compound 41 can be calculated to be about 3.12%.

Example 26: Synthesis of Component A-26

(1) Synthesis of Compound 42. The synthesis was carried out according to the method disclosed in the reference (Singh, A. K.; Khade, P. K. Tetrahedron. 2005, 61, 10007.).

(2) Synthesis of Compound 43. The solution of Compound 42 (1 g, 3.4 mmol) and ethylenediamine (1.1 mL) dissolved in methanol (50 mL) were reluxed overnight. The solvents were removed by rotary evaporation under reduced pressure, then the residue was re-dissolved in methanol and re-precipitated in ethyl acetate. Compound 43 (0.90 g, 82%) was obtained by filtration and vacuum drying after several times of dissolution-reprecipitation. $^1$H NMR (400 MHz, CDCl$_3$): δ=8.31-7.12 (m, 5H), 4.96 (s, 2H), 4.83 (s, 2H), 3.32 (t, J=5.9 Hz, 2H), 2.82 (t, J=5.9 Hz, 2H). MS (ESI): [M+H] 320.1254.

(3) Synthesis of Component A-26. To a solution of hyaluronic acid sodium (2 g, 340 kDa) in 100 mL 0.01 M 2-(N-morpholine) mesylate (MES) buffer solution (pH=5.2) was added Compound 43 (64 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-26 (1.87 g). According to the nuclear magnetic resonance spectrum, the grafting degree of Compound 43 can be calculated to be about 3.21%.

Example 28: Synthesis of Component A-28

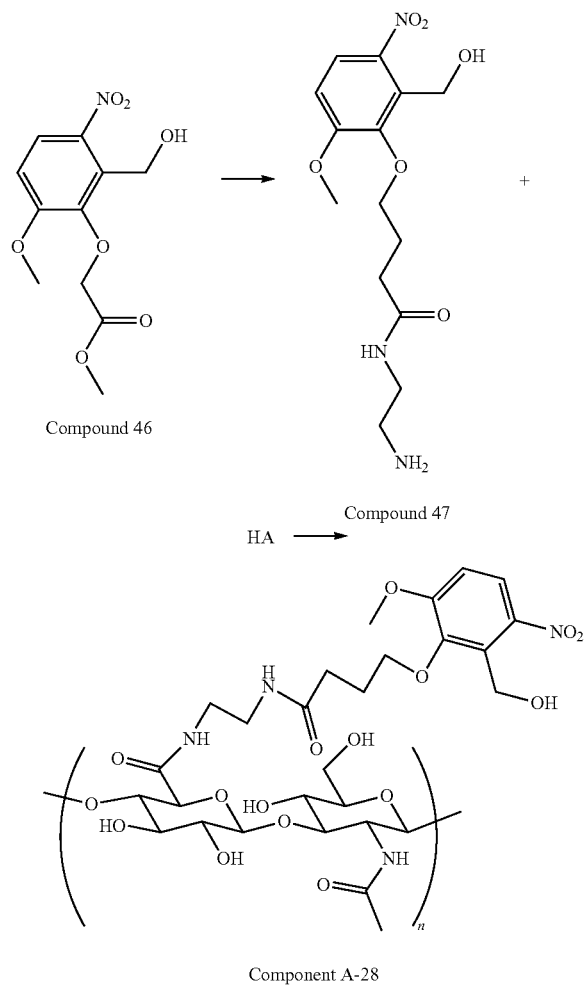

Compound 46

Compound 47

Component A-28

(1) Synthesis of Compound 46. The synthesis was carried out according to the method disclosed in the reference (Grazyna Groszek; Agnieszka Nowak-Krol; Barbara Filipek. Eur. J. Med. Chem. 2009, 44, 5103.).

(2) Synthesis of Compound 47. Compound 46 (1 g, 3.3 mmol) and ethylenediamine (1.1 mL) were dissolved in methanol (50 mL) and refluxed overnight. After steaming by rotary evaporation under reduced pressure, the crude product was dissolved in methanol and re-precipitated from ethyl acetate. After several times of dissolution-reprecipitation, filtration and vacuum drying gave Compound 47 (0.97 g, 89%). $^1$H NMR (400 MHz, CDCl$_3$): δ=8.04 (s, 1H), 7.42 (s, 1H), 4.96 (s, 2H), 4.13 (t, J=6.1 Hz, 2H), 3.99 (s, 3H), 3.32 (dd, J=11.6, 5.7 Hz, 2H), 2.82 (t, J=5.9 Hz, 2H), 2.44 (t, J=7.2 Hz, 2H), 2.26-2.17 (m, 2H). MS (ESI): [M+H] 328.1507.

(3) Synthesis of Component A-28. To a solution of hyaluronic acid sodium (2 g, 340 kDa) in 100 mL 0.01 M 2-(N-morpholine) mesylate (MES) buffer solution (pH=5.2) was added Compound 47 (65 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-28 (1.85 g). According to the nuclear magnetic resonance spectrum, the grafting degree of Compound 47 can be calculated to be about 3.43%.

Example 29: Synthesis of Component A-29

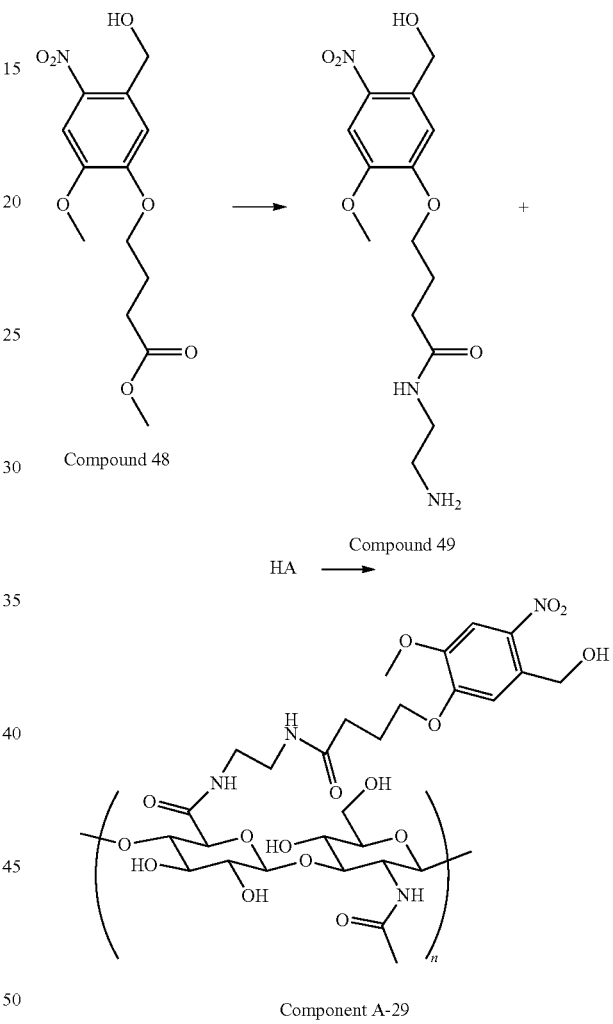

Compound 48

Compound 49

Component A-29

(1) Synthesis of Compound 48. The synthesis was carried out according to the method disclosed in the reference (Thomas F. Greene; Shu Wang; Mary J. Meegan. J. Med. Chem. 2016, 59, 90.).

(2) Synthesis of Compound 49. Compound 48 (1 g, 3.3 mmol) and ethylenediamine (1.1 mL) were dissolved in methanol (50 mL) and refluxed overnight. The solvent was removed by rotary evaporation under reduced pressure, the obtained crude product was dissolved in methanol and re-precipitated from ethyl acetate for several times to obtain Compound 49 (0.95 g, 87%). $^1$H NMR (400 MHz, CDCl$_3$): δ=7.95 (s, 1H), 7.12 (s, 1H), 4.96 (s, 2H), 4.13 (t, J=6.1 Hz, 2H), 3.99 (s, 3H), 3.32 (dd, J=11.6, 5.7 Hz, 2H), 2.82 (t, J=5.9 Hz, 2H), 2.44 (t, J=7.2 Hz, 2H), 2.26-2.17 (m, 2H). MS (ESI): [M+H] 328.1507.

(3) Synthesis of Component A-29. To a solution of hyaluronic acid sodium (2 g, 340 kDa) in 100 mL 0.01 M 2-(N-morpholine) mesylate (MES) buffer solution (pH=5.2) was added Compound 49 (65 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-29 (1.86 g). According to the nuclear magnetic resonance spectrum, the grafting degree of Compound 49 can be calculated to be about 3.52%.

Example 30: Synthesis of Component A-30

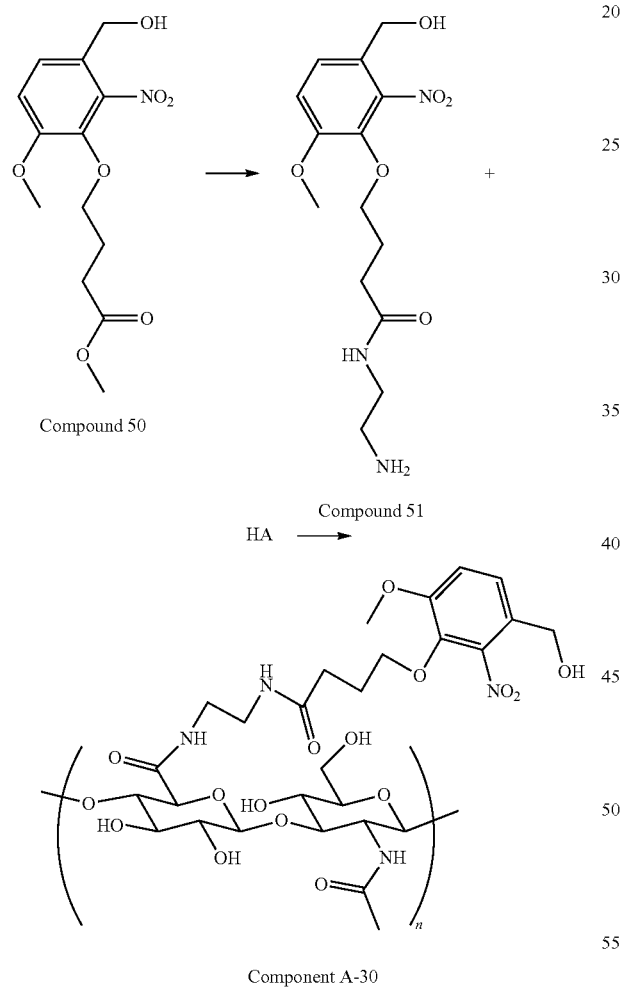

Component A-30

(1) Synthesis of Compound 50. The synthesis was carried out according to the method disclosed in the reference (Yu-Shan; Mohane Selvaraj Coumar; Hsing-Pang Hsieh. J. Med. Chem. 2009, 52, 4941.).

(2) Synthesis of Compound 51. Compound 50 (1 g, 3.3 mmol) and ethylenediamine (1.1 mL) were dissolved in methanol (50 mL) and refluxed overnight. The solvent was removed by rotary evaporation under reduced pressure, the obtained crude product was dissolved in methanol and re-precipitated from ethyl acetate for several times to obtain Compound 51 (0.89 g, 81%). $^1$H NMR (400 MHz, CDCl$_3$): δ=7.64 (s, 1H), 7.02 (s, 1H), 4.96 (s, 2H), 4.13 (t, J=6.1 Hz, 2H), 3.99 (s, 3H), 3.32 (dd, J=11.6, 5.7 Hz, 2H), 2.82 (t, J=5.9 Hz, 2H), 2.44 (t, J=7.2 Hz, 2H), 2.26-2.17 (m, 2H). MS (ESI): [M+H] 328.1507.

(3) Synthesis of Component A-30. To a solution of hyaluronic acid sodium (2 g, 340 kDa) in 100 mL 0.01 M 2-(N-morpholine) mesylate (MES) buffer solution (pH=5.2) was added Compound 51 (65 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-30 (1.85 g). According to the nuclear magnetic resonance spectrum, the grafting degree of Compound 51 can be calculated to be about 3.39%.

Example 31: Synthesis of Component A-31

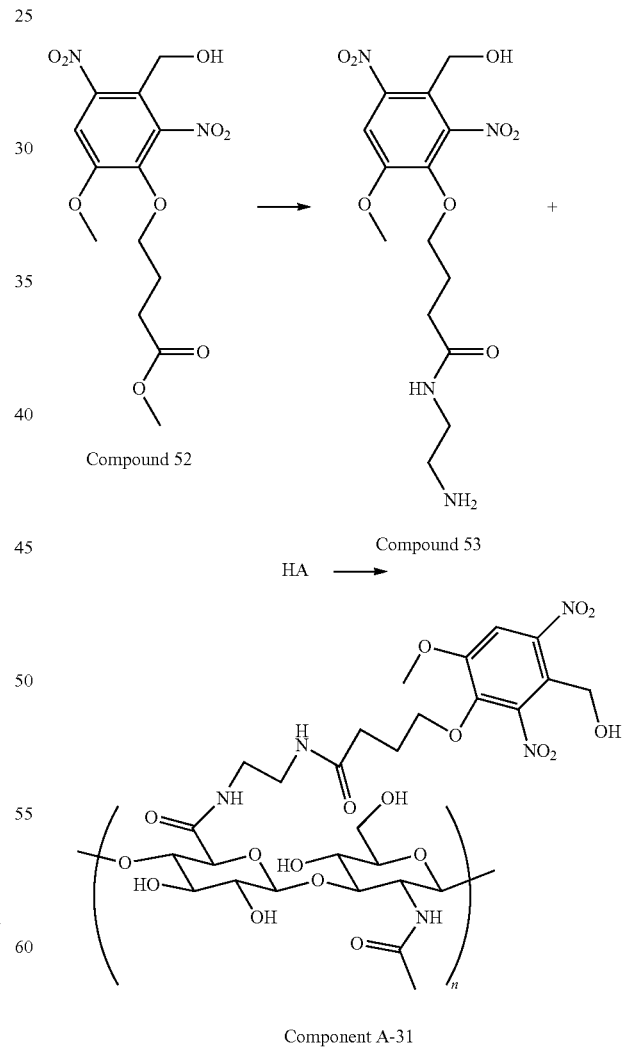

Component A-31

(1) Synthesis of Compound 52. The synthesis was carried out according to the method disclosed in the reference (Sarit S. Agasti; Apiwat Chompoosor; Vincent M. Rotello. J. Am. Chem. Soc. 2009, 131, 5728.).

(2) Synthesis of Compound 53. Compound 52 (1 g, 2.9 mmol) and ethylenediamine (1.1 mL) were dissolved in methanol (50 mL) and refluxed overnight. After steaming by rotary evaporation under reduced pressure, the crude product was dissolved in methanol and re-precipitated from ethyl acetate for several times to obtain Compound 53 (0.91 g, 84%). $^1$H NMR (400 MHz, CDCl$_3$): δ=7.91 (s, 1H), 4.96 (s, 2H), 4.13 (t, J=6.1 Hz, 2H), 3.99 (s, 3H), 3.32 (dd, J=11.6, 5.7 Hz, 2H), 2.82 (t, J=5.9 Hz, 2H), 2.44 (t, J=7.2 Hz, 2H), 2.26-2.17 (m, 2H). MS (ESI): [M+H] 373.1373.

(3) Synthesis of Component A-31. To a solution of hyaluronic acid sodium (2 g, 340 kDa) in 100 mL 0.01 M 2-(N-morpholine) mesylate (MES) buffer solution (pH=5.2) was added Compound 53 (75 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-31 (1.87 g). According to the nuclear magnetic resonance spectrum, the grafting degree of Compound 53 can be calculated to be about 3.45%.

Example 33: Synthesis of Component A-33

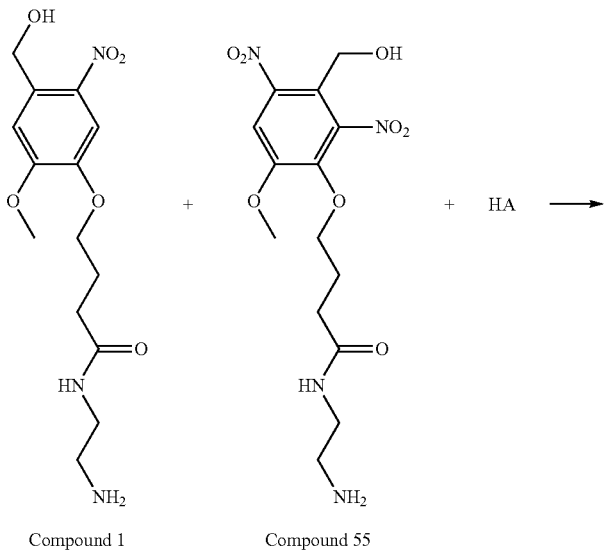

Compound 1          Compound 55

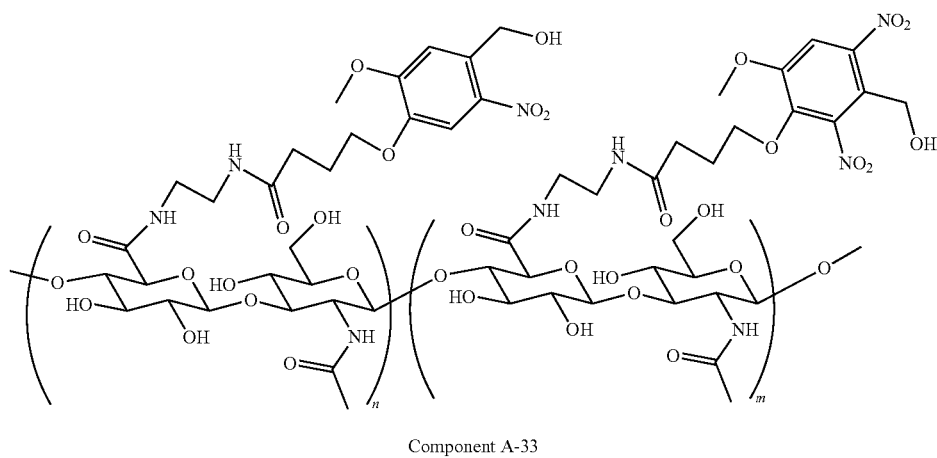

Component A-33

Synthesis of Component A-33. To a solution of hyaluronic acid sodium (2 g, 340 kDa) in 100 mL 0.01 M 2-(N-morpholine) mesylate (MES) buffer solution (pH=5.2) was added the mixture of Compound 1 and Compound 55 (60 mg, weight ratio 1:1) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-33 (1.87 g). According to the nuclear magnetic resonance spectrum, the grafting degree of the NB mixture (Compound 1/Compound 55) can be calculated to be about 3.52%.

Example 34: Synthesis of Component A-34

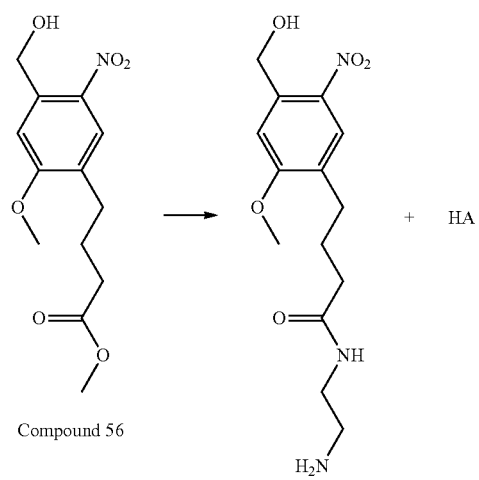

Compound 56

Compound 57

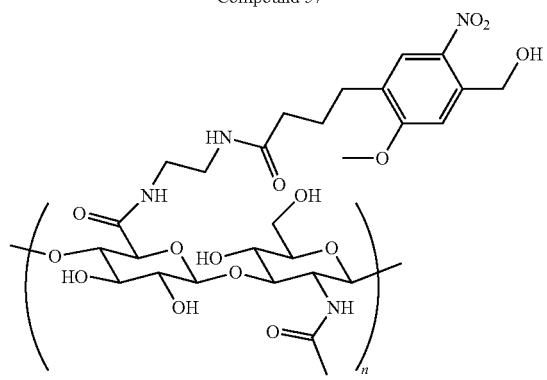

Component A-34

(1) Synthesis of Compound 56. The synthesis was carried out according to the method disclosed in the reference (Pauloehrl, T.; Delaittre, G.; Bruns, M.; Meißler, M.; Börner, H. G.; Bastmeyer, M.; Bamer-Kowollik, C. Angew. Chem. Int. Ed. 2012, 51, 9181.).

(2) Synthesis of Compound 57. Compound 56 (1 g, 3.3 mmol) and ethylenediamine (1.1 mL) were dissolved in methanol (50 mL) and refluxed overnight. After steaming by rotary evaporation under reduced pressure, the crude product was dissolved in methanol and re-precipitated from ethyl acetate. After several times of dissolution-reprecipitation, filtration and vacuum drying gave Compound 57 (0.93 g, 85%). $^1$H NMR (400 MHz, CDCl$_3$): δ=7.71 (s, 1H), 7.22 (s, 1H), 4.96 (s, 2H), 3.99 (s, 3H), 3.32 (t, J=5.7 Hz, 2H), 2.82 (t, J=5.9 Hz, 2H), 2.55 (t, J=6.1 Hz, 2H), 2.44 (t, J=7.2 Hz, 2H), 2.26-2.17 (m, 2H). MS (ESI): [M+H]326.1721.

(3) Synthesis of Component A-34. To a solution of hyaluronic acid sodium (2 g, 340 kDa) in 100 mL 0.01 M 2-(N-morpholine) mesylate (MES) buffer solution (pH=5.2) was added Compound 57 (65 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-34 (1.82 g). According to the nuclear magnetic resonance spectrum, the grafting degree of Compound 57 can be calculated to be about 3.21%.

Example 35: Synthesis of Component A-35

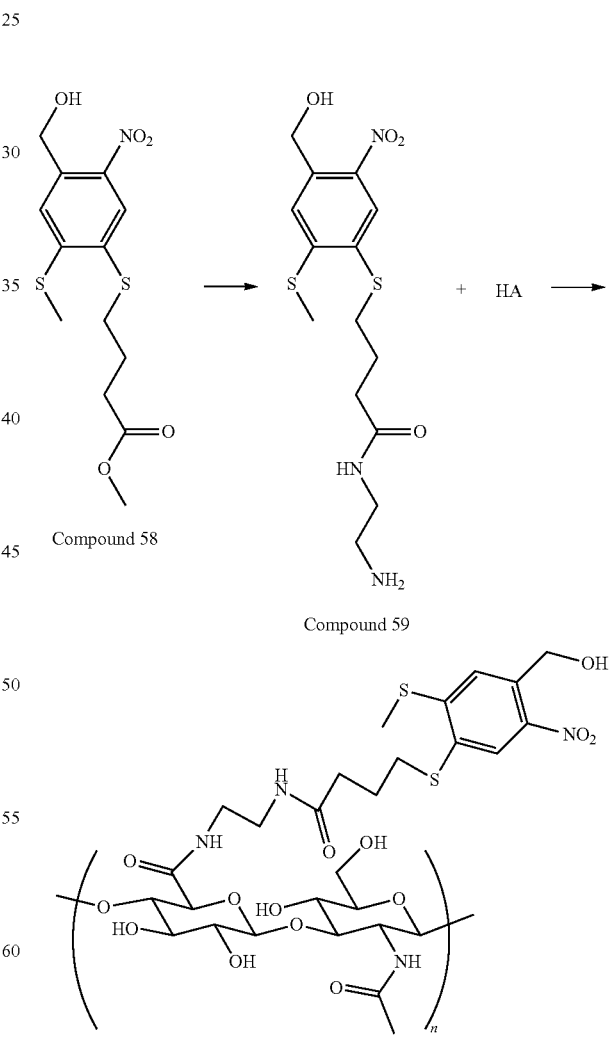

Compound 58

Compound 59

Component A-35

(1) Synthesis of Compound 58. The synthesis was carried out according to the method disclosed in the reference (Pauloehrl, T.; Delaittre, G.; Bruns, M.; Meißler, M.; Börner, H. G.; Bastmeyer, M.; Bamer-Kowollik, C. Angew. Chem. Int. Ed. 2012, 51, 9181.).

(2) Synthesis of Compound 59. Compound 58 (1 g, 3.3 mmol) and ethylenediamine (1.1 mL) were dissolved in methanol (50 mL) and refluxed overnight. After steaming by rotary evaporation under reduced pressure, the crude product was dissolved in methanol and re-precipitated from ethyl acetate. After several times of dissolution-reprecipitation, filtration and vacuum drying gave Compound 59 (0.82 g, 75%). $^1$H NMR (400 MHz, CDCl$_3$): δ=7.71 (s, 1H), 7.22 (s, 1H), 4.96 (s, 2H), 4.03 (t, J=6.1 Hz, 2H), 3.99 (s, 3H), 3.32 (dd, J=11.6, 5.7 Hz, 2H), 2.82 (t, J=5.9 Hz, 2H), 2.44 (t, J=7.2 Hz, 2H), 2.26-2.17 (m, 2H). MS (ESI): [M+H] 360.1213.

(3) Synthesis of Component A-35. To a solution of hyaluronic acid sodium (2 g, 340 kDa) in 100 mL 0.01 M 2-(N-morpholine) mesylate (MES) buffer solution (pH=5.2) was added Compound 59 (65 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-35 (1.87 g). According to the nuclear magnetic resonance spectrum, the grafting degree of Compound 59 can be calculated to be about 2.76%.

Example 36: Synthesis of Component A-36

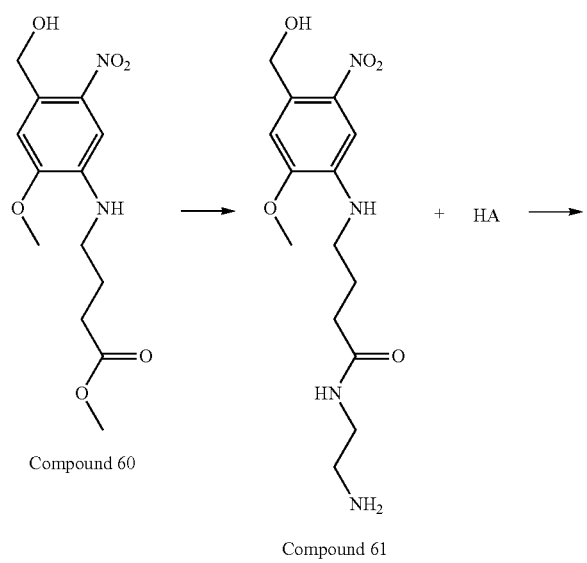

Compound 60

Compound 61

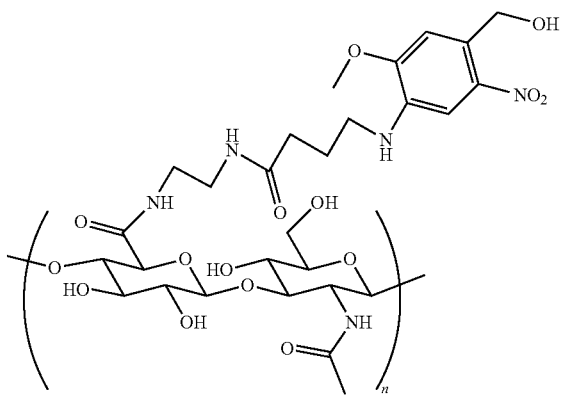

Component A-36

(1) Synthesis of Compound 60. The synthesis was carried out according to the method disclosed in the reference (Pauloehrl, T.; Delaittre, G.; Bruns, M.; Meißler, M.; Börner, H. G.; Bastmeyer, M.; Bamer-Kowollik, C. Angew. Chem. Int. Ed. 2012, 51, 9181.).

(2) Synthesis of Compound 61. Compound 60 (1 g, 3.3 mmol) and ethylenediamine (1.1 mL) were dissolved in methanol (50 mL) and refluxed overnight. After steaming by rotary evaporation under reduced pressure, the crude product was dissolved in methanol and re-precipitated from ethyl acetate. After several times of dissolution-reprecipitation, filtration and vacuum drying gave Compound 61 (0.80 g, 73%). $^1$H NMR (400 MHz, CDCl$_3$): δ=7.71 (s, 1H), 7.22 (s, 1H), 4.96 (s, 2H), 3.99 (s, 3H), 3.45 (t, J=6.1 Hz, 2H), 3.32 (dd, J=11.6, 5.7 Hz, 2H), 2.82 (t, J=5.9 Hz, 2H), 2.44 (t, J=7.2 Hz, 2H), 2.26-2.17 (m, 2H). MS (ESI): [M+H] 327.1625.

(3) Synthesis of Component A-36. To a solution of hyaluronic acid sodium (2 g, 340 kDa) in 100 mL 0.01 M 2-(N-morpholine) mesylate (MES) buffer solution (pH=5.2) was added Compound 61 (65 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-36 (1.76 g). According to the nuclear magnetic resonance spectrum, the grafting degree of Compound 61 can be calculated to be about 3.21%.

107

Example 37: Synthesis of Component A-37

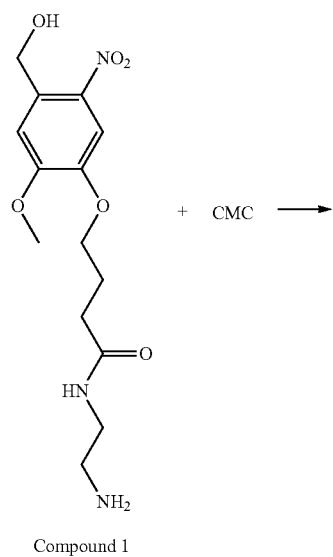

Compound 1

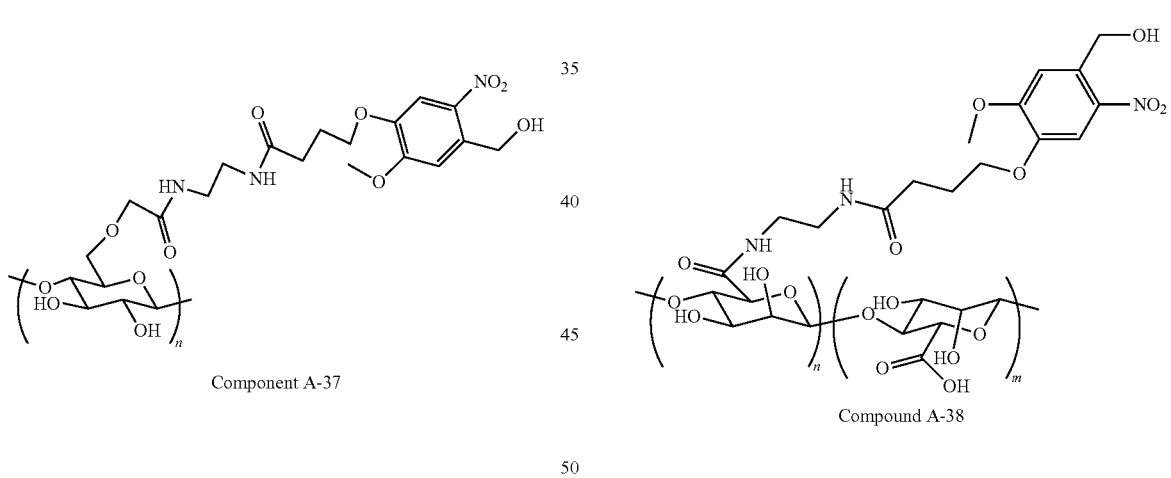

Component A-37

Synthesis of Component A-37: To a solution of carboxymethyl cellulose (2 g, 90 kDa) in 100 mL 0.01 M 2-(N-morpholine) mesylate (MES) buffer solution (pH=5.2) was added Compound 1 (65 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive carboxymethylcellulose derivative Compound A-37 (1.89 g). According to the nuclear magnetic resonance spectrum, the grafting degree of Compound 1 can be calculated to be about 2.25%.

108

Example 38: Synthesis of Component A-38

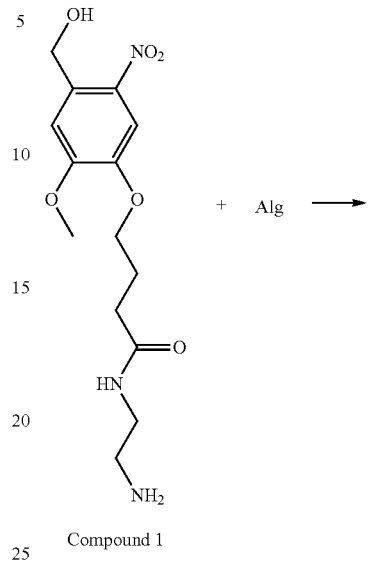

Compound 1

Compound A-38

Synthesis of Component A-38: To a solution of alginic acid (2 g) in 100 mL 0.01 M 2-(N-morpholine) mesylate (MES) buffer solution (pH=5.2) was added Compound 1 (65 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive alginic acid derivative Compound A-38 (1.82 g). According to the nuclear magnetic resonance spectrum, the grafting degree of Compound 1 can be calculated to be about 3.17%.

Example 39: Synthesis of Component A-39

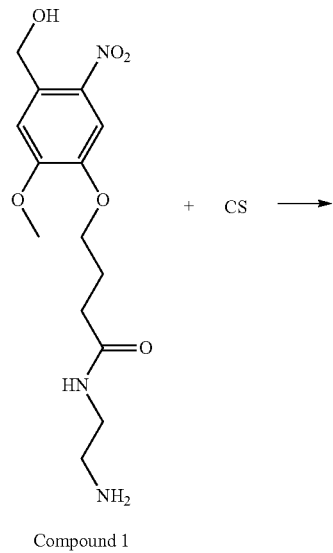

Compound 1

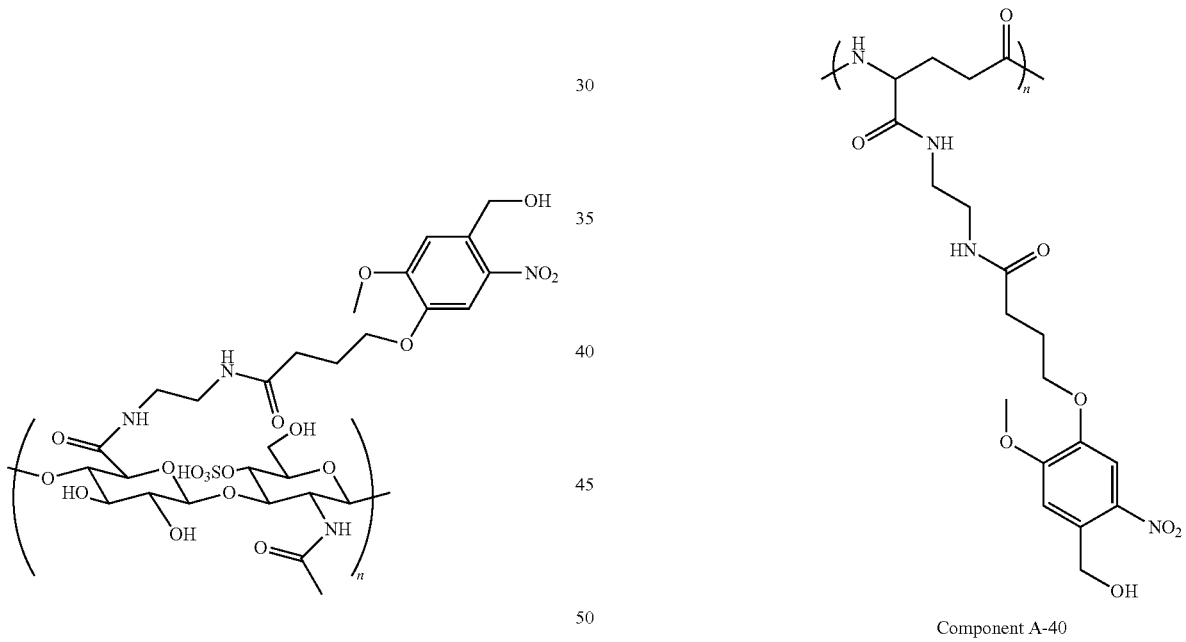

Synthesis of Component A-39. To a solution of chondroitin sulfate (2 g) in 100 mL 0.01 M 2-(N-morpholine) mesylate (MES) buffer solution (pH=5.2) was added Compound 1 (65 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive chondroitin sulfate derivative Compound A-39 (1.73 g). According to the nuclear magnetic resonance spectrum, the grafting degree of Compound 1 can be calculated to be about 2.98%.

Example 40: Synthesis of Component A-40

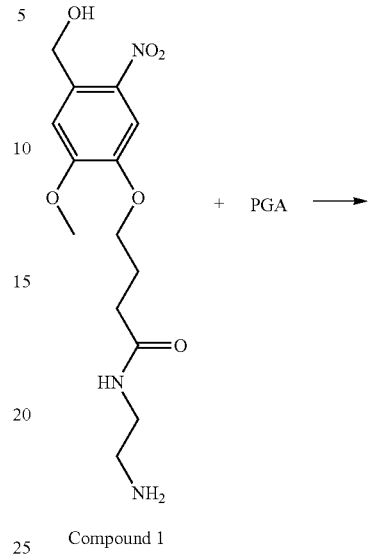

Compound 1

Component A-40

Synthesis of Component A-40. To a solution of polyglutamic acid (PGA, 1 g) in 50 mL distilled water was added hydroxybenzotriazole (HOBt, 0.3 g, 2.3 mmol). Then Compound 1 (0.5 g, 1.6 mmol) and 1-ethyl-(3-dimethylaminopropyl) carbodiimine hydrochloride (EDC-HCl, 0.5 g, 2.6 mmol) dissolved in methanol were added to the above solution, and the mixture was stirred at room temperature for 48 h. The solution was firstly dialyzed with dilute hydrochloric acid solution containing sodium chloride (pH=3.5) for 1 d, and then dialyzed against pure water for 1 d, then freeze-dried to obtain photosensitive polyglutamic acid derivative Compound A-40 (0.92 g). According to its nuclear magnetic resonance spectrum, the grafting degree of Compound 1 can be calculated to be about 21.3%.

Example 41: Synthesis of Component A-41

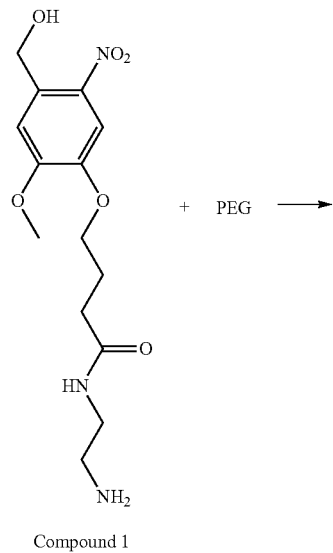

Synthesis of Component A-41. To a solution of four-arm polyglycol carboxylic acid derivative 4-PEG-COOH (0.5 g, 10 kDa) dissolved in 20 mL dry dimethyl sulfoxide (DMSO) was added Compound 1 (130 mg, 0.4 mmol) dissolved in 5 mL dimethyl sulfoxide (DMSO). And then, 0.2 ml triethylamine TEA and benzotriazol-1-yl-oxytripyrrolidinylphosphonium (PyBop, 210 mg, 0.4 mmol) were added into the above solution. The mixture was reacted at room temperature for 24 h. Then, it was re-precipitated in diethyl ether, and the crude product was re-dissolved in water and poured into a dialysis bag (MWCO 3500) to dialyze against deionized water for 2-3 d. The photosensitive polyethylene glycol derivative Compound A-41 (0.45 g) was obtained by freeze-drying. According to the nuclear magnetic resonance spectrum, the grafting degree of Compound 1 can be calculated to be about 98%.

Example 42: Synthesis of Component A-42

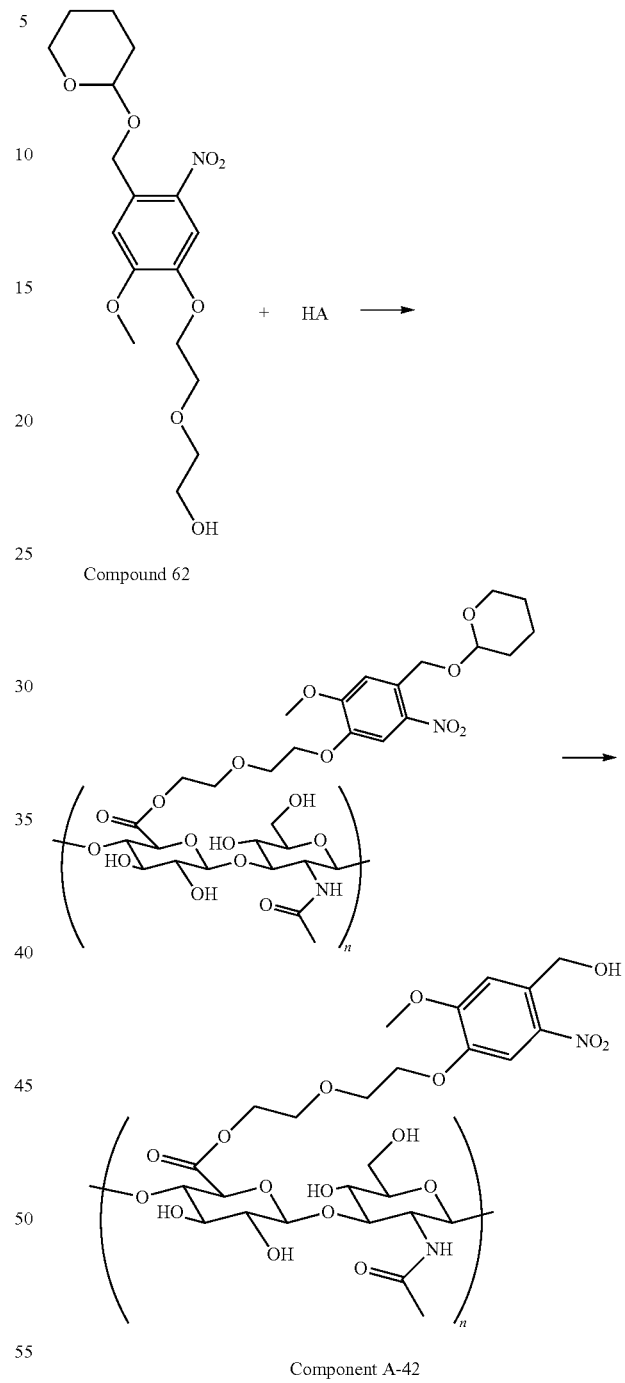

(1) Synthesis of Compound 62. The synthesis was carried out according to the method disclosed in the reference (Pauloehrl, T.; Delaittre, G.; Bruns, M.; Meißler, M.; Börner, H. G.; Bastmeyer, M.; Barner-Kowollik, C. Angew. Chem. Int. Ed. 2012, 51, 9181.). $^1$H NMR (400 MHz, CDCl$_3$): δ=7.71 (s, 1H), 7.22 (s, 1H), 4.96 (s, 2H), 4.13 (t, J=6.1 Hz, 2H), 3.99 (s, 3H), 3.90-3.80 (m, 1H), 3.79 (t, J=6.1 Hz, 2H), 3.70 (t, J=7.2 Hz, 2H), 3.63-3.52 (m, 1H), 3.56 (t, J=7.2 Hz, 2H), 2.00-1.34 (m, 6H). MS (ESI): [M+H] 372.1627.

(2) Synthesis of Component A-42. To a solution of hyaluronic acid (1 g, 340 kDa) dissolved in 50 mL of water was sequentially added Compound 62 (0.2 g, 0.48 mmol), EDC-HCl (0.76 g, 3.96 mmol) and DPTS (0.12 g, 0.48 mmol), and the reaction was stirred at room temperature for 48 h. The reaction solution was re-precipitated in cold ethanol, and the crude product was re-dissolved in water and re-precipitated several times. The collected precipitate was dried and dissolved in anhydrous DMSO, and the above solution was added p-toluenesulfonic acid to remove dihydropyran protecting group to obtain the photosensitive hyaluronic acid derivative Compound A-42 (0.86 g). According to its nuclear magnetic resonance spectrum, the grafting degree of Compound 62 can be calculated to be about 10%.

Example 43: Synthesis of Component A-43

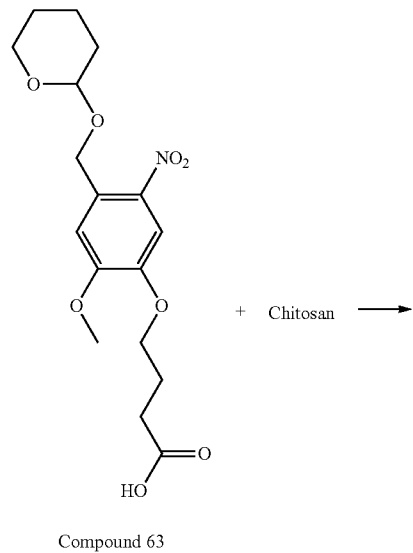

Compound 63

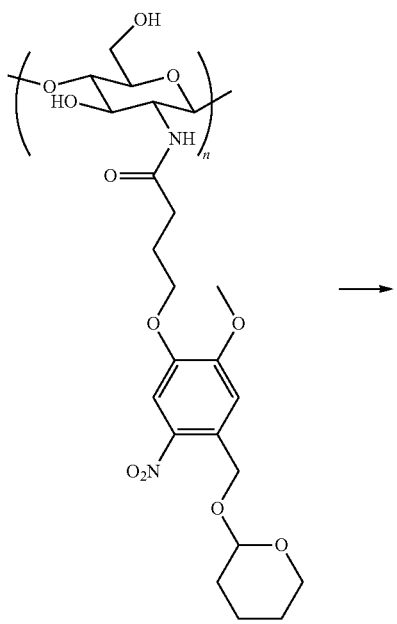

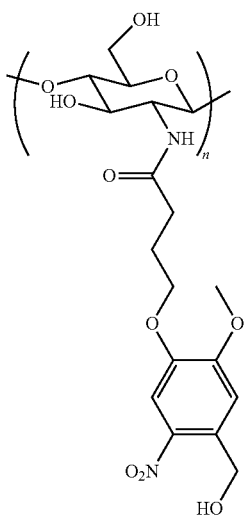

Component A-43

(1) Synthesis of Compound 63. The synthesis was carried out according to the method disclosed in the reference (Pauloehrl, T.; Delaittre, G.; Bruns, M.; Meißler, M.; Börner, H. G.; Bastmeyer, M.; Bamer-Kowollik, C. Angew. Chem. Int. Ed. 2012, 51, 9181.). $^1$H NMR (400 MHz, CDCl$_3$): δ=7.71 (s, 1H), 7.22 (s, 1H), 4.96 (s, 2H), 4.13 (t, J=6.1 Hz, 2H), 3.99 (s, 3H), 3.90-3.80 (m, 1H), 3.63-3.52 (m, 1H), 2.44 (t, J=7.2 Hz, 2H), 2.26-2.17 (m, 2H), 2.00-1.34 (m, 6H). MS (ESI): [M+H] 370.1512.

(2) Synthesis of Component A-43. To a suspension liquid of chitosan (1 g) dissolved in 75 mL isopropanol was sequentially added Compound 63 (0.2 g, 0.54 mmol), EDC-HCl (0.76 g, 3.96 mmol) and NHS (0.46 g, 4.0 mmol), and the reaction was stirred at room temperature for 48 h. After completion of the reaction, the mixture solution was filtered, and the filtrate was dialyzed three times with a methanol/water mixed solvent and twice with methanol, and then freeze-dried to obtain chitosan modified by Compound 63 (0.9 g). The chitosan modified by Compound 63 was dissolved in anhydrous DMSO, and the solution was added p-toluenesulfonic acid to remove dihydropyran protecting group to obtain the photosensitive chitosan derivative Compound A-43. According to its nuclear magnetic resonance spectrum, the grafting degree of the Compound 63 can be calculated to be about 12.5%.

Example 44: Synthesis of Component A-44

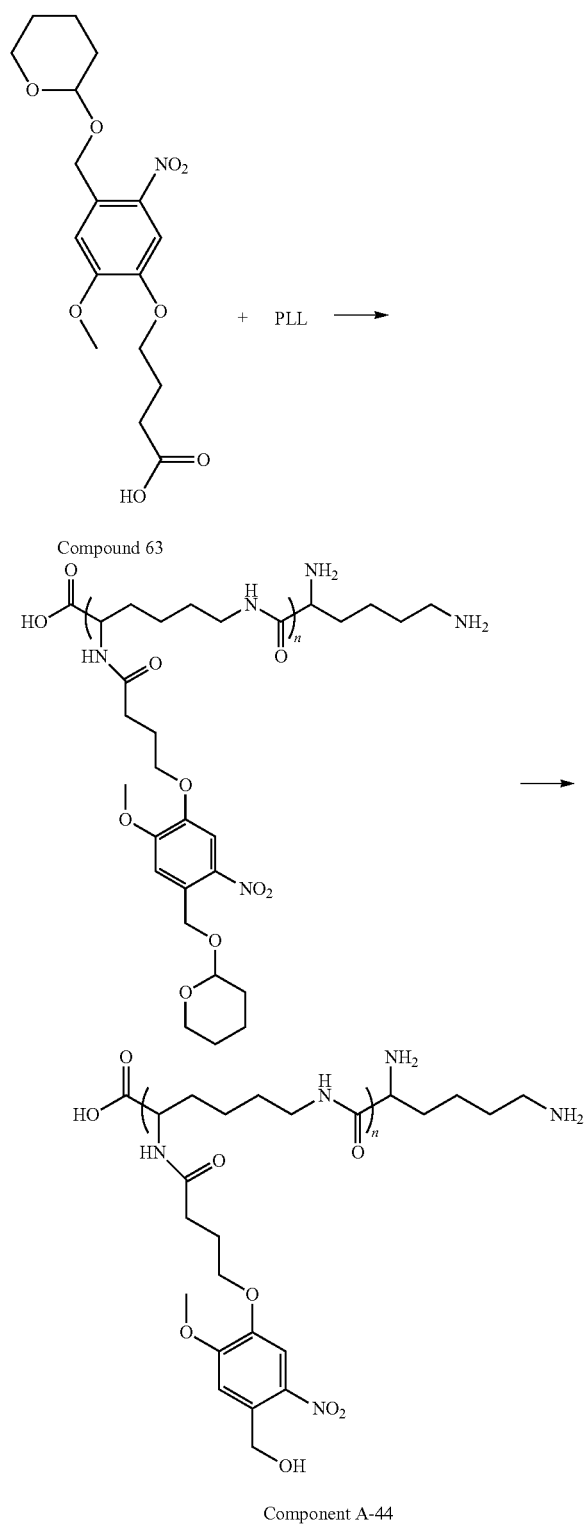

Component A-44

Synthesis of Component A-44. To a solution of polylysine (PLL, 1 g) dissolved in 50 mL water was sequentially added Compound 63 (0.2 g, 0.54 mmol), EDC-HCl (0.76 g, 3.96 mmol) and NHS (0.46 g, 4.0 mmol), and the reaction was stirred at room temperature for 48 h. After completion of the reaction, the reaction solution was reprecipitated in cold ethanol, and the crude product was re-dissolved in water and reprecipitated several times. The collected precipitate was dried and dissolved in anhydrous DMSO, and the above solution was added p-toluenesulfonic acid to remove dihydropyran protecting group to obtain the photosensitive hyaluronic acid derivative Compound A-44 (0.84 g). According to its nuclear magnetic resonance spectrum, the grafting degree of Compound 63 can be calculated to be about 15.6%.

Example 45: Synthesis of Component A-45

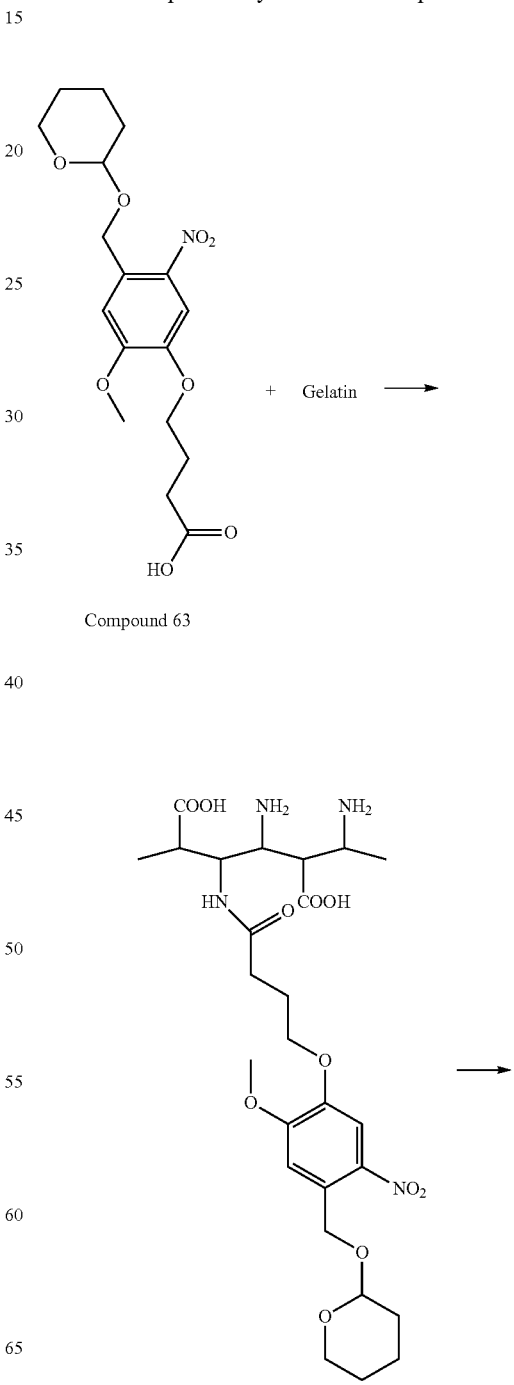

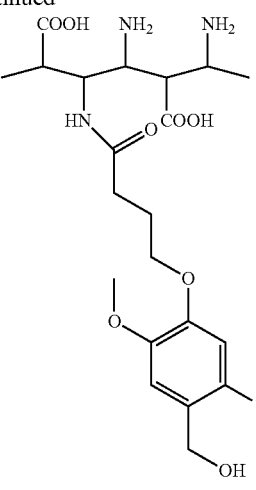

Component A-45

Synthesis of Component A-45: To a solution of gelatin (1 g) dissolved in 50 mL water was sequentially added Compound 63 (0.2 g, 0.54 mmol), EDC-HCl (0.76 g, 3.96 mmol) and NHS (0.46 g, 4.0 mmol), and the reaction was stirred at room temperature for 48 h. After completion of the reaction, the reaction solution was reprecipitated in cold ethanol, and the crude product was re-dissolved in water and reprecipitated several times. The collected precipitate was dried and dissolved in anhydrous DMSO, and the above solution was added p-toluenesulfonic acid to remove dihydropyran protecting group to obtain the photosensitive gelatin derivative Compound A-45 (0.83 g). According to its nuclear magnetic resonance spectrum, the grafting degree of Compound 63 can be calculated to be about 11.2%

Example 46: Synthesis of Component A-46

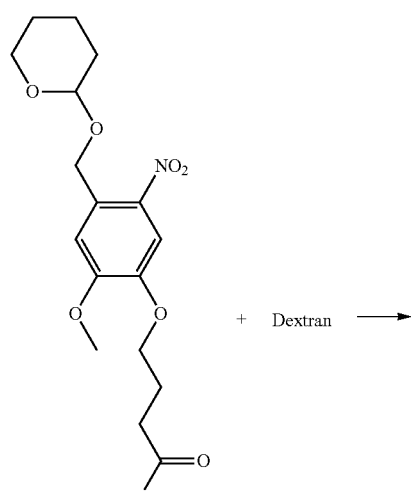

Compound 63

+ Dextran →

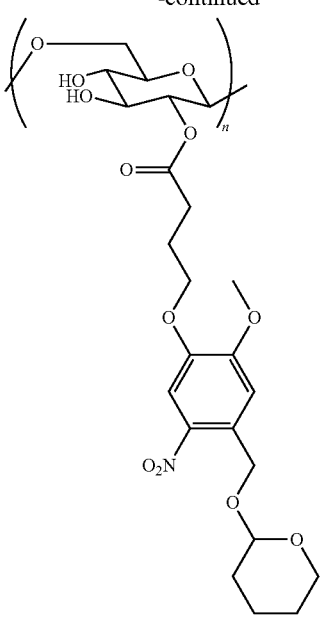

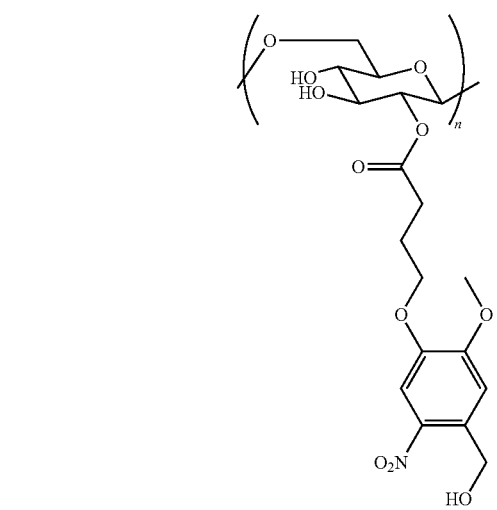

Component A-46

Synthesis of Component A-46: To a solution of dextran (1 g) dissolved in 50 mL water was sequentially added Compound 63 (0.2 g, 0.54 mmol), EDC-HCl (0.76 g, 3.96 mmol) and NHS (0.46 g, 4.0 mmol), and the reaction was stirred at room temperature for 48 h. After completion of the reaction, the reaction solution was reprecipitated in cold ethanol, and the crude product was re-dissolved in water and reprecipitated several times. The collected precipitate was dried and dissolved in anhydrous DMSO, and the above solution was added p-toluenesulfonic acid to remove dihydropyran protecting group to obtain the photosensitive hyaluronic acid derivative Compound A-46 (0.92 g). According to its nuclear magnetic resonance spectrum, the grafting degree of Compound 63 can be calculated to be about 18.2%.

Example 47: Synthesis of Component A-47

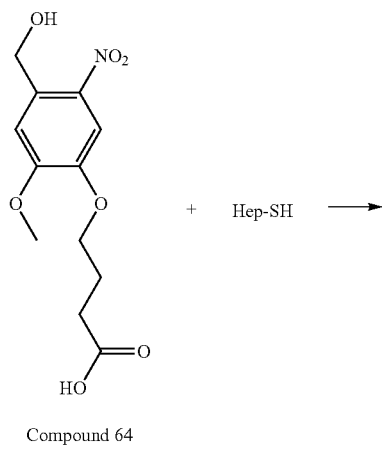

Compound 64

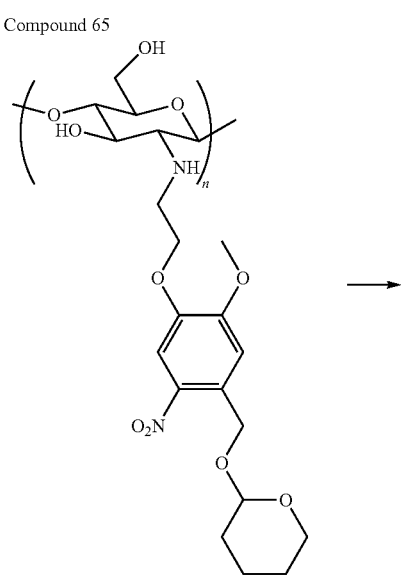

Component A-47

(1) Synthesis of Compound 64. The synthesis was carried out according to the method disclosed in the reference (Pauloehrl, T.; Delaittre, G.; Bruns, M.; Meißler, M.; Börner, H. G.; Bastmeyer, M.; Bamer-Kowollik, C. Angew. Chem. Int. Ed. 2012, 51, 9181.). $^1$H NMR (400 MHz, CDCl$_3$): δ=7.71 (s, 1H), 7.22 (s, 1H), 4.96 (s, 2H), 4.13 (t, J=6.1 Hz, 2H), 3.99 (s, 3H), 2.44 (t, J=7.2 Hz, 2H), 2.26-2.17 (m, 2H). MS (ESI): [M+H] 286.0943.

(2) Synthesis of Component A-47. To a solution of sulphydryl-modified heparin Hep-SH (1 g) dissolved in 50 mL distilled water was added hydroxybenzotriazole (HOBt, 0.3 g, 2.3 mmol). Then Compound 64 (0.5 g, 1.6 mmol) and 1-ethyl-(3-dimethyl amino propyl) carbodiimine hydrochloride (EDC-HCl, 0.5 g, 2.6 mmol) dissolved in methanol were added to the above solution, and the mixture was stirred at room temperature for 48 h. The solution was firstly dialyzed with dilute hydrochloric acid solution containing sodium chloride (pH=3.5) for 1 d, and then dialyzed against pure water for 1 d, then freeze-dried to obtain photosensitive heparin derivative Compound A-47 (0.86 g). According to its nuclear magnetic resonance spectrum, the grafting degree of Compound 64 can be calculated to be about 10.2%.

Example 48: Synthesis of Component A-48

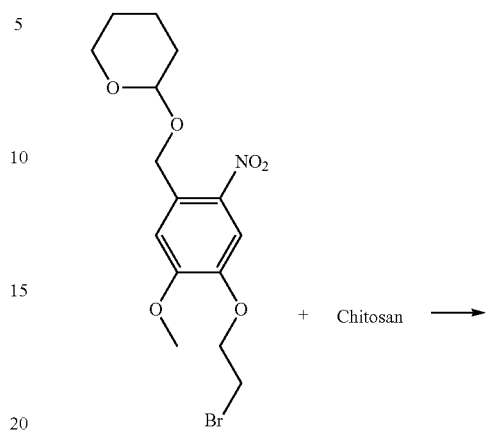

Compound 65

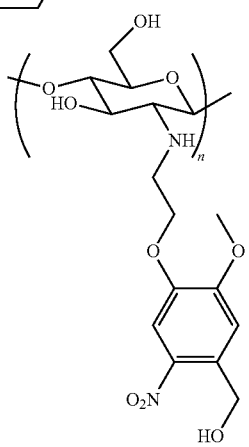

Component A-48

(1) Synthesis of Compound 65. The synthesis was carried out according to the method disclosed in the reference (Pauloehrl, T.; Delaittre, G.; Bruns, M.; Meißler, M.; Börner, H. G.; Bastmeyer, M.; Bamer-Kowollik, C. Angew. Chem. Int. Ed. 2012, 51, 9181.). $^1$H NMR (400 MHz, CDCl$_3$):

δ=7.71 (s, 1H), 7.22 (s, 1H), 4.96 (s, 2H), 4.13 (t, J=6.1 Hz, 2H), 3.99 (s, 3H), 3.90-3.80 (m, 1H), 3.63-3.52 (m, 1H), 3.04 (t, J=7.2 Hz, 2H), 2.00-1.34 (m, 6H). MS (ESI): [M+H] 391.0518.

(2) Synthesis of Component A-48. To a suspension liquid of chitosan (1 g) in 75 mL isopropanol was slowly added 25 mL of NaOH solution (10 mol/L) for five times, and the solution was stirred for 0.5 h. Compound 65 (0.2 g) was then added to the above solution and reacted at 60° C. for 3 h. After completion of the reaction, the mixture solution was filtered, and the filtrate was dialyzed three times with a methanol/water mixed solvent and twice with methanol, and then freeze-dried to obtain chitosan modified by Compound 65 (0.92 g). The chitosan modified by Compound 65 was dissolved in DMSO, and the solution was added p-toluenesulfonic acid to remove dihydropyran protecting group to obtain the photosensitive chitosan derivative Compound A-48 (0.84 g). According to its nuclear magnetic resonance spectrum, the grafting degree of the Compound 65 can be calculated to be about 12.4%.

Example 49: Synthesis of Component A-49

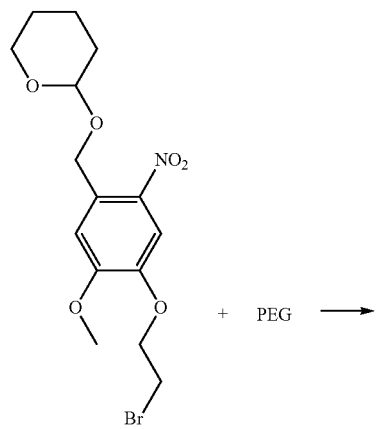

Compound 65

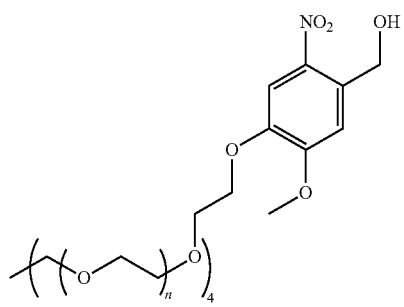

Component A-49

Synthesis of Component A-49: To a solution of PEG-4OH (1 g, 0.05 mmol) dissolved in anhydrous acetonitrile was added K₂CO₃ (55.3 mg, 0.4 mmol) and stirred for 30 min. Then the solution was added Compound 65 (0.17 g, 0.4 mmol) and continued to react at room temperature for 24 h. After the reaction was completed, most of the solvent was removed, the residue was polyreprecipitated in diethyl ether, and washed several times. The PEG-4OH modified by Compound 65 was dissolved in DMSO, and the solution was added p-toluenesulfonic acid to remove dihydropyran protecting group to obtain the photosensitive polyethelene glycol derivative Compound A-49 (0.93 g). According to its nuclear magnetic resonance spectrum, the grafting degree of the Compound 65 can be calculated to be about 95%.

Example 50: Synthesis of Component A-50

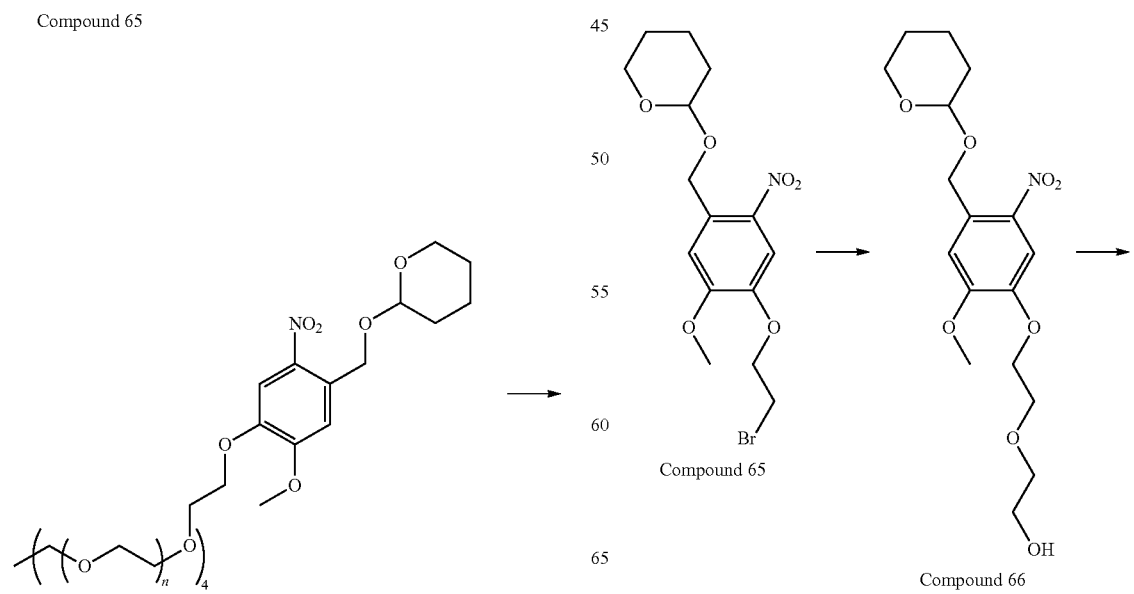

Compound 65

Compound 66

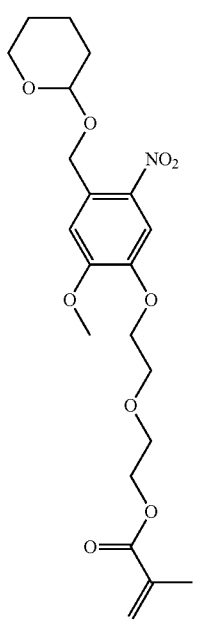

Compound 67

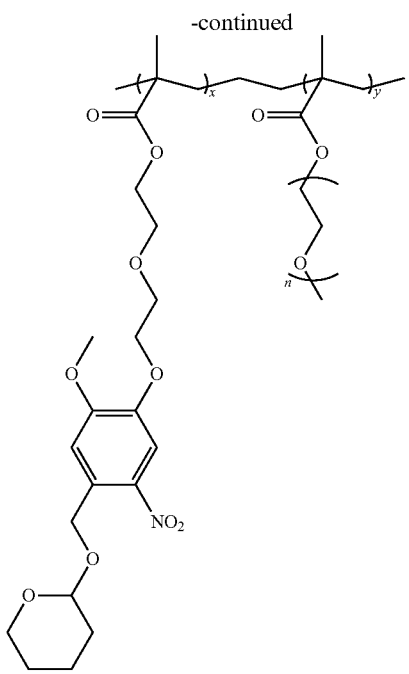

Component A-50

(1) Synthesis of Compound 66. To a solution of Compound 65 (0.5 g, 1.29 mmol) and ethylene glycol (0.24 g, 3.87 mmol) dissolved in anhydrous acetonitrile was added $K_2CO_3$ (0.5 g, 3.87 mmol) as a base and refluxed overnight. After completion of the reaction, the solvent was removed by rotary evaporation under reduced pressure and purified by column chromatography to afford Compound 66 (0.34 g, 72%). $^1$H NMR (400 MHz, $CDCl_3$): δ=7.71 (s, 1H), 7.22 (s, 1H), 4.96 (s, 2H), 4.13 (t, J=6.1 Hz, 2H), 3.99 (s, 3H), 3.90-3.80 (m, 1H), 3.79 (t, J=6.1 Hz, 2H), 3.70 (t, J=7.2 Hz, 2H), 3.63-3.52 (m, 1H), 3.56 (t, J=7.2 Hz, 2H), 2.00-1.34 (m, 6H). MS (ESI): [M+H] 372.1627.

(2) Synthesis of Compound 67. To a solution of Compound 66 (0.64 g, 1.72 mmol) and triethylamine (0.34 g, 3.44 mmol) dissolved in dry dichloromethane was slowly dropwise added methacryloyl chloride (0.27 g, 2.58 mmol) under ice bath conditions, and the reaction was carried out overnight at room temperature after the dropwise addition. After completion of the reaction, the solvent was removed by rotary evaporation under reduced pressure and purified to afford Compound 67 (0.49 g, 65%). $^1$H NMR (400 MHz, CDCl$_3$): δ=7.71 (s, 1H), 7.22 (s, 1H), 6.25 (s, 1H), 5.68 (s, 1H), 4.96 (s, 2H), 4.13 (t, J=6.1 Hz, 2H), 3.99 (s, 3H), 3.90-3.80 (m, 1H), 3.79 (t, J=6.1 Hz, 2H), 3.70 (t, J=7.2 Hz, 2H), 3.63-3.52 (m, 1H), 3.56 (t, J=7.2 Hz, 2H), 2.00-1.34 (m, 6H), 1.87 (s, 3H). MS (ESI): [M+H] 440.1942.

(3) Synthesis of Component A-50. Compound 67 (0.28 g, 0.63 mmol), comonomer PEG-MA (0.882 g, 2.52 mmol) and the initiator azobisisobutyronitrile (11 mg) were added into the Shrek tube and dissolved by anhydrous THF. After repeated freeze-vacuum cycle operation, the reaction system was reacted at 75° C. for 24 h. After the reaction was completed, the reaction solution was poured into cold diethyl ether and reprecipitated several times. The collected precipitate was dried and dissolved in anhydrous DMSO, and the solution was added p-toluenesulfonic acid to remove dihydropyran protecting group to obtain the photosensitive polyethelene glycol derivative Compound A-50 (0.84 g). According to its nuclear magnetic resonance spectrum, it can be calculated that the content of the Compound 67 in the copolymer is about 15.5%. According to GPC, the molecular weight of the synthetic polymer is about 25 kDa. According to the feed ratio, n is 12, x is 10, and y is 40.

Example 51: Synthesis of Component A-51

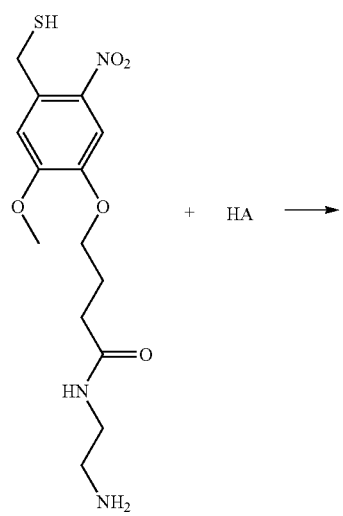

Component A-51

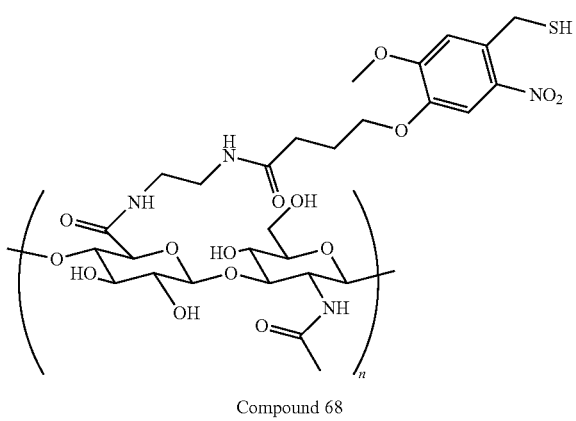

Compound 68

(1) Synthesis of Compound 68. The synthesis was carried out according to the method disclosed in the reference (Kunihiko Morihiro; Tetsuya Kodama; Shohei Mori; Satoshi Obika. Org. Biomol. Chem. 2014, 12, 2468.). $^1$H NMR (400 MHz, CDCl$_3$): δ=7.71 (s, 1H), 7.22 (s, 1H), 4.03 (s, 2H), 4.13 (t, J=6.1 Hz, 2H), 3.99 (s, 3H), 3.32 (dd, J=11.6, 5.7 Hz, 2H), 2.82 (t, J=5.9 Hz, 2H), 2.44 (t, J=7.2 Hz, 2H), 2.26-2.17 (m, 2H). MS (ESI): [M+H]344.1207.

(2) Synthesis of Component A-51. To a solution of hyaluronic acid sodium (2 g, 340 kDa) dissolved in 100 mL 0.01 M 2-(N-morpholine) mesylate (MES) buffer solution (pH=5.2) was added Compound 68 (69 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-51 (1.85 g). According to the nuclear magnetic resonance spectrum, the grafting degree of Compound 68 can be calculated to be about 3.34%.

Example 52: Synthesis of Component A-52

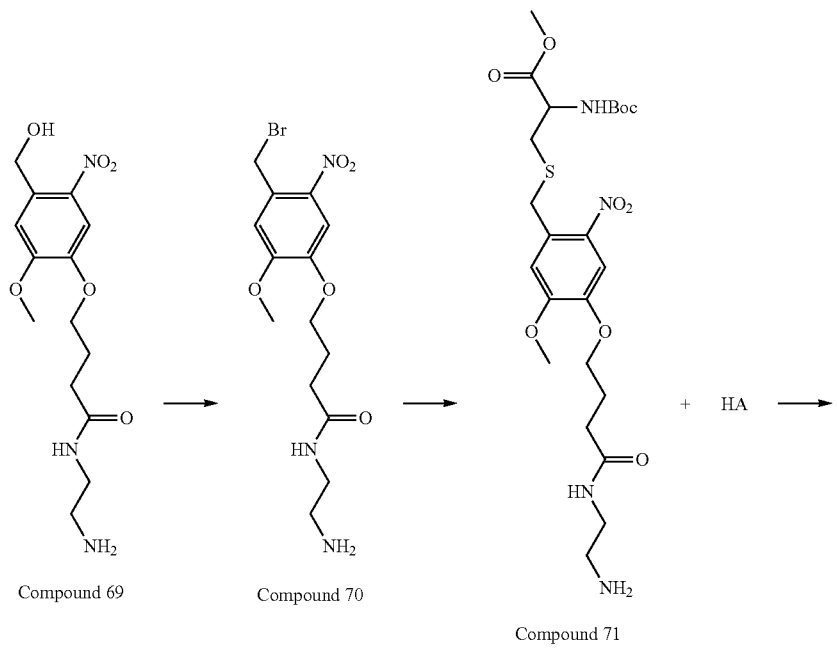

Compound 69     Compound 70     Compound 71

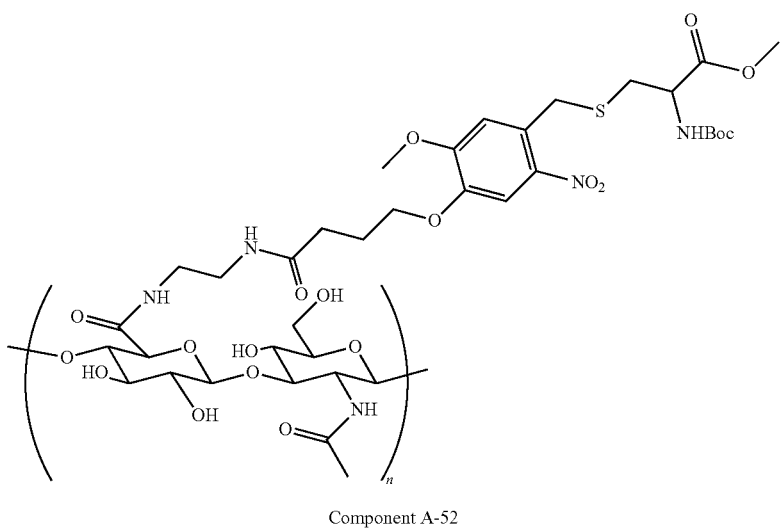

Component A-52

(1) Synthesis of Compound 69. The synthesis was carried out according to the method disclosed in the reference (Yunlong Yang; Jieyuan Zhang; Zhenzhen Liu; Qiuning Lin; Xiaolin Liu; Chunyan Bao; Yang Wang; Linyong Zhu. Adv. Mater. 2016, 28, 2724.)

(2) Synthesis of Compound 70. To a solution of Compound 69 (1 g, 3.0 mmol) dissolved in 50 mL tetrahydrofuran was added carbon tetrabromide ($CBr_4$, 2 g, 6.0 mmol) and triphenylphosphine ($PPh_3$, 1.6 g, 6.0 mmol), and the reaction was stirred at room temperature for 2 h under the protection of argon. After completion of the reaction, 5 mL of water was added to quench the reaction. Then, the solvent was removed by rotary evaporation under reduced pressure, the crude was extracted with ethyl acetate and separated by column chromatography (PE:DCM=4:1) to obtain Compound 70 (1.0 g, yield 84%). $^1$H NMR (400 MHz, $CDCl_3$): δ=7.71 (s, 1H), 7.22 (s, 1H), 4.56 (s, 2H), 4.13 (t, J=6.1 Hz, 2H), 3.99 (s, 3H), 3.32 (dd, J=11.6, 5.7 Hz, 2H), 2.82 (t, J=5.9 Hz, 2H), 2.44 (t, J=7.2 Hz, 2H), 2.26-2.17 (m, 2H). MS (ESI): [M+H] 390.0623.

(3) Synthesis of Compound 71. To a solution of Compound 70 (0.5 g, 1.3 mmol) dissolved in 50 mL acetone was added L-cysteine methyl ester hydrochloride (0.45 g, 2.6 mmol) and sodium hydroxide (0.2 g, 5.2 mmol), the reaction was stirred at room temperature for 2 h under the protection of argon. After completion of the reaction, the solution was added 4 M HCl to adjust the pH=7. The solvent was removed by ratary evaporation under reduced pressure, and the crude was extracted with ethyl acetate and purified by column chromatography (PE:DCM=4:1) to obtain Compound 71 (0.7 g, 88%). $^1$H NMR (400 MHz, CDCl$_3$): δ=7.71 (s, 1H), 7.22 (s, 1H), 4.76 (s, 2H), 4.42 (m, 1H), 4.13 (t, J=6.1 Hz, 2H), 3.99 (s, 3H), 3.95 (s, 3H), 3.43 (d, J=5.6, 2H), 3.32 (dd, J=11.6, 5.7 Hz, 2H), 2.82 (t, J=5.9 Hz, 2H), 2.44 (t, J=7.2 Hz, 2H), 2.26-2.17 (m, 2H), 1.42 (s, 9H). MS (ESI): [M+H]545.2219.

(4) Synthesis of Component A-52. To a solution of hyaluronic acid sodium (2 g, 340 kDa) dissolved in 100 mL 0.01 M 2-(N-morpholine) mesylate (MES) buffer solution (pH=5.2) was added Compound 71 (109 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-52 (1.92 g). According to the nuclear magnetic resonance spectrum, the grafting degree of Compound 71 can be calculated to be about 3.32%.

Example 53: Synthesis of Component A-53

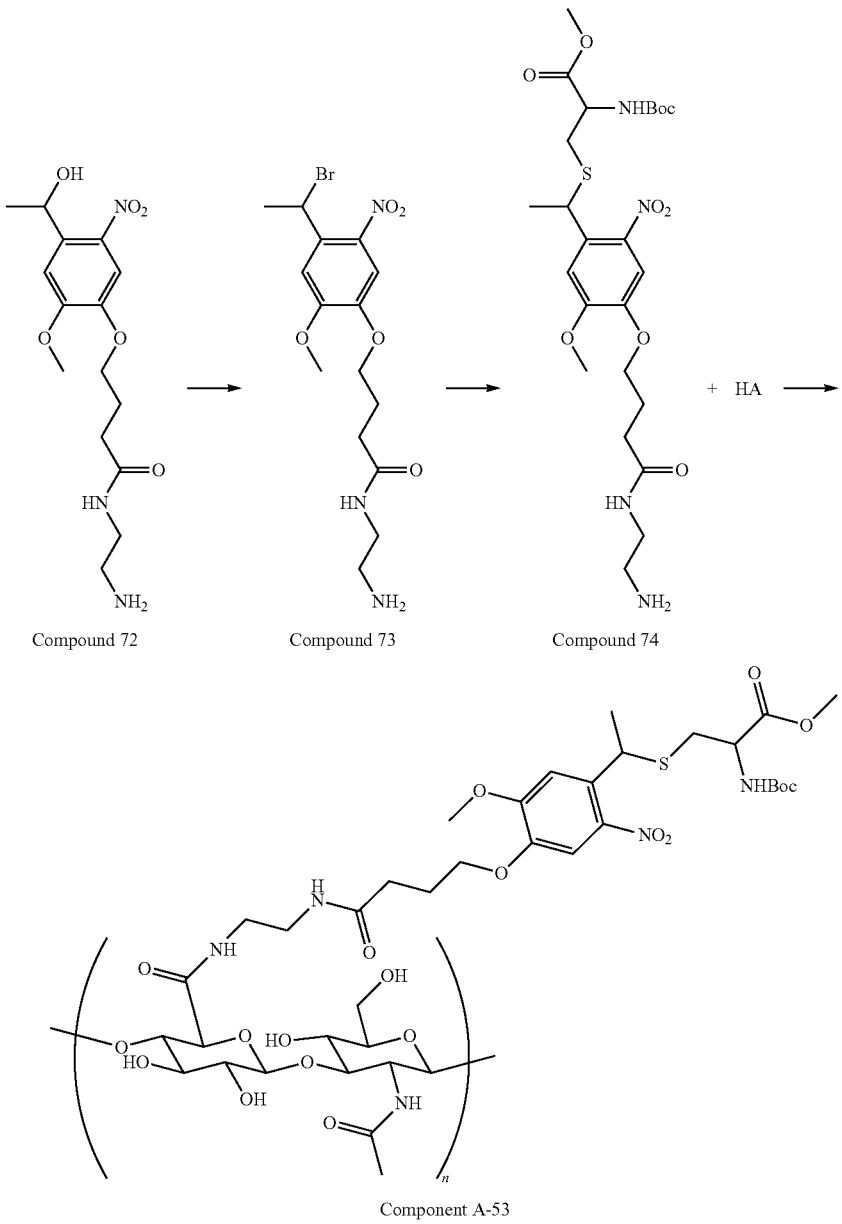

Component A-53

(1) Synthesis of Compound 72. The synthesis was carried out according to the method disclosed in the reference (James F. Cameron; Jean M. J. Frechet. J. Am. Chem. Soc. 1991, 113, 4303.)

(2) Synthesis of Compound 73. According to the method in Example 52, Compound 73 was obtained from Compound 72 (yield: 73%). $^1$H NMR (400 MHz, CDCl$_3$): δ=7.71 (s, 1H), 7.22 (s, 1H), 4.66 (m, 1H), 4.13 (t, J=6.1 Hz, 2H), 3.99 (s, 3H), 3.32 (dd, J=11.6, 5.7 Hz, 2H), 2.82 (t, J=5.9 Hz, 2H), 2.44 (t, J=7.2 Hz, 2H), 2.26-2.17 (m, 2H), 1.33 (d, J=6.9 Hz, 3H). MS (ESI): [M+H] 404.0863.

(3) Synthesis of Compound 74. According to the method in Example 52, Compound 74 was obtained from Compound 73 (yield: 70%). $^1$H NMR (400 MHz, CDCl$_3$): δ=7.71 (s, 1H), 7.22 (s, 1H), 4.86 (m, 1H), 4.42 (m, 1H), 4.13 (t, J=6.1 Hz, 2H), 3.99 (s, 3H), 3.95 (s, 3H), 3.43 (d, J=5.6, 2H), 3.32 (dd, J=11.6, 5.7 Hz, 2H), 2.82 (t, J=5.9 Hz, 2H), 2.44 (t, J=7.2 Hz, 2H), 2.26-2.17 (m, 2H), 1.42 (s, 9H), 1.33 (d, J=6.9 Hz, 3H). MS (ESI): [M+H]559.2402.

(4) Synthesis of Component A-53. To a solution of hyaluronic acid sodium (2 g, 340 kDa) dissolved in 100 mL 0.01 M 2-(N-morpholine) mesylate (MES) buffer solution (pH=5.2) was added Compound 74 (112 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-53 (1.75 g). According to the nuclear magnetic resonance spectrum, the grafting degree of Compound 74 can be calculated to be about 2.34%.

Example 54: Synthesis of Component A-54

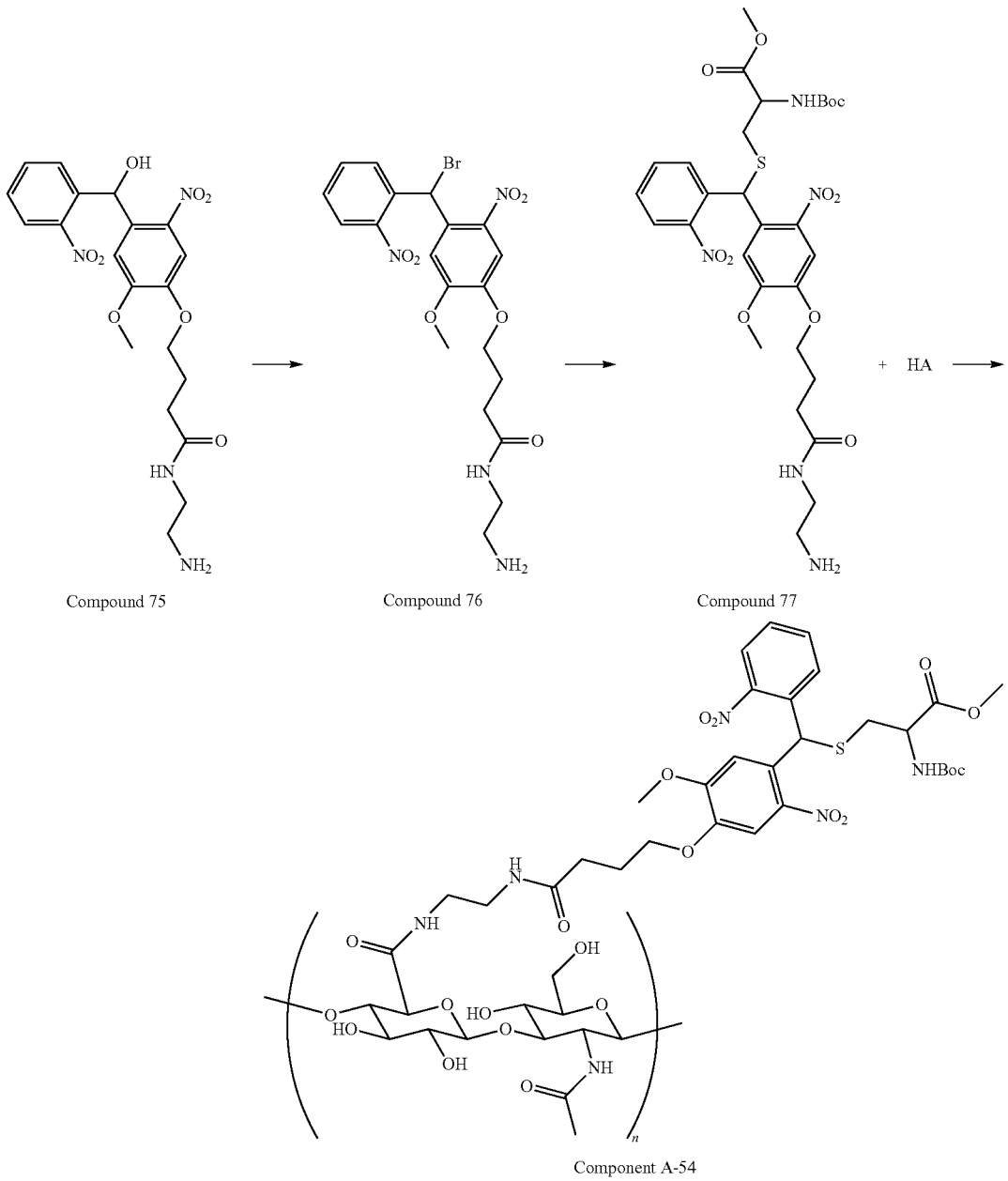

Component A-54

(1) Synthesis of Compound 75. The synthesis was carried out according to the method disclosed in the reference (Jack E. Baldwin; Adrian W. McConnaughie; Sung Bo Shin Tetrahedron. 1990, 46, 6879.)

(2) Synthesis of Compound 76. According to the method in Example 52, Compound 76 was obtained from Compound 75 (yield: 64%). $^1$H NMR (400 MHz, CDCl$_3$): δ=7.71 (s, 1H), 7.75 (ddd, J=8.2, 1.4, 0.4 Hz, 1H), 7.22 (s, 1H), 7.57 (tdd, J=7.3, 1.4, 0.7 Hz, 1H), 7.49 (dd, J=7.9, 1.4 Hz, 1H), 7.36 (ddd, J=8.1, 7.3, 1.4 Hz, 1H), 4.66 (s, 1H), 4.13 (t, J=6.1 Hz, 2H), 3.99 (s, 3H), 3.32 (dd, J=11.6, 5.7 Hz, 2H), 2.82 (t, J=5.9 Hz, 2H), 2.44 (t, J=7.2 Hz, 2H), 2.26-2.17 (m, 2H). MS (ESI): [M+H] 511.0881.

(3) Synthesis of Compound 77. According to the method in Example 52, Compound 77 was obtained from Compound 76 (yield: 58%). $^1$H NMR (400 MHz, CDCl$_3$): δ=7.71 (s, 1H), 7.75 (ddd, J=8.2, 1.4, 0.4 Hz, 1H), 7.22 (s, 1H), 7.57 (tdd, J=7.3, 1.4, 0.7 Hz, 1H), 7.49 (dd, J=7.9, 1.4 Hz, 1H), 7.36 (ddd, J=8.1, 7.3, 1.4 Hz, 1H), 4.86 (s, 1H), 4.42 (m, 1H), 4.13 (t, J=6.1 Hz, 2H), 3.99 (s, 3H), 3.95 (s, 3H), 3.43 (d, J=5.6, 2H), 3.32 (dd, J=11.6, 5.7 Hz, 2H), 2.82 (t, J=5.9 Hz, 2H), 2.44 (t, J=7.2 Hz, 2H), 2.26-2.17 (m, 2H), 1.42 (s, 9H). MS (ESI): [M+H] 666.2423.

(4) Synthesis of Component A-54. To a solution of hyaluronic acid sodium (2 g, 340 kDa) in 100 mL 0.01 M 2-(N-morpholine) mesylate (MES) buffer solution (pH=5.2) was added Compound 77 (133 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-54 (1.8 g). According to the nuclear magnetic resonance spectrum, the grafting degree of Compound 77 can be calculated to be about 3.35%.

Example 55: Synthesis of Component A-55

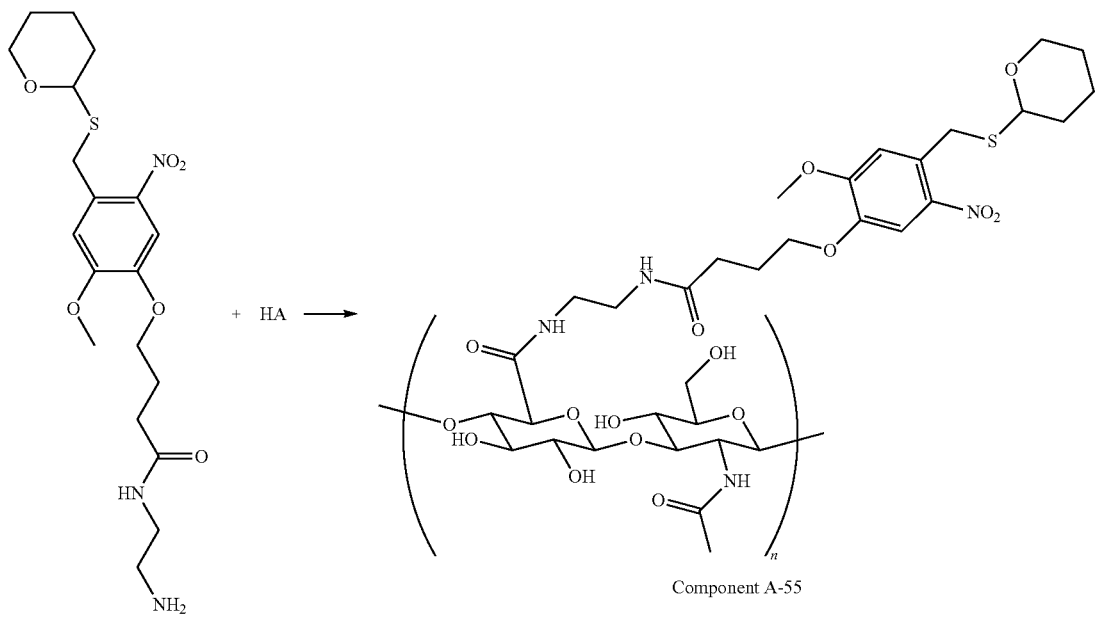

Compound 78

Component A-55

(1) Synthesis of Compound 78. The synthesis was carried out according to the method disclosed in the reference (Pauloehrl, T.; Delaittre, G.; Bruns, M.; Meißler, M.; Börner, H. G.; Bastmeyer, M.; Bamer-Kowollik, C. Angew. Chem. Int. Ed. 2012, 51, 9181.) $^1$H NMR (400 MHz, CDCl$_3$): δ=7.71 (s, 1H), 7.22 (s, 1H), 4.76 (s, 2H), 4.13 (t, J=6.1 Hz, 2H), 3.99 (s, 3H), 3.90-3.80 (m, 1H), 3.63-3.52 (m, 1H), 3.32 (dd, J=11.6, 5.7 Hz, 2H), 2.82 (t, J=5.9 Hz, 2H), 2.44 (t, J=7.2 Hz, 2H), 2.26-2.17 (m, 2H), 2.00-1.34 (m, 6H). MS (ESI): [M+H]428.1831.

(2) Synthesis of Component A-55. To a solution of hyaluronic acid sodium (2 g, 340 kDa) dissolved in 100 mL 0.01 M 2-(N-morpholine) mesylate (MES) buffer solution (pH=5.2) was added Compound 78 (85 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-55 (1.85 g). According to the nuclear magnetic resonance spectrum, the grafting degree of Compound 78 can be calculated to be about 3.42%.

Example 56: Synthesis of Component A-56

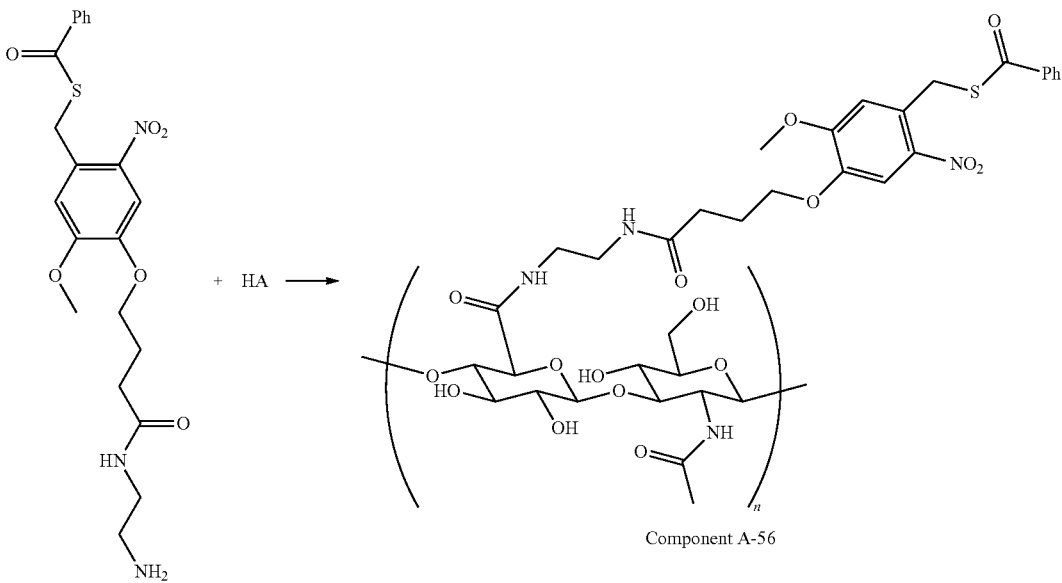

Compound 79

Component A-56

(1) Synthesis of Compound 79. The synthesis was carried out according to the method disclosed in the reference (Patchornik Abraham; Amit B.; Woodward R. B. J. Am. Chem. Soc. 1970, 92, 6333.). $^1$H NMR (400 MHz, CDCl$_3$): δ=8.02-7.23 (m, 5H), 7.71 (s, 1H), 7.22 (s, 1H), 4.76 (s, 2H), 4.13 (t, J=6.1 Hz, 2H), 3.99 (s, 3H), 3.32 (dd, J=11.6, 5.7 Hz, 2H), 2.82 (t, J=5.9 Hz, 2H), 2.44 (t, J=7.2 Hz, 2H), 2.26-2.17 (m, 2H). MS (ESI): [M+H]448.1561.

(2) Synthesis of Component A-56. To a solution of hyaluronic acid sodium (2 g, 340 kDa) dissolved in 100 mL 0.01 M 2-(N-morpholine) mesylate (MES) buffer solution (pH=5.2) was added Compound 79 (89 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-56 (1.87 g). According to the nuclear magnetic resonance spectrum, the grafting degree of Compound 79 can be calculated to be about 3.21%.

Example 57: Synthesis of Component A-57

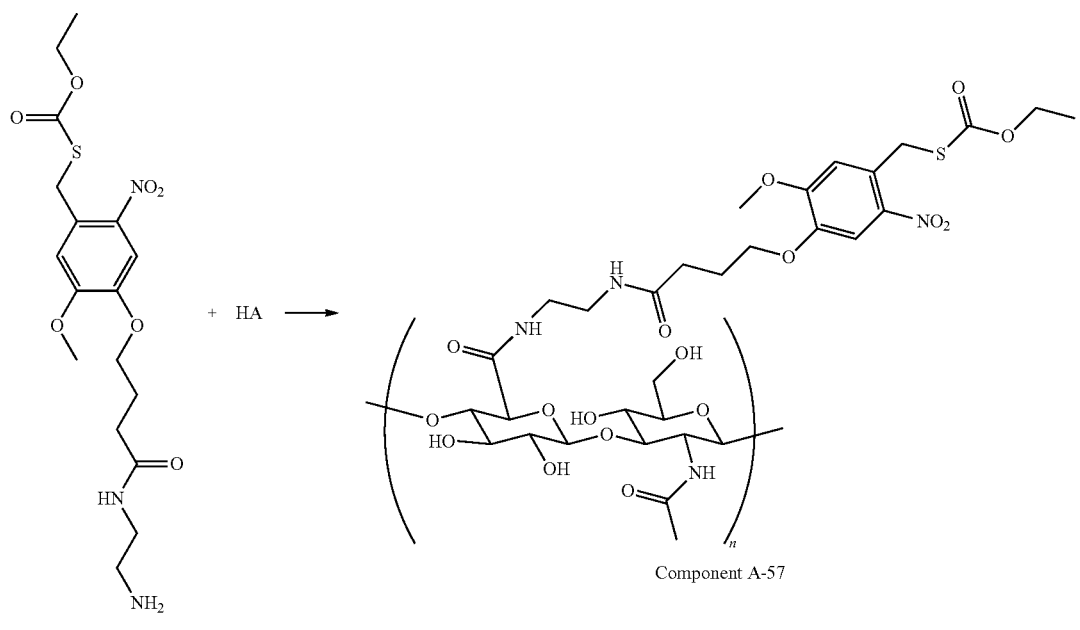

Compound 80

Component A-57

(1) Synthesis of Compound 80. The synthesis was carried out according to the method disclosed in the reference (Patchomrnik Abraham; Amit B.; Woodward R. B. J. Am. Chem. Soc. 1970, 92, 6333.). $^1$H NMR (400 MHz, CDCl$_3$): δ=7.71 (s, 1H), 7.22 (s, 1H), 4.76 (s, 2H), 4.25 (q, J=6.5 Hz, 2H), 4.13 (t, J=6.1 Hz, 2H), 3.99 (s, 3H), 3.32 (dd, J=11.6, 5.7 Hz, 2H), 2.82 (t, J=5.9 Hz, 2H), 2.44 (t, J=7.2 Hz, 2H), 2.26-2.17 (m, 2H), 1.32 (t, J=6.5 Hz, 3H). MS (ESI): [M+H] 416.1432.

(2) Synthesis of Component A-57. To a solution of hyaluronic acid sodium (2 g, 340 kDa) dissolved in 100 mL 0.01 M 2-(N-morpholine) mesylate (MES) buffer solution (pH=5.2) was added Compound 80 (83 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-57 (1.74 g). According to the nuclear magnetic resonance spectrum, the grafting degree of Compound 80 can be calculated to be about 2.34%.

Example 58: Synthesis of Component A-58

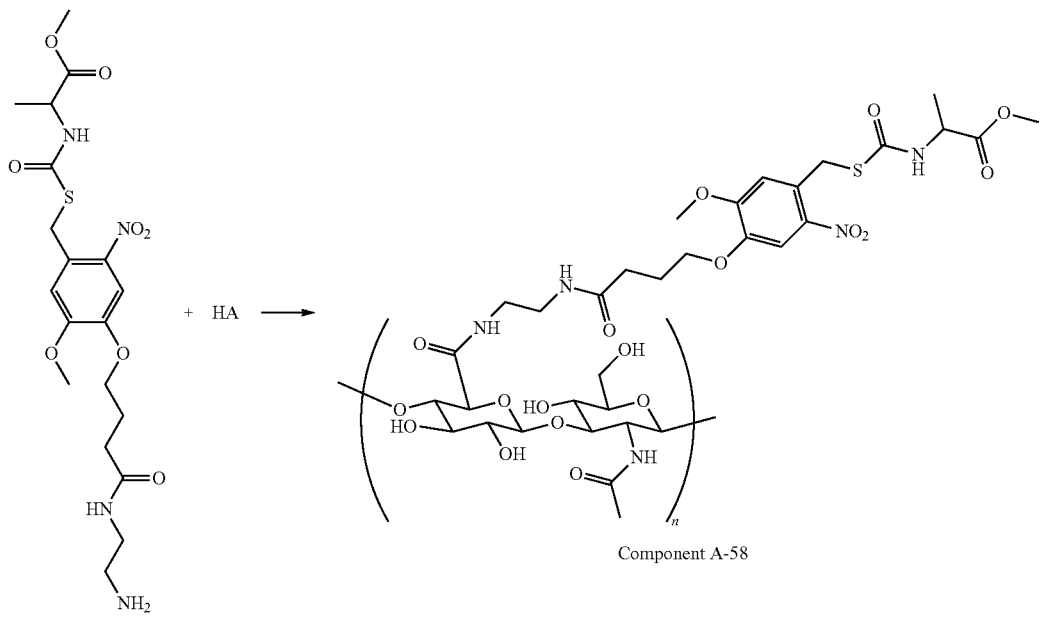

Compound 81

Component A-58

(1) Synthesis of Compound 81. The synthesis was carried out according to the method disclosed in the reference (Kalbag, S. M.; Roeske, R. W. J. Am. Chem. Soc. 1975, 97, 440.). $^1$H NMR (400 MHz, CDCl$_3$): δ=7.71 (s, 1H), 7.22 (s, 1H), 4.76 (s, 2H), 4.63 (q, J=6.9 Hz, 1H), 4.13 (t, J=6.1 Hz, 2H), 3.99 (s, 3H), 3.67 (s, 3H), 3.32 (dd, J=11.6, 5.7 Hz, 2H), 2.82 (t, J=5.9 Hz, 2H), 2.44 (t, J=7.2 Hz, 2H), 2.26-2.17 (m, 2H), 1.48 (d, J=6.9 Hz, 3H). MS (ESI): [M+H] 473.1734.

(2) Synthesis of Component A-58. To a solution of hyaluronic acid sodium (2 g, 340 kDa) dissolved in 100 mL 0.01 M 2-(N-morpholine) mesylate (MES) buffer solution (pH=5.2) was added Compound 81 (94 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-58 (1.72 g). According to the nuclear magnetic resonance spectrum, the grafting degree of Compound 81 can be calculated to be about 2.56%.

Example 59: Synthesis of Component A-59

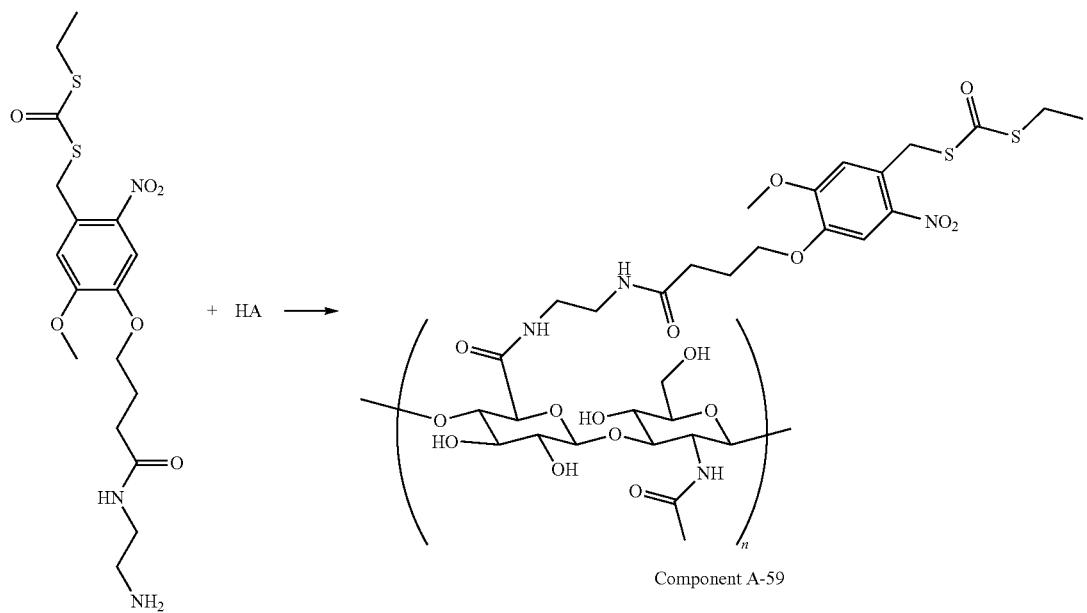

(1) Synthesis of Compound 82. The synthesis was carried out according to the method disclosed in the reference (Patchomik Abraham; Amit B.; Woodward R. B. J. Am. Chem. Soc. 1970, 92, 6333.). $^1$H NMR (400 MHz, CDCl$_3$): δ=7.71 (s, 1H), 7.22 (s, 1H), 4.76 (s, 2H), 4.25 (q, J=6.5 Hz, 2H), 4.13 (t, J=6.1 Hz, 2H), 3.99 (s, 3H), 3.32 (dd, J=11.6, 5.7 Hz, 2H), 2.82 (t, J=5.9 Hz, 2H), 2.44 (t, J=7.2 Hz, 2H), 2.26-2.17 (m, 2H), 1.32 (t, J=6.5 Hz, 3H). MS (ESI): [M+H] 432.1224.

(2) Synthesis of Component A-59. To a solution of hyaluronic acid sodium (2 g, 340 kDa) in 100 mL 0.01 M 2-(N-morpholine) mesylate (MES) buffer solution (pH=5.2) was added Compound 82 (83 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-59 (1.74 g). According to the nuclear magnetic resonance spectrum, the grafting degree of Compound 82 can be calculated to be about 2.34%.

Example 60: Synthesis of Component A-60

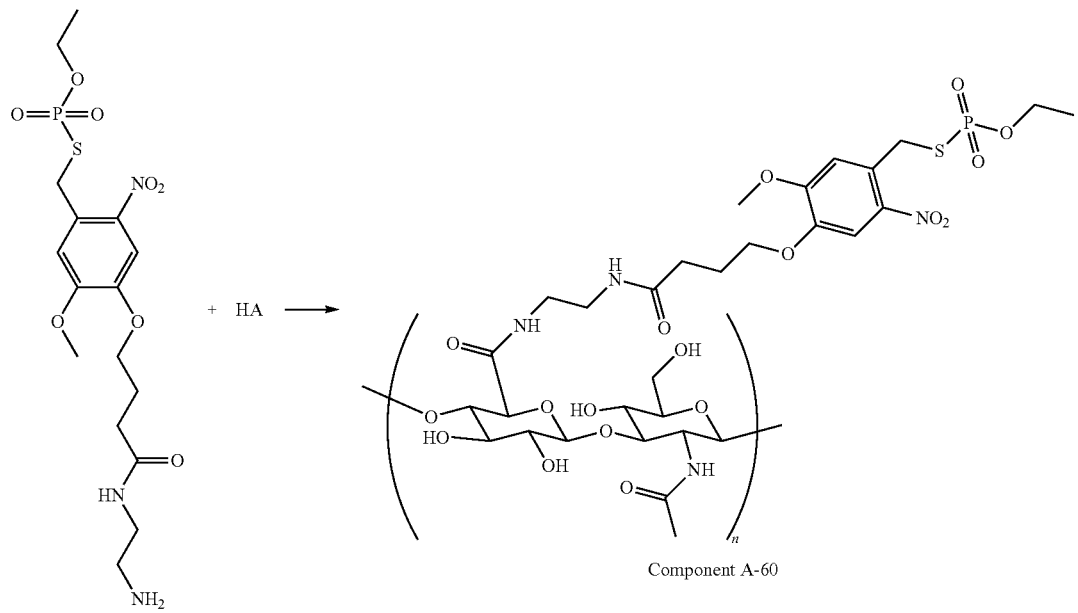

Component A-60

(1) Synthesis of Compound 83. The synthesis was carried out according to the method disclosed in the reference (Engels, J.; Schlaeger, E. J. J. Med. Chem. 1977, 20, 907.). $^1$H NMR (400 MHz, CDCl$_3$): δ=7.71 (s, 1H), 7.22 (s, 1H), 4.76 (s, 2H), 4.25 (q, J=6.5 Hz, 2H), 4.13 (t, J=6.1 Hz, 2H), 3.99 (s, 3H), 3.32 (dd, J=11.6, 5.7 Hz, 2H), 2.82 (t, J=5.9 Hz, 2H), 2.44 (t, J=7.2 Hz, 2H), 2.26-2.17 (m, 2H), 1.32 (t, J=6.5 Hz, 3H). MS (ESI): [M+H]451.1126.

(2) Synthesis of Component A-60. To a solution of hyaluronic acid sodium (2 g, 340 kDa) dissolved in 100 mL 0.01 M 2-(N-morpholine) mesylate (MES) buffer solution (pH=5.2) was added Compound 83 (90 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-60 (1.72 g). According to the nuclear magnetic resonance spectrum, the grafting degree of Compound 83 can be calculated to be about 2.36%.

Example 62: Synthesis of Component A-62

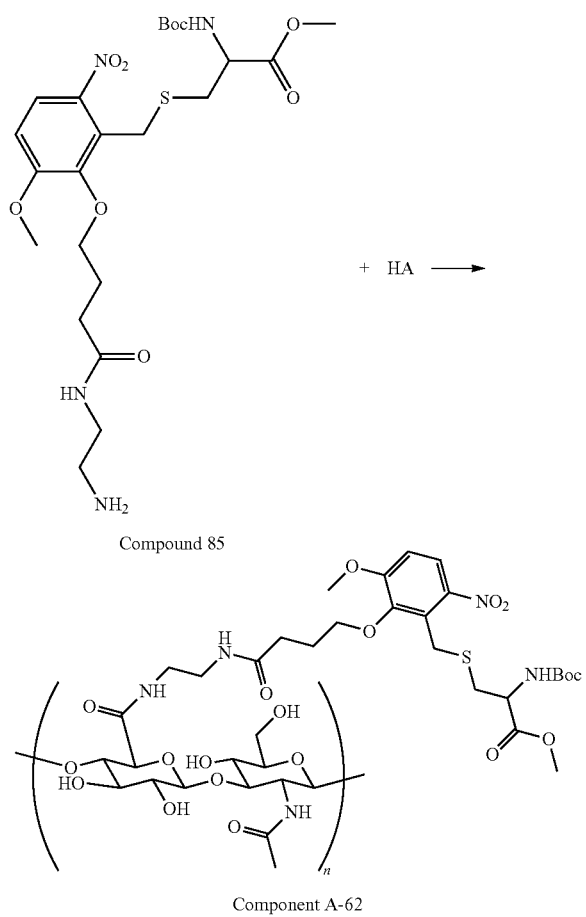

Compound 85

Component A-62

(1) Synthesis of Compound 85. The synthesis was carried out according to the method disclosed in the reference (Grazyna Groszek; Agnieszka Nowak-Krol; Barbara Filipek. Eur. J. Med. Chem. 2009, 44, 5103.). $^1$H NMR (400 MHz, CDCl$_3$): δ=8.04 (s, 1H), 7.42 (s, 1H), 4.76 (s, 2H), 4.42 (m, 1H), 4.13 (t, J=6.1 Hz, 2H), 3.99 (s, 3H), 3.95 (s, 3H), 3.43 (d, J=5.6, 2H), 3.32 (dd, J=11.6, 5.7 Hz, 2H), 2.82 (t, J=5.9 Hz, 2H), 2.44 (t, J=7.2 Hz, 2H), 2.26-2.17 (m, 2H), 1.42 (s, 9H). MS (ESI): [M+H] 545.2234.

(2) Synthesis of Component A-62. To a solution of hyaluronic acid sodium (2 g, 340 kDa) dissolved in 100 mL 0.01 M 2-(N-morpholine) mesylate (MES) buffer solution (pH=5.2) was added Compound 85 (109 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-62 (1.92 g). According to the nuclear magnetic resonance spectrum, the grafting degree of Compound 85 can be calculated to be about 3.14%.

Example 63: Synthesis of Component A-63

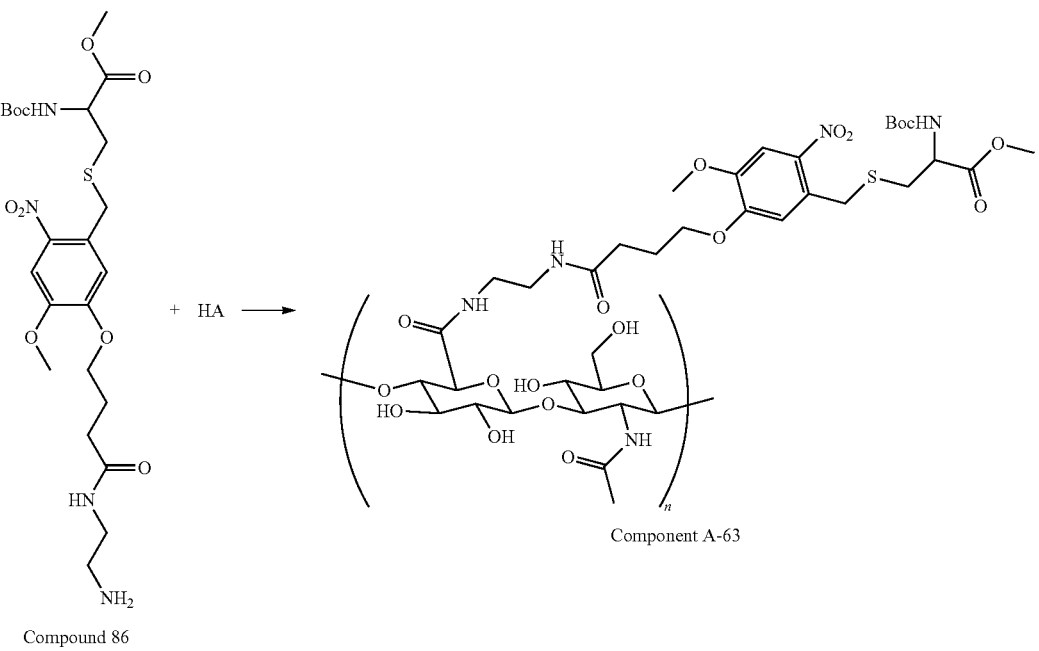

Compound 86

Component A-63

(1) Synthesis of Compound 86. The synthesis was carried out according to the method disclosed in the reference (Thomas F. Greene; Shu Wang; Mary J. Meegan. J. Med. Chem. 2016, 59, 90.). $^1$H NMR (400 MHz, CDCl$_3$): δ=7.95 (s, 1H), 7.12 (s, 1H), 4.76 (s, 2H), 4.42 (m, 1H), 4.13 (t, J=6.1 Hz, 2H), 3.99 (s, 3H), 3.95 (s, 3H), 3.43 (d, J=5.6, 2H), 3.32 (dd, J=11.6, 5.7 Hz, 2H), 2.82 (t, J=5.9 Hz, 2H), 2.44 (t, J=7.2 Hz, 2H), 2.26-2.17 (m, 2H), 1.42 (s, 9H). MS (ESI): [M+H] 545.2262.

(2) Synthesis of Component A-63. To a solution of hyaluronic acid sodium (2 g, 340 kDa) dissolved in 100 mL 0.01 M 2-(N-morpholine) mesylate (MES) buffer solution (pH=5.2) was added Compound 86 (109 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-63 (1.88 g). According to the nuclear magnetic resonance spectrum, the grafting degree of Compound 68 can be calculated to be about 3.45%.

Example 64: Synthesis of Component A-64

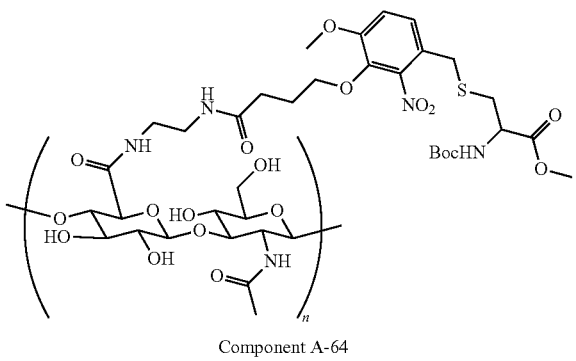

Component A-64

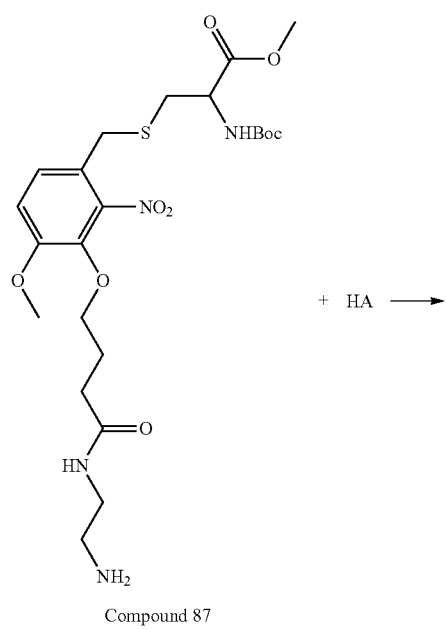

Compound 87 + HA →

(1) Synthesis of Compound 87. The synthesis was carried out according to the method disclosed in the reference (Yu-Shan; Mohane Selvaraj Coumar; Hsing-Pang Hsieh. J. Med. Chem. 2009, 52, 4941.). $^1$H NMR (400 MHz, CDCl$_3$): δ=7.64 (s, 1H), 7.02 (s, 1H), 4.76 (s, 2H), 4.42 (m, 1H), 4.13 (t, J=6.1 Hz, 2H), 3.99 (s, 3H), 3.95 (s, 3H), 3.43 (d, J=5.6, 2H), 3.32 (dd, J=11.6, 5.7 Hz, 2H), 2.82 (t, J=5.9 Hz, 2H), 2.44 (t, J=7.2 Hz, 2H), 2.26-2.17 (m, 2H), 1.42 (s, 9H). MS (ESI): [M+H] 545.2231.

(2) Synthesis of Component A-64. To a solution of hyaluronic acid sodium (2 g, 340 kDa) dissolved in 100 mL 0.01 M 2-(N-morpholine) mesylate (MES) buffer solution (pH=5.2) was added Compound 87 (109 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-64 (1.85 g). According to the nuclear magnetic resonance spectrum, the grafting degree of Compound 87 can be calculated to be about 3.32%.

Example 65: Synthesis of Component A-65

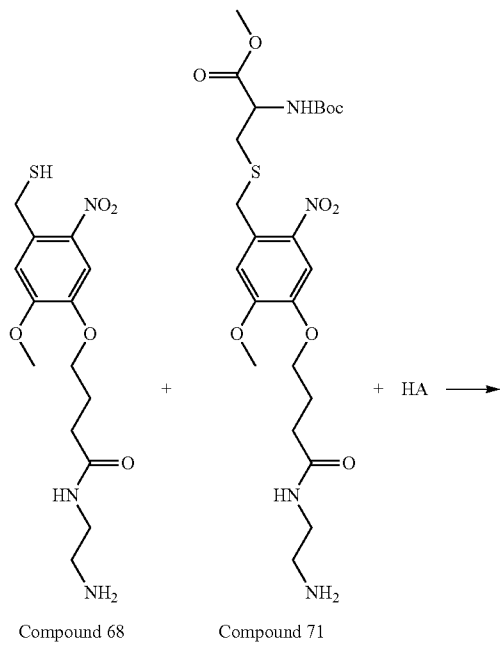

Compound 68    Compound 71

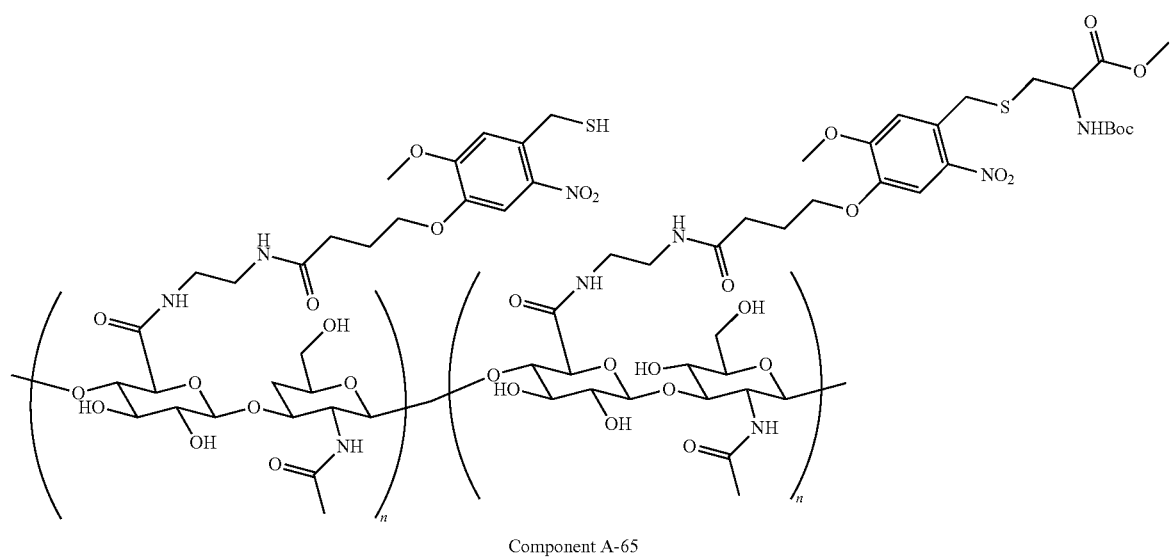

Component A-65

Synthesis of Component A-65: To a solution of hyaluronic acid sodium (2 g, 340 kDa) dissolved in 100 mL 0.01 M 2-(N-morpholine) mesylate (MES) buffer solution (pH=5.2) was added NB mixture (Compound 68/Compound 71, 60 mg, weight ratio is 1:1) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-65 (1.89 g). According to the nuclear magnetic resonance spectrum, the grafting degree of Compound NB mixture is calculated to be about 3.41%.

Example 66: Synthesis of Component A-66

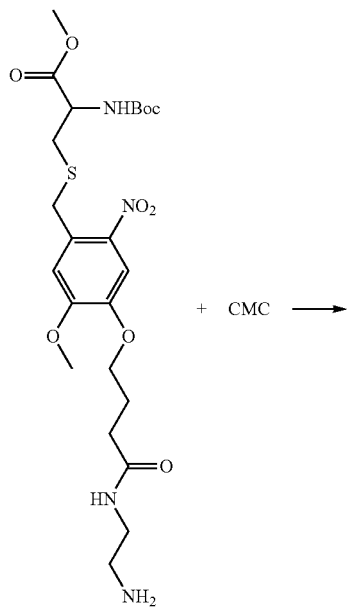

Compound 71

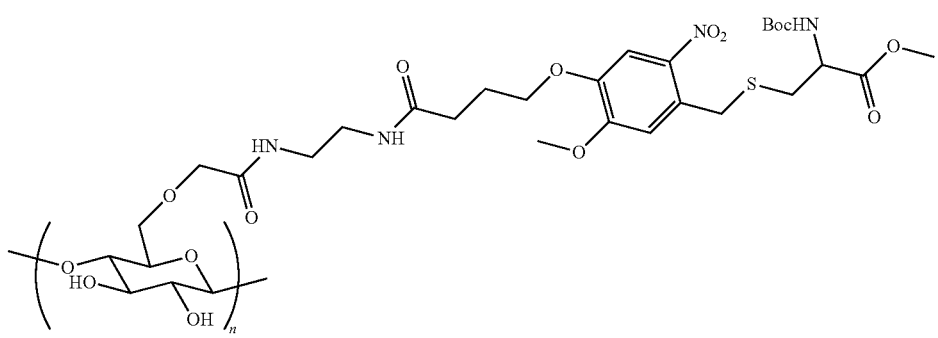

Component A-66

Synthesis of Component A-66. To a solution of carboxymethylcellulose (2 g, 340 kDa) dissolved in 100 mL 0.01 M 2-(N-morpholine) mesylate (MES) buffer solution (pH=5.2) was added Compound 71 (109 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive carboxymethyl-cellulose derivative Compound A-66 (1.74 g). According to the nuclear magnetic resonance spectrum, the grafting degree of Compound 71 can be calculated to be about 2.34%.

Example 67: Synthesis of Component A-67

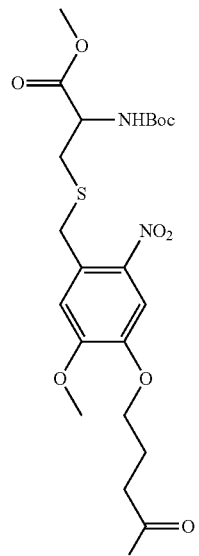

Compound 88

+ Chitosan ⟶

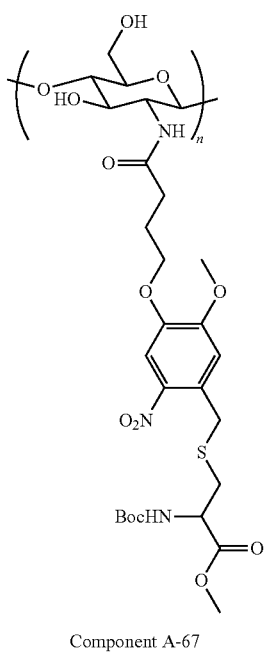

Component A-67

(1) Synthesis of Compound 88. According to the method in Example 52, Compound 88 was prepared by conventional chemical methods. $^1$H NMR (400 MHz, CDCl$_3$): δ=7.71 (s, 1H), 7.22 (s, 1H), 4.76 (s, 2H), 4.42 (m, 1H), 4.13 (t, J=6.1 Hz, 2H), 3.99 (s, 3H), 3.95 (s, 3H), 3.43 (d, J=5.6, 2H), 2.44 (t, J=7.2 Hz, 2H), 2.26-2.17 (m, 2H), 1.42 (s, 9H). MS (ESI): [M+H] 503.1732.

(2) Synthesis of Component A-67. To a suspension liquid of chitosan (1 g) dissolved in 75 mL isopropanol was sequentially added Compound 88 (0.2 g, 0.54 mmol), EDC-HCl (0.76 g, 3.96 mmol) and NHS (0.46 g, 4.0 mmol), and the reaction was stirred at room temperature for 48 h. After completion of the reaction, the mixture solution was dialyzed with diluted hydrochloric acid solution for 1 d, dialyzed with distilled water for 1 d, and then freeze-dried to obtain photosensitive chitosan derivatives Compound A-67 (0.89 g). According to its nuclear PEG-4OHmagnetic resonance spectrum, the grafting degree of the Compound 88 can be calculated to be about 12.5%.

Example 68: Synthesis of Component A-68

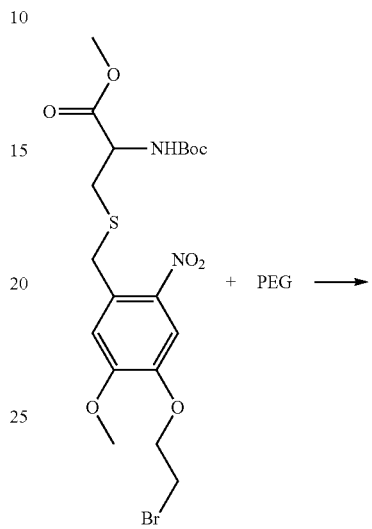

Compound 89

+ PEG ⟶

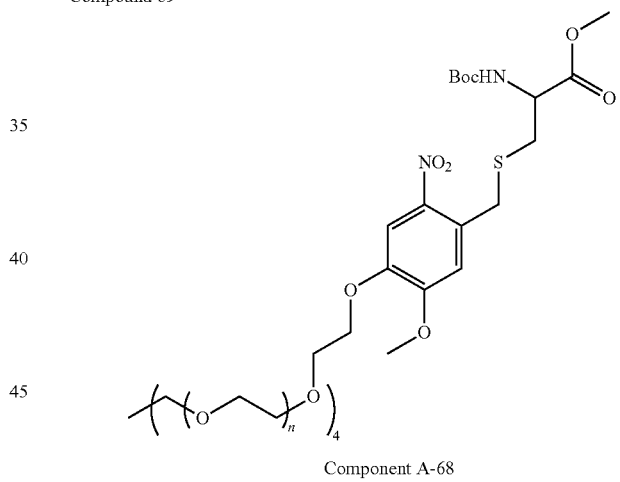

Component A-68

(1) Synthesis of Compound 89. According to the method in Example 52, Compound 89 was prepared by conventional chemical methods. $^1$H NMR (400 MHz, CDCl$_3$): δ=7.71 (s, 1H), 7.22 (s, 1H), 4.76 (s, 2H), 4.42 (m, 1H), 4.13 (t, J=6.1 Hz, 2H), 3.99 (s, 3H), 3.95 (s, 3H), 3.43 (d, J=5.6, 2H), 3.04 (t, J=7.2 Hz, 2H), 1.42 (s, 9H). MS (ESI): [M+H] 523.0731.

(2) Synthesis of Component A-68. To a solution of PEG-4OH (1 g, 0.05 mmol) in anhydrous acetonitrile was added K$_2$CO$_3$ (55.3 mg, 0.4 mmol) and stirred for 30 min. Then the solution was added Compound 89 (0.20 g, 0.4 mmol) and continued to react at room temperature for 24 h. After completion of the reaction, most of the solvent was removed, reprecipitated in diethyl ether, and washed several times to obtain the photosensitive polyethelene glycol derivative Compound A-68 (0.85 g). According to its nuclear magnetic resonance spectrum, the grafting degree of the Compound 89 can be calculated to be about 95%.

Example 69: Synthesis of Component A-69

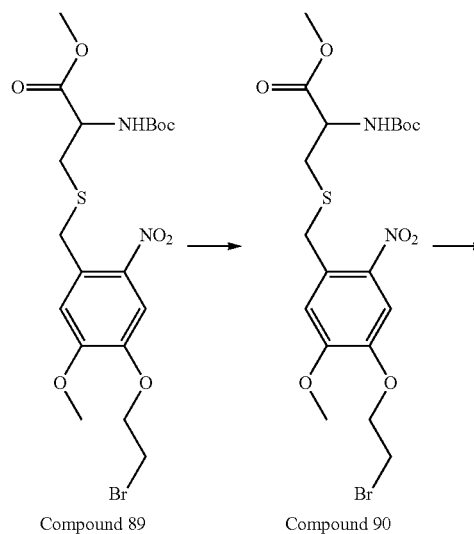

Compound 89 → Compound 90

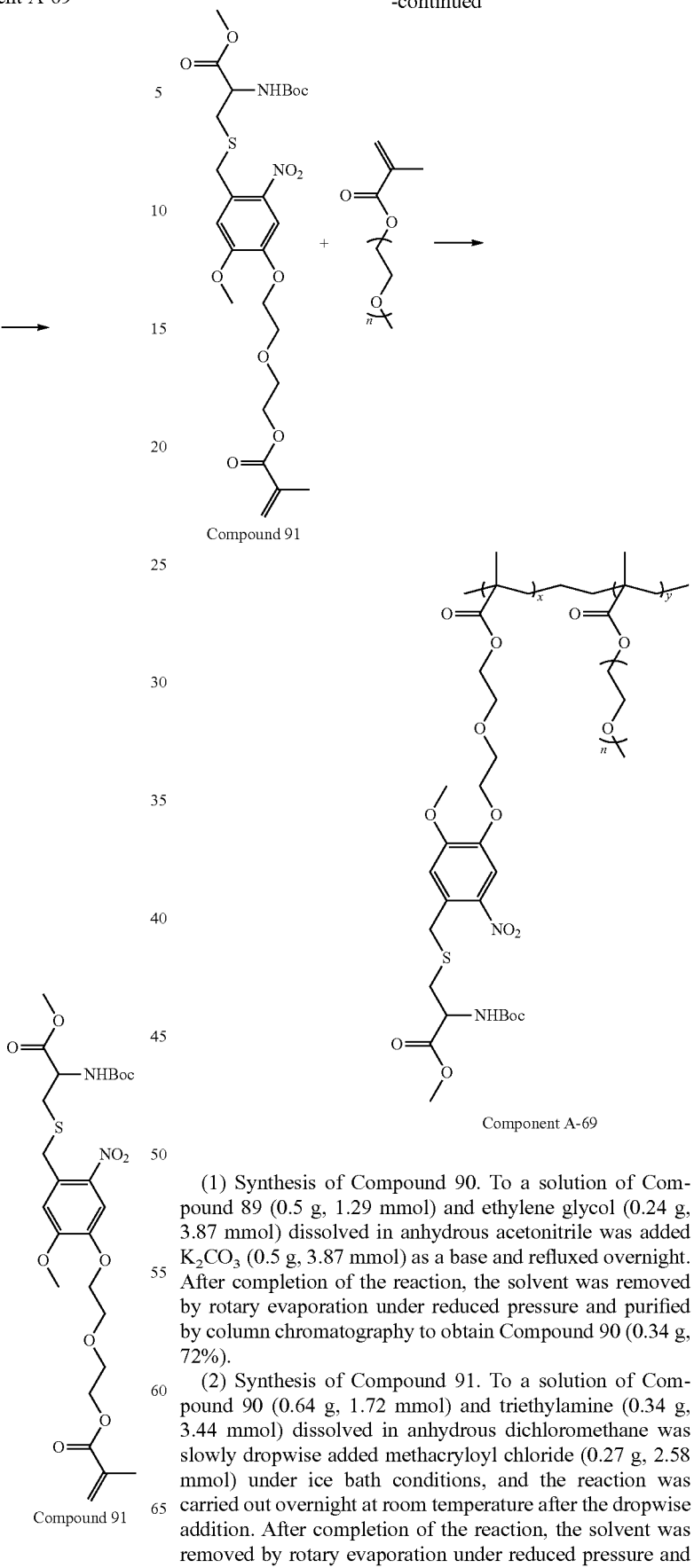

(1) Synthesis of Compound 90. To a solution of Compound 89 (0.5 g, 1.29 mmol) and ethylene glycol (0.24 g, 3.87 mmol) dissolved in anhydrous acetonitrile was added $K_2CO_3$ (0.5 g, 3.87 mmol) as a base and refluxed overnight. After completion of the reaction, the solvent was removed by rotary evaporation under reduced pressure and purified by column chromatography to obtain Compound 90 (0.34 g, 72%).

(2) Synthesis of Compound 91. To a solution of Compound 90 (0.64 g, 1.72 mmol) and triethylamine (0.34 g, 3.44 mmol) dissolved in anhydrous dichloromethane was slowly dropwise added methacryloyl chloride (0.27 g, 2.58 mmol) under ice bath conditions, and the reaction was carried out overnight at room temperature after the dropwise addition. After completion of the reaction, the solvent was removed by rotary evaporation under reduced pressure and purified by column chromatography to afford Compound 91 (0.49 g, 65%). $^1$H NMR (400 MHz, CDCl$_3$): δ=7.71 (s, 1H), 7.22 (s, 1H), 6.25 (s, 1H), 5.68 (s, 1H), 4.76 (s, 2H), 4.42 (m, 1H), 4.13 (t, J=6.1 Hz, 2H), 3.99 (s, 3H), 3.95 (s, 3H), 3.79 (t, J=6.1 Hz, 2H), 3.70 (t, J=7.2 Hz, 2H), 3.56 (t, J=7.2 Hz, 2H), 3.43 (d, J=5.6, 2H), 1.87 (s, 3H), 1.42 (s, 9H). MS (ESI): [M+H] 573.2125.

(3) Synthesis of Component A-69. Compound 91 (0.28 g, 0.63 mmol), comonomer PEG-MA (0.882 g, 2.52 mmol) and the initiator azobisisobutyronitrile (11 mg) were added into the Shrek tube and dissolved by anhydrous THF. After repeated freeze-vacuum cycle operation, the reaction system was reacted at 75° C. for 24 h. After the reaction was completed, the reaction solution was poured into cold diethyl ether and reprecipitated several times to obtain the photosensitive copolymer derivative Compound A-69 (0.86 g). According to its nuclear magnetic resonance spectrum, it can be calculated that the content of the Compound 91 in the copolymer is about 15.3%. According to GPC, the molecular weight of the synthetic polymer is about 25 kDa. According to the feed ratio, n is 12, x is 10, and y is 40.

Example 70: Synthesis of Component A-70

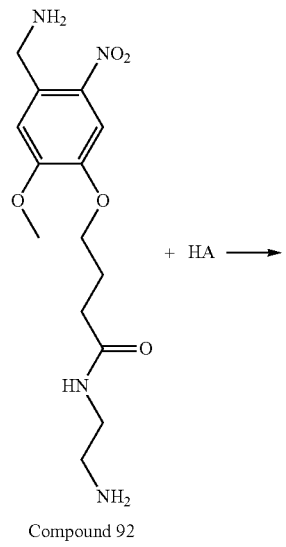

Compound 92

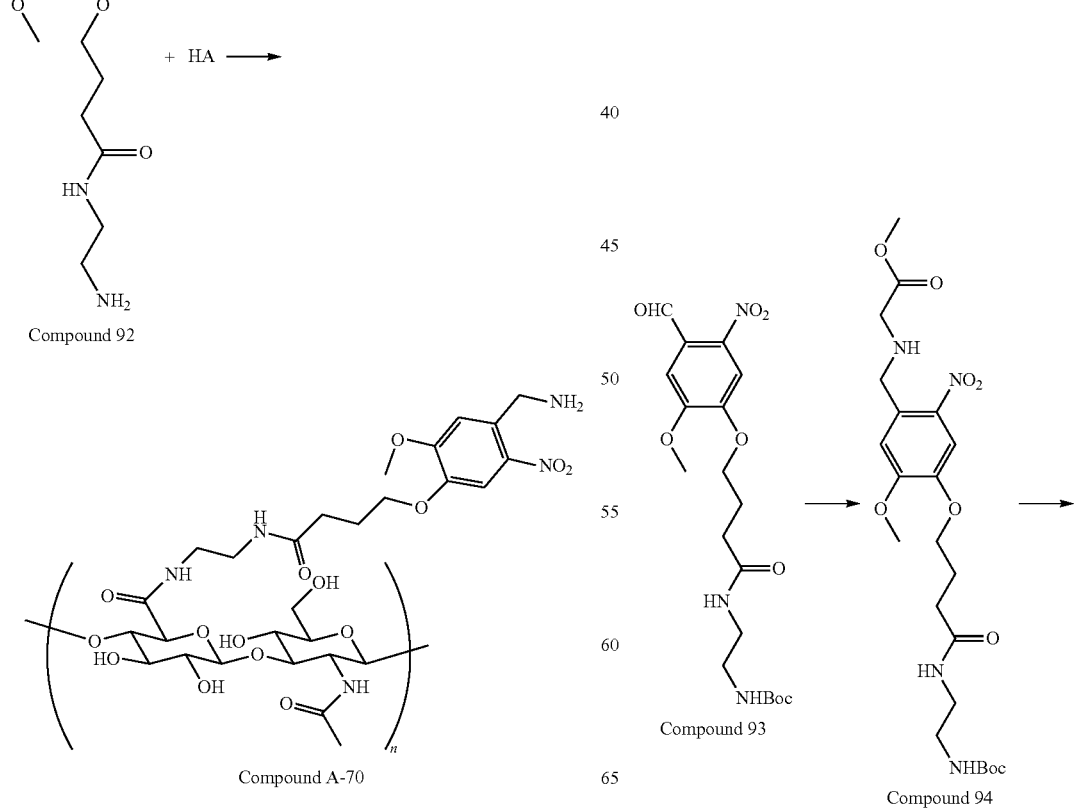

Compound A-70

(1) Synthesis of Compound 92. The synthesis was carried out according to the method disclosed in the reference (Takahiro Muraoka; Honggang Cui; Samuel I. Stupp. J. Am. Chem. Soc. 2008, 130, 2946.). $^1$H NMR (400 MHz, CDCl$_3$): δ=7.71 (s, 1H), 7.22 (s, 1H), 4.35 (s, 2H), 4.13 (t, J=6.1 Hz, 2H), 3.99 (s, 3H), 3.32 (dd, J=11.6, 5.7 Hz, 2H), 2.82 (t, J=5.9 Hz, 2H), 2.44 (t, J=7.2 Hz, 2H), 2.26-2.17 (m, 2H). MS (ESI): [M+H] 327.1617.

(2) Synthesis of Component A-70. To a solution of hyaluronic acid sodium (2 g, 340 kDa) dissolved in 100 mL 0.01 M 2-(N-morpholine) mesylate (MES) buffer solution (pH=5.2) was added Compound 92 (65 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-70 (1.8 g). According to the nuclear magnetic resonance spectrum, the grafting degree of Compound 92 is calculated to be about 3.26%.

Example 71: Synthesis of Component A-71

-continued

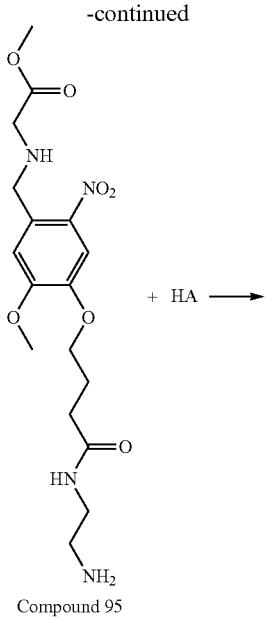

Compound 95

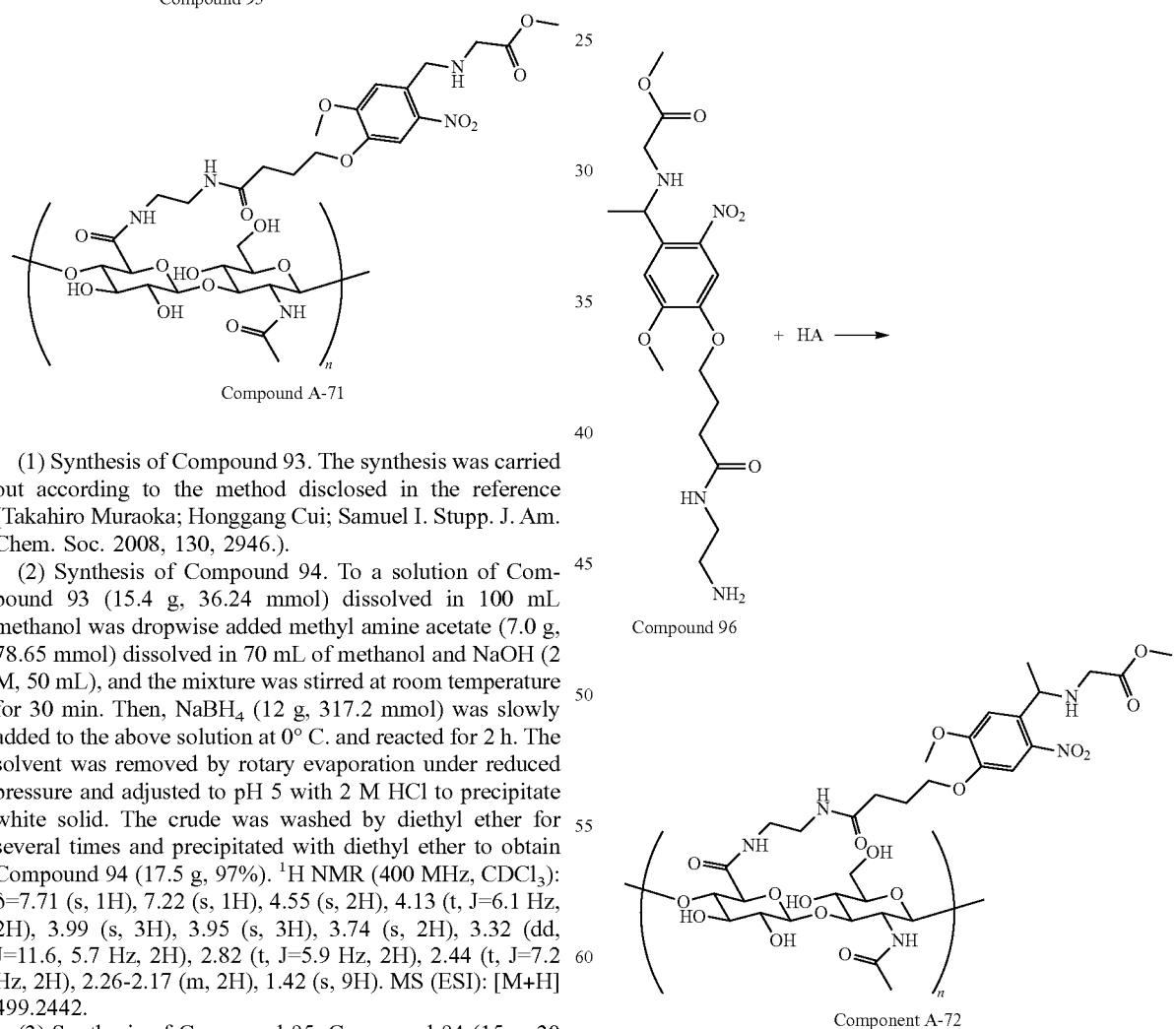

Compound A-71

(1) Synthesis of Compound 93. The synthesis was carried out according to the method disclosed in the reference (Takahiro Muraoka; Honggang Cui; Samuel I. Stupp. J. Am. Chem. Soc. 2008, 130, 2946.).

(2) Synthesis of Compound 94. To a solution of Compound 93 (15.4 g, 36.24 mmol) dissolved in 100 mL methanol was dropwise added methyl amine acetate (7.0 g, 78.65 mmol) dissolved in 70 mL of methanol and NaOH (2 M, 50 mL), and the mixture was stirred at room temperature for 30 min. Then, NaBH$_4$ (12 g, 317.2 mmol) was slowly added to the above solution at 0° C. and reacted for 2 h. The solvent was removed by rotary evaporation under reduced pressure and adjusted to pH 5 with 2 M HCl to precipitate white solid. The crude was washed by diethyl ether for several times and precipitated with diethyl ether to obtain Compound 94 (17.5 g, 97%). $^1$H NMR (400 MHz, CDCl$_3$): δ=7.71 (s, 1H), 7.22 (s, 1H), 4.55 (s, 2H), 4.13 (t, J=6.1 Hz, 2H), 3.99 (s, 3H), 3.95 (s, 3H), 3.74 (s, 2H), 3.32 (dd, J=11.6, 5.7 Hz, 2H), 2.82 (t, J=5.9 Hz, 2H), 2.44 (t, J=7.2 Hz, 2H), 2.26-2.17 (m, 2H), 1.42 (s, 9H). MS (ESI): [M+H] 499.2442.

(3) Synthesis of Compound 95. Compound 94 (15 g, 30 mmol) was dissolved in a mixed solution of dichloromethane/trifluoroacetic acid (3:1), and the reaction was stirred at room temperature for 30 min. Then the solvent was removed by reduced pressure, and the crude product was precipitated by ethyl ether to obtain Compound 95 (11.4 g, 95%). $^1$H NMR (400 MHz, CDCl$_3$): δ=7.71 (s, 1H), 7.22 (s, 1H), 4.55 (s, 2H), 4.13 (t, J=6.1 Hz, 2H), 3.99 (s, 3H), 3.95 (s, 3H), 3.74 (s, 2H), 3.32 (dd, J=11.6, 5.7 Hz, 2H), 2.82 (t, J=5.9 Hz, 2H), 2.44 (t, J=7.2 Hz, 2H), 2.26-2.17 (m, 2H). MS (ESI): [M+H] 399.1823.

(4) Synthesis of Component A-71. To a solution of hyaluronic acid sodium (2 g, 340 kDa) in 100 mL 0.01 M 2-(N-morpholine) mesylate (MES) buffer solution (pH=5.2) was added Compound 95 (80 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-71 (1.87 g). According to the nuclear magnetic resonance spectrum, the grafting degree of Compound 95 is calculated to be about 3.42%.

Example 72: Synthesis of Component A-72

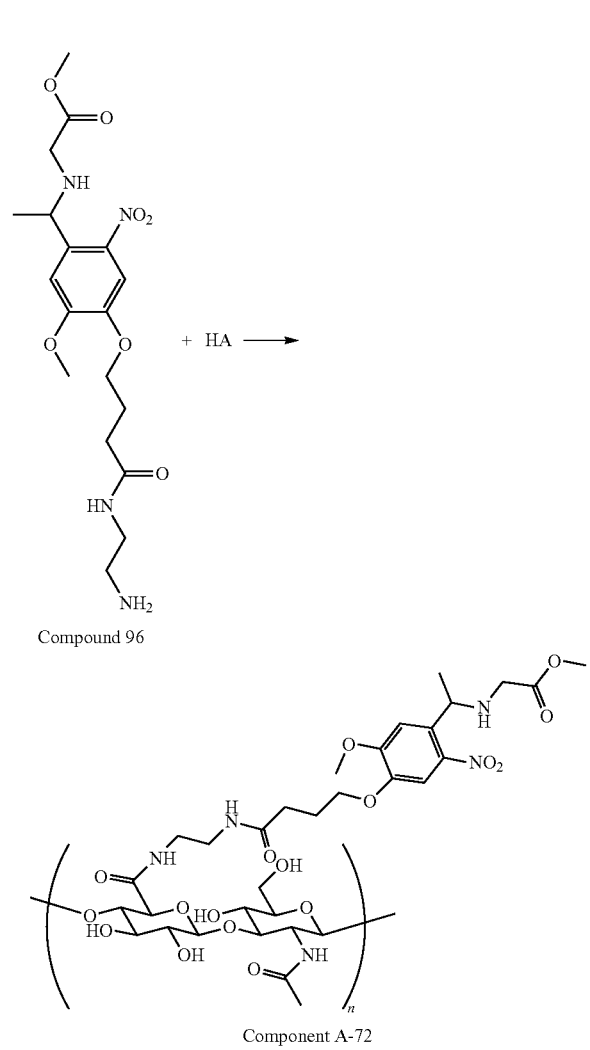

Compound 96

Component A-72

(1) Synthesis of Compound 96. The synthesis was carried out according to the method disclosed in the reference (James F. Cameron; Jean M. J. Frechet. J. Am. Chem. Soc.

1991, 113, 4303.). H NMR (400 MHz, CDCl$_3$): δ=7.71 (s, 1H), 7.22 (s, 1H), 4.75 (m, 1H), 4.13 (t, J=6.1 Hz, 2H), 3.99 (s, 3H), 3.95 (s, 3H), 3.74 (s, 2H), 3.32 (dd, J=11.6, 5.7 Hz, 2H), 2.82 (t, J=5.9 Hz, 2H), 2.44 (t, J=7.2 Hz, 2H), 2.26-2.17 (m, 2H), 1.33 (d, J=6.9 Hz, 3H). MS (ESI): [M+H] 413.2041.

(2) Synthesis of Component A-72. To a solution of hyaluronic acid sodium (2 g, 340 kDa) dissolved in 100 mL 0.01 M 2-(N-morpholine) mesylate (MES) buffer solution (pH=5.2) was added Compound 96 (82 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-72 (1.84 g). According to the nuclear magnetic resonance spectrum, the grafting degree of Compound 96 is calculated to be about 3.21%.

Example 74: Synthesis of Component A-74

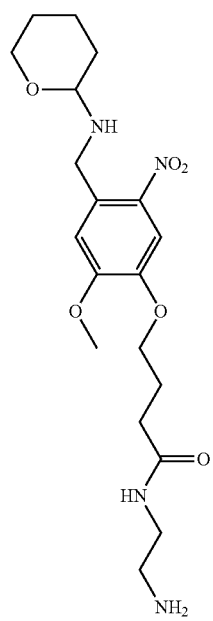

Compound 98

(1) Synthesis of Compound 98. The synthesis was carried out according to the method disclosed in the reference (Pauloehrl, T.; Delaittre, G.; Bruns, M.; Meißler, M.; Börner, H. G.; Bastmeyer, M.; Barner-Kowollik, C. Angew. Chem. Int. Ed. 2012, 51, 9181.). $^1$H NMR (400 MHz, CDCl$_3$): δ=7.71 (s, 1H), 7.22 (s, 1H), 4.55 (s, 2H), 4.13 (t, J=6.1 Hz, 2H), 3.99 (s, 3H), 3.90-3.80 (m, 1H), 3.63-3.52 (m, 1H), 3.32 (dd, J=11.6, 5.7 Hz, 2H), 2.82 (t, J=5.9 Hz, 2H), 2.44 (t, J=7.2 Hz, 2H), 2.26-2.17 (m, 2H), 2.00-1.34 (m, 6H). MS (ESI): [M+H]411.2231.

(2) Synthesis of Component A-74. To a solution of hyaluronic acid sodium (2 g, 340 kDa) in 100 mL 0.01 M 2-(N-morpholine) mesylate (MES) buffer solution (pH=5.2) was added Compound 98 (82 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-74 (1.88 g). According to the nuclear magnetic resonance spectrum, the grafting degree of Compound 98 is calculated to be about 3.38%.

Example 75: Synthesis of Component A-75

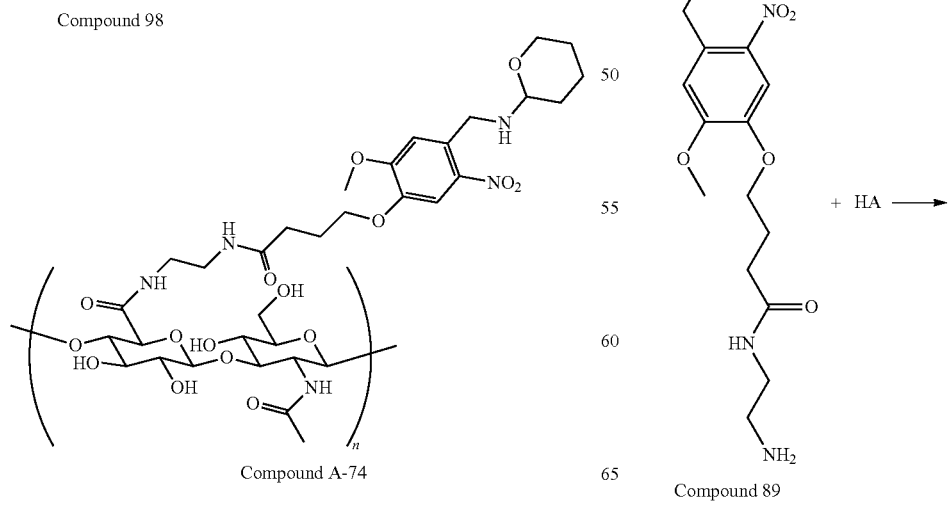

Compound A-74

Compound 89

Example 76: Synthesis of Component A-76

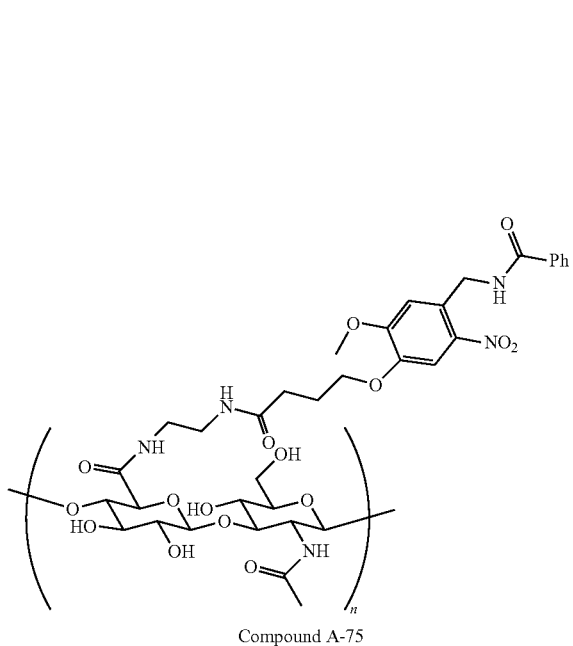

Compound A-75

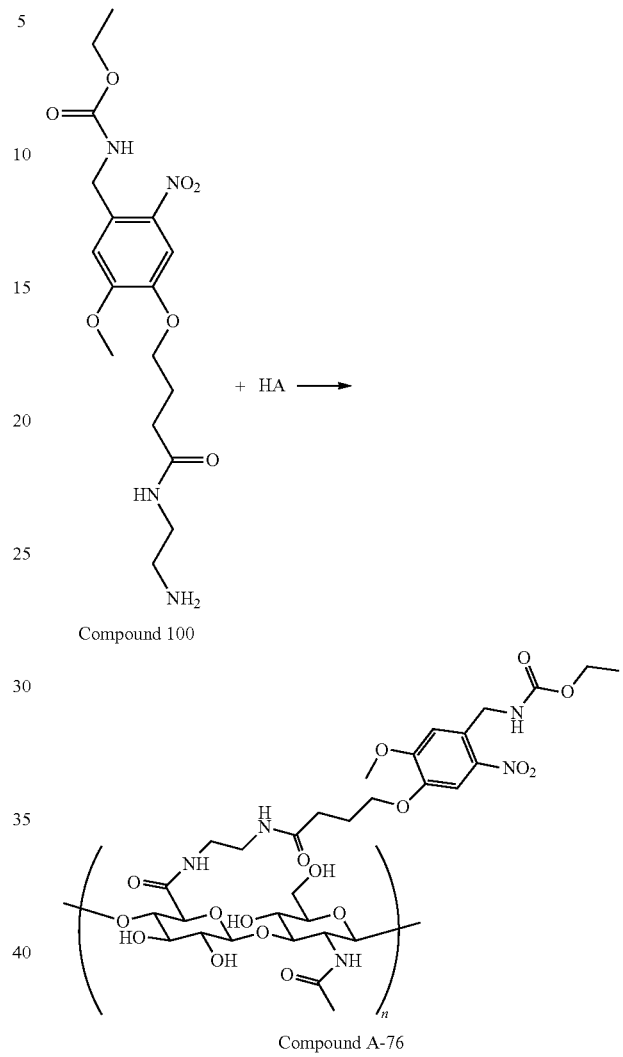

Compound 100

Compound A-76

(1) Synthesis of Compound 99. The synthesis was carried out according to the method disclosed in the reference (Patchomrnik Abraham; Amit B.; Woodward R. B. J. Am. Chem. Soc. 1970, 92, 6333.). $^1$H NMR (400 MHz, CDCl$_3$): δ=8.02-7.23 (m, 5H), 7.71 (s, 1H), 7.22 (s, 1H), 4.55 (m, 1H), 4.13 (t, J=6.1 Hz, 2H), 3.99 (s, 3H), 3.32 (dd, J=11.6, 5.7 Hz, 2H), 2.82 (t, J=5.9 Hz, 2H), 2.44 (t, J=7.2 Hz, 2H), 2.26-2.17 (m, 2H). MS (ESI): [M+H]431.1926.

(2) Synthesis of Component A-75. To a solution of hyaluronic acid sodium (2 g, 340 kDa) dissolved in 100 mL 0.01 M 2-(N-morpholine) mesylate (MES) buffer solution (pH=5.2) was added Compound 99 (86 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-75 (1.85 g). According to the nuclear magnetic resonance spectrum, the grafting degree of Compound 99 is calculated to be about 3.21%.

(1) Synthesis of Compound 100. The synthesis was carried out according to the method disclosed in the reference (Patchomik Abraham; Amit B.; Woodward R. B. J. Am. Chem. Soc. 1970, 92, 6333.). $^1$H NMR (400 MHz, CDCl$_3$): δ=7.71 (s, 1H), 7.22 (s, 1H), 4.55 (s, 2H), 4.25 (q, J=6.5 Hz, 2H), 4.13 (t, J=6.1 Hz, 2H), 3.99 (s, 3H), 3.32 (dd, J=11.6, 5.7 Hz, 2H), 2.82 (t, J=5.9 Hz, 2H), 2.44 (t, J=7.2 Hz, 2H), 2.26-2.17 (m, 2H), 1.32 (t, J=6.5 Hz, 3H). MS (ESI): [M+H] 399.1818.

(2) Synthesis of Component A-76. To a solution of hyaluronic acid sodium (2 g, 340 kDa) dissolved in 100 mL 0.01 M 2-(N-morpholine) mesylate (MES) buffer solution (pH=5.2) was added Compound 100 (80 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-76 (1.69 g). According to the nuclear magnetic resonance spectrum, the grafting degree of Compound 92 is calculated to be about 2.31%.

Example 77: Synthesis of Component A-77

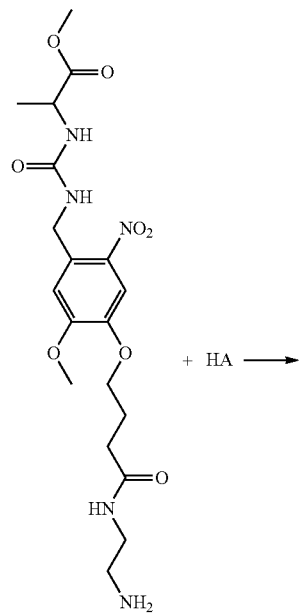

Compound 101

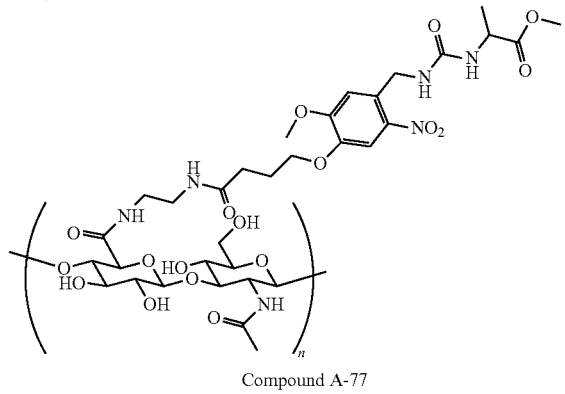

Compound A-77

(1) Synthesis of Compound 101. The synthesis was carried out according to the method disclosed in the reference (Kalbag, S. M.; Roeske, R. W. J. Am. Chem. Soc. 1975, 97, 440.). $^1$H NMR (400 MHz, CDCl$_3$): δ=7.71 (s, 1H), 7.22 (s, 1H), 4.55 (s, 2H), 4.63 (q, J=6.9 Hz, 1H), 4.13 (t, J=6.1 Hz, 2H), 3.99 (s, 3H), 3.67 (s, 3H), 3.32 (dd, J=11.6, 5.7 Hz, 2H), 2.82 (t, J=5.9 Hz, 2H), 2.44 (t, J=7.2 Hz, 2H), 2.26-2.17 (m, 2H), 1.48 (d, J=6.9 Hz, 3H). MS (ESI): [M+H] 456.2036.

(2) Synthesis of Component A-77. To a solution of hyaluronic acid sodium (2 g, 340 kDa) in 100 mL 0.01 M 2-(N-morpholine) mesylate (MES) buffer solution (pH=5.2) was added Compound 101 (91 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-77 (1.82 g). According to the nuclear magnetic resonance spectrum, the grafting degree of Compound 92 is calculated to be about 3.21%.

Example 80: Synthesis of Component A-80

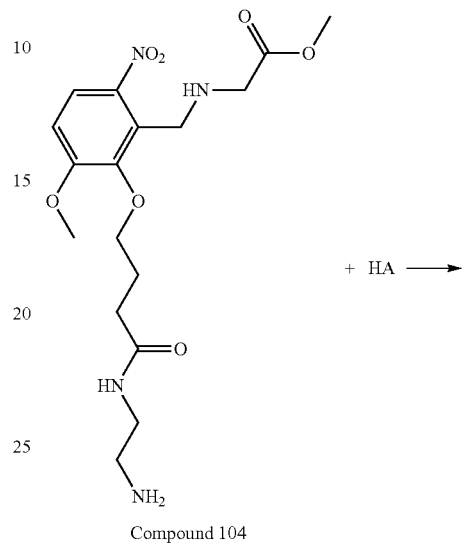

Compound 104

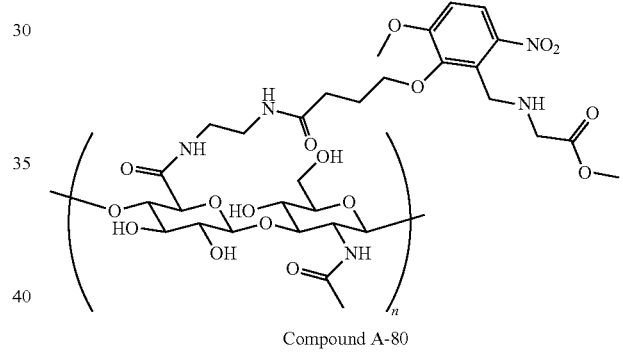

Compound A-80

(1) Synthesis of Compound 104. The synthesis was carried out according to the method disclosed in the reference (Grazyna Groszek; Agnieszka Nowak-Krol; Barbara Filipek. the J. Med. Chem. 2009, 44, 5103.). $^1$H NMR (400 MHz, CDCl$_3$): δ=8.04 (s, 1H), 7.42 (s, 1H), 4.55 (s, 2H), 4.13 (t, J=6.1 Hz, 2H), 3.99 (s, 3H), 3.95 (s, 3H), 3.74 (s, 2H), 3.32 (dd, J=11.6, 5.7 Hz, 2H), 2.82 (t, J=5.9 Hz, 2H), 2.44 (t, J=7.2 Hz, 2H), 2.26-2.17 (i, 2H). MS (ESI): [M+H] 399.1832.

(2) Synthesis of Component A-80. To a solution of hyaluronic acid sodium (2 g, 340 kDa) dissolved in 100 mL 0.01 M 2-(N-morpholine) mesylate (MES) buffer solution (pH=5.2) was added Compound 104 (80 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-80 (1.8 g). According to the nuclear magnetic resonance spectrum, the grafting degree of Compound 104 is calculated to be about 3.32%.

Example 81: Synthesis of Component A-81

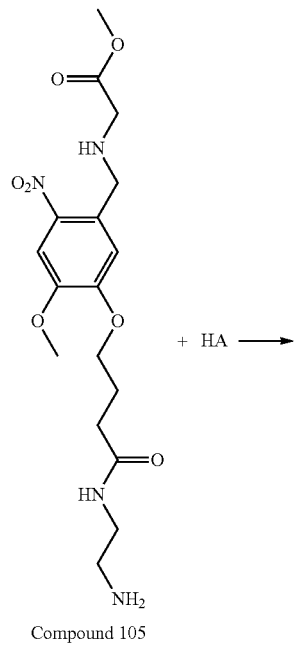

Compound 105

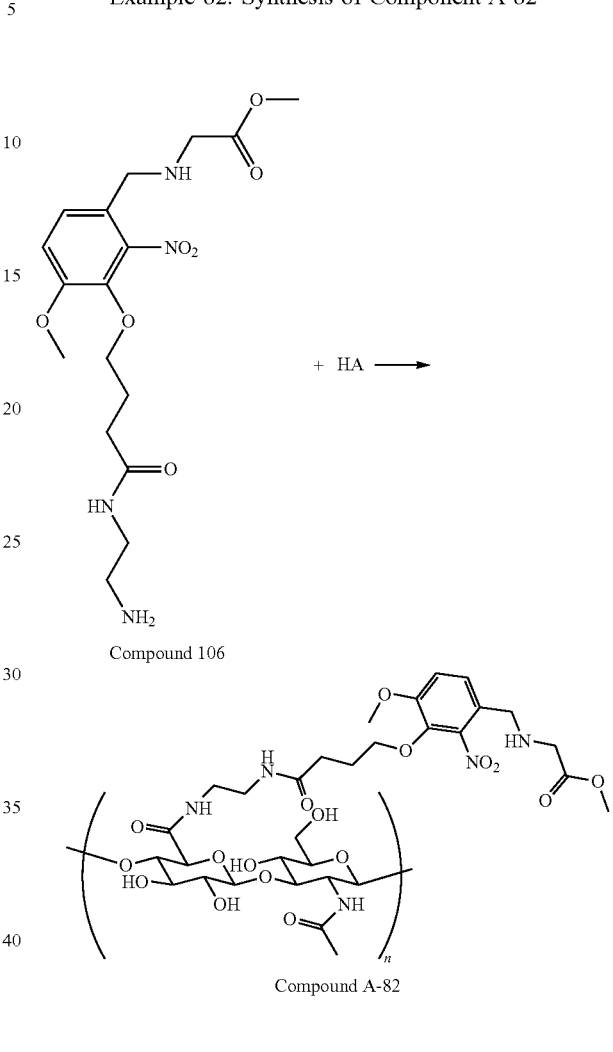

Compound 106

Compound A-82

(1) Synthesis of Compound 105. The synthesis was carried out according to the method disclosed in the reference (Thomas F. Greene; Shu Wang; Mary J. Meegan. J. Med. Chem. 2016, 59, 90.). $^1$H NMR (400 MHz, CDCl$_3$): δ=7.95 (s, 1H), 7.12 (s, 1H), 4.55 (s, 2H), 4.13 (t, J=6.1 Hz, 2H), 3.99 (s, 3H), 3.95 (s, 3H), 3.74 (s, 2H), 3.32 (dd, J=11.6, 5.7 Hz, 2H), 2.82 (t, J=5.9 Hz, 2H), 2.44 (t, J=7.2 Hz, 2H), 2.26-2.17 (m, 2H). MS (ESI): [M+H]399.1832.

(2) Synthesis of Component A-81. To a solution of hyaluronic acid sodium (2 g, 340 kDa) in 100 mL 0.01 M 2-(N-morpholine) mesylate (MES) buffer solution (pH=5.2) was added Compound 105 (80 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-81 (1.89 g). According to the nuclear magnetic resonance spectrum, the grafting degree of Compound 105 is calculated to be about 3.28%.

Example 82: Synthesis of Component A-82

(1) Synthesis of Compound 106. The synthesis was carried out according to the method disclosed in the reference (Yu-Shan; Mohane Selvaraj Coumar; Hsing-Pang Hsieh. J. Med. Chem. 2009, 52, 4941.). $^1$H NMR (400 MHz, CDCl$_3$): δ=7.64 (s, 1H), 7.02 (s, 1H), 4.55 (s, 2H), 4.13 (t, J=6.1 Hz, 2H), 3.99 (s, 3H), 3.95 (s, 3H), 3.74 (s, 2H), 3.32 (dd, J=11.6, 5.7 Hz, 2H), 2.82 (t, J=5.9 Hz, 2H), 2.44 (t, J=7.2 Hz, 2H), 2.26-2.17 (m, 2H). MS (ESI): [M+H] 399.1832.

(2) Synthesis of Component A-82. To a solution of hyaluronic acid sodium (2 g, 340 kDa) dissolved in 100 mL 0.01 M 2-(N-morpholine) mesylate (MES) buffer solution (pH=5.2) was added Compound 106 (80 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-82 (1.91 g). According to the nuclear magnetic resonance spectrum, the grafting degree of Compound 106 is calculated to be about 3.26%.

Example 83: Synthesis of Component A-83

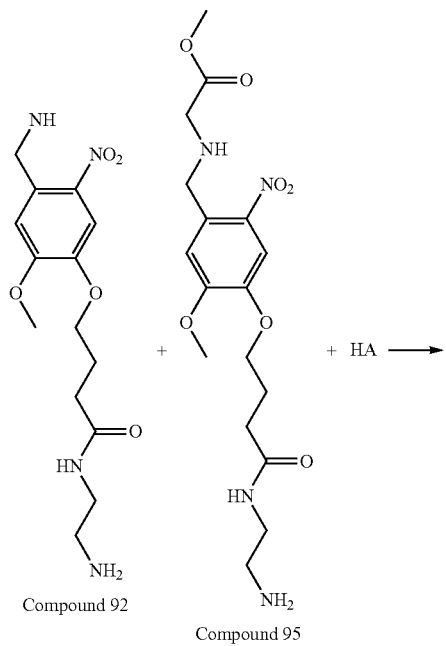

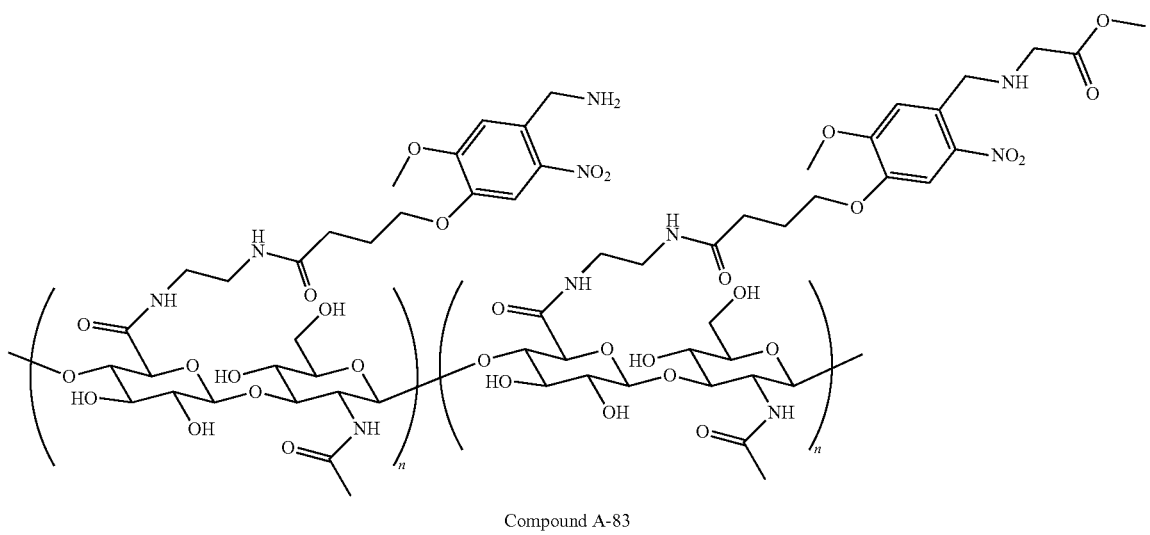

Synthesis of Component A-83. To a solution of hyaluronic acid sodium (2 g, 340 kDa) dissolved in 100 mL 0.01 M 2-(N-morpholine) mesylate (MES) buffer solution (pH=5.2) was added nNB mixture (Compound 92/Compound 95, 60 mg, weight ratio is 1:1) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-83 (1.89 g). According to the nuclear magnetic resonance spectrum, the grafting degree of Compound NB mixture is calculated to be about 3.42%.

Example 84: Synthesis of Component A-84

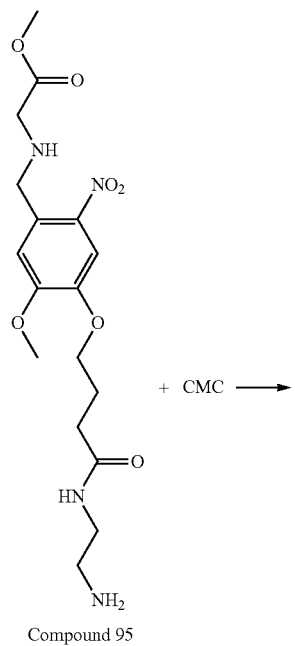

Compound 95

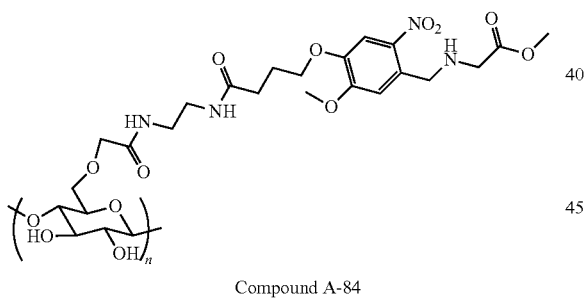

Compound A-84

Synthesis of Component A-84. To a solution of carboxymethyl cellulose (2 g, 90 kDa) dissolved in 100 mL 0.01 M 2-(N-morpholine) mesylate (MES) buffer solution (pH=5.2) was added Compound 95 (80 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-84 (1.72 g). According to the nuclear magnetic resonance spectrum, the grafting degree of Compound 95 is calculated to be about 2.21%.

Example 85: Synthesis of Component A-85

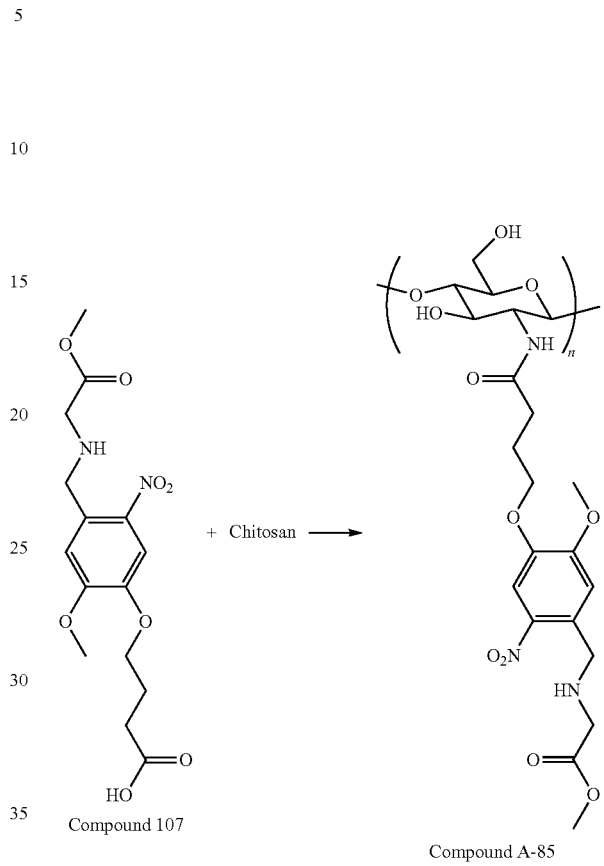

Compound 107

Compound A-85

(1) Synthesis of Compound 107. According to the method in Example 71, Compound 107 was prepared by conventional chemical means. $^1$H NMR (400 MHz, CDCl$_3$): δ=7.71 (s, 1H), 7.22 (s, 1H), 4.55 (s, 2H), 4.13 (t, J=6.1 Hz, 2H), 3.99 (s, 3H), 3.95 (s, 3H), 3.74 (s, 2H), 2.44 (t, J=7.2 Hz, 2H), 2.26-2.17 (m, 2H). MS (ESI): [M+H] 357.1342.

(2) Synthesis of Component A-85. To a suspension liquid of chitosan (1 g) dissolved in 75 mL isopropanol was sequentially added Compound 107 (0.2 g, 0.56 mmol), EDC·HCl (0.76 g, 3.96 mmol) and NHS (0.46 g, 4.0 mmol), and the reaction was stirred at room temperature for 48 h. After completion of the reaction, the mixture solution was dialyzed with diluted hydrochloric acid solution containing sodium chloride (pH=3.5) for 1 d, dialyzed with distilled water for 1 d, and then freeze-dried to obtain photosensitive chitosan derivatives Compound A-85 (0.82 g). According to its nuclear magnetic resonance spectrum, the grafting degree of the Compound 107 can be calculated to be about 11.3%.

Example 86: Synthesis of Component A-86

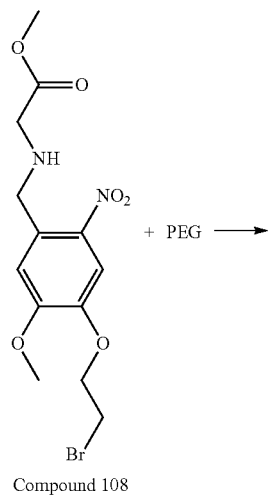

Compound 108

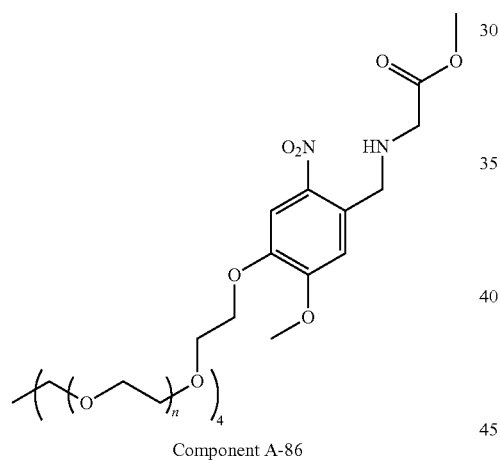

Component A-86

Example 87: Synthesis of Component A-87

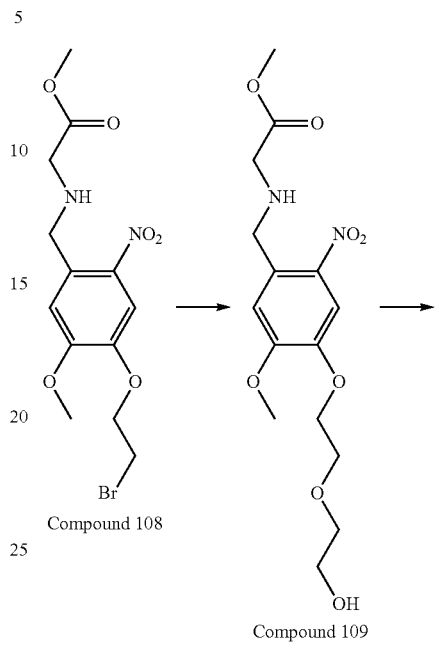

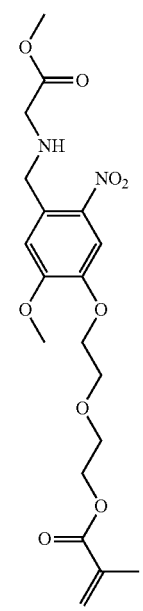

Compound 110

(1) Synthesis of Compound 108. According to the method in Example 71, Compound 108 was prepared by conventional chemical means. $^1$H NMR (400 MHz, CDCl$_3$): δ=7.71 (s, 1H), 7.22 (s, 1H), 4.55 (s, 2H), 4.13 (t, J=6.1 Hz, 2H), 3.99 (s, 3H), 3.95 (s, 3H), 3.74 (s, 2H), 3.04 (t, J=7.2 Hz, 2H). MS (ESI): [M+H] 377.0346.

(2) Synthesis of Component A-86. To a solution of PEG-4OH (1 g, 0.05 mmol) dissolved in anhydrous acetonitrile was added K$_2$CO$_3$ (55.3 mg, 0.4 mmol) and stirred for 30 min. Then the solution was added Compound 108 (0.15 g, 0.4 mmol) and continued to react at room temperature for 24 h. After completion of the reaction, most of the solvent was removed, reprecipitated in diethyl ether, and washed several times to obtain the photosensitive polyethelene glycol derivative Compound A-86 (0.93 g). According to its nuclear magnetic resonance spectrum, the grafting degree of the Compound 89 can be calculated to be about 95%.

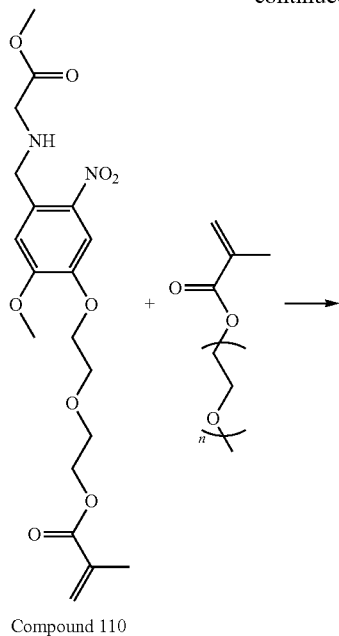

Compound 110

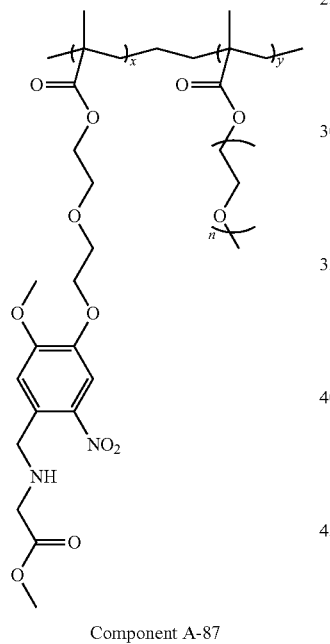

Component A-87

(1) Synthesis of Compound 109. To a solution of Compound 108 (0.5 g, 1.29 mmol) and ethylene glycol (0.24 g, 3.87 mmol) dissolved in anhydrous acetonitrile was added $K_2CO_3$ (0.5 g, 3.87 mmol) as a base and refluxed overnight. After completion of the reaction, the solvent was removed by rotary evaporation under reduced pressure and purified by column chromatography to afford Compound 109 (0.34 g, 72C %). $^1$H NMR (400 MHz, CDCl$_3$): δ=7.71 (s, 1H), 7.22 (s, 1H), 4.55 (s, 2H), 4.13 (t, J=6.1 Hz, 2H), 3.99 (s, 3H), 3.95 (s, 3H), 3.79 (t, J=6.1 Hz, 2H), 3.74 (s, 2H), 3.70 (t, J=7.2 Hz, 2H), 3.56 (t, J=7.2 Hz, 2H). MS (ESI): [M+H] 359.1462.

(2) Synthesis of Compound 110. To a solution of Compound 109 (0.64 g, 1.72 mmol) and triethylamine (0.34 g, 3.44 mmol) dissolved in anhydrous dichloromethane was slowly dropwise added methacryloyl chloride (0.27 g, 2.58 mmol) under ice bath conditions, and the reaction was carried out overnight at room temperature. After completion of the reaction, the solvent was removed by rotary evaporation under reduced pressure and purified by column chromatography to afford Compound 110 (0.49 g, 65C %). $^1$H NMR (400 MHz, CDCl$_3$): δ=7.71 (s, 1H), 7.22 (s, 1H), 6.25 (s, 1H), 5.68 (s, 1H), 4.55 (s, 2H), 4.13 (t, J=6.1 Hz, 2H), 3.99 (s, 3H), 3.95 (s, 3H), 3.79 (t, J=6.1 Hz, 2H), 3.74 (s, 2H), 3.70 (t, J=7.2 Hz, 2H), 3.56 (t, J=7.2 Hz, 2H), 1.87 (s, 3H). MS (ESI): [M+H] 427.1725.

(3) Synthesis of Component A-87. Compound 110 (0.28 g, 0.63 mmol), comonomer PEG-MA (0.882 g, 2.52 mmol) and the initiator azobisisobutyronitrile (11 mg) were added into the Shrek tube and dissolved by anhydrous THF. After repeated freeze-vacuum cycle operation, the reaction system was reacted at 75° C. for 24 h. After completion of the reaction, the solution was poured into cold diethyl ether and reprecipitated several times to obtain the photosensitive copolymer derivative Compound A-87 (0.85 g). According to its nuclear magnetic resonance spectrum, it can be calculated that the content of the Compound 110 in the copolymer is about 14.6%. According to GPC, the molecular weight of the synthetic polymer is about 25 kDa. According to the feed ratio, n is 12, x is 10, and y is 40

Example 88: Synthesis of Component A-88

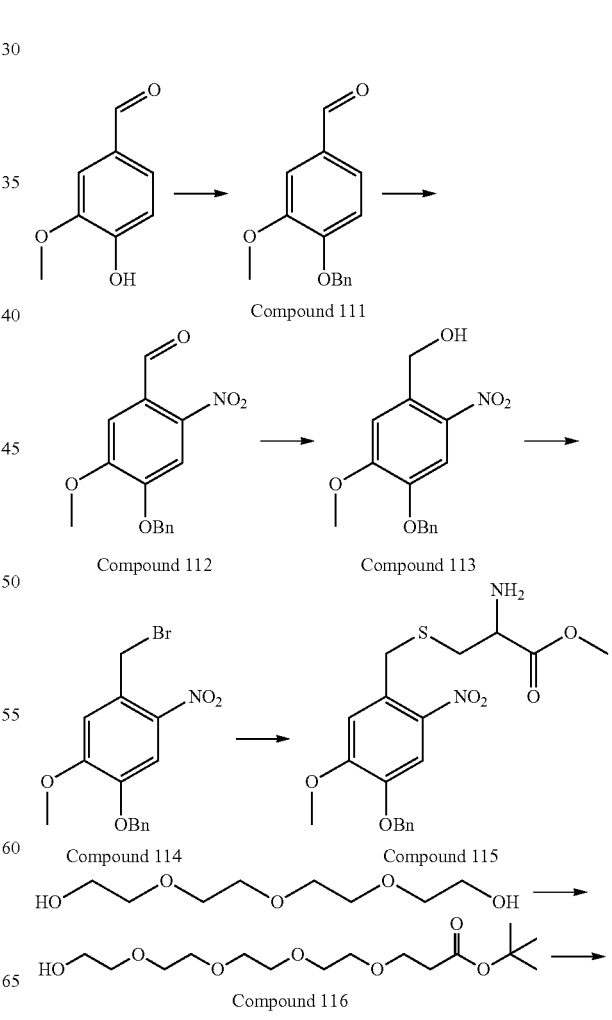

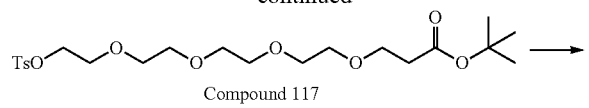

Compound 117

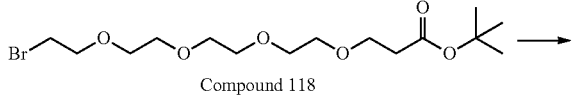

Compound 118

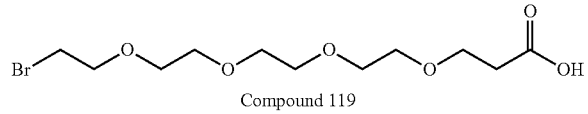

Compound 119

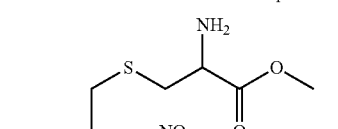

Compound 115

+

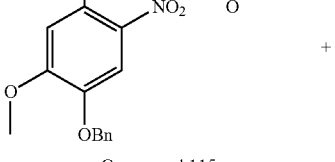

Compound 119

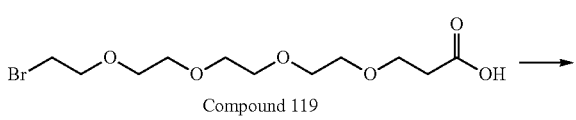

Compound 120

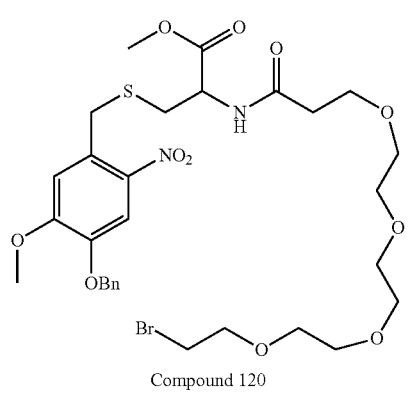

Compound 121

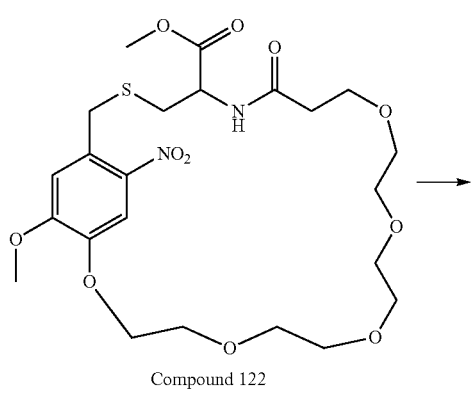

Compound 122

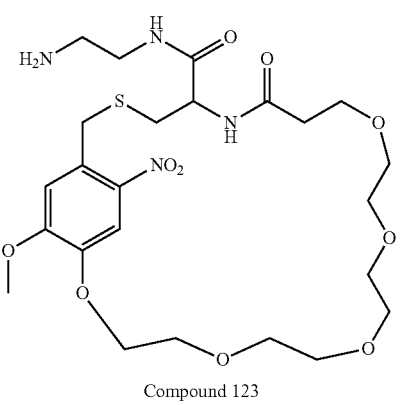

Compound 123

(1) Synthesis of Compound 111. To a solution of vanillin (25 g, 165 mmol) and potassium carbonate (11.4 g, 83 mmol) dissolved in 200 mL acetone was dropwise added benzyl bromide (21.2 g, 181 mmol), and the solution was refluxed at 90° C. for 8 h. Then the reaction was cooled to room temperature, the solvent was removed by rotary evaporation under reduced pressure. The crude was added 100 mL water and extracted three times with ethyl acetate. The combined organic layers were dried over anhydrous $Na_2SO_4$, filtered and removed the solvent under reduced pressure to give the colorless liquid. It was then recrystallized from 100 mL ethanol to give Compound 111 as white powder (36.2 g, 91%). $^1$H NMR (400 MHz, $CDCl_3$): δ=9.83 (s, 1H), 7.39 (ddd, J=24.2, 20.7, 7.4 Hz, 7H), 6.98 (d, J=8.2 Hz, 1H), 5.24 (s, 2H), 3.94 (d, J=0.9 Hz, 3H). MS (ESI): [M+Na] 265.0824.

(2) Synthesis of Compound 112. To a solution of Compound 111 (10 g, 41.3 mmol) dissolved in 50 mL acetic anhydride was dropwise added 50 mL nitric acid (65%) under ice bath. The mixture was reacted at room temperature for 30 min. After completion of the reaction, the reaction system was slowly poured into 600 mL ice water to precipitate a yellow solid. The crude was crystallised from ethanol to obtain yellow needle-like product as Compound 112 (9.72 g, 82%). $^1$H NMR (400 MHz, $CDCl_3$): δ=10.42 (s, 1H), 7.67 (s, 1H), 7.43-7.39 (m, 3H), 7.37 (d, J=7.0 Hz, 1H), 5.26 (s, 2H), 4.01 (s, 3H). MS (ESI): [M+Na]310.0689.

(3) Synthesis of Compound 113. To a solution of Compound 112 (9 g, 31.3 mmol) dissolved in 200 mL methanol was slowly added sodium borohydride (2.37 g, 62.6 mmol) under ice bath, and the mixture was carried out for 30 min at room temperature. After completion of the reaction, the system was acidified with 2 mol/L hydrochloric acid to pH 7.0, and methanol was removed by rotary evaporation under reduced pressure. The crude was added 100 mL water and extracted three times with ethyl acetate, and the combined organic phases was dried over anhydrous $Na_2SO_4$, filtered and removed the solvent by rotary evaporation under reduced pressure to give Compound 113 as yellow solid (9.06 g, 92%). $^1$H NMR (400 MHz, $CDCl_3$): δ=7.77 (s, 1H), 7.49-7.42 (m, 2H), 7.40 (dd, J=8.1, 6.4 Hz, 3H), 7.18 (s, 1H), 5.20 (s, 2H), 4.95 (s, 2H), 4.00 (s, 3H). MS (ESI): [M+Na] 312.0834.

(4) Synthesis of Compound 114. To a solution of Compound 113 (3 g, 10.4 mmol) dissolved in 100 mL anhydrous tetrahydrofuran under protection of $Ar_2$ was simultaneously added triphenylphosphine (4.08 g, 15.6 mmol) and carbon tetrabromide (5.16 g, 15.6 mmol) under ice bath, and the reaction was carried out for 2 h at room temperature. After completion of the reaction, 6 mL of water was added to quench the reaction system, and then the tetrahydrofuran was removed by rotary evaporation under reduced pressure. The crude was extracted twice with saturated brine and ethyl acetate, and then extracted three times with water and ethyl acetate. The combined organic phases was dried over anhydrous $Na_2SO_4$, filtered and removed the solvent by rotary evaporation under reduced pressure, then purified by column chromatography ($PE:CH_2Cl_2$=4:1) to obtain Compound 114 as yellow powder (3.09 g, 85%). $^1$H NMR (400 MHz, $CDCl_3$): δ=7.71 (s, 1H), 7.46-7.41 (m, 2H), 7.40-7.30 (m, 3H), 6.93 (s, 1H), 5.17-5.13 (m, 2H), 4.8-4.79 (m, 2H), 3.95 (s, 3H), 1.42 (s, 9H). MS (ESI): [M+Na] 374.0003.

(5) Synthesis of Compound 115. To a solution of Compound 114 (3 g, 8.5 mmol) dissolved in 120 mL acetone under protection of $Ar_2$ was added L-cysteine methyl ester hydrochloride (2.9 g, 17 mmol) and sodium hydroxide (0.85 g, 21.25 mmol), and the mixture was reacted at room temperature for 2 h. After completion of the reaction, the system was acidified with 4 mol/L hydrochloric acid to pH 7.0, and the acetone was removed by rotary evaporation under reduced pressure. The crude was extracted three times with saturated brine and ethyl acetate, and then extracted three times with water and ethyl acetate. The combined organic phases was dried over anhydrous $Na_2SO_4$, filtered and removed the solvent by rotary evaporation under reduced pressure, then purified by column chromatography ($CH_2Cl_2:CH_3OH$=100:3) to obtain Compound 115 as a yellow solid (2.71 g, 78%). $^1$H NMR (400 MHz, $CDCl_3$): δ=7.71 (s, 1H), 7.45 (d, J=7.0 Hz, 2H), 7.39 (t, J=7.2 Hz, 3H), 6.95 (s, 1H), 5.18 (s, 2H), 4.13 (q, J=13.6 Hz, 2H), 3.98 (s, 3H), 3.73 (s, 3H), 3.65 (m, 1H), 2.91 (dd, J=13.7, 4.6 Hz, 1H), 2.75 (dd, J=13.6, 7.5 Hz, 1H). MS (ESI): [M+H] 407.1277.

(6) Synthesis of Compound 116. To a solution of triethylene glycol (22 g, 113.2 mmol) dissolved in dry tetrahydrofuran was added sodium metal (40 mg, 1.74 mmol), the mixture was stirred until sodium was completely dissolved. The mixture was added tert-butyl acrylate (8 g, 62.4 mmol) and reacted at room temperature for 20 h. After completion of the reaction, the system was acidified with 1 mol/L hydrochloric acid to pH 7.0, and tetrahydrofuran was removed by rotary evaporation under reduced pressure. The crude was extracted three times with saturated brine and ethyl acetate, and then extracted three times with water and ethyl acetate. The combined organic phases was dried over anhydrous $Na_2SO_4$, filtered and removed the solvent by rotary evaporation under reduced pressure. Without further purification, Compound 116 (16.0 g, 80%) as a colorless oily liquid was obtained. $^1$H NMR (400 MHz, $CDCl_3$): δ=3.78-3.69 (m, 4H), 3.69-3.54 (m, 14H), 2.52 (dd, J=4.3, 2.1 Hz, 2H), 1.45 (s, 9H). MS (ESI): [M+Na] 345.1872.

(7) Synthesis of Compound 117. To a solution of Compound 116 (10 g, 31.2 mmol) dissolved in anhydrous dichloromethane was added anhydrous triethylamine (5.2 mm L, 37.4 mmol) and gradually dropwise added p-methylbenzenesulfonyl chloride (8.9 g, 46.8 mmol) in 40 mL dry dichloromethane under ice bath conditions, and the mixture was reacted at room temperature for 6 h. After completion of the reaction, the system was added 200 mL of water and extracted three times with dichloromethane. The combined organic phases were dried over anhydrous $Na_2SO_4$, filtered and removed the solvent by rotary evaporation under reduced pressure, then purified by column chromatography ($CH_2Cl_2:CH_3OH$=50:1) to obtain Compound 117 (12.6 g, 85%) as a pale yellow oily liquid. $^1$H NMR (400 MHz, $CDCl_3$): δ=7.79-7.74 (m, 2H), 7.32 (d, J=8.5 Hz, 2H), 4.21-3.90 (m, 2H), 3.66 (dd, J=5.7, 2.8 Hz, 4H), 3.62-3.35 (m, 12H), 2.47 (dd, J=8.3, 4.8 Hz, 2H), 2.42 (d, J=3.2 Hz, 3H), 1.42 (d, J=3.4 Hz, 9H). MS (ESI): [M+Na] 499.1964.

(8) Synthesis of Compound 118. Compound 117 (10 g, 21.0 mmol) and lithium bromide (4.8 g, 31.5 mmol) were dissolved in 30 mL of N,N-dimethylformamide and heated to 80° C. to react for 1 h. After completion of the reaction, N,N-dimethylformamide was removed the solvent by rotary evaporation under reduced pressure. The crude was extracted three times with water and dichloromethane. The combined organic phases were dried over anhydrous $Na_2SO_4$, filtered and removed the solvent by rotary evaporation under reduced pressure, then purified by column chromatography to obtain Compound 118 (7.3 g, 90%) as a pale yellow oily liquid. $^1$H NMR (400 MHz, $CDCl_3$): δ=3.72 (t, J=6.3 Hz, 2H), 3.62 (t, J=6.6 Hz, 2H), 3.58 (dd, J=2.6, 1.5 Hz, 8H), 3.54 (d, J=2.2 Hz, 4H), 3.39 (t, J=6.3 Hz, 2H), 2.42 (t, J=6.6 Hz, 2H), 1.36 (s, 9H). MS (ESI): [M+Na] 409.1005.

(9) Synthesis of Compound 119. To a solution of Compound 118 (5 g, 13.0 mmol) dissolved in 30 mL anhydrous dichloromethane was added 10 mL trifluoroacetic acid, and the mixture was reacted at room temperature for 30 min. After completion of the reaction, the solvent was removed by rotary evaporation under reduced pressure. Then the crude was re-dissolved with dichloromethane and ethyl acetate and the solvent was removed by rotary evaporation under reduced pressure to absolutely remove trifluoroacetic acid. Without further purification, Compound 119 (3.9 g, 92%) as a yellow oily liquid was obtained. $^1$H NMR (400 MHz, $CDCl_3$): δ=3.72 (t, J=6.3 Hz, 2H), 3.67 (t, J=6.3 Hz, 2H), 3.58 (dd, J=4.1, 1.7 Hz, 4H), 3.57 (s, 4H), 3.55 (s, 4H), 3.39 (t, J=6.3 Hz, 2H), 2.54 (t, J=6.3 Hz, 2H). MS (ESI): [M+Na] 353.0414.

(10) Synthesis of Compound 120. To a solution of Compound 115 (2.0 g, 4.9 mmol) and Compound 119 (2.0 g, 5.9 mmol) dissolved in 40 mL anhydrous dichloromethane was added benzotriazol-1-yl-oxytripyrrolidinyl hexafluorophosphate (5.1 g, 9.8 mmol) and anhydrous triethylamine (1.4 mL, 9.8 mmol), and the mixture was reacted at room temperature for 1 h. After completion of the reaction, the system was extracted three times with dichloromethane and water. The combined organic phases were dried over anhydrous $Na_2SO_4$, filtered and removed the solvent by rotary evaporation under reduced pressure, then purified by column chromatography ($CH_2Cl_2$:$CH_3OH$=100:3) to obtain Compound 120 (2.2 g, 62%) as a yellow solid. $^1$H NMR (400 MHz, CDCl$_3$): δ=7.71 (s, 1H), 7.45 (d, J=7.0 Hz, 2H), 7.39 (t, J=7.2 Hz, 3H), 6.95 (s, 1H), 5.18 (s, 2H), 4.42 (m, 1H), 4.13 (q, J=13.6 Hz, 2H), 3.98 (s, 3H), 3.73 (s, 3H), 3.68-3.63 (m, 2H), 3.62-3.55 (m, 4H), 3.58-3.53 (m, 12H), 3.37 (t, J=6.3 Hz, 2H), 2.43 (t, J=5.8 Hz, 2H). MS (ESI): [M+Na] 741.1529.

(11) Synthesis of Compound 121. Compound 120 (2 g, 2.8 mmol) was dissolved in 20 mL trifluoroacetic acid and reacted at 45° C. for 8 h. After completion of the reaction, trifluoroacetic acid was removed by rotary evaporation under reduced pressure and extracted three times with dichloromethane and water. The combined organic phases were dried over anhydrous $Na_2SO_4$, filtered and removed the solvent by rotary evaporation under reduced pressure, then purified by column chromatography ($CH_2Cl_2$: $CH_3OH$=25:1) to obtain Compound 121 (1.4 g, 82%) as a yellow liquid. $^1$H NMR (400 MHz, CDCl$_3$): δ=7.60 (s, 1H), 6.79 (s, 1H), 4.73-4.66 (m, 1H), 3.99 (d, J=12.9 Hz, 2H), 3.97 (s, 3H), 3.73 (s, 3H), 3.70 (d, J=6.3 Hz, 2H), 3.62-3.55 (m, 4H), 3.58-3.53 (m, 12H), 3.37 (t, J=6.3 Hz, 2H), 2.43 (t, J=5.8 Hz, 2H). MS (ESI): [M+Na] 651.1026.

(12) Synthesis of Compound 122. To a solution of Compound 121 (0.5 g, 0.8 mmol) in 400 mL acetone was added potassium carbonate (0.2 g, 1.6 mmol), and the mixture was refluxed at 75° C. for 4 h. After completion of the reaction, the system was filtrated to remove insoluble matter and removed solvent by rotary evaporation under reduced pressure. Then, the crude was purified by column chromatography ($CH_2Cl_2$:$CH_3OH$=25:1) to obtain Compound 122 (0.27 g, 61%) as a yellow solid. $^1$H NMR (400 MHz, DMSO): δ=7.71 (s, 1H), 7.17 (s, 1H), 4.76 (s, 2H), 4.42 (m, 1H), 3.97 (s, 3H), 3.73 (s, 3H), 3.72 (d, J=6.3 Hz, 2H), 3.62-3.55 (m, 4H), 3.52-3.39 (m, 14H), 2.49-2.35 (m, 2H). MS (ESI): [M+Na]569.1782.

(13) Synthesis of Compound 123. Compound 122 (0.2 g, 3.7 mmol) was dissolve in 20 mL anhydrous ethylenediamine and reacted at room temperature for 6 h. After completion of the reaction, the ethylenediamine was removed by rotary evaporation under reduced pressure. The crude was purified by column chromatography ($CH_2Cl_2$: $CH_3OH$:triethylamine=100:8:0.5) to obtain Compound 123 (0.19 g, 89%) as a yellow powder. $^1$H NMR (400 MHz, DMSO): δ=7.71 (s, 1H), 7.17 (s, 1H), 4.76 (s, 2H), 4.42 (m, 1H), 3.97 (s, 3H), 3.72 (d, J=6.3 Hz, 2H), 3.62-3.55 (m, 2H), 3.52-3.39 (m, 16H), 2.86 (d, J=7.6 Hz, 2H), 2.76 (d, J=7.6 Hz, 2H), 2.49-2.35 (m, 2H). MS (ESI): [M+Na] 597.2211.

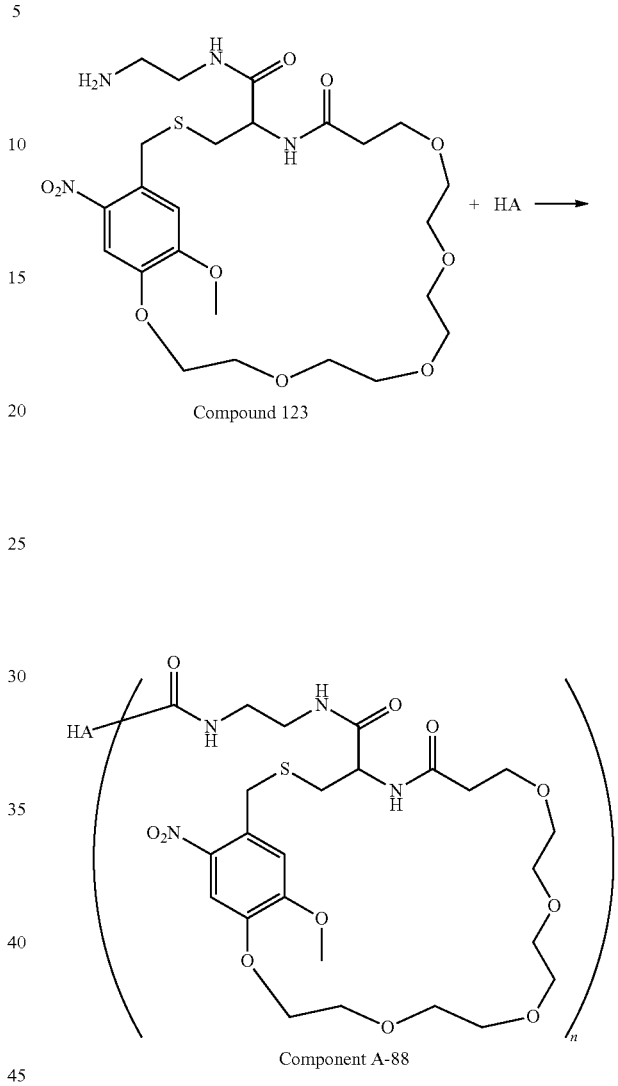

(14) Synthesis of Component A-88. To a solution of hyaluronic acid sodium (2 g, 340 kDa) dissolved in 100 mL 0.01 M 2-(N-morpholine) mesylate (MES) buffer solution (pH=5.2) was added Compound 123 (115 mg, 0.2 mmol) in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-88 (1.87 g). According to the nuclear magnetic resonance spectrum, the grafting degree of Compound 123 can be calculated to be about 3.49%.

Example 89: Synthesis of Component A-89

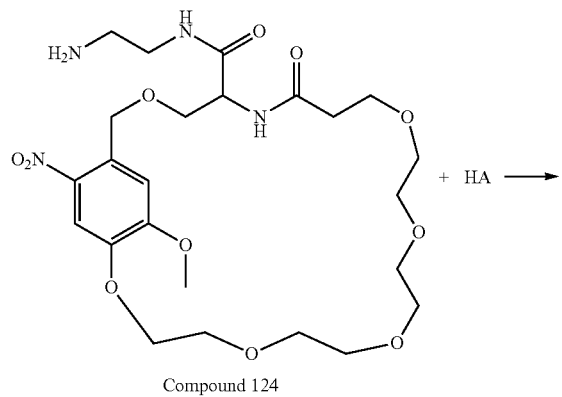

Compound 124

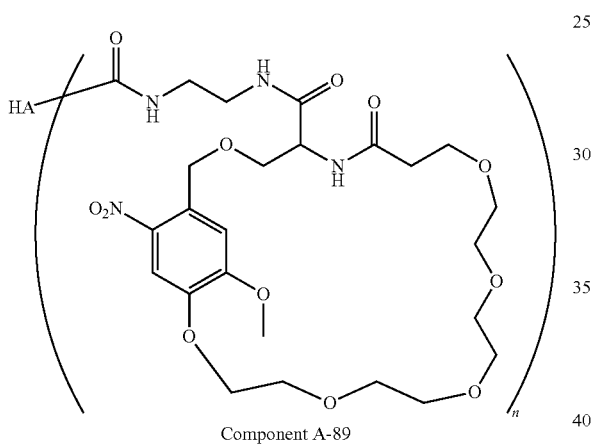

Component A-89

(1) Synthesis of Compound 124. According to the method in Example 88, Compound 124 was prepared by conventional chemical means. $^1$H NMR (400 MHz, DMSO): δ=7.71 (s, 1H), 7.17 (s, 1H), 4.96 (s, 2H), 4.42 (m, 1H), 3.97 (s, 3H), 3.72 (d, J=6.3 Hz, 2H), 3.62-3.55 (m, 2H), 3.52-3.39 (m, 16H), 2.86 (d, J=7.6 Hz, 2H), 2.76 (d, J=7.6 Hz, 2H), 2.49-2.35 (m, 2H). MS (ESI): [M+Na] 559.2642.

(2) Synthesis of Component A-89. To a solution of hyaluronic acid sodium (2 g, 340 kDa) dissolved in 100 mL 0.01 M 2-(N-morpholine) mesylate (MES) buffer solution (pH=5.2) was added Compound 124 (111 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-89 (1.82 g). According to the nuclear magnetic resonance spectrum, the grafting degree of Compound 124 can be calculated to be about 3.15%.

Example 90: Synthesis of Component A-90

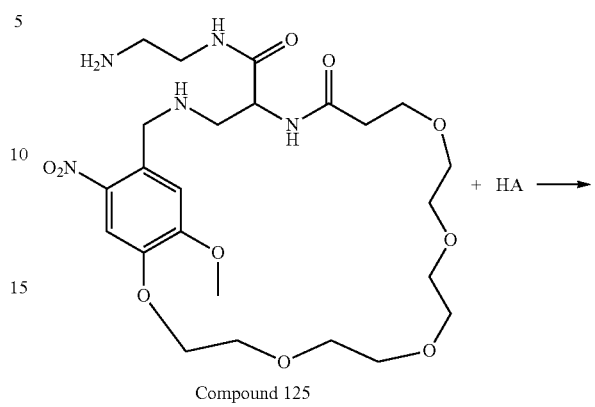

Compound 125

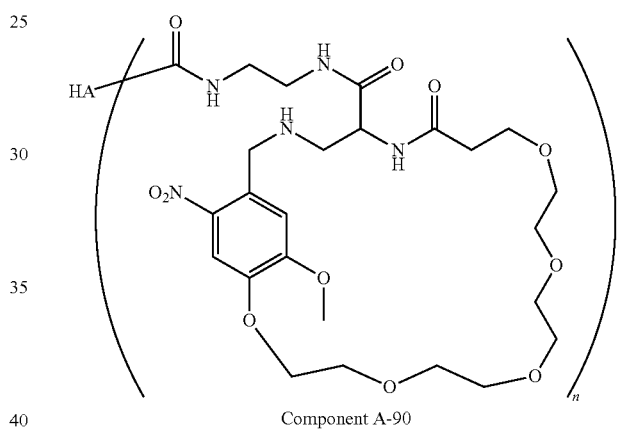

Component A-90

(1) Synthesis of Compound 125. According to the method in Example 88, Compound 125 was prepared by conventional chemical means. $^1$H NMR (400 MHz, DMSO): δ=7.71 (s, 1H), 7.17 (s, 1H), 4.26 (s, 2H), 4.42 (m, 1H), 3.97 (s, 3H), 3.42 (d, J=6.3 Hz, 2H), 3.62-3.55 (m, 2H), 3.52-3.39 (m, 16H), 2.86 (d, J=7.6 Hz, 2H), 2.76 (d, J=7.6 Hz, 2H), 2.49-2.35 (m, 2H). MS (ESI): [M+Na] 558.2725.

(2) Synthesis of Component A-90. To a solution of hyaluronic acid sodium (2 g, 340 kDa) dissolved in 100 mL 0.01 M 2-(N-morpholine) mesylate (MES) buffer solution (pH=5.2) was added Compound 125 (111 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-90 (1.87 g). According to the nuclear magnetic resonance spectrum, the grafting degree of Compound 125 can be calculated to be about 3.27%.

Example 91: Synthesis of Component A-91

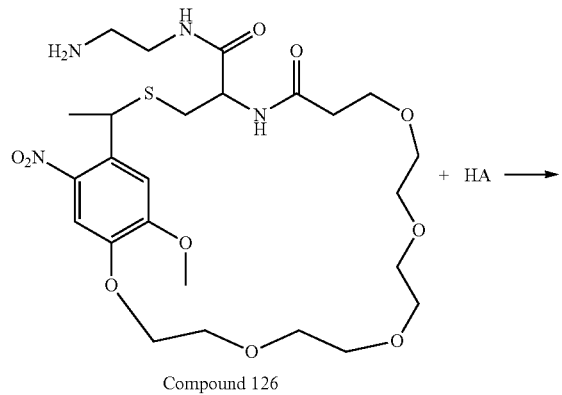

Compound 126

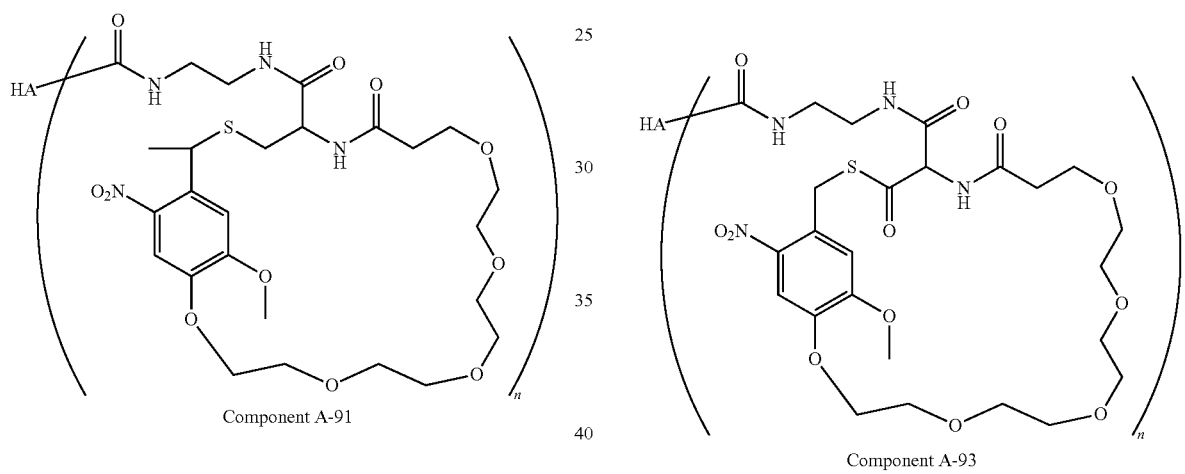

Component A-91

(1) Synthesis of Compound 126. According to the method in Example 88, Compound 126 was prepared by conventional chemical means. $^1$H NMR (400 MHz, DMSO): δ=7.71 (s, 1H), 7.17 (s, 1H), 5.16 (m, 1H), 4.42 (m, 1H), 3.97 (s, 3H), 3.72 (d, J=6.3 Hz, 2H), 3.62-3.55 (m, 2H), 3.52-3.39 (m, 16H), 2.86 (d, J=7.6 Hz, 2H), 2.76 (d, J=7.6 Hz, 2H), 2.49-2.35 (m, 2H), 1.33 (d, J=6.9 Hz, 3H). MS (ESI): [M+Na] 589.2517.

(2) Synthesis of Component A-91. To a solution of hyaluronic acid sodium (2 g, 340 kDa) dissolved in 100 mL 0.01 M 2-(N-morpholine) mesylate (MES) buffer solution (pH=5.2) was added Compound 126 (118 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-91 (1.73 g). According to the nuclear magnetic resonance spectrum, the grafting degree of Compound 126 can be calculated to be about 3.14%.

Example 93: Synthesis of Component A-93

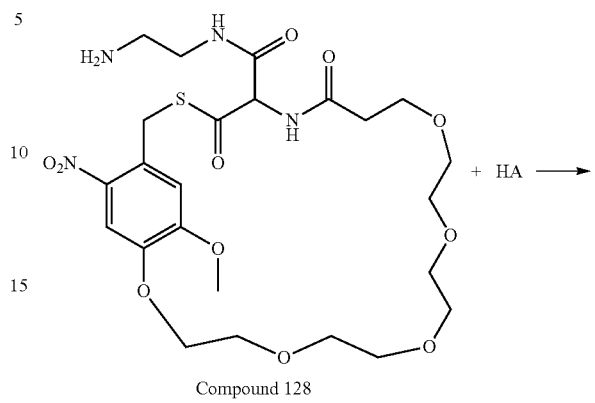

Compound 128

Component A-93

(1) Synthesis of Compound 128. According to the method in Example 88, Compound 128 was prepared by conventional chemical means. $^1$H NMR (400 MHz, DMSO): δ=7.71 (s, 1H), 7.17 (s, 1H), 5.82 (m, 1H), 4.76 (s, 2H), 3.97 (s, 3H), 3.62-3.55 (m, 2H), 3.52-3.39 (m, 16H), 2.86 (d, J=7.6 Hz, 2H), 2.76 (d, J=7.6 Hz, 2H), 2.49-2.35 (m, 2H). MS (ESI): [M+Na] 589.2143.

(2) Synthesis of Component A-93. To a solution of hyaluronic acid sodium (2 g, 340 kDa) dissolved in 100 mL 0.01 M 2-(N-morpholine) mesylate (MES) buffer solution (pH=5.2) was added Compound 128 (118 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-93 (1.73 g). According to the nuclear magnetic resonance spectrum, the grafting degree of Compound 128 can be calculated to be about 3.15%.

Example 94: Synthesis of Component A-94

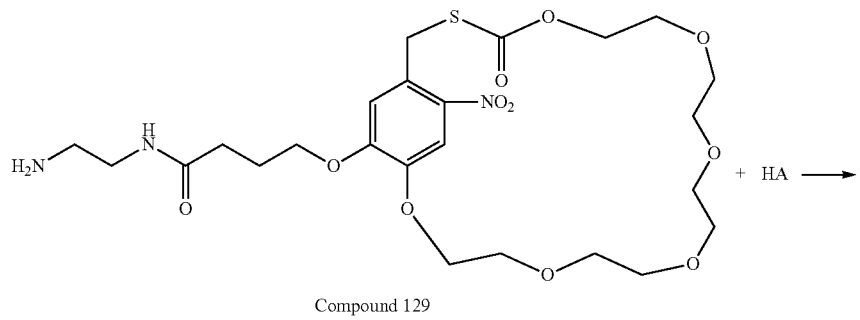

Compound 129

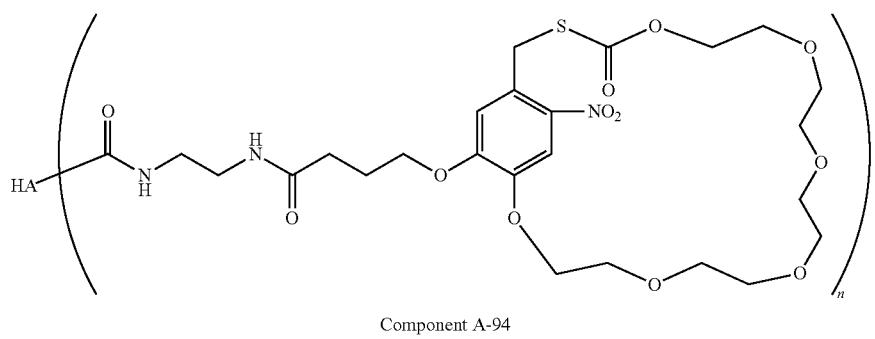

Component A-94

(1) Synthesis of Compound 129. According to the method in Example 88, Compound 129 was prepared by conventional chemical means. $^1$H NMR (400 MHz, DMSO): δ=7.71 (s, 1H), 7.17 (s, 1H), 4.76 (s, 2H), 4.13 (t, J=7.2 Hz, 2H), 3.62-3.55 (m, 2H), 3.52-3.39 (m, 16H), 2.86 (d, J=7.6 Hz, 2H), 2.76 (d, J=7.6 Hz, 2H), 2.49-2.35 (m, 2H), 2.44 (t, J=7.2 Hz, 2H), 2.26-2.17 (m, 2H). MS (ESI): [M+Na] 575.2332.

(2) Synthesis of Component A-94. To a solution of hyaluronic acid sodium (2 g, 340 kDa) dissolved in 100 mL 0.01 M 2-(N-morpholine) mesylate (MES) buffer solution (pH=5.2) was added Compound 129 (115 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-94 (1.84 g). According to the nuclear magnetic resonance spectrum, the grafting degree of Compound 129 can be calculated to be about 2.47%.

Example 95: Synthesis of Component A-95

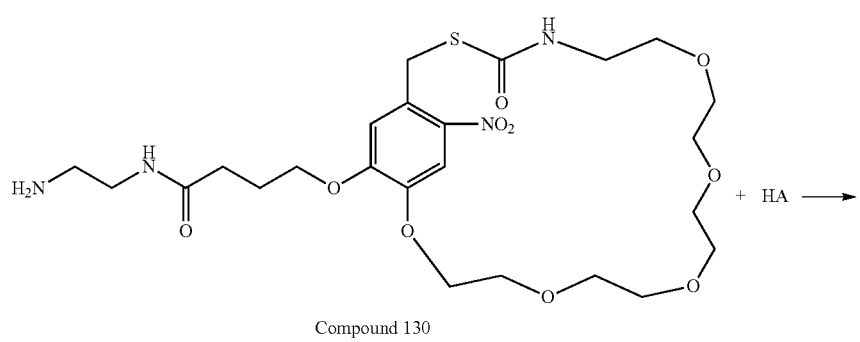

Compound 130

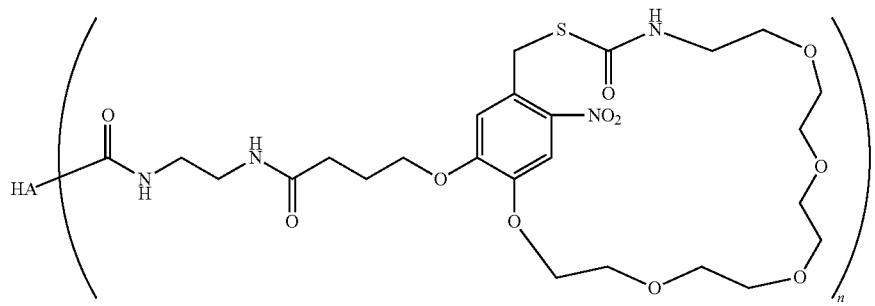

Component A-95

(1) Synthesis of Compound 130. According to the method in Example 88, Compound 130 was prepared by conventional chemical means. $^1$H NMR (400 MHz, DMSO): δ=7.71 (s, 1H), 7.17 (s, 1H), 4.76 (s, 2H), 4.13 (t, J=7.2 Hz, 2H), 3.62-3.55 (m, 2H), 3.52-3.39 (m, 16H), 2.86 (d, J=7.6 Hz, 2H), 2.76 (d, J=7.6 Hz, 2H), 2.69-2.55 (m, 2H), 2.44 (t, J=7.2 Hz, 2H), 2.26-2.17 (m, 2H). MS (ESI): [M+Na] 576.2242.

(2) Synthesis of Component A-95. To a solution of hyaluronic acid sodium (2 g, 340 kDa) dissolved in 100 mL 0.01 M 2-(N-morpholine) mesylate (MES) buffer solution (pH=5.2) was added Compound 130 (115 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-95 (1.75 g). According to the nuclear magnetic resonance spectrum, the grafting degree of Compound 130 can be calculated to be about 3.07%.

Example 98: Synthesis of Component A-98

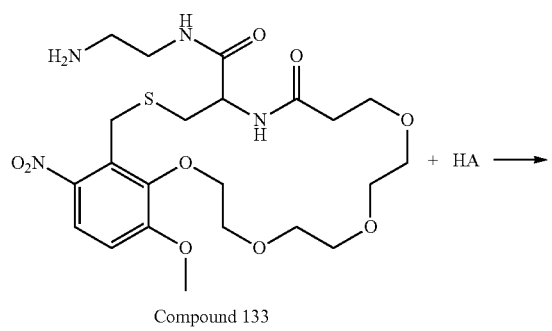

Compound 133

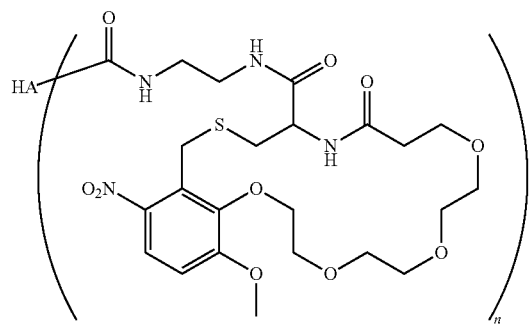

Component A-98

(1) Synthesis of Compound 133. According to the method in Example 88, Compound 133 was prepared by conventional chemical means. $^1$H NMR (400 MHz, DMSO): δ=8.11 (m, 1H), 7.27 (m, 1H), 4.76 (s, 2H), 4.42 (m, 1H), 3.97 (s, 3H), 3.72 (d, J=6.3 Hz, 2H), 3.62-3.55 (m, 2H), 3.52-3.39 (m, 12H), 2.86 (d, J=7.6 Hz, 2H), 2.76 (d, J=7.6 Hz, 2H), 2.49-2.35 (m, 2H). MS (ESI): [M+Na] 531.2143.

(2) Synthesis of Component A-98. To a solution of hyaluronic acid sodium (2 g, 340 kDa) dissolved in 100 mL 0.01 M 2-(N-morpholine) mesylate (MES) buffer solution (pH=5.2) was added Compound 133 (106 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-98 (1.78 g). According to the nuclear magnetic resonance spectrum, the grafting degree of Compound 133 can be calculated to be about 3.31%.

Example 99: Synthesis of Component A-99

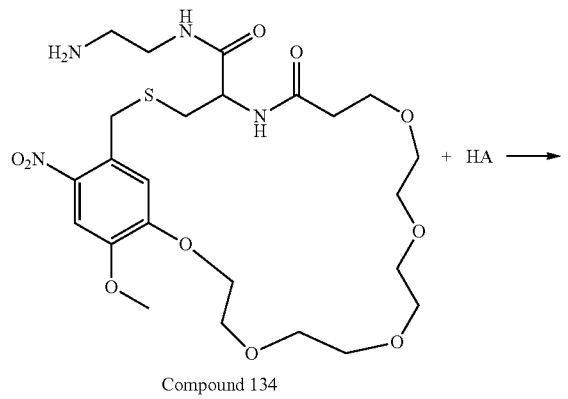

Compound 134

Example 100: Synthesis of Component A-100

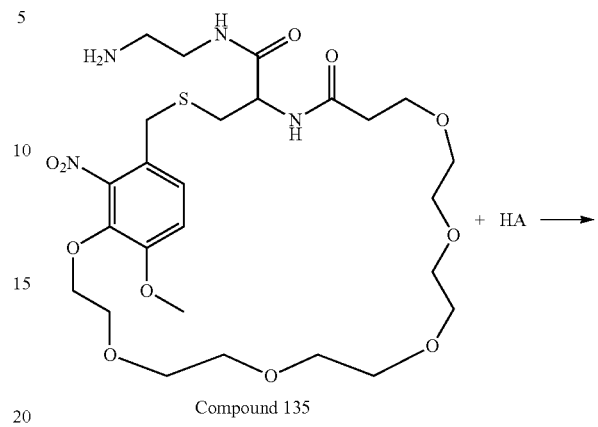

Compound 135

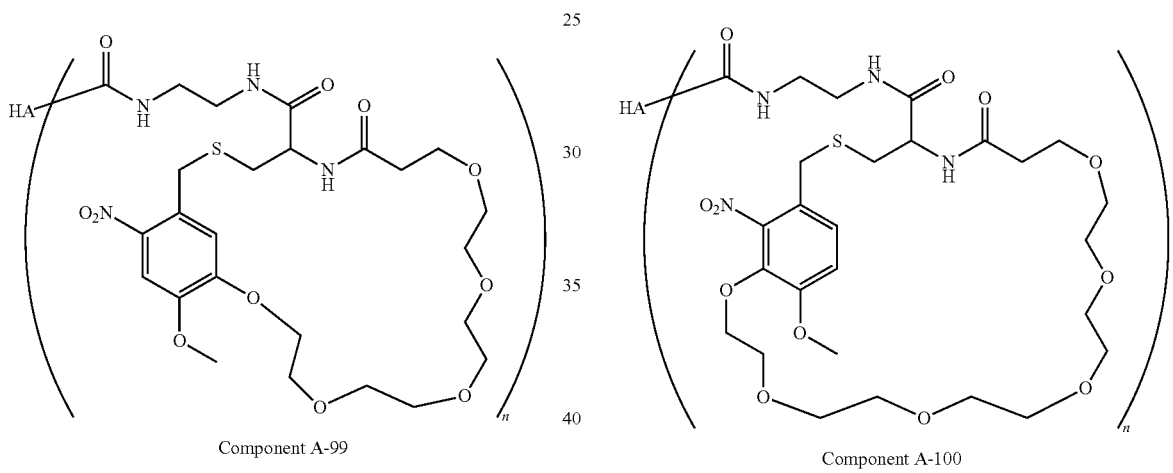

Component A-99                                      Component A-100

(1) Synthesis of Compound 134. According to the method in Example 88, Compound 134 was prepared by conventional chemical means. $^1$H NMR (400 MHz, DMSO): δ=7.71 (s, 1H), 7.17 (s, 1H), 4.76 (s, 2H), 4.42 (m, 1H), 3.97 (s, 3H), 3.72 (d, J=6.3 Hz, 2H), 3.62-3.55 (m, 2H), 3.52-3.39 (m, 16H), 2.86 (d, J=7.6 Hz, 2H), 2.76 (d, J=7.6 Hz, 2H), 2.49-2.35 (m, 2H). MS (ESI): [M+Na] 575.2342.

(2) Synthesis of Component A-99. To a solution of hyaluronic acid sodium (2 g, 340 kDa) dissolved in 100 mL 0.01 M 2-(N-morpholine) mesylate (MES) buffer solution (pH=5.2) was added Compound 134 (115 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-99 (1.84 g). According to the nuclear magnetic resonance spectrum, the grafting degree of Compound 134 can be calculated to be about 3.06%.

(1) Synthesis of Compound 135. According to the method in Example 88, Compound 135 was prepared by conventional chemical means. $^1$H NMR (400 MHz, DMSO): δ=7.54 (m, 1H), 7.03 (m, 1H), 4.76 (s, 2H), 4.42 (m, 1H), 3.97 (s, 3H), 3.72 (d, J=6.3 Hz, 2H), 3.62-3.55 (m, 2H), 3.52-3.39 (m, 20H), 2.86 (d, J=7.6 Hz, 2H), 2.76 (d, J=7.6 Hz, 2H), 2.49-2.35 (m, 2H). MS (ESI): [M+Na] 619.2652.

(2) Synthesis of Component A-100. To a solution of hyaluronic acid sodium (2 g, 340 kDa) dissolved in 100 mL 0.01 M 2-(N-morpholine) mesylate (MES) buffer solution (pH=5.2) was added Compound 135 (124 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-100 (1.84 g). According to the nuclear magnetic resonance spectrum, the grafting degree of Compound 135 can be calculated to be about 3.16%.

Example 101: Synthesis of Component A-101

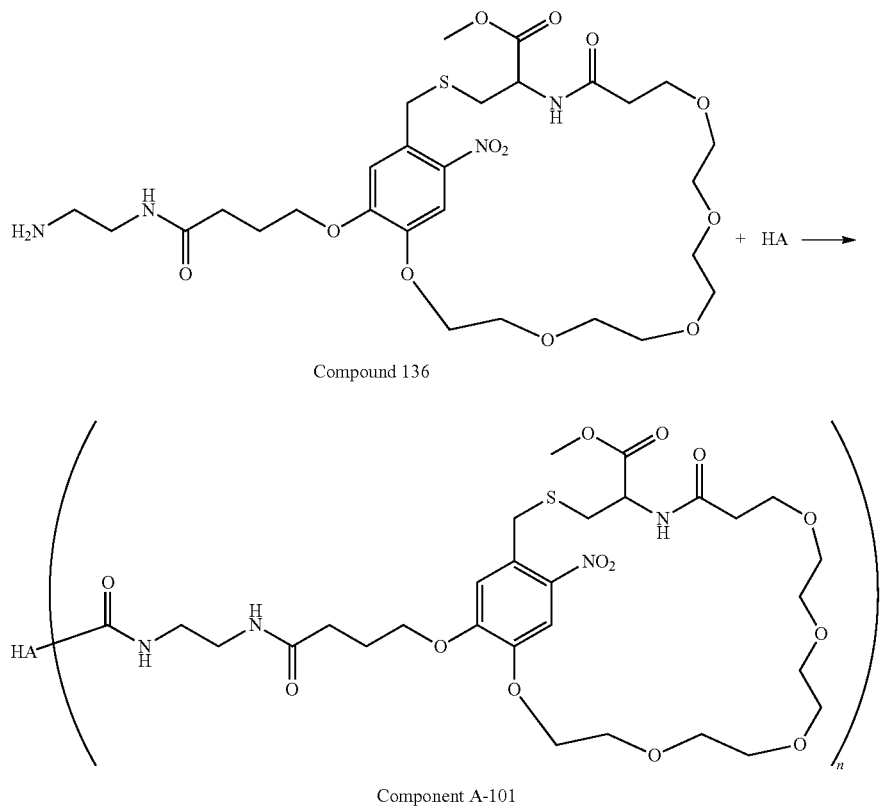

Compound 136

Component A-101

(1) Synthesis of Compound 136. According to the method in Example 88, Compound 136 was prepared by conventional chemical means. $^1$H NMR (400 MHz, DMSO): δ=7.71 (s, 1H), 7.17 (s, 1H), 4.76 (s, 2H), 4.42 (m, 1H), 4.13 (t, J=7.2 Hz, 2H), 3.73 (s, 3H), 3.72 (d, J=6.3 Hz, 2H), 3.62-3.55 (m, 2H), 3.52-3.39 (m, 16H), 2.86 (d, J=7.6 Hz, 2H), 2.76 (d, J=7.6 Hz, 2H), 2.49-2.35 (m, 2H), 2.44 (t, J=7.2 Hz, 2H), 2.26-2.17 (m, 2H). MS (ESI): [M+Na] 661.2745.

(2) Synthesis of Component A-101. To a solution of hyaluronic acid sodium (2 g, 340 kDa) dissolved in 100 mL 0.01 M 2-(N-morpholine) mesylate (MES) buffer solution (pH=5.2) was added Compound 136 (132 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-101 (1.77 g). According to the nuclear magnetic resonance spectrum, the grafting degree of Compound 136 can be calculated to be about 3.21%.

Example 102: Synthesis of Component A-102

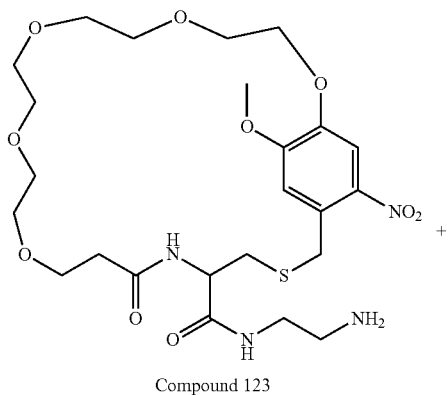

Compound 123

-continued

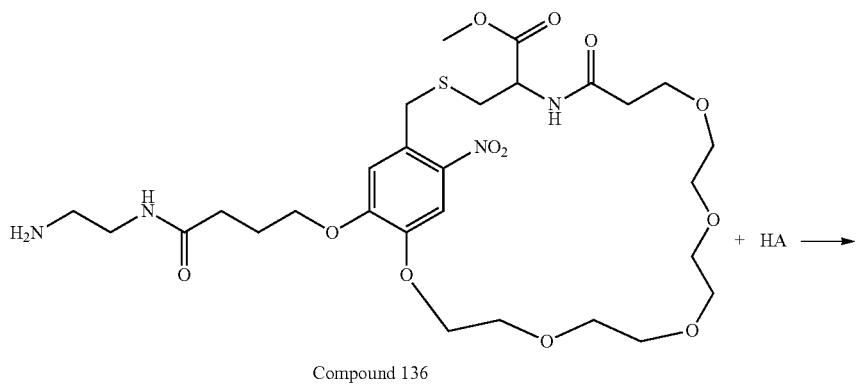
Compound 136

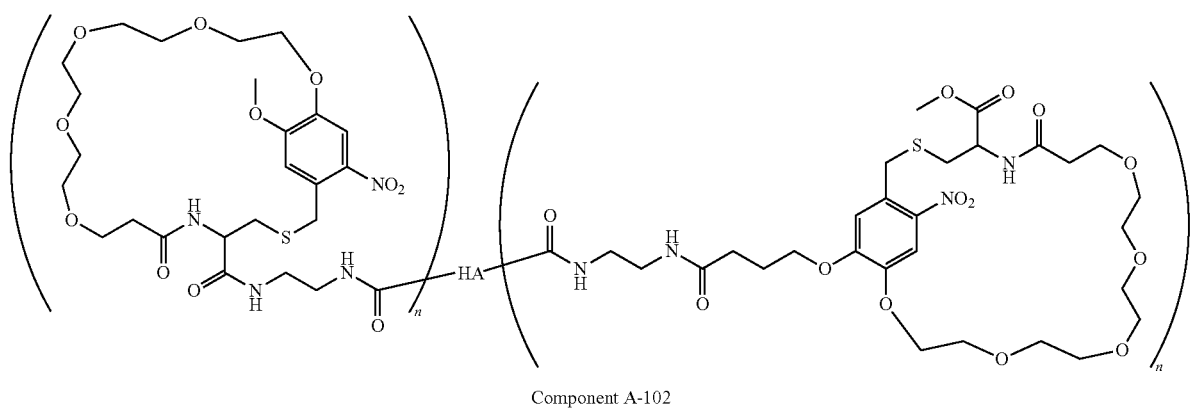
Component A-102

Synthesis of Component A-102. To a solution of hyaluronic acid sodium (2 g, 340 kDa) dissolved in 100 mL 0.01 M 2-(N-morpholine) mesylate (MES) buffer solution (pH=5.2) was added cNB mixture (Compound 123/Compound 136, 60 mg, mass ratio 1:1) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive hyaluronic acid derivative Compound A-102 (1.89 g). According to the nuclear magnetic resonance spectrum, the grafting degree of the cNB mixture (Compound 123/Compound 136) can be calculated to be about 3.52%.

Example 103: Synthesis of Component A-103

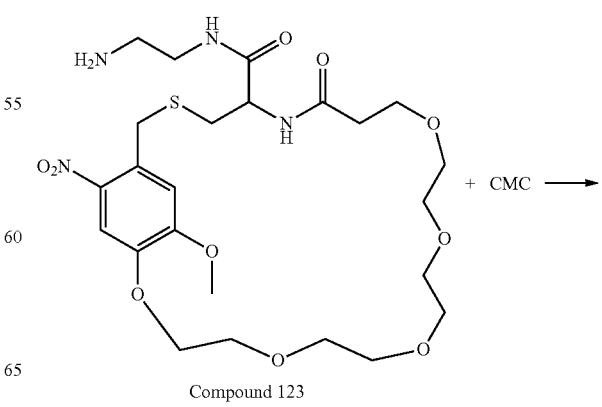
Compound 123

-continued

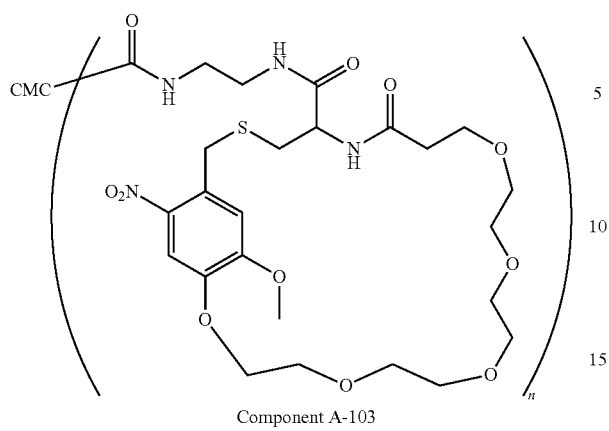

Component A-103

-continued

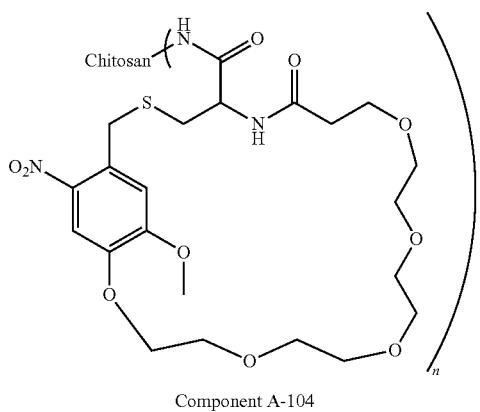

Component A-104

Synthesis of Component A-103. To a solution of carboxymethyl cellulose (2 g, 90 kDa) dissolved in 100 mL 0.01 M 2-(N-morpholine) mesylate (MES) buffer solution (pH=5.2) was added Compound 123 (115 mg, 0.2 mmol) dissolved in 10 mL dimethyl sulfoxide (DMSO). Then, DMTMM (0.4 g, 1.5 mmol) dissolved in 3 mL water was added into the above solution three times with an interval of 1 h, and the mixture was stirred for 24 hours in the dark 35° C. Then, the reaction solution was poured into a dialysis bag (MWCO 7000), dialyzed against deionized water for 2-3 d, and lyophilized to obtain a photosensitive carboxymethyl cellulose derivative Compound A-103 (1.71 g). According to the nuclear magnetic resonance spectrum, the grafting degree of Compound 123 can be calculated to be about 2.41%.

Example 104: Synthesis of Component A-104

(1) Synthesis of Compound 137. According to the method in Example 88, Compound 137 was prepared by conventional chemical means. $^1$H NMR (400 MHz, DMSO): δ=7.71 (s, 1H), 7.17 (s, 1H), 4.76 (s, 2H), 4.42 (m, 1H), 3.97 (s, 3H), 3.72 (d, J=6.3 Hz, 2H), 3.62-3.55 (m, 2H), 3.52-3.39 (m, 16H), 2.49-2.35 (m, 2H). MS (ESI): [M+Na] 533.1845.

(2) Synthesis of Component A-104. To a suspension liquid of chitosan (1 g) dissolved in 75 mL isopropanol was sequentially added Compound 137 (0.2 g, 0.35 mmol), EDC-HCl (0.76 g, 3.96 mmol) and NHS (0.46 g, 4.0 mmol), and the reaction was stirred at room temperature for 48 h. After completion of the reaction, the mixture solution was dialyzed with diluted hydrochloric acid solution containing sodium chloride (pH=3.5) for 1 d, dialyzed with distilled water for 1 d, and then freeze-dried to obtain photosensitive chitosan derivatives Compound A-104 (0.82 g). According to its nuclear magnetic resonance spectrum, the grafting degree of the Compound 137 can be calculated to be about 12.5%.

Example 105: Synthesis of Component A-105

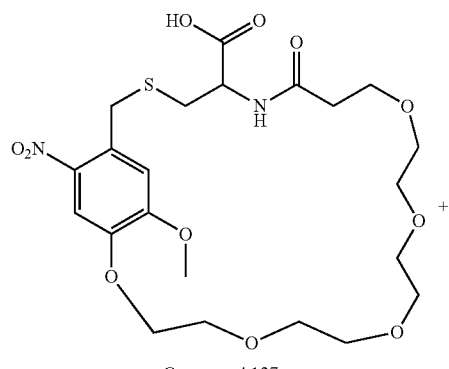

Compound 137

Chitosan ⟶

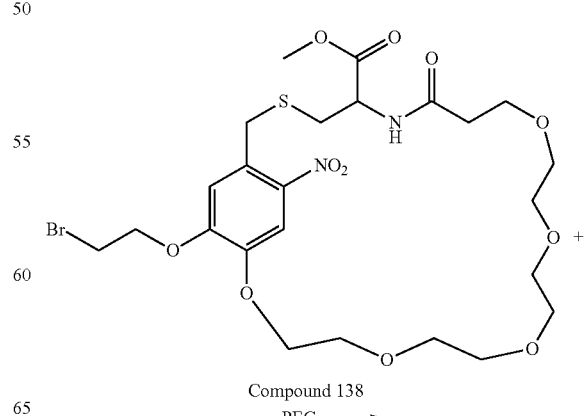

Compound 138

PEG ⟶

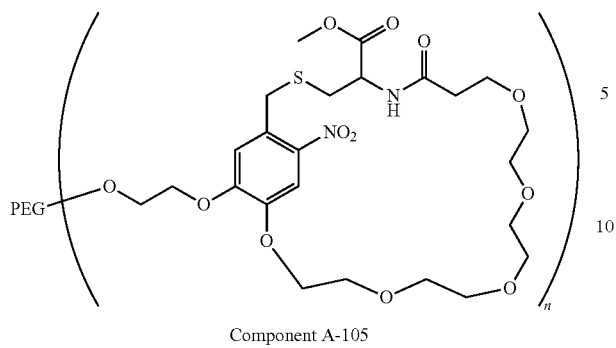

Component A-105

(1) Synthesis of Compound 138. According to the method in Example 88, Compound 138 was prepared by conventional chemical means. $^1$H NMR (400 MHz, DMSO): δ=7.71 (s, 1H), 7.17 (s, 1H), 4.76 (s, 2H), 4.42 (m, 1H), 4.13 (t, J=6.1 Hz, 2H), 3.93 (s, 3H), 3.72 (d, J=6.3 Hz, 2H), 3.62-3.55 (m, 2H), 3.52-3.39 (m, 16H), 3.04 (t, J=7.2 Hz, 2H), 2.49-2.35 (m, 2H). MS (ESI): [M+Na] 640.1134.

(2) Synthesis of Component A-105. To a solution of PEG-4OH (1 g, 0.05 mmol) dissolved in anhydrous acetonitrile was added $K_2CO_3$ (55.3 mg, 0.4 mmol) and stirred for 30 min. Then the solution was added Compound 138 (0.23 g, 0.4 mmol) and continued to react at room temperature for 24 h. After the reaction was completed, most of the solvent was removed, reprecipitated in diethyl ether, and washed several times to obtain the photosensitive polyethelene glycol derivative Compound A-105 (0.85 g). According to its nuclear magnetic resonance spectrum, the grafting degree of the Compound 138 can be calculated to be about 95.3%.

Example 106: Synthesis of Component A-106

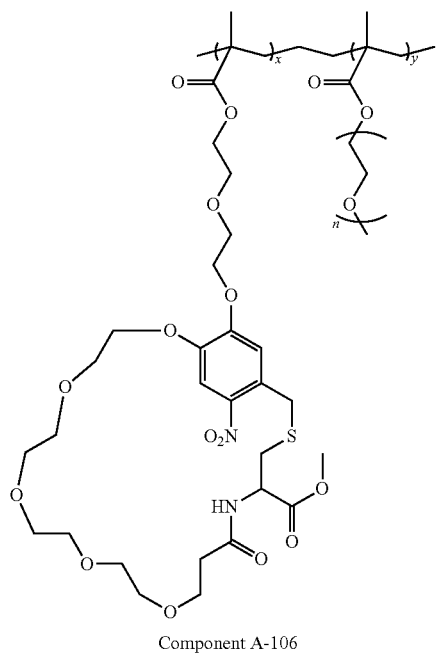

Component A-106

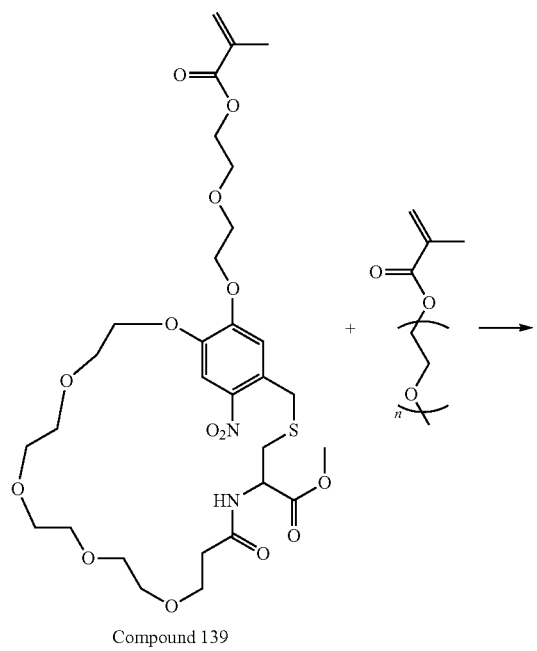

Compound 139

(1) Synthesis of Compound 139. According to the method in Example 88, Compound 139 was prepared by conventional chemical means. $^1$H NMR (400 MHz, DMSO): δ=7.71 (s, 1H), 7.17 (s, 1H), 6.25 (s, 1H), 5.68 (s, 1H), 4.76 (s, 2H), 4.42 (m, 1H), 4.13 (t, J=6.1 Hz, 2H), 3.93 (s, 3H), 3.79 (t, J=6.1 Hz, 2H), 3.72 (d, J=6.3 Hz, 2H), 3.70 (t, J=7.2 Hz, 2H), 3.62-3.55 (m, 2H), 3.56 (t, J=7.2 Hz, 2H), 3.52-3.39 (m, 16H), 2.49-2.35 (m, 2H), 1.87 (s, 3H). MS (ESI): [M+Na] 689.2523.

(2) Synthesis of Component A-106. Compound 139 (0.28 g, 0.63 mmol), comonomer PEG-MA (0.882 g, 2.52 mmol) and the initiator azobisisobutyronitrile (11 mg) were added into the Shrek tube and dissolved by anhydrous THF. After repeated freeze-vacuum cycle operation, the reaction system was reacted at 75° C. for 24 h. After completion of the reaction, the solution was poured into cold diethyl ether and reprecipitated several times to obtain the photosensitive copolymer derivative Compound A-106 (0.85 g). According to its nuclear magnetic resonance spectrum, it can be calculated that the content of the Compound 139 in the copolymer is about 15.4%. According to GPC, the molecular weight of the synthetic polymer is about 25 kDa. According to the feed ratio, n is 12, x is 10, and y is 40.

Example 107: Synthesis of Component A-107

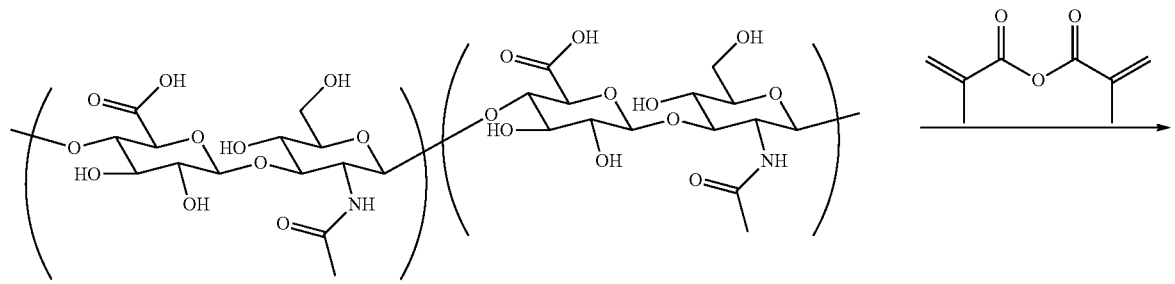

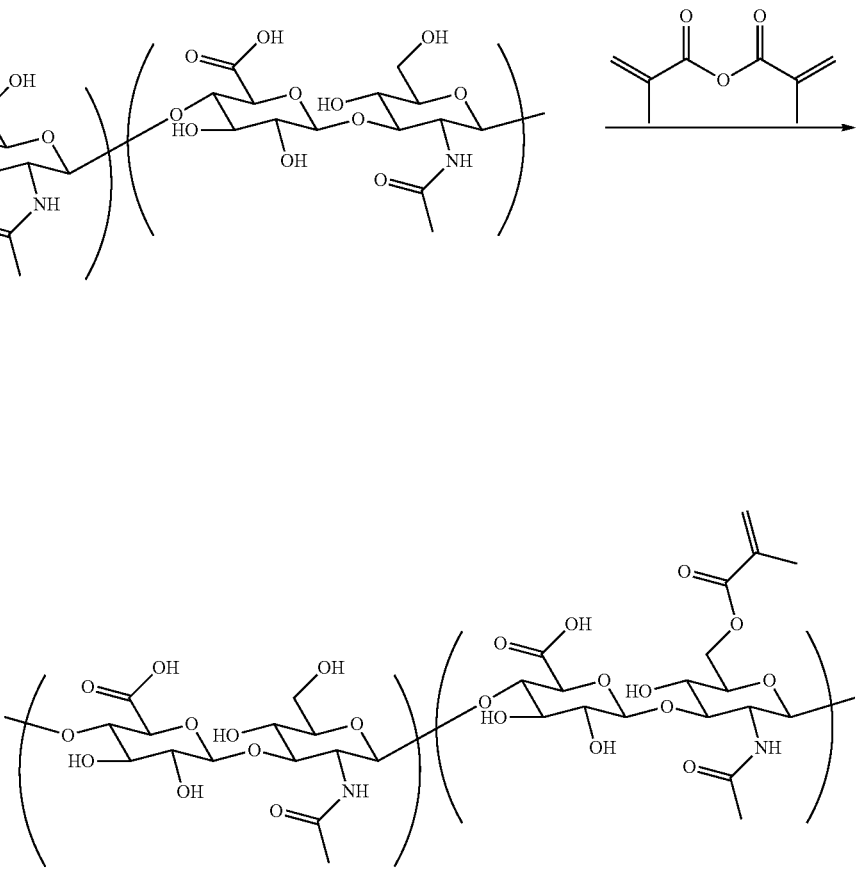

Synthesis of Component A-107. To a solution of hyaluronic acid (1 g, 48 kDa) dissolved in 100 mL deionized water was added 4 mL methacrylic anhydride at 0-4° C. The solution was slowly added 2 mL 5 M NaOH and reacted for 24 h. Then, the reaction solution was poured into a dialysis bag (MWCO 3500), dialyzed against deionized water for 2-3 d, and lyophilized to obtain a photosensitive hyaluronic acid derivative Compound A-107 (0.92 g). According to the nuclear magnetic resonance spectrum, the double bond content can be calculated to be about 54%.

Example 108: Synthesis of Component A-108

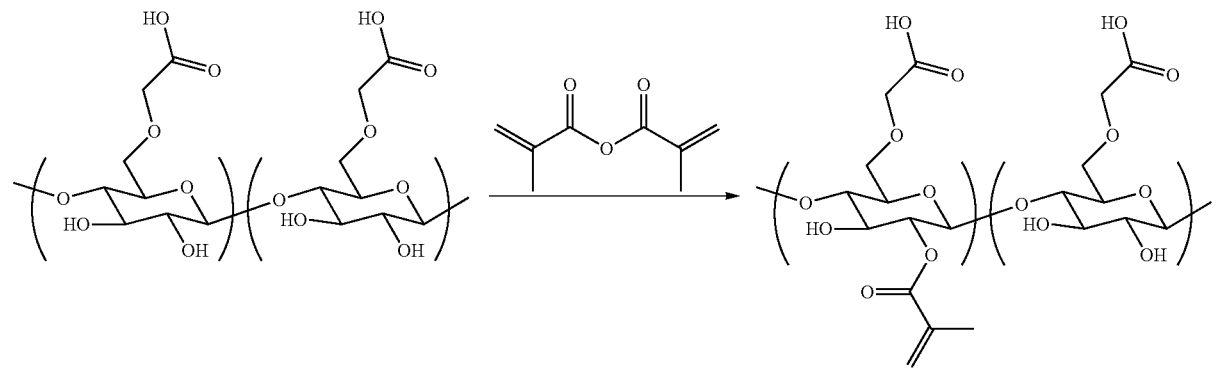

Synthesis of Component A-108. To a solution of carboxymethyl cellulose (1 g, 90 kDa) dissolved in 100 mL deionized water was added 4 mL methacrylic anhydride at 0-4° C. The solution was slowly added 2 mL 5 M NaOH and reacted for 24 h. Then, the reaction solution was poured into a dialysis bag (MWCO 3500), dialyzed against deionized water for 2-3 d, and lyophilized to obtain a photosensitive carboxymethyl cellulose derivative Compound A-108 (0.89 g). According to the nuclear magnetic resonance spectrum, the double bond content can be calculated to be about 43%.

Example 109: Synthesis of Component A-109

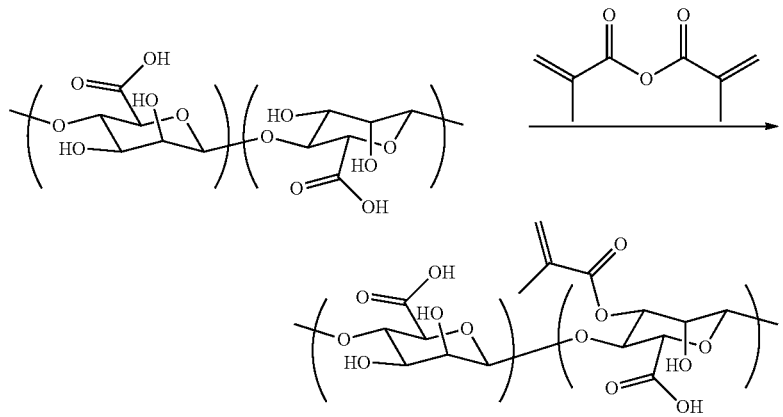

Synthesis of Component A-109. To a solution of alginate (1 g, 48 kDa) in 100 mL deionized water was added 4 mL methacrylic anhydride at 0-4° C. The solution was slowly added 2 mL 5 M NaOH and reacted for 24 h. Then, the reaction solution was poured into a dialysis bag (MWCO 3500), dialyzed against deionized water for 2-3 d, and lyophilized to obtain a photosensitive carboxymethyl cellulose derivative Compound A-109 (0.87 g). According to the nuclear magnetic resonance spectrum, the double bond content can be calculated to be about 57%.

Example 110: Synthesis of Component A-110

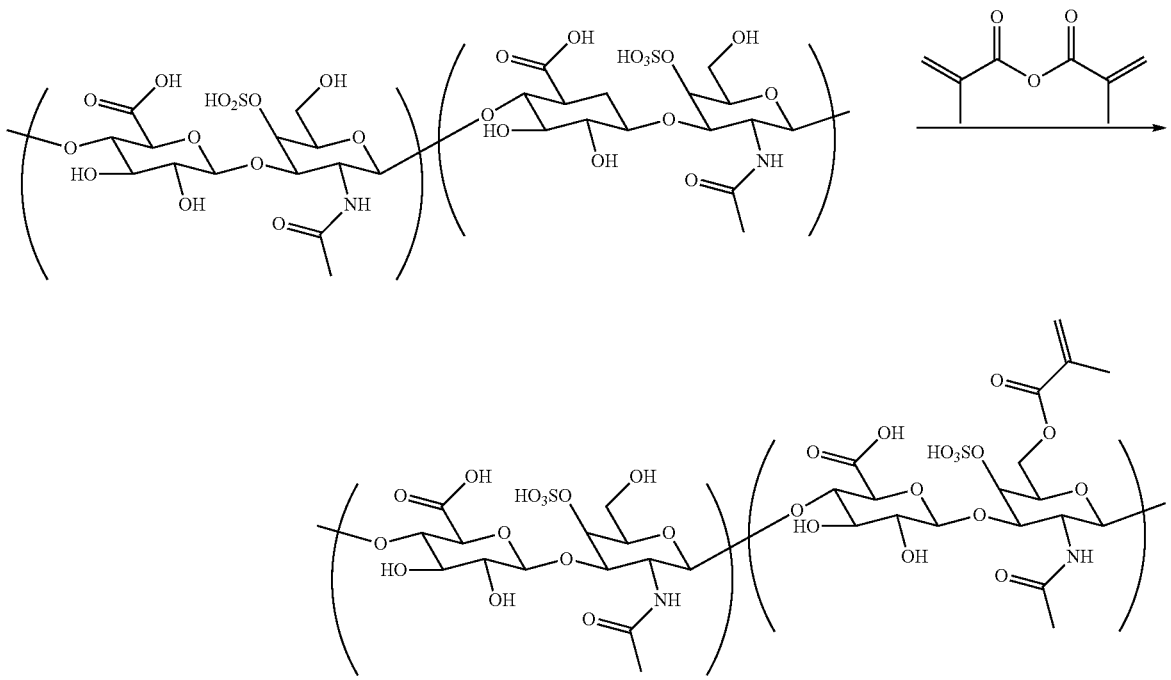

Synthesis of Component A-110. To a solution of chondroitin sulfate (1 g) in 100 mL deionized water was added 4 mL methacrylic anhydride at 0-4° C. The solution was slowly added 2 mL 5 M NaOH and reacted for 24 h. Then, the reaction solution was poured into a dialysis bag (MWCO 3500), dialyzed against deionized water for 2-3 d, and lyophilized to obtain a photosensitive carboxymethyl cellulose derivative Compound A-110 (0.91 g). According to the nuclear magnetic resonance spectrum, the double bond content can be calculated to be about 49%.

Example 111: Synthesis of Component A-111

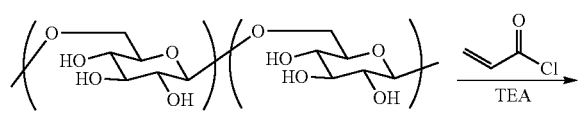

-continued

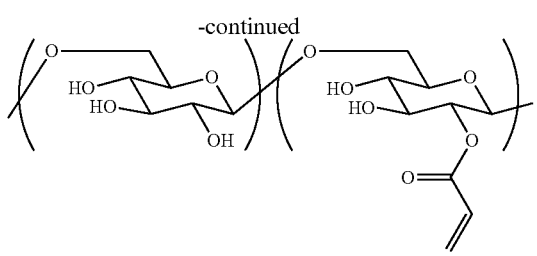

Synthesis of Component A-111. To a solution of dextran (6 g, 70 kDa) dissolved in 60 mL anhydrous dimethyl sulfoxide (DMSO) was added 2 mL triethylamine (TEA) and 0.56 mL acryloyl chloride dissolved in 10 mL dichloromethane (DCM), the mixture was reacted for 10 h. After completion of the reaction, the reaction solution was poured into ethanol to reprecipitate. The crude product obtained by filtration was redissolved in deionized water and dialyzed for 2-3 d, and then lyophilized to obtain photosensitive dextran derivative Compound A-111 (5.8 g). According to the nuclear magnetic resonance spectrum, the content of the double bond can be calculated to be about 24%.

Example 112: Synthesis of Component A-112

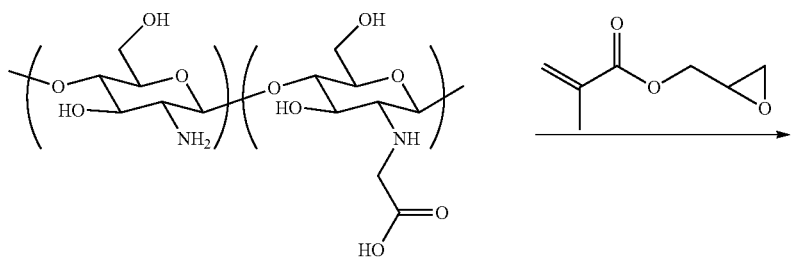

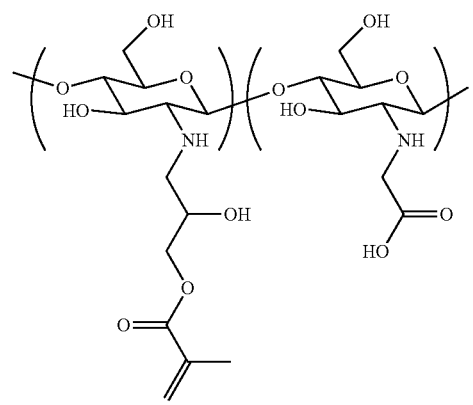

Synthesis of Component A-112. To a solution of carboxymethylchitosan (1 g) dissolved in 100 mL deionized water was added 4 mL glycidyl methacrylate and 2 mL 5M NaOH at 40° C., the mixture was reacted for 2-3 h. The reaction solution was poured into a dialysis bag (MWCO 3500), dialyzed against deionized water for 2-3 d, and freeze-dried to obtain a photosensitive carboxymethylchitosan derivative Compound A-112 (0.88 g). According to the nuclear magnetic resonance spectrum, the content of the double bond can be calculated to be about 32%.

Example 113: Synthesis of Component A-113

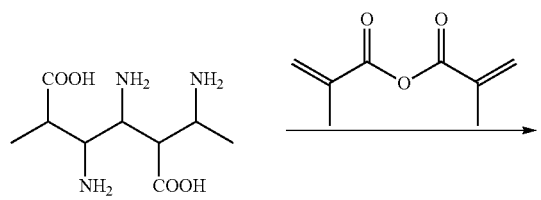

Synthesis of Component A-113. To a solution of gelatin (1 g) dissolved in 10 mL D-PBS was added 0.5 mL methacrylic anhydride, and the mixture was reacted for 2-3 h at 50° C. After completion of the reaction, the system was diluted with 40 mL D-PBS. Then, it was poured into a dialysis bag (MWCO 3500), dialyzed against deionized water for 2-3 d, and lyophilized to obtain a photosensitive gelatin derivative Compound A-113 (0.93 g). According to the nuclear magnetic resonance spectrum, the content of the double bond can be calculated to be about 56%.

Example 114: Synthesis of Component A-114

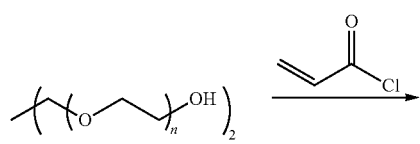

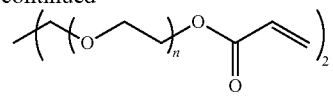

Synthesis of Component A-114. To a solution of PEG-20H (10 kDa, 10 g) dissolved in anhydrous dichloromethane was added triethylamine (0.28 mL, 2 mmol) and then slowly dropwise added acryloyl chloride (0.18 g, 2 mmol) dissolved in dichloromethane, and the reaction was stirred for 12 h. Then, the reaction solution was poured into a dialysis bag (MWCO 3500), dialyzed against deionized water for 2-3 d, and lyophilized to obtain a photosensitive polyethylene glycol derivative Compound A-114 (9.8 g). According to the nuclear magnetic resonance spectrum, the content of the double bond can be calculated to be about 98%.

Example 115: Synthesis of Component A-115

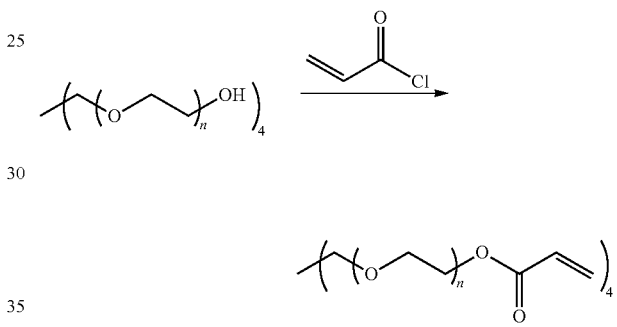

Synthesis of Component A-115. To a solution of PEG-4OH (10 kDa, 10 g) dissolved in anhydrous dichloromethane was added triethylamine (0.56 mL, 4 mmol) and slowly dropwise added acryloyl chloride (0.36 g, 4 mmol) dissolved in dichloromethane, and the reaction was stirred for 12 h. Then, the reaction solution was poured into a dialysis bag (MWCO 3500), dialyzed against deionized water for 2-3 d, and lyophilized to obtain a photosensitive polyethylene glycol derivative Compound A-115 (9.3 g). According to the nuclear magnetic resonance spectrum, the content of the double bond can be calculated to be about 96%.

Example 116: Synthesis of Component A-116

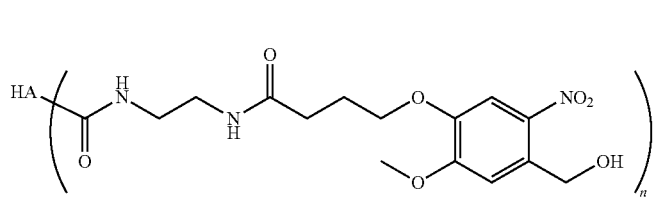

Component A-1

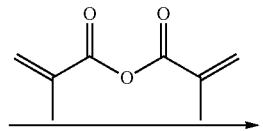

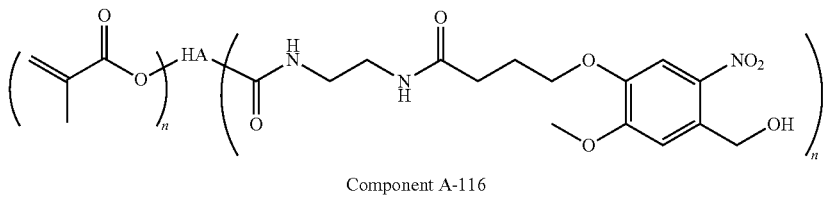

Component A-116

Synthesis of Component A-116. To a solution of Component A-1 chondroitin sulfate (1 g) in 100 mL deionized water was added 4 mL methacrylic anhydride at 0-4° C. The solution was slowly added 2 mL 5M NaOH and reacted for 24 h. Then, the reaction solution was poured into a dialysis bag (MWCO 3500), dialyzed against deionized water for 2-3 d, and lyophilized to obtain a photosensitive carboxymethyl cellulose derivative Compound A-116 (0.91 g). According to the nuclear magnetic resonance spectrum, the double bond content can be calculated to be about 54%.

Example 117: Synthesis of Component A-117

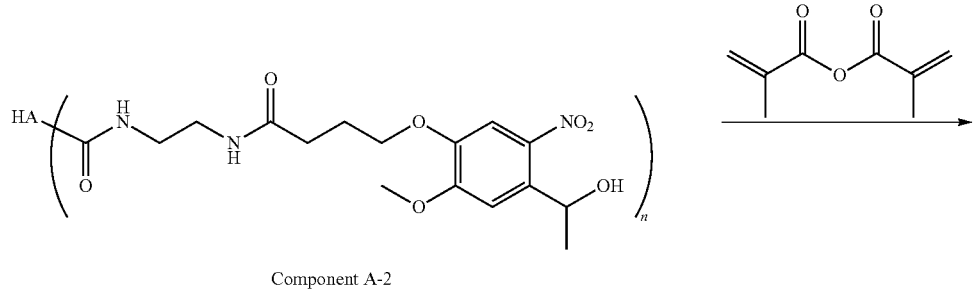

Component A-2

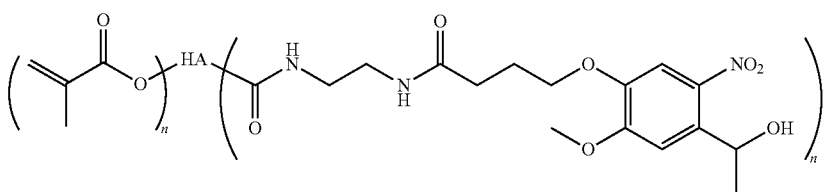

Component A-117

Synthesis of Component A-117. To a solution of Component A-2 dissolved in 100 mL deionized water was added 4 mL methacrylic anhydride at 0-4° C. The solution was slowly added 2 mL 5 M NaOH and reacted for 24 h. Then, the reaction solution was poured into a dialysis bag (MWCO 3500), dialyzed against deionized water for 2-3 d, and lyophilized to obtain a photosensitive carboxymethyl cellulose derivative Compound A-117 (0.87 g). According to the nuclear magnetic resonance spectrum, the double bond content can be calculated to be about 51%.

Example 118: Synthesis of Component A-118

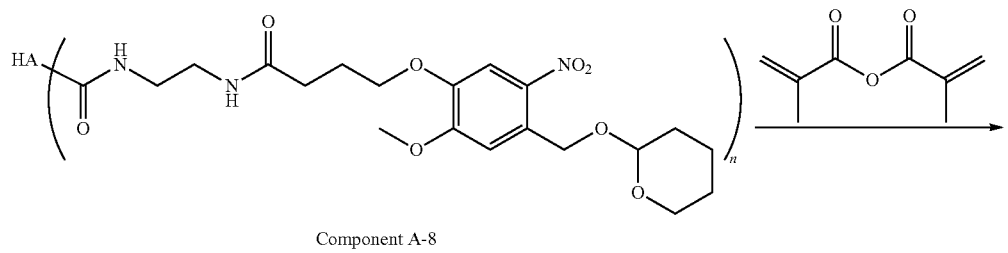

Component A-8

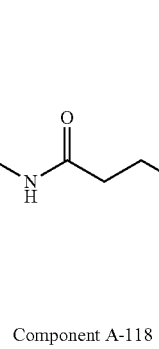

Component A-118

Synthesis of Component A-118. To a solution of Component A-8 dissolved in 100 mL deionized water was added 4 mL methacrylic anhydride at 0-4° C. The solution was slowly added 2 mL 5 M NaOH and reacted for 24 h. Then, the reaction solution was poured into a dialysis bag (MWCO 3500), dialyzed against deionized water for 2-3 d, and lyophilized to obtain a photosensitive carboxymethyl cellulose derivative Compound A-118 (0.86 g). According to the nuclear magnetic resonance spectrum, the double bond content can be calculated to be about 44%.

Example 119: Synthesis of Component A-119

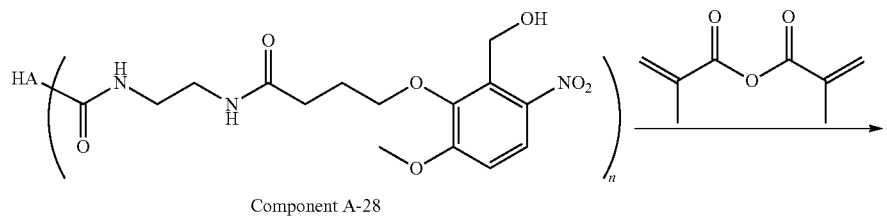

Component A-28

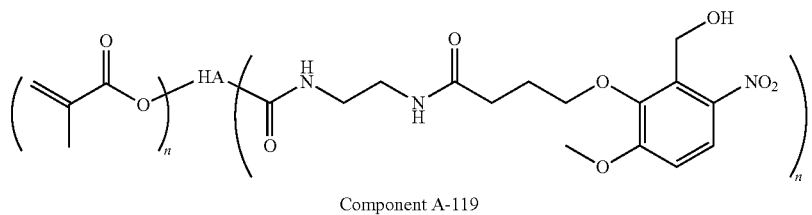

Component A-119

Synthesis of Component A-119. To a solution of Component A-28 dissolved in 100 mL deionized water was added 4 mL methacrylic anhydride at 0-4° C. The solution was slowly added 2 mL 5 M NaOH and reacted for 24 h. Then, the reaction solution was poured into a dialysis bag (MWCO 3500), dialyzed against deionized water for 2-3 d, and lyophilized to obtain a photosensitive carboxymethyl cellulose derivative Compound A-119 (0.85 g). According to the nuclear magnetic resonance spectrum, the double bond content can be calculated to be about 43%.

Example 120: Synthesis of Component A-120

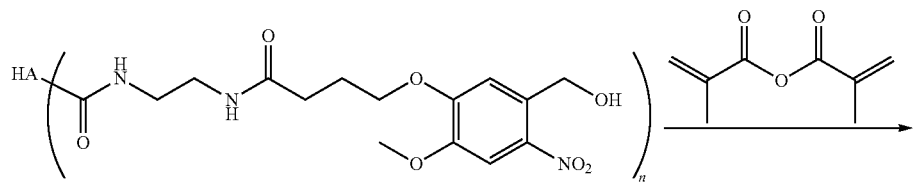

Component A-29

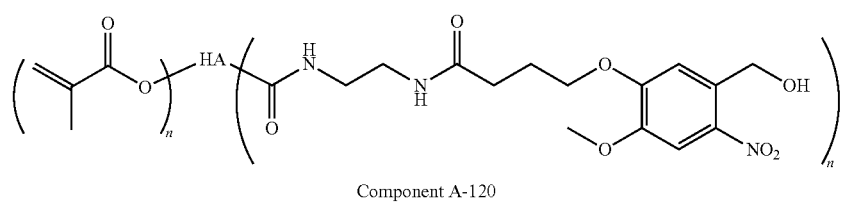

Component A-120

Synthesis of Component A-120. To a solution of Component A-29 dissolved in 100 mL deionized water was added 4 mL methacrylic anhydride at 0-4° C. The solution was slowly added 2 mL 5 M NaOH and reacted for 24 h. Then, the reaction solution was poured into a dialysis bag (MWCO 3500), dialyzed against deionized water for 2-3 d, and lyophilized to obtain a photosensitive carboxymethyl cellulose derivative Compound A-120 (0.93 g). According to the nuclear magnetic resonance spectrum, the double bond content can be calculated to be about 55%.

Example 121: Synthesis of Component A-121

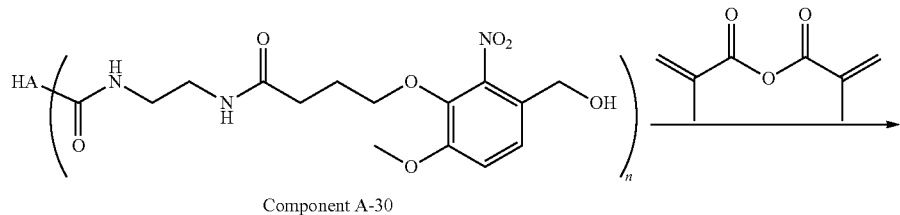

Component A-30

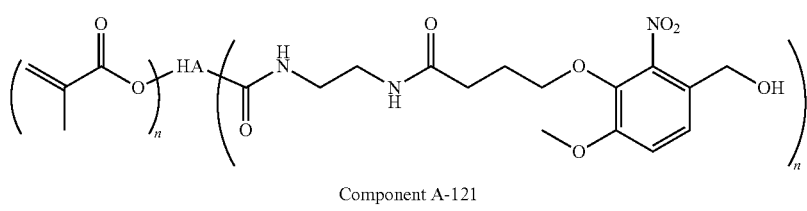

Component A-121

Synthesis of Component A-121. To a solution of Component A-30 dissolved in 100 mL deionized water was added 4 mL methacrylic anhydride at 0-4° C. The solution was slowly added 2 mL 5 M NaOH and reacted for 24 h. Then, the reaction solution was poured into a dialysis bag (MWCO 3500), dialyzed against deionized water for 2-3 d, and lyophilized to obtain a photosensitive carboxymethyl cellulose derivative Compound A-121 (0.85 g). According to the nuclear magnetic resonance spectrum, the double bond content can be calculated to be about 49%.

Example 122: Synthesis of Component A-122

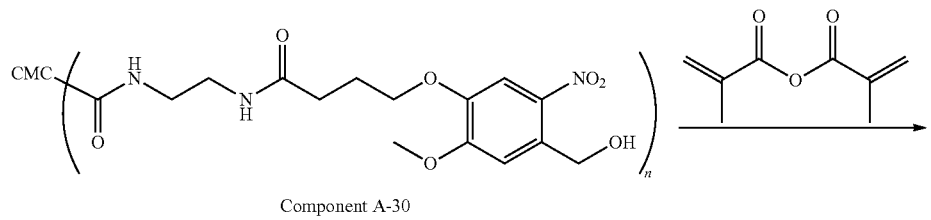
Component A-30

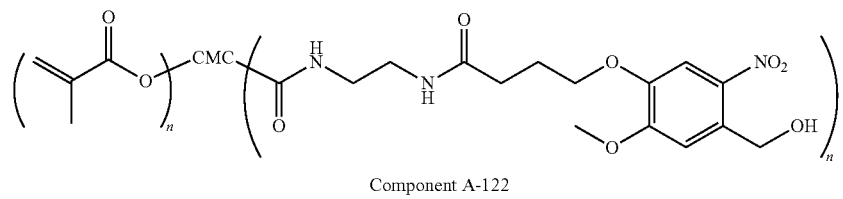
Component A-122

Synthesis of Component A-122. To a solution of Component A-37 dissolved in 100 mL deionized water was added 4 mL methacrylic anhydride at 0-4° C. The solution was slowly added 2 mL 5 M NaOH and reacted for 24 h. Then, the reaction solution was poured into a dialysis bag (MWCO 3500), dialyzed against deionized water for 2-3 d, and lyophilized to obtain a photosensitive carboxymethyl cellulose derivative Compound A-122 (0.91 g). According to the nuclear magnetic resonance spectrum, the double bond content can be calculated to be about 42%.

Example 123: Synthesis of Component A-123

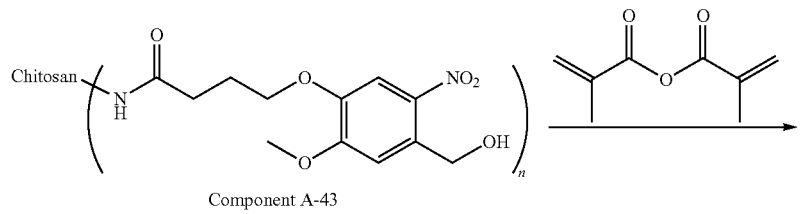
Component A-43

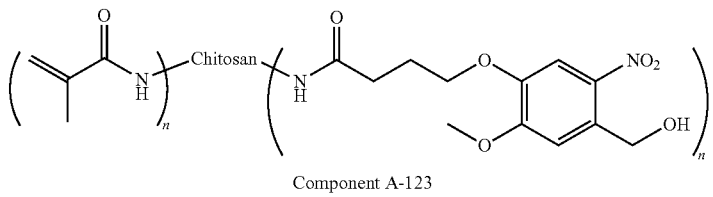
Component A-123

Synthesis of Component A-123. To a solution of Component A-43 in 100 mL deionized water was added 4 mL methacrylic anhydride at 0-4° C. The solution was slowly added 2 mL 5 M NaOH and reacted for 24 h. Then, the reaction solution was poured into a dialysis bag (MWCO 3500), dialyzed against deionized water for 2-3 d, and lyophilized to obtain a photosensitive carboxymethyl cellulose derivative Compound A-123 (0.84 g). According to the nuclear magnetic resonance spectrum, the double bond content can be calculated to be about 56%.

Example 124: Synthesis of Component A-124

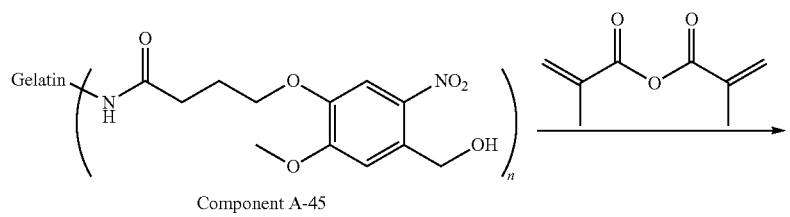

Component A-45

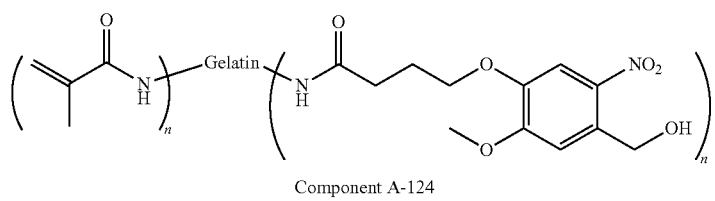

Component A-124

Synthesis of Component A-124. To a solution of Component A-45 dissolved in 100 mL deionized water was added 4 mL methacrylic anhydride at 0-4° C. The solution was slowly added 2 mL 5 M NaOH and reacted for 24 h. Then, the reaction solution was poured into a dialysis bag (MWCO 3500), dialyzed against deionized water for 2-3 d, and lyophilized to obtain a photosensitive carboxymethyl cellulose derivative Compound A-124 (0.92 g). According to the nuclear magnetic resonance spectrum, the double bond content can be calculated to be about 48%.

Example 125: Synthesis of Component A-125

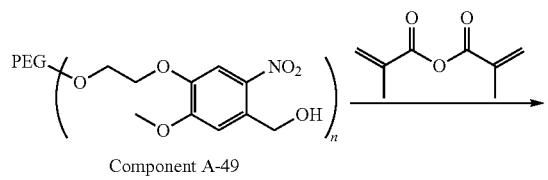

Component A-49

-continued

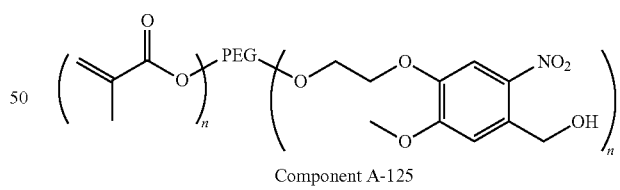

Component A-125

Synthesis of Component A-125. To a solution of Component A-49 dissolved in 100 mL deionized water was added 4 mL methacrylic anhydride at 0-4° C. The solution was slowly added 2 mL 5M NaOH and reacted for 24 h. Then, the reaction solution was poured into a dialysis bag (MWCO 3500), dialyzed against deionized water for 2-3 d, and lyophilized to obtain a photosensitive carboxymethyl cellulose derivative Compound A-125 (0.94 g). According to the nuclear magnetic resonance spectrum, the double bond content can be calculated to be about 24%.

Example 126: Synthesis of Component A-126

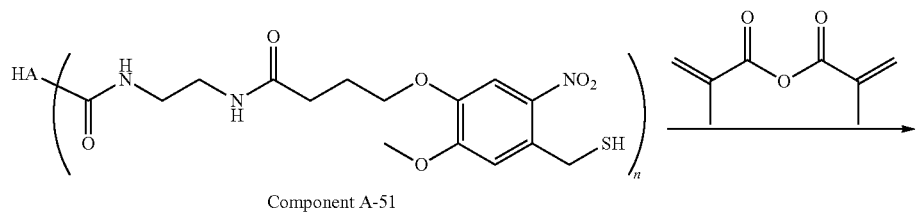

Component A-51

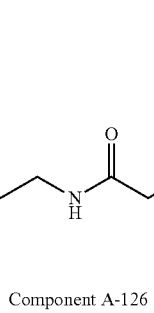

Component A-126

Synthesis of Component A-126. To a solution of Component A-51 in 100 mL deionized water was added 4 mL methacrylic anhydride at 0-4° C. The solution was slowly added 2 mL 5M NaOH and reacted for 24 h. Then, the reaction solution was poured into a dialysis bag (MWCO 3500), dialyzed against deionized water for 2-3 d, and lyophilized to obtain a photosensitive carboxymethyl cellulose derivative Compound A-126 (0.87 g). According to the nuclear magnetic resonance spectrum, the double bond content can be calculated to be about 46%.

Example 127: Synthesis of Component A-127

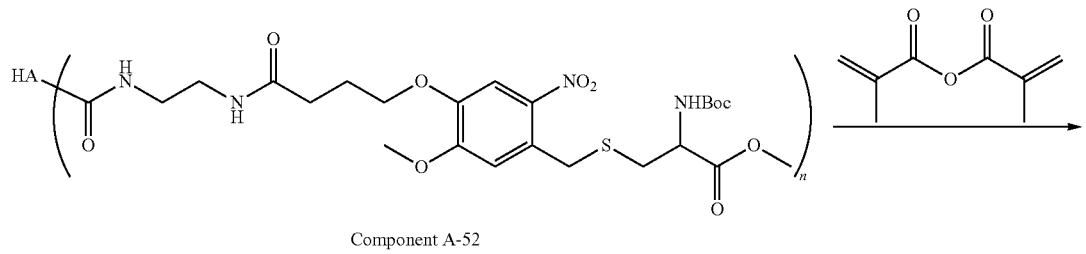

Component A-52

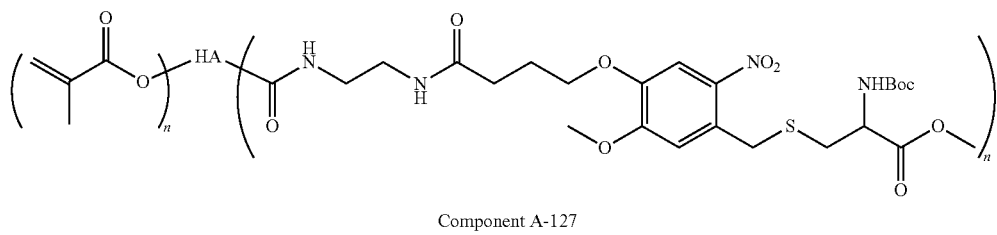

Component A-127

Synthesis of Component A-127. To a solution of Component A-52 dissolved in 100 mL deionized water was added 4 mL methacrylic anhydride at 0-4° C. The solution was slowly added 2 mL 5 M NaOH and reacted for 24 h. Then, the reaction solution was poured into a dialysis bag (MWCO 3500), dialyzed against deionized water for 2-3 d, and lyophilized to obtain a photosensitive carboxymethyl cellulose derivative Compound A-127 (0.85 g). According to the nuclear magnetic resonance spectrum, the double bond content can be calculated to be about 57%.

Example 128: Synthesis of Component A-128

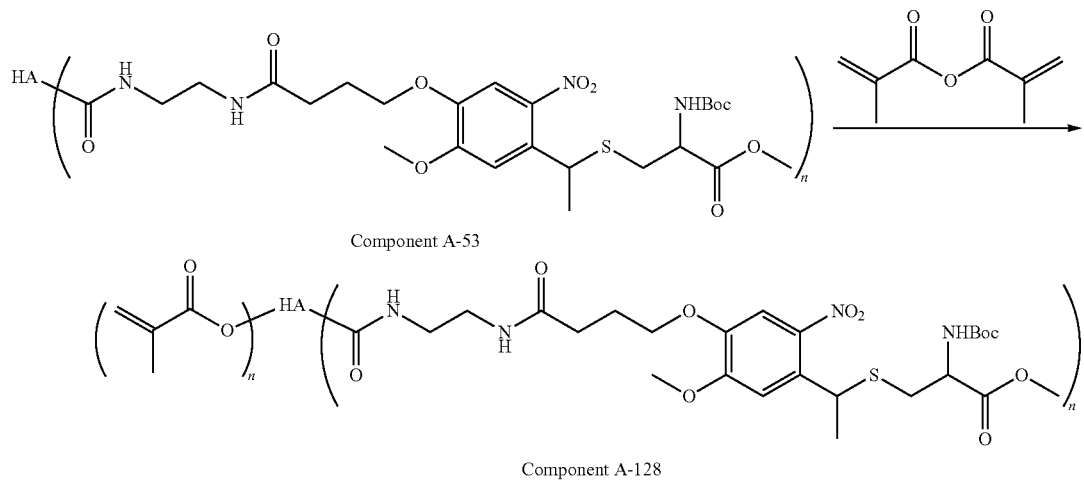

Component A-53

Component A-128

Synthesis of Component A-128. To a solution of Component A-53 dissolved in 100 mL deionized water was added 4 mL methacrylic anhydride at 0-4° C. The solution was slowly added 2 mL 5 M NaOH and reacted for 24 h. Then, the reaction solution was poured into a dialysis bag (MWCO 3500), dialyzed against deionized water for 2-3 d, and lyophilized to obtain a photosensitive carboxymethyl cellulose derivative Compound A-128 (0.93 g). According to the nuclear magnetic resonance spectrum, the double bond content can be calculated to be about 47%.

Example 129: Synthesis of Component A-129

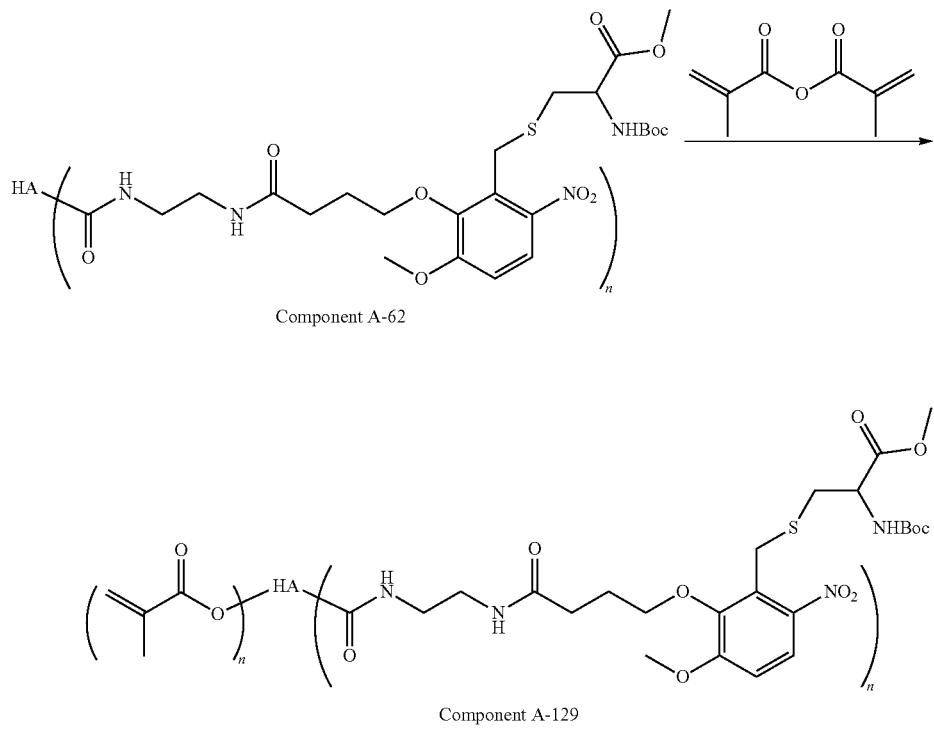

Component A-62

Component A-129

Synthesis of Component A-129. To a solution of Component A-62 dissolved in 100 mL deionized water was added 4 mL methacrylic anhydride at 0-4° C. The solution was slowly added 2 mL 5 M NaOH and reacted for 24 h. Then, the reaction solution was poured into a dialysis bag (MWCO 3500), dialyzed against deionized water for 2-3 d, and lyophilized to obtain a photosensitive carboxymethyl cellulose derivative Compound A-129 (0.90 g). According to the nuclear magnetic resonance spectrum, the double bond content can be calculated to be about 58%.

Example 130: Synthesis of Component A-130

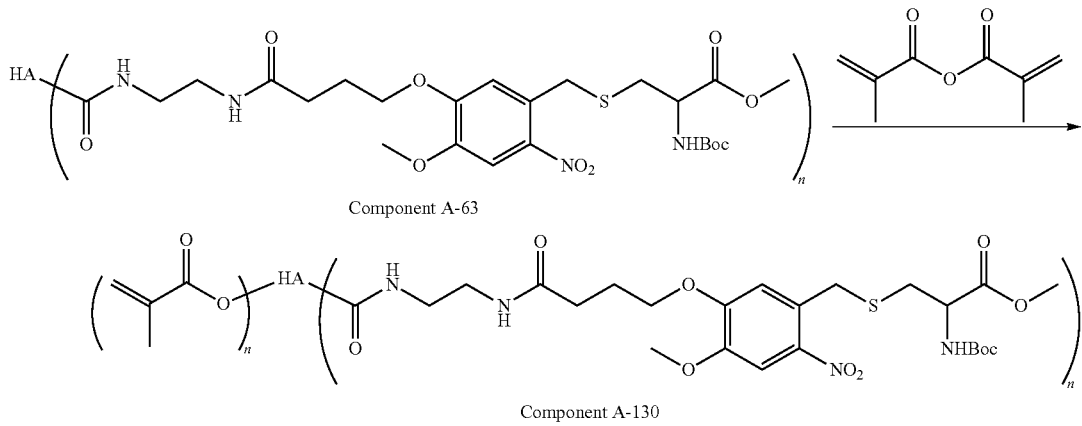

Synthesis of Component A-130. To a solution of Component A-63 in 100 mL deionized water was added 4 mL methacrylic anhydride at 0-4° C. The solution was slowly added 2 mL 5 M NaOH and reacted for 24 h. Then, the reaction solution was poured into a dialysis bag (MWCO 3500), dialyzed against deionized water for 2-3 d, and lyophilized to obtain a photosensitive carboxymethyl cellulose derivative Compound A-130 (0.89 g). According to the nuclear magnetic resonance spectrum, the double bond content can be calculated to be about 46%.

Example 131: Synthesis of Component A-131

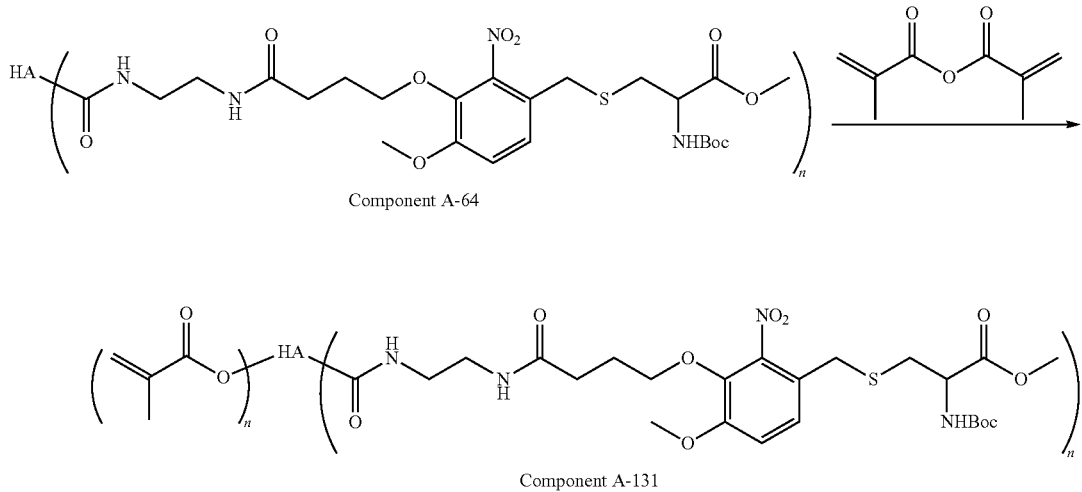

Synthesis of Component A-131. To a solution of Component A-64 in 100 mL deionized water was added 4 mL methacrylic anhydride at 0-4° C. The solution was slowly added 2 mL 5 M NaOH and reacted for 24 h. Then, the reaction solution was poured into a dialysis bag (MWCO 3500), dialyzed against deionized water for 2-3 d, and lyophilized to obtain a photosensitive carboxymethyl cellulose derivative Compound A-131 (0.87 g). According to the nuclear magnetic resonance spectrum, the double bond content can be calculated to be about 58%.

Example 132: Synthesis of Component A-132

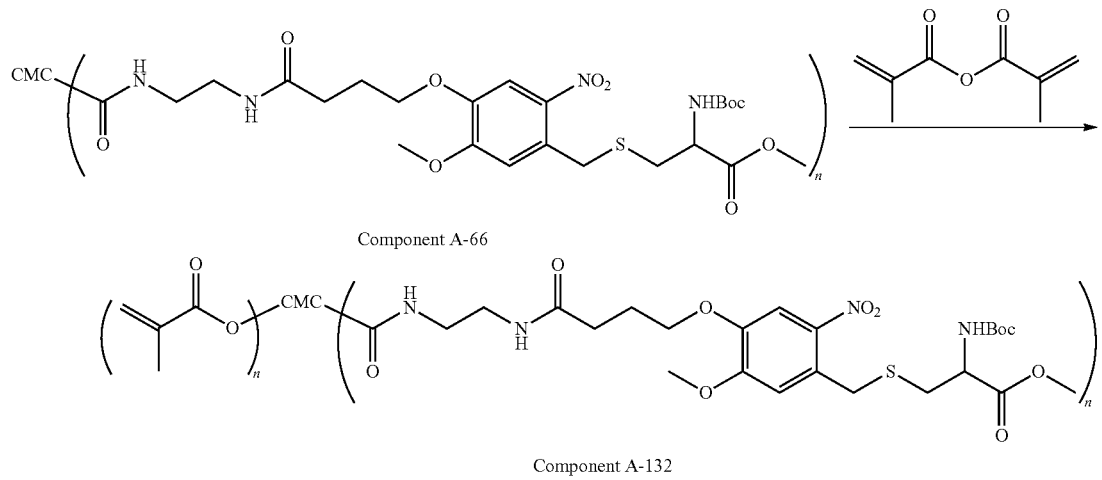

Synthesis of Component A-132. To a solution of Component A-66 in 100 mL deionized water was added 4 mL methacrylic anhydride at 0-4° C. The solution was slowly added 2 mL 5 M NaOH and reacted for 24 h. Then, the reaction solution was poured into a dialysis bag (MWCO 3500), dialyzed against deionized water for 2-3 d, and lyophilized to obtain a photosensitive carboxymethyl cellulose derivative Compound A-132 (0.92 g). According to the nuclear magnetic resonance spectrum, the double bond content can be calculated to be about 46%.

Example 133: Synthesis of Component A-133

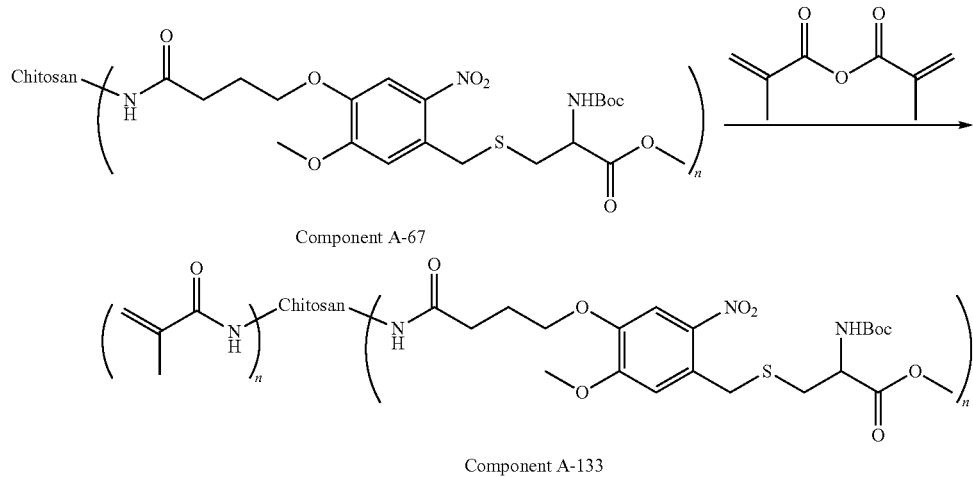

Synthesis of Component A-133. To a solution of Component A-67 dissolved in 100 mL deionized water was added 4 mL methacrylic anhydride at 0-4° C. The solution was slowly added 2 mL 5 M NaOH and reacted for 24 h. Then, the reaction solution was poured into a dialysis bag (MWCO 3500), dialyzed against deionized water for 2-3 d, and lyophilized to obtain a photosensitive carboxymethyl cellulose derivative Compound A-133 (0.91 g). According to the nuclear magnetic resonance spectrum, the double bond content can be calculated to be about 47%.

Example 134: Synthesis of Component A-134

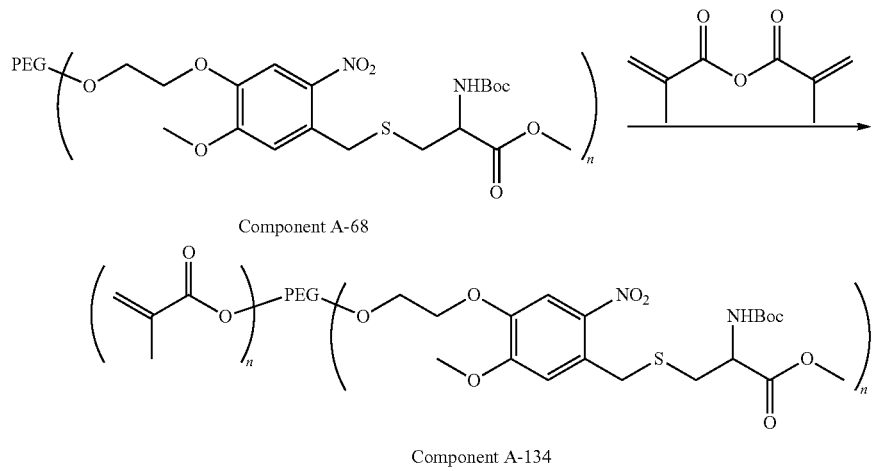

Synthesis of Component A-134. To a solution of Component A-68 dissolved in 100 mL deionized water was added 4 mL methacrylic anhydride at 0-4° C. The solution was slowly added 2 mL 5M NaOH and reacted for 24 h. Then, the reaction solution was poured into a dialysis bag (MWCO 3500), dialyzed against deionized water for 2-3 d, and lyophilized to obtain a photosensitive carboxymethyl cellulose derivative Compound A-134 (0.87 g). According to the nuclear magnetic resonance spectrum, the double bond content can be calculated to be about 52%.

Example 135: Synthesis of Component A-135

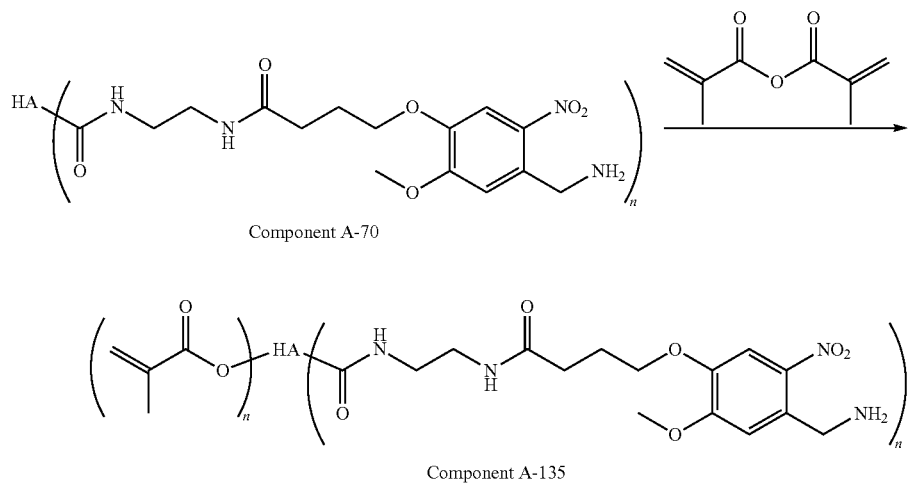

Synthesis of Component A-135. To a solution of Component A-70 dissolved in 100 mL deionized water was added 4 mL methacrylic anhydride at 0-4° C. The solution was slowly added 2 mL 5M NaOH and reacted for 24 h. Then, the reaction solution was poured into a dialysis bag (MWCO 3500), dialyzed against deionized water for 2-3 d, and lyophilized to obtain a photosensitive carboxymethyl cellulose derivative Compound A-135 (0.92 g). According to the nuclear magnetic resonance spectrum, the double bond content can be calculated to be about 47%.

Example 136: Synthesis of Component A-136

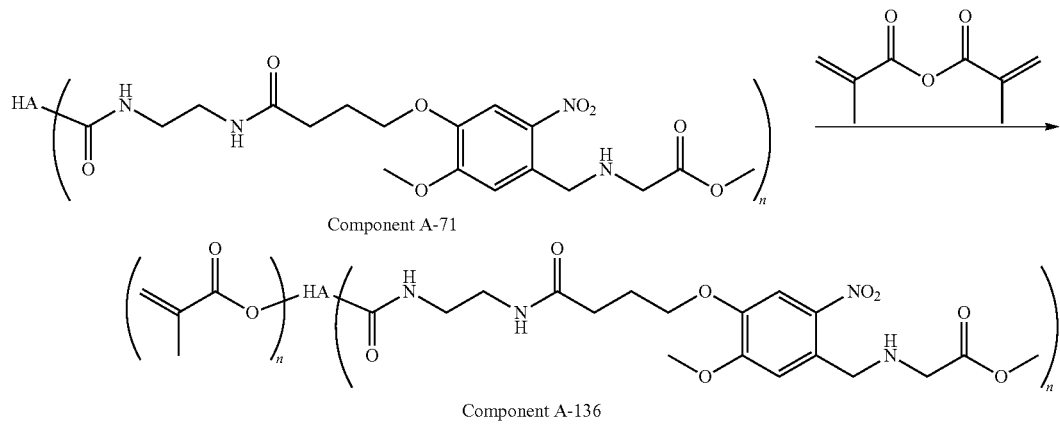

Synthesis of Component A-136. To a solution of Component A-71 dissolved in 100 mL deionized water was added 4 mL methacrylic anhydride at 0-4° C. The solution was slowly added 2 mL 5 M NaOH and reacted for 24 h. Then, the reaction solution was poured into a dialysis bag (MWCO 3500), dialyzed against deionized water for 2-3 d, and lyophilized to obtain a photosensitive carboxymethyl cellulose derivative Compound A-136 (0.86 g). According to the nuclear magnetic resonance spectrum, the double bond content can be calculated to be about 51%.

Example 137: Synthesis of Component A-137

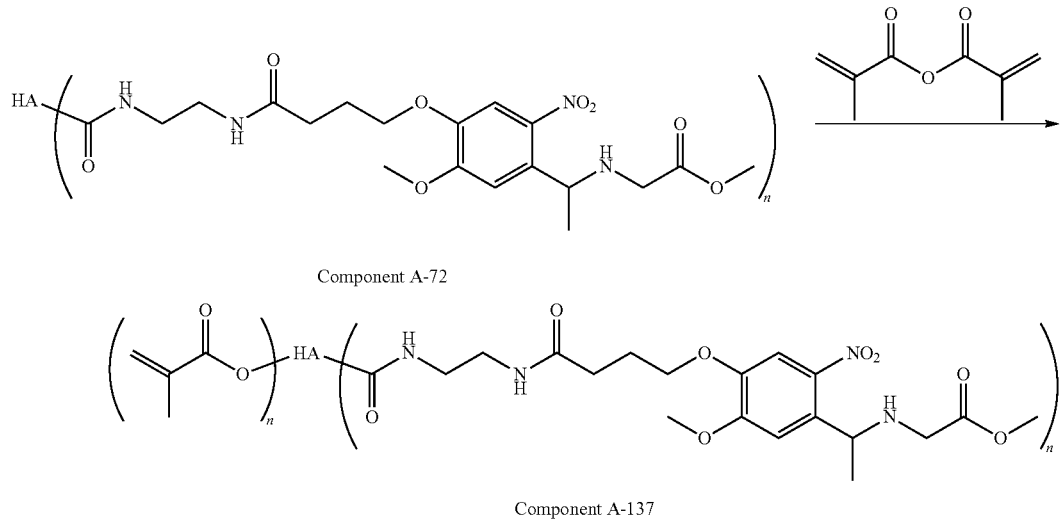

Synthesis of Component A-137. To a solution of Component A-72 in 100 mL deionized water was added 4 mL methacrylic anhydride at 0-4° C. The solution was slowly added 2 mL 5M NaOH and reacted for 24 h. Then, the reaction solution was poured into a dialysis bag (MWCO 3500), dialyzed against deionized water for 2-3 d, and lyophilized to obtain a photosensitive carboxymethyl cellulose derivative Compound A-137 (0.93 g). According to the nuclear magnetic resonance spectrum, the double bond content can be calculated to be about 45%.

Example 138: Synthesis of Component A-138

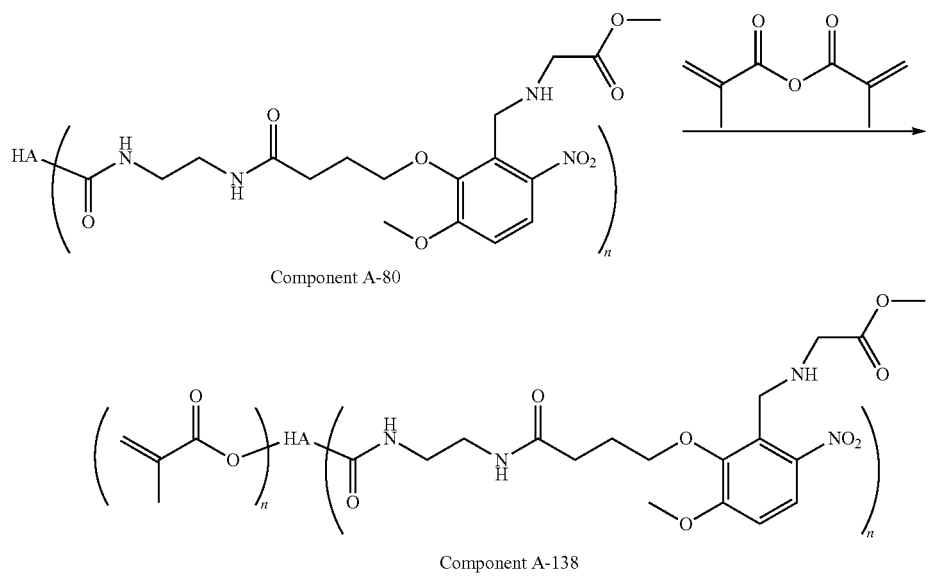

Component A-80

Component A-138

Synthesis of Component A-138. To a solution of Component A-80 dissolved in 100 mL deionized water was added 4 mL methacrylic anhydride at 0-4° C. The solution was slowly added 2 mL 5 M NaOH and reacted for 24 h. Then, the reaction solution was poured into a dialysis bag (MWCO 3500), dialyzed against deionized water for 2-3 d, and lyophilized to obtain a photosensitive carboxymethyl cellulose derivative Compound A-138 (0.88 g). According to the nuclear magnetic resonance spectrum, the double bond content can be calculated to be about 48%.

Example 139: Synthesis of Component A-139

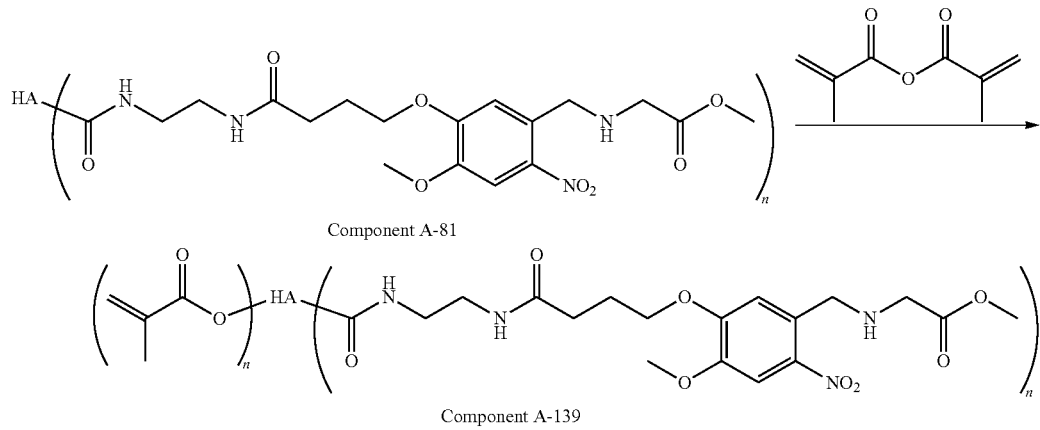

Component A-81

Component A-139

Synthesis of Component A-139. To a solution of Component A-81 dissolved in 100 mL deionized water was added 4 mL methacrylic anhydride at 0-4° C. The solution was slowly added 2 mL 5M NaOH and reacted for 24 h. Then, the reaction solution was poured into a dialysis bag (MWCO 3500), dialyzed against deionized water for 2-3 d, and lyophilized to obtain a photosensitive carboxymethyl cellulose derivative Compound A-139 (0.88 g). According to the nuclear magnetic resonance spectrum, the double bond content can be calculated to be about 46%.

Example 140: Synthesis of Component A-140

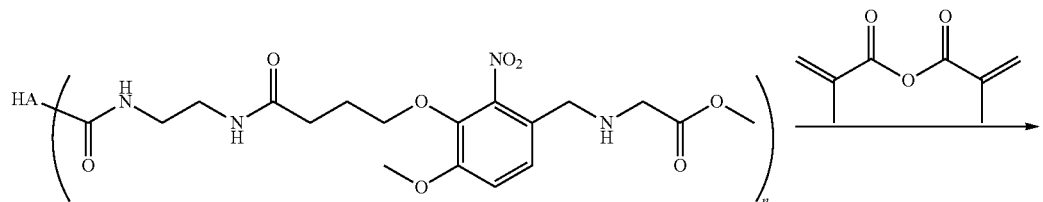

Component A-82

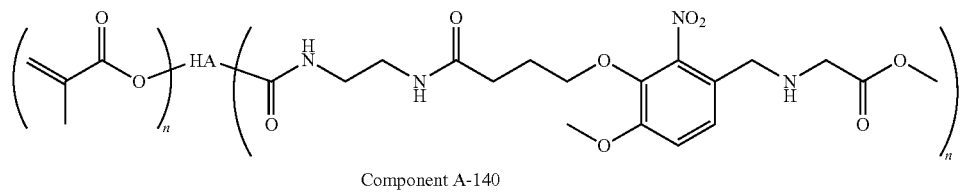

Component A-140

Synthesis of Component A-140. To a solution of Component A-82 in 100 mL deionized water was added 4 mL methacrylic anhydride at 0-4° C. The solution was slowly added 2 mL 5 M NaOH and reacted for 24 h. Then, the reaction solution was poured into a dialysis bag (MWCO 3500), dialyzed against deionized water for 2-3 d, and lyophilized to obtain a photosensitive carboxymethyl cellulose derivative Compound A-140 (0.91 g). According to the nuclear magnetic resonance spectrum, the double bond content can be calculated to be about 57%.

Example 141: Synthesis of Component A-141

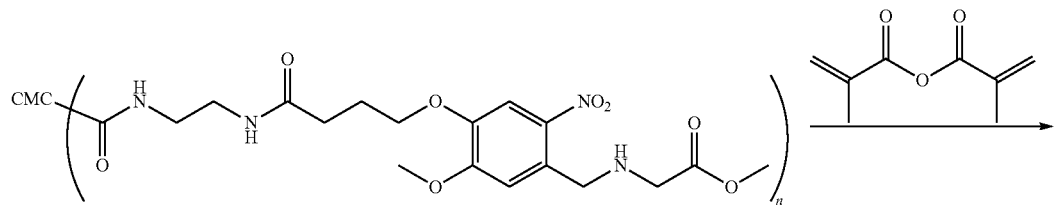

Component A-84

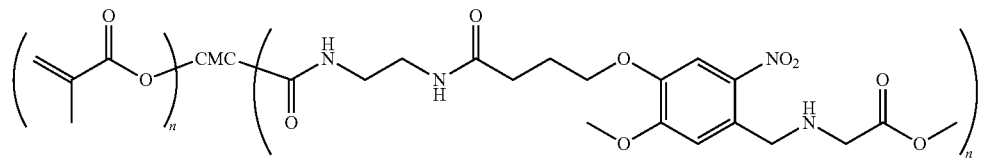

Component A-141

Synthesis of Component A-141. To a solution of Component A-84 in 100 mL deionized water was added 4 mL methacrylic anhydride at 0-4° C. The solution was slowly added 2 mL 5M NaOH and reacted for 24 h. Then, the reaction solution was poured into a dialysis bag (MWCO 3500), dialyzed against deionized water for 2-3 d, and lyophilized to obtain a photosensitive carboxymethyl cellulose derivative Compound A-141 (0.92 g). According to the nuclear magnetic resonance spectrum, the double bond content can be calculated to be about 44%.

Example 142: Synthesis of Component A-142

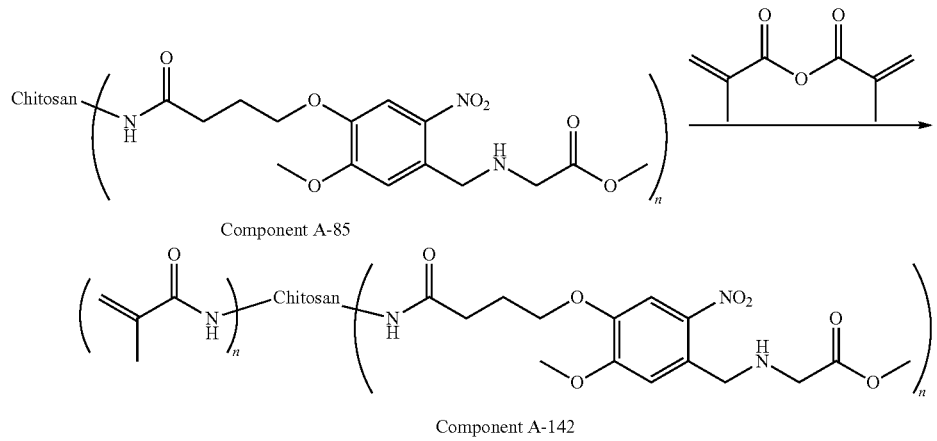

Synthesis of Component A-142. To a solution of Component A-85 in 100 mL deionized water was added 4 mL methacrylic anhydride at 0-4° C. The solution was slowly added 2 mL 5M NaOH and reacted for 24 h. Then, the reaction solution was poured into a dialysis bag (MWCO 3500), dialyzed against deionized water for 2-3 d, and lyophilized to obtain a photosensitive carboxymethyl cellulose derivative Compound A-142 (0.87 g). According to the nuclear magnetic resonance spectrum, the double bond content can be calculated to be about 56%.

Example 143: Synthesis of Component A-143

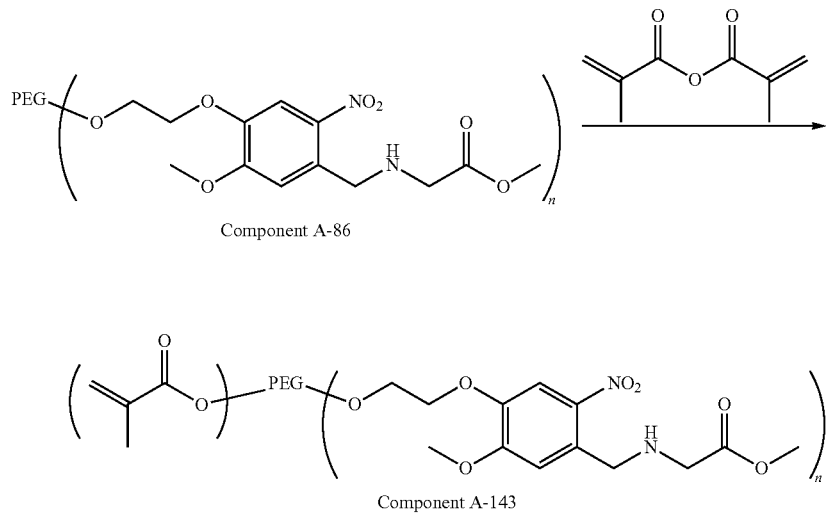

Synthesis of Component A-143. To a solution of Component A-86 in 100 mL deionized water was added 4 mL methacrylic anhydride at 0-4° C. The solution was slowly added 2 mL 5 M NaOH and reacted for 24 h. Then, the reaction solution was poured into a dialysis bag (MWCO 3500), dialyzed against deionized water for 2-3 d, and lyophilized to obtain a photosensitive carboxymethyl cellulose derivative Compound A-143 (0.91 g). According to the nuclear magnetic resonance spectrum, the double bond content can be calculated to be about 48%.

Example 144: Synthesis of Component A-144

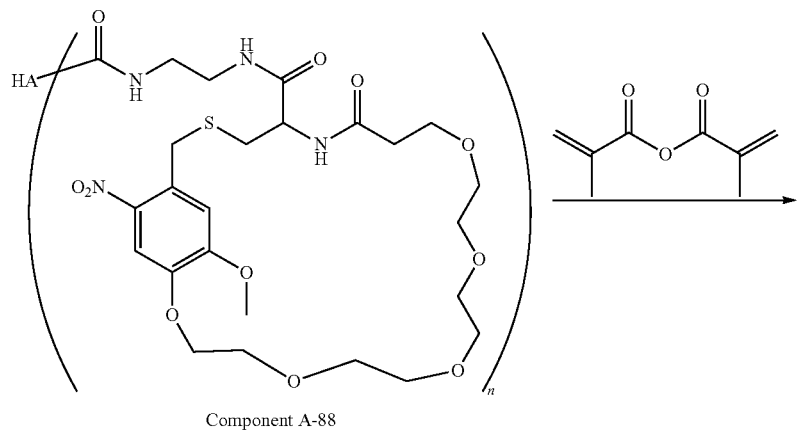

Component A-88

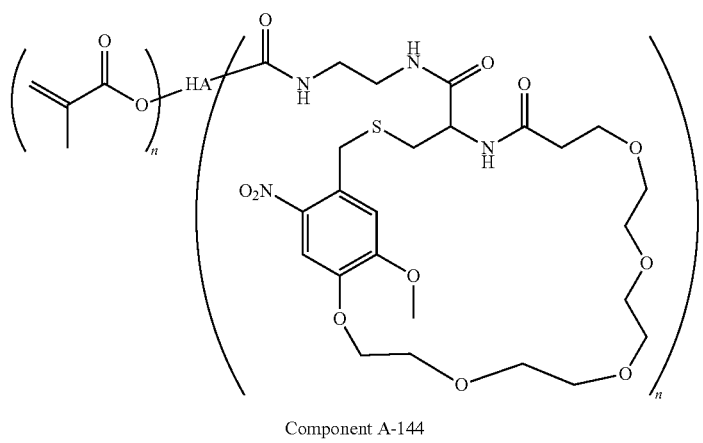

Component A-144

Synthesis of Component A-144. To a solution of Component A-88 in 100 mL deionized water was added 4 mL methacrylic anhydride at 0-4° C. The solution was slowly added 2 mL 5M NaOH and reacted for 24 h. Then, the reaction solution was poured into a dialysis bag (MWCO 3500), dialyzed against deionized water for 2-3 d, and lyophilized to obtain a photosensitive carboxymethyl cellulose derivative Compound A-144 (0.89 g). According to the nuclear magnetic resonance spectrum, the double bond content can be calculated to be about 52%.

Example 145: Synthesis of Component A-145

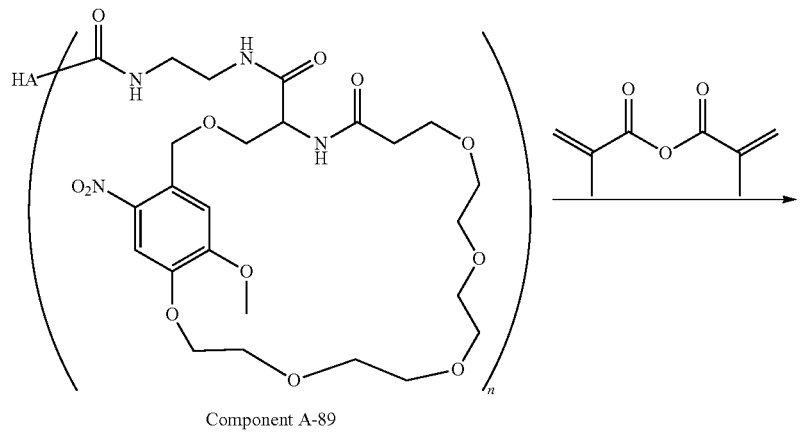

Component A-89

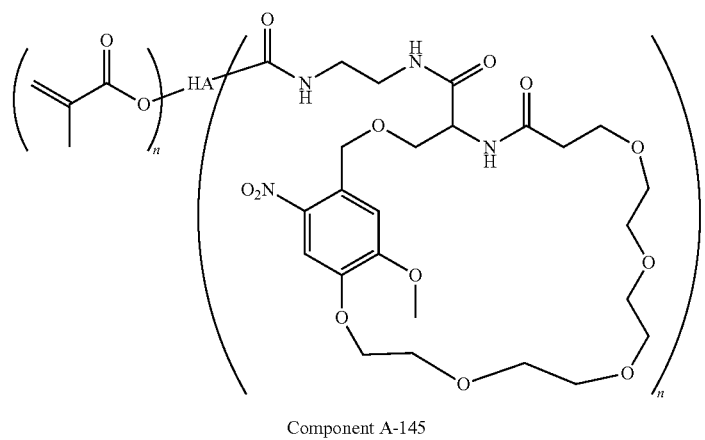

Component A-145

Synthesis of Component A-145. To a solution of Component A-89 in 100 mL deionized water was added 4 mL methacrylic anhydride at 0-4° C. The solution was slowly added 2 mL 5 M NaOH and reacted for 24 h. Then, the reaction solution was poured into a dialysis bag (MWCO 3500), dialyzed against deionized water for 2-3 d, and lyophilized to obtain a photosensitive carboxymethyl cellulose derivative Compound A-145 (0.81 g). According to the nuclear magnetic resonance spectrum, the double bond content can be calculated to be about 43%.

Example 146: Synthesis of Component A-146

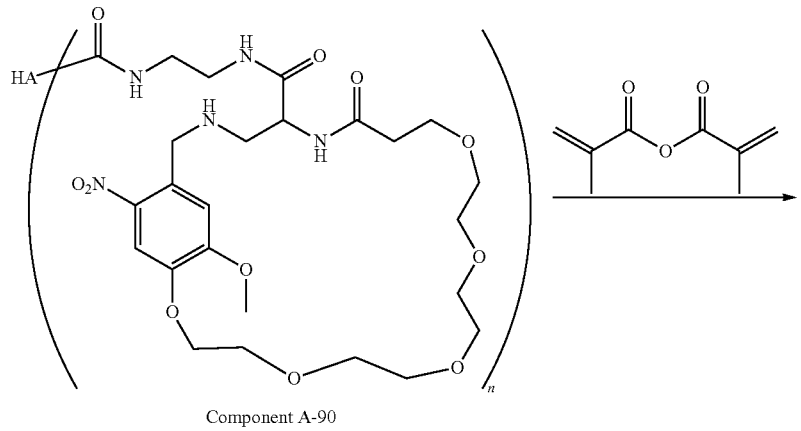

Component A-90

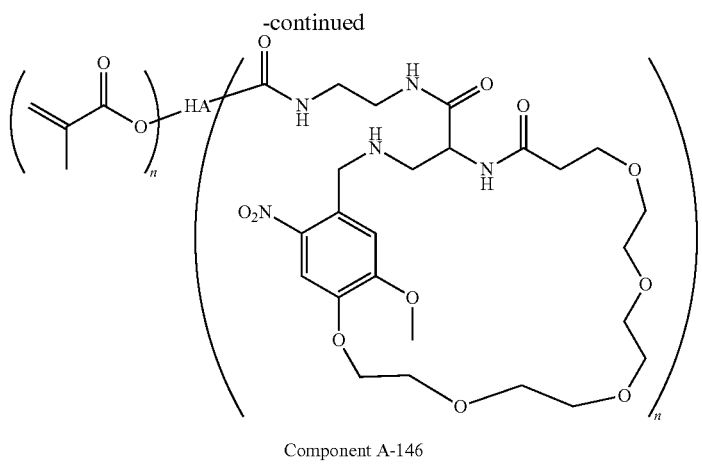

Component A-146

Synthesis of Component A-146. To a solution of Component A-90 in 100 mL deionized water was added 4 mL methacrylic anhydride at 0-4° C. The solution was slowly added 2 mL 5 M NaOH and reacted for 24 h. Then, the reaction solution was poured into a dialysis bag (MWCO 3500), dialyzed against deionized water for 2-3 d, and lyophilized to obtain a photosensitive carboxymethyl cellulose derivative Compound A-146 (0.84 g). According to the nuclear magnetic resonance spectrum, the double bond content can be calculated to be about 49%.

Example 147: Synthesis of Component A-147

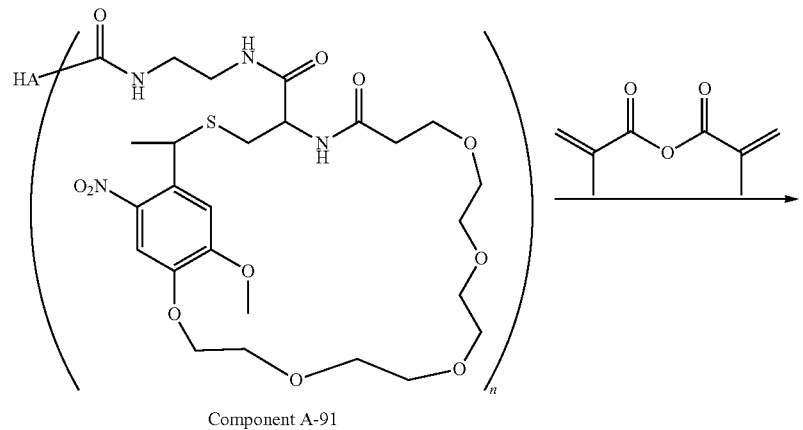

Component A-91

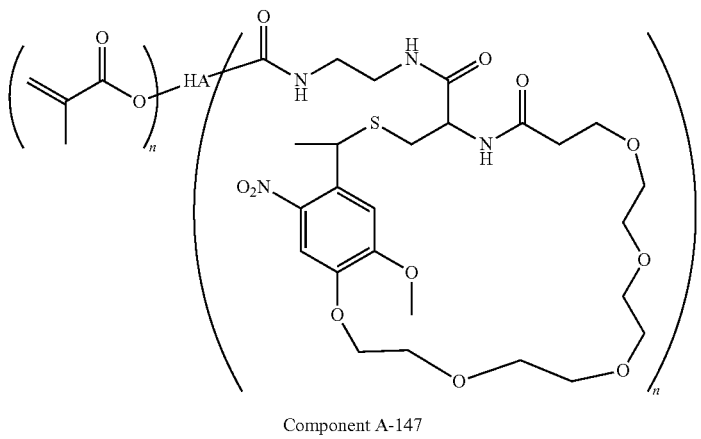

Component A-147

Synthesis of Component A-147. To a solution of Component A-91 in 100 mL deionized water was added 4 mL methacrylic anhydride at 0-4° C. The solution was slowly added 2 mL 5M NaOH and reacted for 24 h. Then, the reaction solution was poured into a dialysis bag (MWCO 3500), dialyzed against deionized water for 2-3 d, and lyophilized to obtain a photosensitive carboxymethyl cellulose derivative Compound A-147 (0.92 g). According to the nuclear magnetic resonance spectrum, the double bond content can be calculated to be about 46%.

Example 148: Synthesis of Component A-148

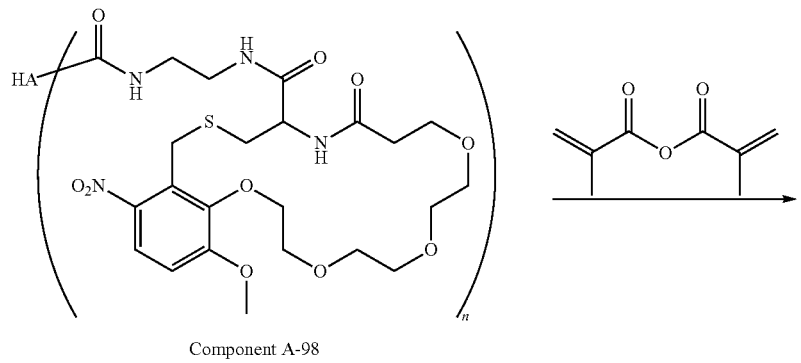

Component A-98

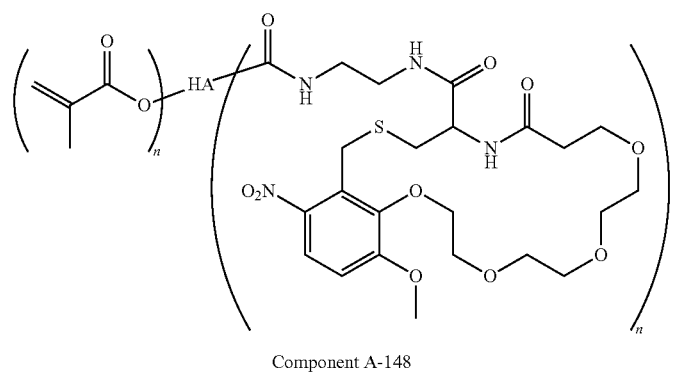

Component A-148

Synthesis of Component A-148. To a solution of Component A-98 in 100 mL deionized water was added 4 mL methacrylic anhydride at 0-4° C. The solution was slowly added 2 mL 5 M NaOH and reacted for 24 h. Then, the reaction solution was poured into a dialysis bag (MWCO 3500), dialyzed against deionized water for 2-3 d, and lyophilized to obtain a photosensitive carboxymethyl cellulose derivative Compound A-148 (0.94 g). According to the nuclear magnetic resonance spectrum, the double bond content can be calculated to be about 56%.

Example 149: Synthesis of Component A-149

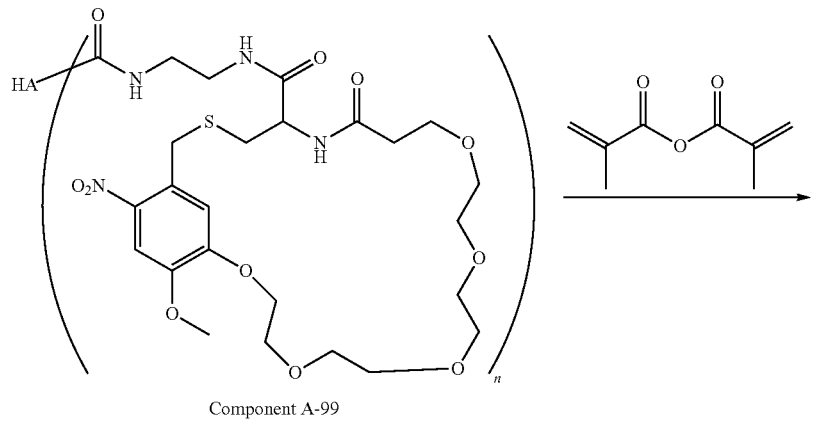

Synthesis of Component A-149. To a solution of Component A-99 in 100 mL deionized water was added 4 mL methacrylic anhydride at 0-4° C. The solution was slowly added 2 mL 5M NaOH and reacted for 24 h. Then, the reaction solution was poured into a dialysis bag (MWCO 3500), dialyzed against deionized water for 2-3 d, and lyophilized to obtain a photosensitive carboxymethyl cellulose derivative Compound A-149 (0.87 g). According to the nuclear magnetic resonance spectrum, the double bond content can be calculated to be about 51%.

Example 150: Synthesis of Component A-150

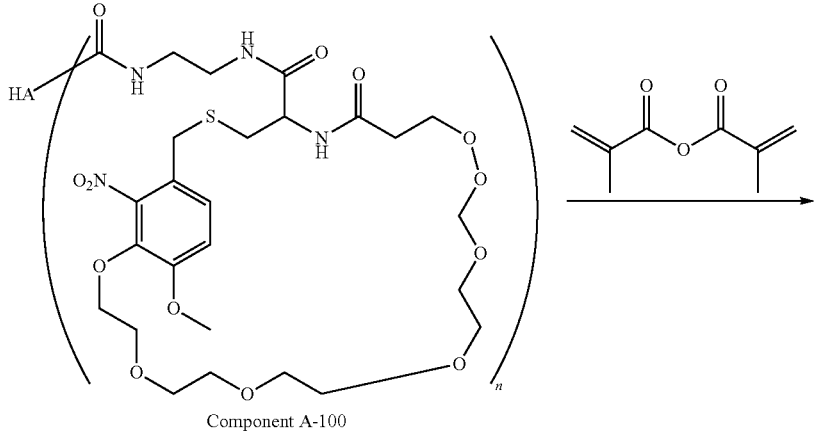

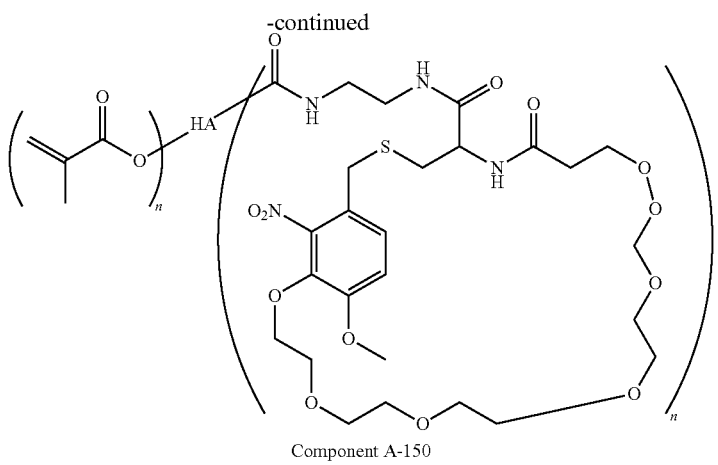

Component A-150

Synthesis of Component A-150. To a solution of Component A-100 in 100 mL deionized water was added 4 mL methacrylic anhydride at 0-4° C. The solution was slowly added 2 mL 5M NaOH and reacted for 24 h. Then, the reaction solution was poured into a dialysis bag (MWCO 3500), dialyzed against deionized water for 2-3 d, and lyophilized to obtain a photosensitive carboxymethyl cellulose derivative Compound A-150 (0.88 g). According to the nuclear magnetic resonance spectrum, the double bond content can be calculated to be about 47%.

Example 151: Synthesis of Component A-151

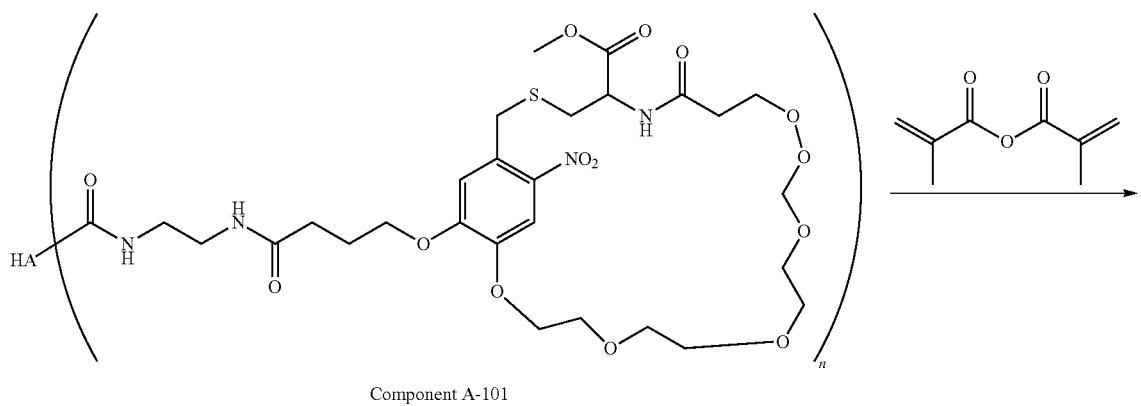

Component A-101

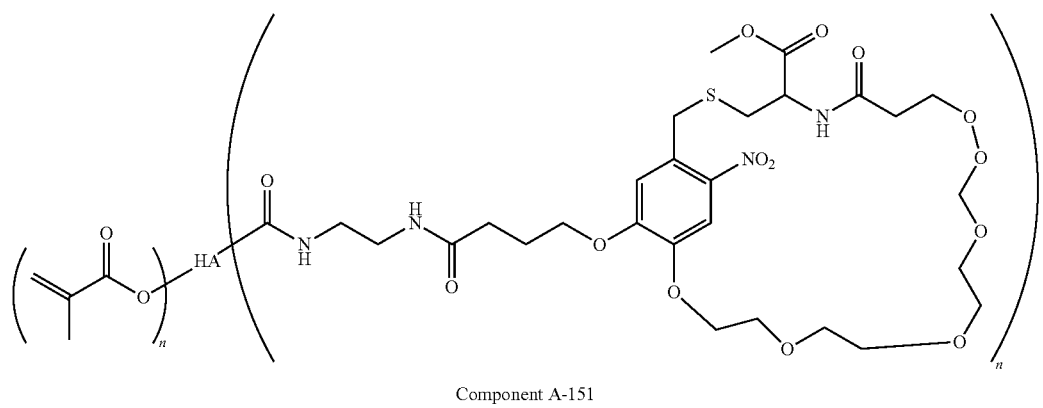

Component A-151

Synthesis of Component A-151. To a solution of Component A-101 in 100 mL deionized water was added 4 mL methacrylic anhydride at 0-4° C. The solution was slowly added 2 mL 5M NaOH and reacted for 24 h. Then, the reaction solution was poured into a dialysis bag (MWCO 3500), dialyzed against deionized water for 2-3 d, and lyophilized to obtain a photosensitive carboxymethyl cellulose derivative Compound A-151 (0.91 g). According to the nuclear magnetic resonance spectrum, the double bond content can be calculated to be about 45%.

Example 152: Synthesis of Component A-152

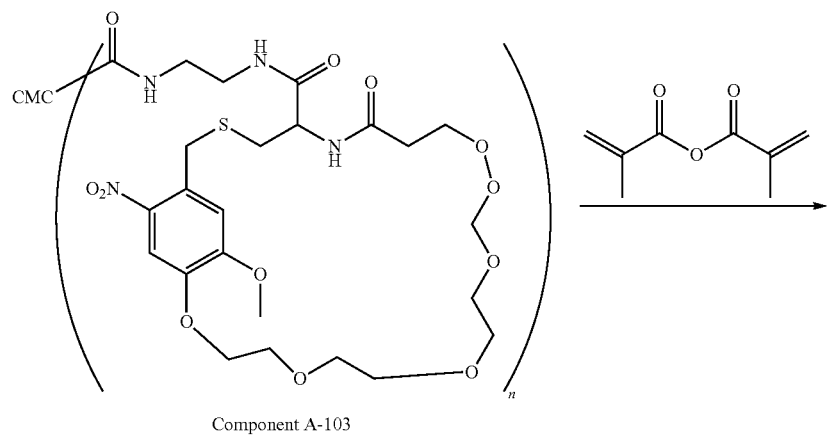

Component A-103

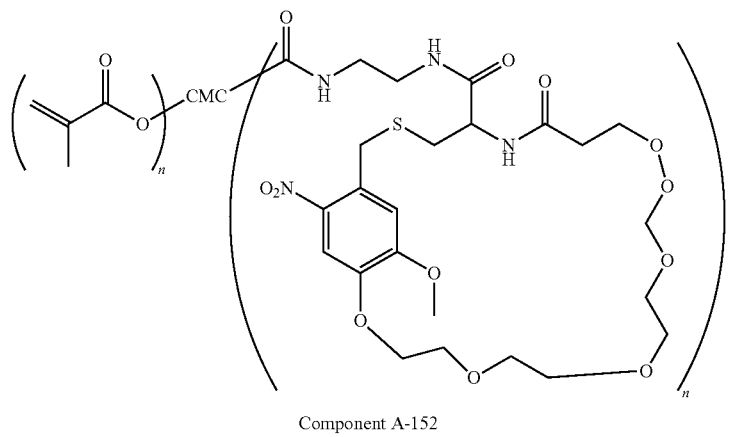

Component A-152

Synthesis of Component A-152. To a solution of Component A-103 in 100 mL deionized water was added 4 mL methacrylic anhydride at 0-4° C. The solution was slowly added 2 mL 5M NaOH and reacted for 24 h. Then, the reaction solution was poured into a dialysis bag (MWCO 3500), dialyzed against deionized water for 2-3 d, and lyophilized to obtain a photosensitive carboxymethyl cellulose derivative Compound A-152 (0.84 g). According to the nuclear magnetic resonance spectrum, the double bond content can be calculated to be about 43%.

Example 153: Synthesis of Component A-153

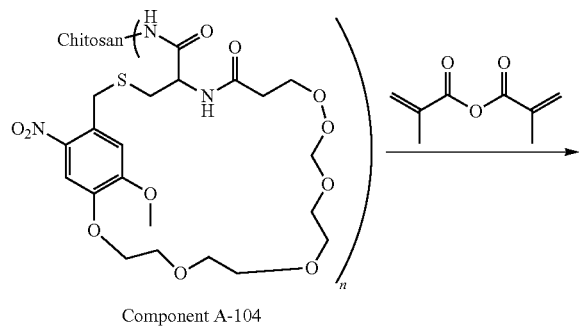

Component A-104

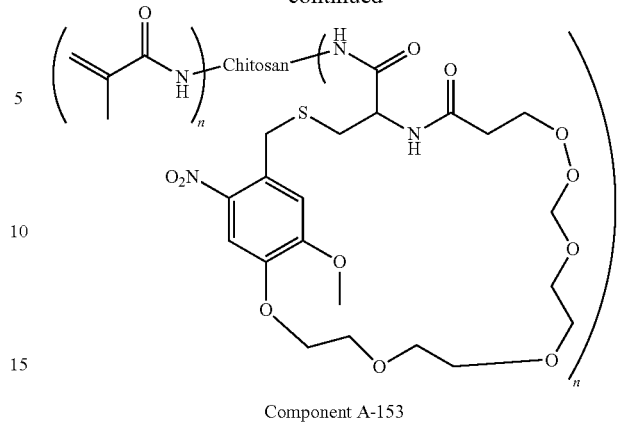

Component A-153

Synthesis of Component A-153. To a solution of Component A-104 in 100 mL deionized water was added 4 mL methacrylic anhydride at 0-4° C. The solution was slowly added 2 mL 5M NaOH and reacted for 24 h. Then, the reaction solution was poured into a dialysis bag (MWCO 3500), dialyzed against deionized water for 2-3 d, and lyophilized to obtain a photosensitive carboxymethyl cellulose derivative Compound A-153 (0.89 g). According to the nuclear magnetic resonance spectrum, the double bond content can be calculated to be about 50%.

Example 154: Synthesis of Component A-154

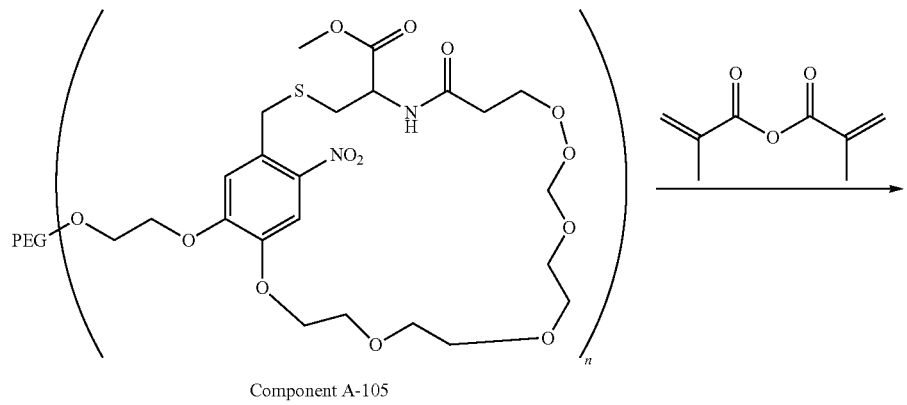

Component A-105

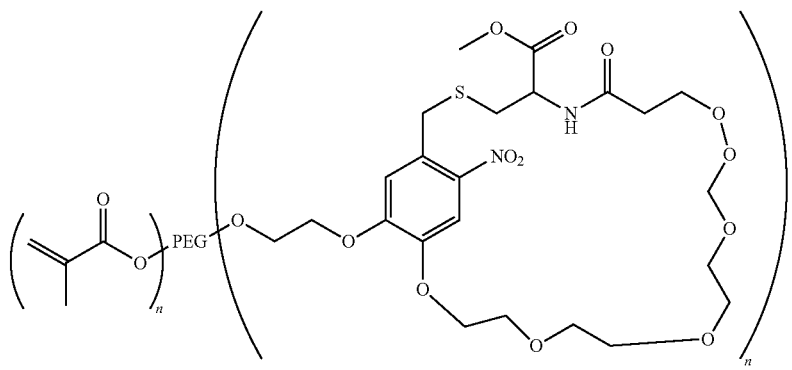

Component A-154

Synthesis of Component A-154. To a solution of Component A-105 in 100 mL deionized water was added 4 mL methacrylic anhydride at 0-4° C. The solution was slowly added 2 mL 5M NaOH and reacted for 24 h. Then, the reaction solution was poured into a dialysis bag (MWCO 3500), dialyzed against deionized water for 2-3 d, and lyophilized to obtain a photosensitive carboxymethyl cellulose derivative Compound A-154 (0.94 g). According to the nuclear magnetic resonance spectrum, the double bond content can be calculated to be about 43%.

Example 155: Synthesis of Photoinitiator-LAP

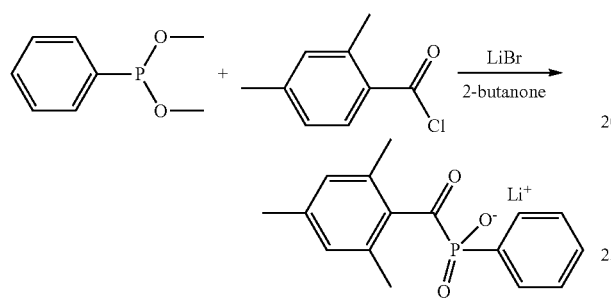

Synthesis of LAP. Dimethoxyphenylphosphine (3.0 g, 0.018 mol) placed in 250 mL three-necked flask under protection of argon was added 2, 4, 6-trimethylbenzoyl chloride (3.2 g, 0.018 mol), and the reaction was stirred at room temperature for 18 h. Then, lithium bromide (6.1 g, 0.072 mol) dissolved in 100 mL of 2-butanone was added to the above reaction solution and heated to 50° C. for 10 min, a precipitate formed. After cooling to room temperature for 4 h, it was filtered, and the obtained crude product was washed twice with 2-butanone, and dried to obtain LAP (6.0 g) as a white solid.

Example 156: Synthesis of Component C-10

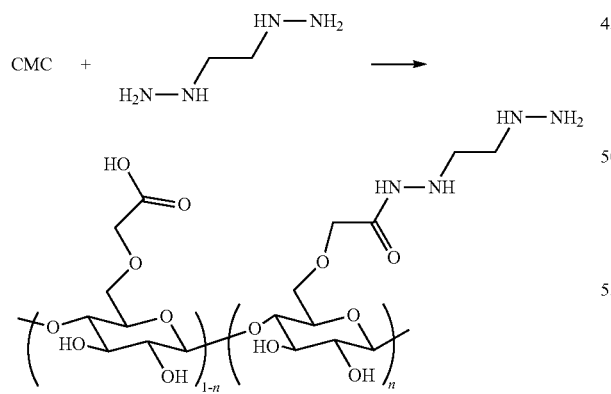

Synthesis of Component C-10. To a solution of carboxymethylcellulose (CMC, 400 mg) in 50 mL distilled water was added hydroxybenzotriazole (HOBt, 153 mg), dihydrazine (90 mg) and 1-ethyl-(3-dimethyl amine propyl) carbodiimine hydrochloride (EDC-HCl, 90 mg), the mixture was stirred at room temperature for 48 h. After completion of the reaction, the reaction solution was added to a dialysis bag and dialyzed against dilute hydrochloric acid solution containing sodium chloride (pH=3.5) for 1 d, and dialyzed against distilled water for 1 d, then freeze-dried to obtain the carboxymethylcellulose photosensitive polymer derivative modified by hydrazine (410 mg). The grafting degree of hydrazine tested by TBNS method was about 10%.

Example 157: Synthesis of Component C-11

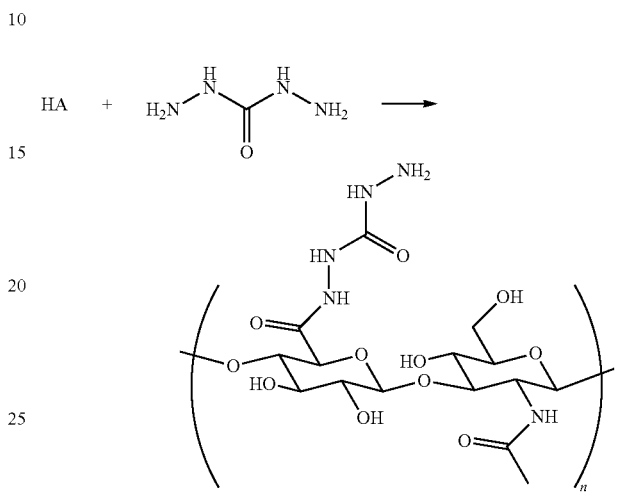

Synthesis of Component C-11. To a solution of hyaluronic acid (HA, 400 mg) in 50 mL distilled water was added hydroxybenzotriazole (HOBt, 153 mg), carbonyl hydrazide (CDH, 90 mg) and 1-ethyl-(3-dimethyl amine propyl) carbodiimine hydrochloride (EDC-HCl, 90 mg), the mixture was stirred at room temperature for 48 h. After completion of the reaction, the reaction solution was added to a dialysis bag and dialyzed against dilute hydrochloric acid solution containing sodium chloride (pH=3.5) for 1 d, and dialyzed against distilled water for 1 d, then freeze-dried to obtain the HA-CDH (410 mg). The grafting degree of hydrazine tested by TBNS method was about 10%.

Example 158: Synthesis of Component C-12

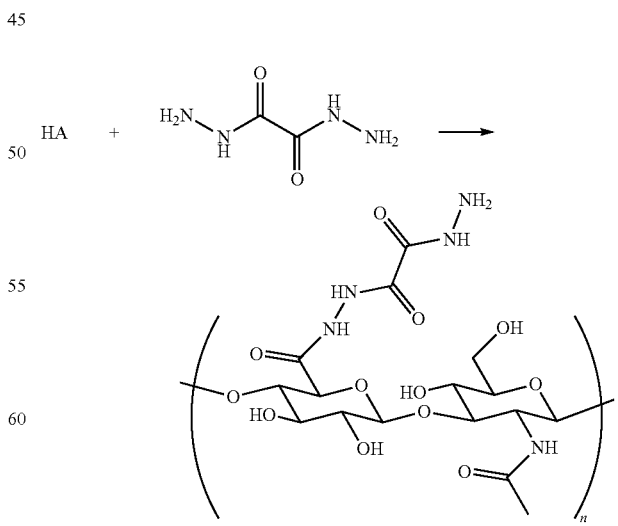

Synthesis of Component C-12. To a solution of hyaluronic acid (HA, 400 mg) in 50 mL distilled water was added hydroxybenzotriazole (HOBt, 153 mg), dihydrazide oxalate (ODH, 90 mg) and 1-ethyl-(3-dimethyl amine propyl) carbodiimine hydrochloride (EDC-HCl, 90 mg), the mixture was stirred at room temperature for 48 h. After completion of the reaction, the reaction solution was added to a dialysis bag and dialyzed against dilute hydrochloric acid solution containing sodium chloride (pH=3.5) for 1 d, and dialyzed against distilled water for 1 d, then freeze-dried to obtain HA-ODH (410 mg). The grafting degree of hydrazine tested by TBNS method was about 10%.

Example 159: Synthesis of Component C-13

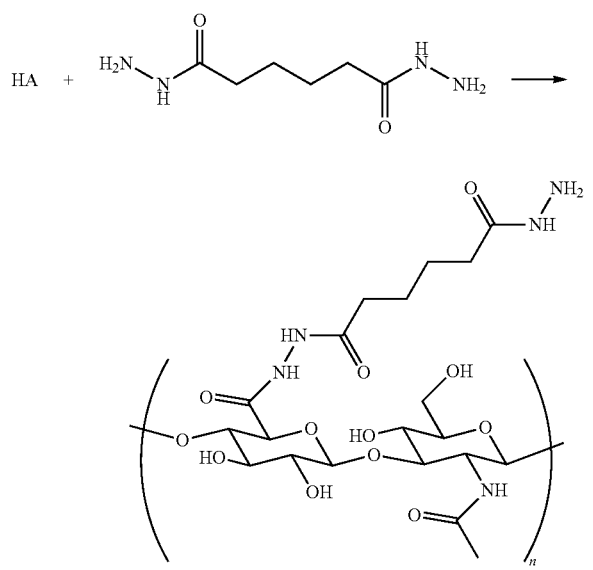

Synthesis of Component C-13. To a solution of hyaluronic acid (HA, 400 mg) in 50 mL distilled water was added hydroxybenzotriazole (HOBt, 153 mg), dihydrazide adipate (ADH, 90 mg) and 1-ethyl-(3-dimethyl amine propyl) carbodiimine hydrochloride (EDC-HCl, 90 mg), the mixture was stirred at room temperature for 48 h. After completion of the reaction, the reaction solution was added to a dialysis bag and dialyzed against dilute hydrochloric acid solution containing sodium chloride (pH=3.5) for 1 d, and dialyzed against distilled water for 1 d, then freeze-dried to obtain HA-ADH (410 mg). The grafting degree of hydrazine tested by TBNS method was about 10%.

Example 160: Synthesis of Component C-14

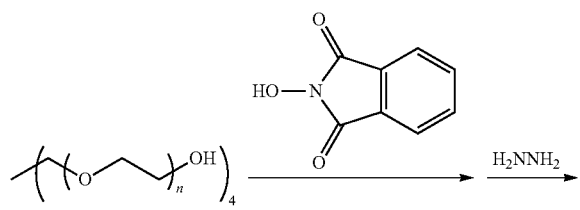

-continued

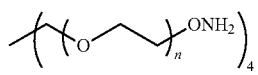

Synthesis of Component C-14. To a solution of PEG-4OH (2 g, 97.3 µmol) and N-hydroxyphthalimide (634.6 mg, 3.89 mmol) in anhydrous dichloromethane was slowly added triphenylphosphine (1.02 g, 3.89 mmol) under ice bath, the mixture was reacted under ice bath for about 30 min. The above solution was slowly added diisopropyl azodicarboxylate (765.9 µL, 3.89 mmol) in dry dichloromethane and reacted at room temperature for 1 d. After completion of the reaction, the system was reprecipitated with diethyl ether. The above precipitate (0.25 g, 11.8 µmol) was re-dissolved in acetonitrile and added hydrazine monohydrate (22.9 µL, 473 µmol), the mixture was stirred for 2 h. The above mixture solution was added dichloromethane and filtered. The solvent was removed by rotary evaporation under reduced pressure to obtain four-arm polyethylene glycol modified by hydroxylamine (PEG-4ONH$_2$).

Example 161: Synthesis of Component C-15

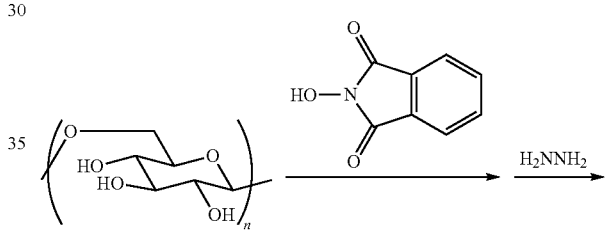

Synthesis of Component C-15. To a solution of dextran (2 g, 97.3 µmol) and N-hydroxyphthalimide (634.6 mg, 3.89 mmol) in anhydrous dichloromethane was slowly added triphenylphosphine (1.02 g, 3.89 mmol) under ice bath, the mixture was reacted under ice bath for about 30 min. The above solution was slowly added diisopropyl azodicarboxylate (765.9 µL, 3.89 mmol) in dry dichloromethane and reacted at room temperature for 1 d. After completion of the reaction, the system was reprecipitated with diethyl ether. The above precipitate (0.25 g, 11.8 µmol) was re-dissolved in acetonitrile and added hydrazine monohydrate (22.9 µL, 473 µmol), the mixture was stirred for 2 h. The above mixture solution was added dichloromethane and filtered. The solvent was removed by rotary evaporation under reduced pressure to obtain dextran modified by hydroxylamine (Dex-ONH$_2$).

Example 162: Synthesis of Component C-18

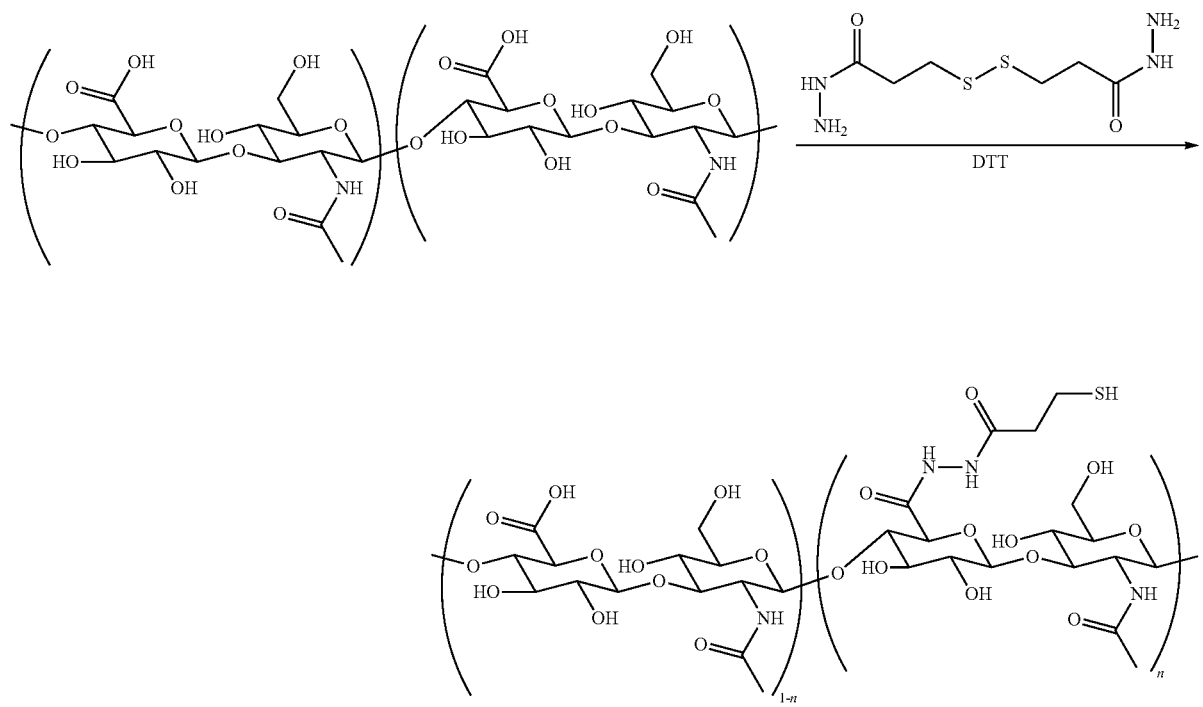

Synthesis of Component C-18. To a solution of hyaluronic acid (0.5 g, 48 kDa) in 50 mL distilled water was added hydroxybenzotriazole (HOBt, 0.2 g), 1-ethyl-(3-dimethyl-aminopropyl) carbodiimine hydrochloride (EDC-HCl, 0.1 g), 3, 3'-dithiobis (propionide) (DTP, 0.1 g). The mixture was adjusted to pH 4.75 with dilute hydrochloric acid solution and reacted for 24 h. Then, the solution was added DTT and continued to react for 5 h. After completion of the reaction, the solution was poured into a dialysis bag (MWCO 3500), dialyzed against deionized water for 2-3 d, and freeze-dried to obtain HA-SH (0.45 g). According to the nuclear magnetic resonance spectrum, the grafting degree of sulfhydryl group can be calculated to be about 20%.

Example 163: Synthesis of Component C-19

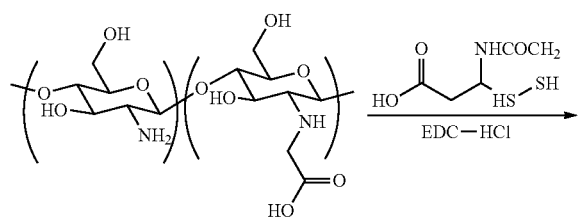

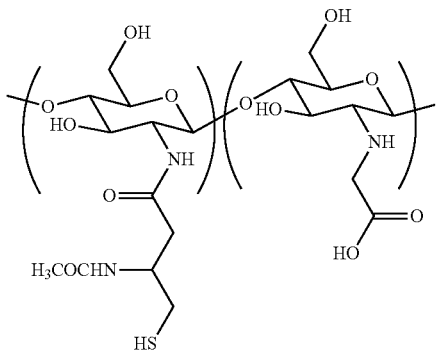

Synthesis of Component C-19. To a solution of carboxymethyl chitosan (1 g) in 100 mL of deionized water was added N-acetylcysteine (1.77 g, 10 mmol) and 1-ethyl-(3-dimethylaminopropyl) carbodiimine hydrochloride (EDC-HCl, 1.91 g, 10 mmol). The mixture was adjusted to pH 5 with hydrochloric acid, and reacted at room temperature for 5 h. Then, the solution was poured into a dialysis bag (MWCO 3500), dialyzed against 5 mM HCl solution for 1 d, and dialyzed against 5 mM HCl/1% NaCl solution for 1 d, then dialyzed against 1 mM HCl solution for 1 d, lyophilized to obtain CMCh-SH (0.9 g). According to the nuclear magnetic resonance spectrum, the grafting degree of sulfhydryl group can be calculated to be about 10%.

Example 164: Synthesis of Component C-20

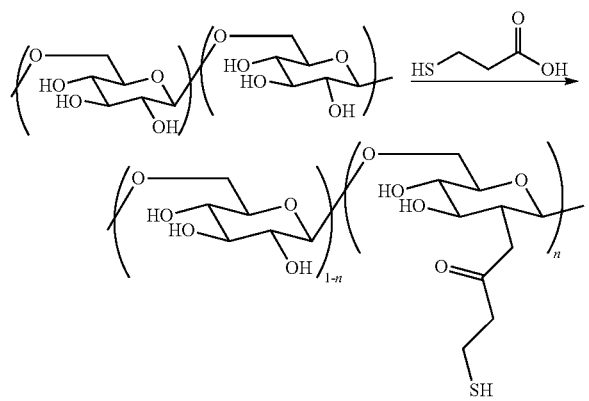

Synthesis of Component C-20. To a solution of dextran (40 kDa, 12 g, 0.3 mmol) in 50 mL DMSO was added 3-mercaptopropionic acid (636.8 mg, 6.0 mmol), 1,3-dicyclohexyl carbodiimine (910.7 mg, 9.0 mmol) and 4-dimethylaminylpyridine (1099.5 mg, 9.0 mmol), and the solution was reacted at room temperature for 48 h. Then, it was reprecipitated in acetone. The crude product was dissolved in water, poured into a dialysis bag (MWCO 3500), dialyzed against deionized water for 2-3 d, and lyophilized to obtain Dex-SH (11.5 g). According to the nuclear magnetic resonance spectrum, the grafting degree of sulfhydryl group can be calculated to be about 20%.

Example 165: Synthesis of Component C-21

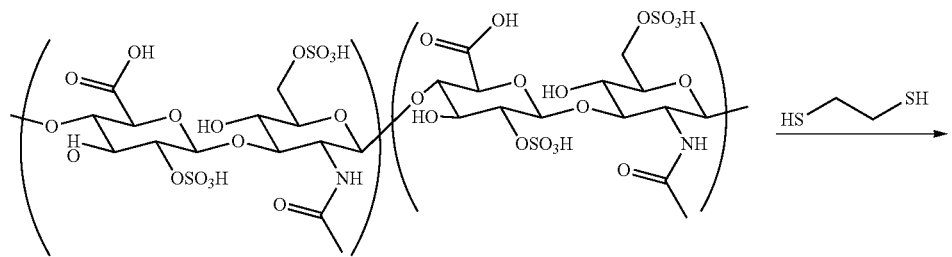

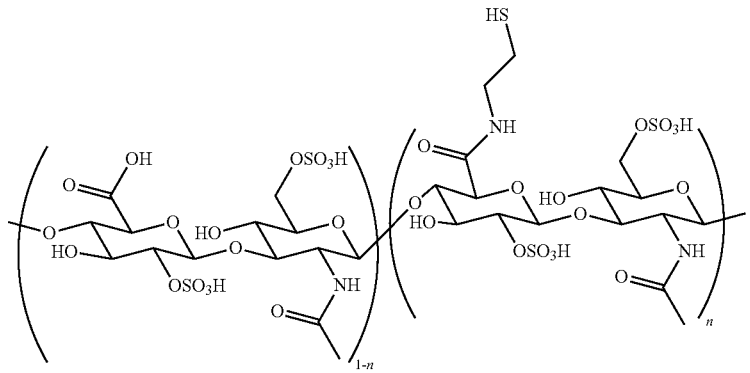

Synthesis of Component C-21. To a solution of heparin (0.5 g, 12 kDa) in 50 mL distilled water was added hydroxybenzotriazole (HOBt, 0.2 g), 1-ethyl-(3-dimethylamine-propyl) carbodiimine hydrochloride (EDC-HCl, 0.1 g) and mercaptoethylamine (0.1 g), the solution was adjusted to pH 5-6 with dilute hydrochloric acid solution and reacted for 24 h. The solution was poured into dialysis bag (MWCO 3500), dialyzed against deionized water for 2-3 d, freeze-dried to obtain Hep-SH (0.45 g). According to the nuclear magnetic resonance spectrum, the grafting degree of sulfhydryl group can be calculated to be about 20%.

Example 166: Photo-Crosslinking Method for Preparing Hydrogel

Different hydrogel precursor solutions were prepared according to the process in the invention at 37° C. as shown in Table 1.

TABLE 1

|  | B | | | | | |
|---|---|---|---|---|---|---|
| A | Component B-1 | Component B-2 | Component B-3 | Component B-1/ Component C . . . | Component B-3/ Component C . . . | Component B-3/ Component C . . . |
|  | concentration | | | | | |
| Component A-1 | 1-20 wt % | 1-20 wt % | 1-20 wt % | 1-20 wt % | 1-20 wt % | 1-20 wt % |
| Component . . . | 1-20 wt % | 1-20 wt % | 1-20 wt % | 1-20 wt % | 1-20 wt % | 1-20 wt % |
| Component A-154 | 1-20 wt % | 1-20 wt % | 1-20 wt % | 1-20 wt % | 1-20 wt % | 1-20 wt % |
| Component A-1/ Component A-2 | 1-20 wt % | 1-20 wt % | 1-20 wt % | 1-20 wt % | 1-20 wt % | 1-20 wt % |
| Component A . . . . . . / Component A . . . . . . | 1-20 wt % | 1-20 wt % | 1-20 wt % | 1-20 wt % | 1-20 wt % | 1-20 wt % |
| Component A-153/ Component A-154 | 1-20 wt % | 1-20 wt % | 1-20 wt % | 1-20 wt % | 1-20 wt % | 1-20 wt % |

The above different gel solutions are irradiated at 365 or 395 nm (20 mW/cm$^2$) for a certain period of time to obtain hydrogels of different chemical compositions. Different gel materials have different biological effects, and the composition of the gel material can be selected in a targeted manner according to different applications.

Note: Component A . . . is Component A-2~A-153; Component A . . . is Component A-1~A-154; Component C . . . is component C-1~C-21.

1-20 wt % in Table 1 is a preferred range of mass concentration of the hydrogel precursor solution.

Example 167: Rheology Test of Photo-Crosslinked Hydrogel

Rheology analysis was performed on a 37° C. test platform ((p=20 mm) using a HAAKE MARS rheometer. In this example, the effects of UV light time, light intensity and mass concentration of polymer derivatives on gelation time and storage modulus of hydrogels were investigated. FIG. 1 shows the gelation curve of the prepared hydrogel precursor solution under illumination of Component A-1 (i.e. HA-NB) prepared in Example 1, Component A-107 (i.e. HAMA) prepared in Example 107, Component C-4 (i.e. Gelatin) prepared in Example 107 and Component C-4 (i.e. Gelatin) and Component B-2 (i.e. LAP) prepared in Example 155, or Component A-88 prepared in Example 88 (i.e., HA-cNB), Component A-144 prepared in Example 144 (i.e., HA-cNB-MA) and Component B-2 (i.e., LAP) prepared in Example 155 (In the rheological test, G' is the storage modulus, G" is the loss modulus, and when G' exceeds G", it is the gel point.). Therefore, both the gelation rate and the gel strength are significantly better than those hydrogels prepared by free radical polymerization crosslinking and photocoupled crosslinking. As shown in FIG. 1, the solution starts to form gel at about 2 s, it is completely gelatinized in about 10 s, and the modulus at the time of complete gel formation can reach 3500-10000 Pa. Further, the strength of the gel is proportional to the mass concentration of the gel solution, and the greater the mass concentration of the gel is, the greater the strength of the gel is. The gel point and final modulus of hydrogel systems composed of other different materials are also different. The specific data are shown in Table 2.

TABLE 2

| The composition of hydrogel material | Gel point (s) | Final Modulus (Pa) |
|---|---|---|
| HA-NB$_0$/CMCh (2% wt:2% wt) | 30 | 200 |
| Component A-1/Component B-1 (2% wt:0.2% wt) | <2 | 1100 |
| Component A-1/Component B-3 (2% wt:0.2% wt) | <2 | 900 |
| Component A-1/Component B-2 (2% wt:0.2% wt) | <2 | 1500 |
| Component A-2/Component B-2 (2% wt:0.2% wt) | <2 | 1400 |
| Component A-8/Component B-2 (2% wt:0.2% wt) | <2 | 1450 |
| Component A-13/Component B-2 (2% wt:0.2% wt) | <2 | 1640 |
| Component A-28/Component B-2 (2% wt:0.2% wt) | <2 | 1550 |
| Component A-33/Component B-2 (2% wt:0.2% wt) | <2 | 2100 |
| Component A-37/Component B-2 (2% wt:0.2% wt) | <2 | 1230 |
| Component A-38/Component B-2 (2% wt:0.2% wt) | <2 | 1050 |
| Component A-39/Component B-2 (2% wt:0.2% wt) | <2 | 990 |
| Component A-40/Component B-2 (2% wt:0.2% wt) | <2 | 860 |
| Component A-41/Component B-2 (2% wt:0.2% wt) | <2 | 880 |
| Component A-43/Component B-2 (2% wt:0.2% wt) | <2 | 1120 |
| Component A-44/Component B-2 (2% wt:0.2% wt) | <2 | 980 |
| Component A-45/Component B-2 (2% wt:0.2% wt) | <2 | 760 |
| Component A-46/Component B-2 (2% wt:0.2% wt) | <2 | 720 |
| Component A-47/Component B-2 (2% wt:0.2% wt) | <2 | 680 |

TABLE 2-continued

| The composition of hydrogel material | Gel point (s) | Final Modulus (Pa) |
|---|---|---|
| Component A-50/Component B-2 (2% wt:0.2% wt) | <2 | 790 |
| Component A-51/Component B-2 (2% wt:0.2% wt) | <2 | 1700 |
| Component A-52/Component B-2 (2% wt:0.2% wt) | <2 | 1890 |
| Component A-53/Component B-2 (2% wt:0.2% wt) | <2 | 1760 |
| Component A-55/Component B-2 (2% wt:0.2% wt) | <2 | 1980 |
| Component A-62/Component B-2 (2% wt:0.2% wt) | <2 | 1680 |
| Component A-65/Component B-2 (2% wt:0.2% wt) | <2 | 2450 |
| Component A-66/Component B-2 (2% wt:0.2% wt) | <2 | 1540 |
| Component A-67/Component B-2 (2% wt:0.2% wt) | <2 | 1320 |
| Component A-68/Component B-2 (2% wt:0.2% wt) | <2 | 1100 |
| Component A-69/Component B-2 (2% wt:0.2% wt) | <2 | 1080 |
| Component A-70/Component B-2 (2% wt:0.2% wt) | <2 | 1670 |
| Component A-71/Component B-2 (2% wt:0.2% wt) | <2 | 1710 |
| Component A-72/Component B-2 (2% wt:0.2% wt) | <2 | 1730 |
| Component A-74/Component B-2 (2% wt:0.2% wt) | <2 | 1780 |
| Component A-80/Component B-2 (2% wt:0.2% wt) | <2 | 1670 |
| Component A-83/Component B-2 (2% wt:0.2% wt) | <2 | 2340 |
| Component A-84/Component B-2 (2% wt:0.2% wt) | <2 | 1310 |
| Component A-85/Component B-2 (2% wt:0.2% wt) | <2 | 1150 |
| Component A-86/Component B-2 (2% wt:0.2% wt) | <2 | 1020 |
| Component A-87/Component B-2 (2% wt:0.2% wt) | <2 | 890 |
| Component A-88/Component B-2 (2% wt:0.2% wt) | <2 | 2140 |
| Component A-89/Component B-2 (2% wt:0.2% wt) | <2 | 2010 |
| Component A-90/Component B-2 (2% wt:0.2% wt) | <2 | 1980 |
| Component A-91/Component B-2 (2% wt:0.2% wt) | <2 | 2040 |
| Component A-93/Component B-2 (2% wt:0.2% wt) | <2 | 1820 |
| Component A-98/Component B-2 (2% wt:0.2% wt) | <2 | 2140 |
| Component A-102/Component B-2 (2% wt:0.2% wt) | <2 | 2790 |
| Component A-103/Component B-2 (2% wt:0.2% wt) | <2 | 2110 |
| Component A-104/Component B-2 (2% wt:0.2% wt) | <2 | 2040 |
| Component A-105/Component B-2 (2% wt:0.2% wt) | <2 | 1890 |
| Component A-106/Component B-2 (2% wt:0.2% wt) | <2 | 1720 |
| Component A-1/Component A-107/Component B-1 (2% wt:1% wt:0.2% wt) | <2 | 2900 |
| Component A-1/Component A-107/Component B-3 (2% wt:1% wt:0.2% wt) | <2 | 2830 |
| Component A-1/Component A-107/Component B-2 (2% wt:1% wt:0.2% wt) | <2 | 3200 |
| Component A-1/Component A-108/Component B-2 (2% wt:1% wt:0.2% wt) | <2 | 2890 |
| Component A-1/Component A-109/Component B-2 (2% wt:1% wt:0.2% wt) | <2 | 2780 |
| Component A-1/Component A-110/Component B-2 (2% wt:1% wt:0.2% wt) | <2 | 2540 |
| Component A-1/Component A-111/Component B-2 (2% wt:1% wt:0.2% wt) | <2 | 2340 |
| Component A-1/Component A-112/Component B-2 (2% wt:1% wt:0.2% wt) | <2 | 2140 |
| Component A-1/Component A-113/Component B-2 (2% wt:1% wt:0.2% wt) | <2 | 1950 |
| Component A-1/Component A-115/Component B-2 (2% wt:1% wt:0.2% wt) | <2 | 1780 |
| Component A-51/Component A-107/Component B-2 (2% wt:1% wt:0.2% wt) | <2 | 3200 |
| Component A-52/Component A-107/Component B-2 (2% wt:1% wt:0.2% wt) | <2 | 3180 |
| Component A-70/Component A-107/Component B-2 (2% wt:1% wt:0.2% wt) | <2 | 3430 |
| Component A-71/Component A-107/Component B-2 (2% wt:1% wt:0.2% wt) | <2 | 3320 |
| Component A-88/Component A-107/Component B-2 (2% wt:1% wt:0.2% wt) | <2 | 8800 |
| Component A-89/Component A-107/Component B-2 (2% wt:1% wt:0.2% wt) | <2 | 7800 |
| Component A-90/Component A-107/Component B-2 (2% wt:1% wt:0.2% wt) | <2 | 6710 |
| Component A-1/Component A-116/Component B-1 (2% wt:1% wt:0.2% wt) | <2 | 4300 |
| Component A-1/Component A-116/Component B-3 (2% wt:1% wt:0.2% wt) | <2 | 4100 |
| Component A-1/Component A-116/Component B-2 (2% wt:1% wt:0.2% wt) | <2 | 4500 |
| Component A-1/Component A-117/Component B-2 (2% wt:1% wt:0.2% wt) | <2 | 4340 |
| Component A-1/Component A-118/Component B-2 (2% wt:1% wt:0.2% wt) | <2 | 4680 |
| Component A-1/Component A-122/Component B-2 (2% wt:1% wt:0.2% wt) | <2 | 4100 |
| Component A-1/Component A-123/Component B-2 (2% wt:1% wt:0.2% wt) | <2 | 4260 |
| Component A-1/Component A-124 Component B-2 (2% wt:1% wt:0.2% wt) | <2 | 3980 |
| Component A-1/Component A-125/Component B-2 (2% wt:1% wt:0.2% wt) | <2 | 3640 |
| Component A-1/Component A-126/Component B-2 (2% wt:1% wt:0.2% wt) | <2 | 5430 |
| Component A-1/Component A-127/Component B-2 (2% wt:1% wt:0.2% wt) | <2 | 5200 |
| Component A-1/Component A-128/Component B-2 (2% wt:1% wt:0.2% wt) | <2 | 4900 |
| Component A-1/Component A-132/Component B-2 (2% wt:1% wt:0.2% wt) | <2 | 4780 |
| Component A-1/Component A-133/Component B-2 (2% wt:1% wt:0.2% wt) | <2 | 4210 |
| Component A-1/Component A-134/Component B-2 (2% wt:1% wt:0.2% wt) | <2 | 4020 |
| Component A-1/Component A-135/Component B-2 (2% wt:1% wt:0.2% wt) | <2 | 5120 |
| Component A-1/Component A-136/Component B-2 (2% wt:1% wt:0.2% wt) | <2 | 4980 |
| Component A-1/Component A-137/Component B-2 (2% wt:1% wt:0.2% wt) | <2 | 4740 |
| Component A-1/Component A-141/Component B-2 (2% wt:1% wt:0.2% wt) | <2 | 3890 |
| Component A-1/Component A-142/Component B-2 (2% wt:1% wt:0.2% wt) | <2 | 3720 |
| Component A-1/Component A-143/Component B-2 (2% wt:1% wt:0.2% wt) | <2 | 3580 |
| Component A-1/Component A-144/Component B-2 (2% wt:1% wt:0.2% wt) | <2 | 8900 |
| Component A-1/Component A-145/Component B-2 (2% wt:1% wt:0.2% wt) | <2 | 8200 |
| Component A-1/Component A-146/Component B-2 (2% wt:1% wt:0.2% wt) | <2 | 7890 |
| Component A-1/Component A-147/Component B-2 (2% wt:1% wt:0.2% wt) | <2 | 8300 |
| Component A-1/Component A-152/Component B-2 (2% wt:1% wt:0.2% wt) | <2 | 7100 |
| Component A-1/Component A-153/Component B-2 (2% wt:1% wt:0.2% wt) | <2 | 6800 |
| Component A-1/Component A-154/Component B-2 (2% wt:1% wt:0.2% wt) | <2 | 6700 |
| Component A-51/Component A-126/Component B-2 (2% wt:1% wt:0.2% wt) | <2 | 5670 |
| Component A-52/Component A-127/Component B-2 (2% wt:1% wt:0.2% wt) | <2 | 5100 |
| Component A-71/Component A-135/Component B-2 (2% wt:1% wt:0.2% wt) | <2 | 4800 |
| Component A-72/Component A-136/Component B-2 (2% wt:1% wt:0.2% wt) | <2 | 4300 |
| Component A-88/Component A-144/Component B-2 (2% wt:1% wt:0.2% wt) | <2 | 10000 |
| Component A-89/Component A-145/Component B-2 (2% wt:1% wt:0.2% wt) | <2 | 9400 |
| Component A-90/Component A-146/Component B-2 (2% wt:1% wt:0.2% wt) | <2 | 8700 |
| Component A-1/Component A-107/Component C-3/Component B-1 (2% wt:1% wt:2% wt:0.2% wt) | <2 | 4600 |
| Component A-1/Component A-107/Component C-3/Component B-3 (2% wt:1% wt:2% wt:0.2% wt) | <2 | 3900 |
| Component A-1/Component A-107/Component C-3/Component B-2 (2% wt:1% wt:2% wt:0.2% wt) | <2 | 5100 |
| Component A-1/Component A-107/Component C-4/Component B-2 (2% wt:1% wt:6% wt:0.2 % wt) | <2 | 3500 |
| Component A-1/Component A-107/Component C-8/Component B-2 (2% wt:1% wt:2% wt:0.2% wt) | <2 | 2300 |
| Component A-1/Component A-107/Component C-10/Component B-2 (2% wt:1% wt:2% wt:0.2% wt) | <2 | 1600 |
| Component A-1/Component A-107/Component C-11/Component B-2 (2% wt:1% wt:2% wt:0.2% wt) | <2 | 5400 |
| Component A-1/Component A-107/Component C-14/Component B-2 (2% wt:1% wt:2% wt:0.2% wt) | <2 | 2400 |

TABLE 2-continued

| The composition of hydrogel material | Gel point (s) | Final Modulus (Pa) |
|---|---|---|
| Component A-51/Component A-107/Component C-3/Component B-2 (2% wt:1% wt:2% wt:0.2% wt) | <2 | 4500 |
| Component A-52/Component A-107/Component C-3/Component B-2 (2% wt:1% wt:2% wt:0.2% wt) | <2 | 4200 |
| Component A-71/Component A-107/Component C-3/Component B-2 (2% wt:1% wt:2% wt:0.2% wt) | <2 | 4100 |
| Component A-72/Component A-107/Component C-3/Component B-2 (2% wt:1% wt:2% wt:0.2% wt) | <2 | 3910 |
| Component A-88/Component A-107/Component C-3/Component B-2 (2% wt:1% wt:2% wt:0.2% wt) | <2 | 7600 |
| Component A-89/Component A-107/Component C-3/Component B-2 (2% wt:1% wt:2% wt:0.2% wt) | <2 | 7300 |
| Component A-90/Component A-107/Component C-3/Component B-2 (2% wt:1% wt:2% wt:0.2% wt) | <2 | 7100 |

Note:
$NB_0$ is o-nitrobenzyl phototriggers used for constructing of hydrogels reported in the literature. (Yunlong Yang; Jieyuan Zhang; Zhenzhen Liu; Qiuning Lin; Xiaolin Liu; Chunyan Bao; Yang Wang; Linyong Zhu. Adv. Mater. 2016, 28, 2724.). $HA-NB_0$ is hyaluronic acid polymer derivative modified by $NB_0$. NB is o-nitrobenzyl phototriggers in Component A-1 of the invention; cNB is cyclic o-nitrobenzyl phototriggers in Component A-88 of the invention; cNB-MA is cyclic o-nitrobenzyl phototriggers and double bond functional group in Component A-144 of the invention. Among them, HA-NB is Component A-1; HA-cNB is Component A-88; HA-cNB-MA is Component A-144.

Example 168: Adhesion Test of Photo-Crosslinked Hydrogel

Fresh pig casings were taken and cutted into 3.5 cm×2.5 cm casing pieces, and then fixed to 6.5 cm×2.5 cm tempered glass piece using 502 glue. The above tempered glass piece was taken, and 150 μL of a certain component of the hydrogel precursor solution was applied to one of the connected casing surfaces. Then, another piece of glass was placed over the above piece of glass to completely opposite, and the excess extruded hydrogel precursor solution was wiped off. The casing was irradiated for 5 min using a 395 nm UV LED source (20 mW/cm$^2$) to allow the hydrogel precursor solution to gel in situ between the two casings. After the glue was completed, one end of the glass piece was vertically fixed, and the other end was connected to a container capable of holding water through a string. The metered water was then continuously added to the container until the two pieces of glass were broken. Thereafter, the mass of the water and the container at this time was recorded and converted into gravity, that was, the tensile force F when the glass piece was broken. The tissue adhesion of the hydrogel was calculated using the following formula:

Hydrogel tissue adhesion=$F/A$

Figure 2:
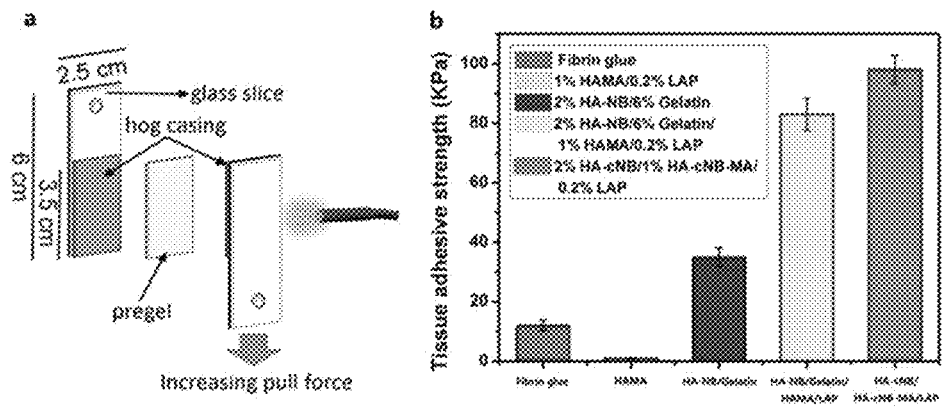
FIG. 2 is a adhesion test graph of the hydrogel (2% HA-NB/6% Gelatin/1% HAMA/0.2% LAP 或 2% HA-cNB/1% HA-cNB-MA/0.2% LAP).

A is the adhesion area of the casing, and the test device is shown in FIG. 2. The tissue adhesion of hydrogel systems composed of other different materials is also different. The specific data is shown in Table 3.

TABLE 3

| Composition of hydrogel material | Tissue adhesion (kPa) |
|---|---|
| HA-NB$_0$/CMCh (2% wt:2% wt) | 24 |
| Component A-1/Component B-1 (2% wt:0.2% wt) | 80 |
| Component A-1/Component B-3 (2% wt:0.2% wt) | 81 |
| Component A-1/Component B-2 (2% wt:0.2% wt) | 84 |
| Component A-2/Component B-2 (2% wt:0.2% wt) | 78 |
| Component A-8/Component B-2 (2% wt:0.2% wt) | 79 |
| Component A-13/Component B-2 (2% wt:0.2% wt) | 74 |
| Component A-28/Component B-2 (2% wt:0.2% wt) | 72 |
| Component A-33/Component B-2 (2% wt:0.2% wt) | 88 |
| Component A-37/Component B-2 (2% wt:0.2% wt) | 82 |
| Component A-38/Component B-2 (2% wt:0.2% wt) | 77 |
| Component A-39/Component B-2 (2% wt:0.2% wt) | 73 |
| Component A-40/Component B-2 (2% wt:0.2% wt) | 68 |
| Component A-41/Component B-2 (2% wt:0.2% wt) | 66 |
| Component A-43/Component B-2 (2% wt:0.2% wt) | 74 |
| Component A-44/Component B-2 (2% wt:0.2% wt) | 63 |
| Component A-45/Component B-2 (2% wt:0.2% wt) | 67 |
| Component A-46/Component B-2 (2% wt:0.2% wt) | 63 |
| Component A-47/Component B-2 (2% wt:0.2% wt) | 65 |
| Component A-50/Component B-2 (2% wt:0.2% wt) | 61 |
| Component A-51/Component B-2 (2% wt:0.2% wt) | 67 |
| Component A-52/Component B-2 (2% wt:0.2% wt) | 63 |
| Component A-53/Component B-2 (2% wt:0.2% wt) | 62 |
| Component A-55/Component B-2 (2% wt:0.2% wt) | 61 |
| Component A-62/Component B-2 (2% wt:0.2% wt) | 65 |
| Component A-65/Component B-2 (2% wt:0.2% wt) | 69 |
| Component A-66/Component B-2 (2% wt:0.2% wt) | 67 |
| Component A-67/Component B-2 (2% wt:0.2% wt) | 66 |
| Component A-68/Component B-2 (2% wt:0.2% wt) | 62 |
| Component A-69/Component B-2 (2% wt:0.2% wt) | 60 |
| Component A-70/Component B-2 (2% wt:0.2% wt) | 68 |
| Component A-71/Component B-2 (2% wt:0.2% wt) | 66 |
| Component A-72/Component B-2 (2% wt:0.2% wt) | 64 |
| Component A-74/Component B-2 (2% wt:0.2% wt) | 62 |
| Component A-80/Component B-2 (2% wt:0.2% wt) | 67 |
| Component A-83/Component B-2 (2% wt:0.2% wt) | 69 |
| Component A-84/Component B-2 (2% wt:0.2% wt) | 66 |
| Component A-85/Component B-2 (2% wt:0.2% wt) | 64 |
| Component A-86/Component B-2 (2% wt:0.2% wt) | 61 |
| Component A-87/Component B-2 (2% wt:0.2% wt) | 60 |
| Component A-88/Component B-2 (2% wt:0.2% wt) | 78 |
| Component A-89/Component B-2 (2% wt:0.2% wt) | 76 |
| Component A-90/Component B-2 (2% wt:0.2% wt) | 74 |
| Component A-91/Component B-2 (2% wt:0.2% wt) | 75 |
| Component A-93/Component B-2 (2% wt:0.2% wt) | 73 |
| Component A-98/Component B-2 (2% wt:0.2% wt) | 75 |
| Component A-102/Component B-2 (2% wt:0.2% wt) | 77 |
| Component A-103/Component B-2 (2% wt:0.2% wt) | 72 |
| Component A-104/Component B-2 (2% wt:0.2% wt) | 71 |
| Component A-105/Component B-2 (2% wt:0.2% wt) | 68 |
| Component A-106/Component B-2 (2% wt:0.2% wt) | 62 |
| Component A-1/Component A-107/Component B-1 (2% wt:1% wt:0.2% wt) | 85 |
| Component A-1/Component A-107/Component B-3 (2% wt:1% wt:0.2% wt) | 81 |
| Component A-1/Component A-107/Component B-3 (2% wt:1% wt:0.2% wt) | 84 |
| Component A-1/Component A-108/Component B-2 (2% wt:1% wt:0.2% wt) | 82 |
| Component A-1/Component A-109/Component B-2 (2% wt:1% wt:0.2% wt) | 80 |
| Component A-1/Component A-110/Component B-2 (2% wt:1% wt:0.2% wt) | 79 |
| Component A-1/Component A-111/Component B-2 (2% wt:1% wt:0.2% wt) | 81 |
| Component A-1/Component A-112/Component B-2 (2% wt:1% wt:0.2% wt) | 82 |
| Component A-1/Component A-113/Component B-2 (2% wt:1% wt:0.2% wt) | 81 |
| Component A-1/Component A-115/Component B-2 (2% wt:1% wt:0.2% wt) | 80 |
| Component A-51/Component A-107/Component B-2 (2% wt:1% wt:0.2% wt) | 76 |
| Component A-52/Component A-107/Component B-2 (2% wt:1% wt:0.2% wt) | 74 |
| Component A-70/Component A-107/Component B-2 (2% wt:1% wt:0.2% wt) | 73 |
| Component A-71/Component A-107/Component B-2 (2% wt:1% wt:0.2% wt) | 71 |
| Component A-88/Component A-107/Component B-2 (2% wt:1% wt:0.2% wt) | 99 |
| Component A-89/Component A-107/Component B-2 (2% wt:1% wt:0.2% wt) | 92 |

TABLE 3-continued

| Composition of hydrogel material | Tissue adhesion (kPa) |
|---|---|
| Component A-90/Component A-107/Component B-2 (2% wt:1% wt:0.2% wt) | 91 |
| Component A-1/Component A-116/Component B-1 (2% wt:1% wt:0.2% wt) | 88 |
| Component A-1/Component A-116/Component B-3 (2% wt:1% wt:0.2% wt) | 86 |
| Component A-1/Component A-116/Component B-2 (2% wt:1% wt:0.2% wt) | 84 |
| Component A-1/Component A-117/Component B-2 (2% wt:1% wt:0.2% wt) | 82 |
| Component A-1/Component A-118/Component B-2 (2% wt:1% wt:0.2% wt) | 81 |
| Component A-1/Component A-122/Component B-2 (2% wt:1% wt:0.2% wt) | 78 |
| Component A-1/Component A-123/Component B-2 (2% wt:1% wt:0.2% wt) | 74 |
| Component A-1/Component A-124 Component B-2 (2% wt:1% wt:0.2% wt) | 71 |
| Component A-1/Component A-125/Component B-2 (2% wt:1% wt:0.2% wt) | 69 |
| Component A-1/Component A-126/Component B-2 (2% wt:1% wt:0.2% wt) | 84 |
| Component A-1/Component A-127/Component B-2 (2% wt:1% wt:0.2% wt) | 82 |
| Component A-1/Component A-128/Component B-2 (2% wt:1% wt:0.2% wt) | 79 |
| Component A-1/Component A-132/Component B-2 (2% wt:1% wt:0.2% wt) | 80 |
| Component A-1/Component A-133/Component B-2 (2% wt:1% wt:0.2% wt) | 76 |
| Component A-1/Component A-134/Component B-2 (2% wt:1% wt:0.2% wt) | 74 |
| Component A-1/Component A-135/Component B-2 (2% wt:1% wt:0.2% wt) | 82 |
| Component A-1/Component A-136/Component B-2 (2% wt:1% wt:0.2% wt) | 80 |
| Component A-1/Component A-137/Component B-2 (2% wt:1% wt:0.2% wt) | 79 |
| Component A-1/Component A-141/Component B-2 (2% wt:1% wt:0.2% wt) | 76 |
| Component A-1/Component A-142/Component B-2 (2% wt:1% wt:0.2% wt) | 74 |
| Component A-1/Component A-143/Component B-2 (2% wt:1% wt:0.2% wt) | 71 |
| Component A-1/Component A-144/Component B-2 (2% wt:1% wt:0.2% wt) | 86 |
| Component A-1/Component A-145/Component B-2 (2% wt:1% wt:0.2% wt) | 82 |
| Component A-1/Component A-146/Component B-2 (2% wt:1% wt:0.2% wt) | 88 |
| Component A-1/Component A-147/Component B-2 (2% wt:1% wt:0.2% wt) | 83 |
| Component A-1/Component A-152/Component B-2 (2% wt:1% wt:0.2% wt) | 82 |
| Component A-1/Component A-153/Component B-2 (2% wt:1% wt:0.2% wt) | 76 |
| Component A-1/Component A-154/Component B-2 (2% wt:1% wt:0.2% wt) | 72 |
| Component A-51/Component A-126/Component B-2 (2% wt:1% wt:0.2% wt) | 81 |
| Component A-52/Component A-127/Component B-2 (2% wt:1% wt:0.2% wt) | 78 |
| Component A-71/Component A-135/Component B-2 (2% wt:1% wt:0.2% wt) | 76 |
| Component A-72/Component A-136/Component B-2 (2% wt:1% wt:0.2% wt) | 79 |
| Component A-88/Component A-144/Component B-2 (2% wt:1% wt:0.2% wt) | 85 |
| Component A-89/Component A-145/Component B-2 (2% wt:1% wt:0.2% wt) | 82 |
| Component A-90/Component A-146/Component B-2 (2% wt:1% wt:0.2% wt) | 81 |
| Component A-1/Component A-107/Component C-3/Component B-1 (2% wt:1% wt:2% wt:0.2% wt) | 85 |
| Component A-1/Component A-107/Component C-3/Component B-3 (2% wt:1% wt:2% wt:0.2% wt) | 83 |
| Component A-1/Component A-107/Component C-3/Component B-2 (2% wt:1% wt:2% wt:0.2% wt) | 84 |
| Component A-1/Component A-107/Component C-4/Component B-2 (2% wt:1% wt:6% wt:0.2% wt) | 81 |
| Component A-1/Component A-107/Component C-8/Component B-2 (2% wt:1% wt:2% wt:0.2% wt) | 83 |
| Component A-1/Component A-107/Component C-10/Component B-2 (2% wt:1% wt:2% wt:0.2% wt) | 80 |
| Component A-1/Component A-107/Component C-11/Component B-2 (2% wt:1% wt:2% wt:0.2% wt) | 78 |
| Component A-1/Component A-107/Component C-14/Component B-2 (2% wt:1% wt:2% wt:0.2% wt) | 77 |
| Component A-51/Component A-107/Component C-3/Component B-2 (2% wt:1% wt:2% wt:0.2% wt) | 76 |
| Component A-52/Component A-107/Component C-3/Component B-2 (2% wt:1% wt:2% wt:0.2% wt) | 77 |
| Component A-71/Component A-107/Component C-3/Component B-2 (2% wt:1% wt:2% wt:0.2% wt) | 75 |
| Component A-72/Component A-107/Component C-3/Component B-2 (2% wt:1% wt:2% wt:0.2% wt) | 79 |
| Component A-88/Component A-107/Component C-3/Component B-2 (2% wt:1% wt:2% wt:0.2% wt) | 83 |
| Component A-89/Component A-107/Component C-3/Component B-2 (2% wt:1% wt:2% wt:0.2% wt) | 85 |
| Component A-90/Component A-107/Component C-3/Component B-2 (2% wt:1% wt:2% wt:0.2% wt) | 87 |

Example 169: Mechanical Properties Test of Photo-Crosslinked Hydrogel

Figure 3:
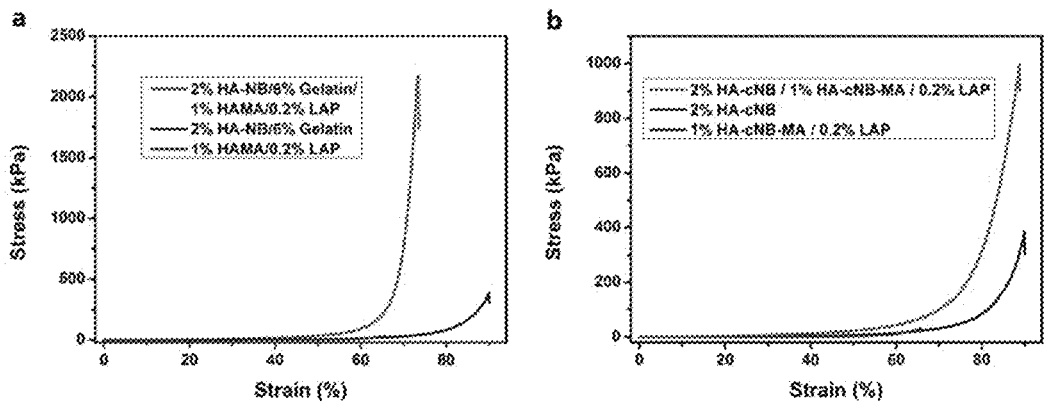
FIG. 3 is a compression test diagram of the hydrogel (2% HA-NB/6% Gelatin/1% HAMA/0.2% LAP 或 2% HA-cNB/1% HA-cNB-MA/0.2% LAP).

The mechanical properties test was performed by GT-TCS-2000 tensile machine (including tensile test and compression test). The tensile test specimen is a dumbbell specimen with a length of 20 mm, a width of 3 mm and a thickness of 2 mm, and the test speed is 5 mm/min. The compression test sample is a cylindrical specimen with a diameter of 10 mm and a height of 3 mm, and the test speed is 1 mm/min. Take the hydrogel compared by Component A-1 (i.e., HA-NB) prepared in Example 1, Component A-107 (i.e., HAMA) prepared in Example 107, Component C-4 (i.e., gelatin) and Component B-2 (i.e., LAP) prepared in Example 155, or Component A-88 (i.e., HA-cNB) prepared in Example 88, Component A-144 (i.e., HA-cNB-MA) prepared in Example 144 and Component B-2 (i.e., LAP) prepared in Example 155 as an example to test the tensile and compressive properties of the hydrogel. As shown in FIG. 3, the hydrogel (HA-NB/HAMA/LAP) can be compressed to about 75% with the compression strength of about 2 MPa. Hydrogels (HA-cNB/HA-cNB-MA/LAP) can be compressed to about 88% with compression strength of about 1 MPa. The mechanical properties of hydrogel systems composed of other different materials are also different. The specific data are shown in Table 4.

TABLE 4

| The composition of hydrogel material | Compression ratio (%) | Compressive strength (kPa) |
|---|---|---|
| HA-NB$_0$/CMCh (2% wt:2% wt) | 45 | 200 |
| Component A-1/Component B-1 (2% wt:0.2% wt) | 71 | 850 |
| Component A-1/Component B-3 (2% wt:0.2% wt) | 68 | 780 |

TABLE 4-continued

| The composition of hydrogel material | Compression ratio (%) | Compressive strength (kPa) |
|---|---|---|
| Component A-1/Component B-2 (2% wt:0.2% wt) | 72 | 960 |
| Component A-2/Component B-2 (2% wt:0.2% wt) | 70 | 880 |
| Component A-8/Component B-2 (2% wt:0.2% wt) | 68 | 820 |
| Component A-13/Component B-2 (2% wt:0.2% wt) | 67 | 800 |
| Component A-28/Component B-2 (2% wt:0.2% wt) | 72 | 880 |
| Component A-33/Component B-2 (2% wt:0.2% wt) | 75 | 990 |
| Component A-37/Component B-2 (2% wt:0.2% wt) | 72 | 930 |
| Component A-38/Component B-2 (2% wt:0.2% wt) | 67 | 850 |
| Component A-39/Component B-2 (2% wt:0.2% wt) | 63 | 840 |
| Component A-40/Component B-2 (2% wt:0.2% wt) | 61 | 760 |
| Component A-41/Component B-2 (2% wt:0.2% wt) | 66 | 730 |
| Component A-43/Component B-2 (2% wt:0.2% wt) | 71 | 760 |
| Component A-44/Component B-2 (2% wt:0.2% wt) | 73 | 790 |
| Component A-45/Component B-2 (2% wt:0.2% wt) | 68 | 820 |
| Component A-46/Component B-2 (2% wt:0.2% wt) | 69 | 850 |
| Component A-47/Component B-2 (2% wt:0.2% wt) | 65 | 760 |
| Component A-50/Component B-2 (2% wt:0.2% wt) | 61 | 720 |
| Component A-51/Component B-2 (2% wt:0.2% wt) | 72 | 880 |
| Component A-52/Component B-2 (2% wt:0.2% wt) | 73 | 850 |
| Component A-53/Component B-2 (2% wt:0.2% wt) | 68 | 810 |
| Component A-55/Component B-2 (2% wt:0.2% wt) | 66 | 830 |
| Component A-62/Component B-2 (2% wt:0.2% wt) | 65 | 800 |
| Component A-65/Component B-2 (2% wt:0.2% wt) | 73 | 860 |
| Component A-66/Component B-2 (2% wt:0.2% wt) | 67 | 870 |
| Component A-67/Component B-2 (2% wt:0.2% wt) | 66 | 850 |
| Component A-68/Component B-2 (2% wt:0.2% wt) | 62 | 750 |
| Component A-69/Component B-2 (2% wt:0.2% wt) | 60 | 720 |
| Component A-70/Component B-2 (2% wt:0.2% wt) | 68 | 820 |
| Component A-71/Component B-2 (2% wt:0.2% wt) | 67 | 800 |
| Component A-72/Component B-2 (2% wt:0.2% wt) | 64 | 790 |
| Component A-74/Component B-2 (2% wt:0.2% wt) | 70 | 810 |
| Component A-80/Component B-2 (2% wt:0.2% wt) | 72 | 830 |
| Component A-83/Component B-2 (2% wt:0.2% wt) | 73 | 880 |
| Component A-84/Component B-2 (2% wt:0.2% wt) | 66 | 850 |
| Component A-85/Component B-2 (2% wt:0.2% wt) | 64 | 790 |
| Component A-86/Component B-2 (2% wt:0.2% wt) | 61 | 770 |
| Component A-87/Component B-2 (2% wt:0.2% wt) | 60 | 720 |
| Component A-88/Component B-2 (2% wt:0.2% wt) | 78 | 980 |
| Component A-89/Component B-2 (2% wt:0.2% wt) | 76 | 940 |
| Component A-90/Component B-2 (2% wt:0.2% wt) | 74 | 920 |
| Component A-91/Component B-2 (2% wt:0.2% wt) | 75 | 900 |
| Component A-93/Component B-2 (2% wt:0.2% wt) | 73 | 910 |
| Component A-98/Component B-2 (2% wt:0.2% wt) | 75 | 900 |
| Component A-102/Component B-2 (2% wt:0.2% wt) | 77 | 970 |
| Component A-103/Component B-2 (2% wt:0.2% wt) | 72 | 950 |
| Component A-104/Component B-2 (2% wt:0.2% wt) | 71 | 850 |
| Component A-105/Component B-2 (2% wt:0.2% wt) | 68 | 820 |
| Component A-106/Component B-2 (2% wt:0.2% wt) | 62 | 800 |
| Component A-1/Component A-107/Component B-1 (2% wt:1% wt:0.2% wt) | 82 | 940 |
| Component A-1/Component A-107/Component B-3 (2% wt:1% wt:0.2% wt) | 81 | 920 |
| Component A-1/Component A-107/Component B-2 (2% wt:1% wt:0.2% wt) | 83 | 980 |
| Component A-1/Component A-108/Component B-2 (2% wt:1% wt:0.2% wt) | 80 | 950 |
| Component A-1/Component A-109/Component B-2 (2% wt:1% wt:0.2% wt) | 78 | 920 |
| Component A-1/Component A-110/Component B-2 (2% wt:1% wt:0.2% wt) | 75 | 900 |
| Component A-1/Component A-111/Component B-2 (2% wt:1% wt:0.2% wt) | 78 | 930 |
| Component A-1/Component A-112/Component B-2 (2% wt:1% wt:0.2% wt) | 80 | 960 |
| Component A-1/Component A-113/Component B-2 (2% wt:1% wt:0.2% wt) | 81 | 940 |
| Component A-1/Component A-115/Component B-2 (2% wt:1% wt:0.2% wt) | 79 | 910 |
| Component A-51/Component A-107/Component B-2 (2% wt:1% wt:0.2% wt) | 78 | 880 |
| Component A-52/Component A-107/Component B-2 (2% wt:1% wt:0.2% wt) | 76 | 890 |
| Component A-70/Component A-107/Component B-2 (2% wt:1% wt:0.2% wt) | 74 | 870 |
| Component A-71/Component A-107/Component B-2 (2% wt:1% wt:0.2% wt) | 73 | 880 |
| Component A-88/Component A-107/Component B-2 (2% wt:1% wt:0.2% wt) | 86 | 970 |
| Component A-89/Component A-107/Component B-2 (2% wt:1% wt:0.2% wt) | 83 | 980 |
| Component A-90/Component A-107/Component B-2 (2% wt:1% wt:0.2% wt) | 84 | 960 |
| Component A-1/Component A-116/Component B-1 (2% wt:1% wt:0.2% wt) | 81 | 870 |
| Component A-1/Component A-116/Component B-3 (2% wt:1% wt:0.2% wt) | 83 | 830 |
| Component A-1/Component A-116/Component B-2 (2% wt:1% wt:0.2% wt) | 84 | 850 |
| Component A-1/Component A-117/Component B-2 (2% wt:1% wt:0.2% wt) | 82 | 820 |
| Component A-1/Component A-118/Component B-2 (2% wt:1% wt:0.2% wt) | 81 | 860 |
| Component A-1/Component A-122/Component B-2 (2% wt:1% wt:0.2% wt) | 78 | 810 |
| Component A-1/Component A-123/Component B-2 (2% wt:1% wt:0.2% wt) | 74 | 890 |
| Component A-1/Component A-124/Component B-2 (2% wt:1% wt:0.2% wt) | 77 | 800 |
| Component A-1/Component A-125/Component B-2 (2% wt:1% wt:0.2% wt) | 79 | 830 |

TABLE 4-continued

| The composition of hydrogel material | Compression ratio (%) | Compressive strength (kPa) |
|---|---|---|
| Component A-1/Component A-126/Component B-2 (2% wt:1% wt:0.2% wt) | 74 | 840 |
| Component A-1/Component A-127/Component B-2 (2% wt:1% wt:0.2% wt) | 73 | 810 |
| Component A-1/Component A-128/Component B-2 (2% wt:1% wt:0.2% wt) | 75 | 790 |
| Component A-1/Component A-132/Component B-2 (2% wt:1% wt:0.2% wt) | 70 | 770 |
| Component A-1/Component A-133/Component B-2 (2% wt:1% wt:0.2% wt) | 76 | 750 |
| Component A-1/Component A-134/Component B-2 (2% wt:1% wt:0.2% wt) | 74 | 730 |
| Component A-1/Component A-135/Component B-2 (2% wt:1% wt:0.2% wt) | 73 | 710 |
| Component A-1/Component A-136/Component B-2 (2% wt:1% wt:0.2% wt) | 76 | 730 |
| Component A-1/Component A-137/Component B-2 (2% wt:1% wt:0.2% wt) | 75 | 720 |
| Component A-1/Component A-141/Component B-2 (2% wt:1% wt:0.2% wt) | 76 | 750 |
| Component A-1/Component A-142/Component B-2 (2% wt:1% wt:0.2% wt) | 74 | 710 |
| Component A-1/Component A-143/Component B-2 (2% wt:1% wt:0.2% wt) | 71 | 700 |
| Component A-1/Component A-144/Component B-2 (2% wt:1% wt:0.2% wt) | 73 | 720 |
| Component A-1/Component A-145/Component B-2 (2% wt:1% wt:0.2% wt) | 72 | 730 |
| Component A-1/Component A-146/Component B-2 (2% wt:1% wt:0.2% wt) | 76 | 780 |
| Component A-1/Component A-147/Component B-2 (2% wt:1% wt:0.2% wt) | 74 | 770 |
| Component A-1/Component A-152/Component B-2 (2% wt:1% wt:0.2% wt) | 72 | 710 |
| Component A-1/Component A-153/Component B-2 (2% wt:1% wt:0.2% wt) | 76 | 700 |
| Component A-1/Component A-154/Component B-2 (2% wt:1% wt:0.2% wt) | 72 | 740 |
| Component A-51/Component A-126/Component B-2 (2% wt:1% wt:0.2% wt) | 71 | 760 |
| Component A-52/Component A-127/Component B-2 (2% wt:1% wt:0.2% wt) | 74 | 730 |
| Component A-71/Component A-135/Component B-2 (2% wt:1% wt:0.2% wt) | 76 | 720 |
| Component A-72/Component A-136/Component B-2 (2% wt:1% wt:0.2% wt) | 79 | 700 |
| Component A-88/Component A-144/Component B-2 (2% wt:1% wt:0.2% wt) | 88 | 1000 |
| Component A-89/Component A-145/Component B-2 (2% wt:1% wt:0.2% wt) | 87 | 980 |
| Component A-90/Component A-146/Component B-2 (2% wt:1% wt:0.2% wt) | 83 | 970 |
| Component A-1/Component A-107/Component C-3/Component B-1 (2% wt:1% wt:2% wt:0.2% wt) | 74 | 1600 |
| Component A-1/Component A-107/Component C-3/Component B-3 (2% wt:1% wt:2% wt: 0.2% wt) | 71 | 1700 |
| Component A-1/Component A-107/Component C-3/Component B-2 (2% wt:1% wt:2% wt: 0.2% wt) | 72 | 1500 |
| Component A-1/Component A-107/Component C-4/Component B-2 (2% wt:1% wt:6% wt: 0.2% wt) | 75 | 2000 |
| Component A-1/Component A-107/Component C-8/Component B-2 (2% wt:1% wt:2% wt: 0.2% wt) | 73 | 1800 |
| Component A-1/Component A-107/Component C-10/Component B-2 (2% wt:1% wt:2% wt: 0.2% wt) | 70 | 1600 |
| Component A-1/Component A-107/Component C-11/Component B-2 (2% wt:1% wt:2% wt: 0.2% wt) | 72 | 1300 |
| Component A-1/Component A-107/Component C-14/Component B-2 (2% wt:1% wt:2% wt: 0.2% wt) | 71 | 1500 |
| Component A-51/Component A-107/Component C-3/Component B-2 (2% wt:1% wt:2% wt: 0.2% wt) | 73 | 1400 |
| Component A-52/Component A-107/Component C-3/Component B-2 (2% wt:1% wt:2% wt: 0.2% wt) | 71 | 1600 |
| Component A-71/Component A-107/Component C-3/Component B-2 (2% wt:1% wt:2% wt: 0.2% wt) | 75 | 1200 |
| Component A-72/Component A-107/Component C-3/Component B-2 (2% wt:1% wt:2% wt:0.2% wt) | 73 | 1500 |
| Component A-88/Component A-107/Component C-3/Component B-2 (2% wt:1% wt:2% wt: 0.2% wt) | 73 | 1300 |
| Component A-89/Component A-107/Component C-3/Component B-2 (2% wt:1% wt:2% wt:0.2% wt) | 75 | 1600 |
| Component A-90/Component A-107/Component C-3/Component B-2 (2% wt:1% wt:2% wt: 0.2% wt) | 77 | 1800 |

Example 170: Biocompatibility Test of Photo-Crosslinked Hydrogel

In this experiment, Component A-1 (i.e., HA-NB) prepared in Example 1, Component A-107 (i.e., HAMA) prepared in Example 107, Component C-4 (i.e., gelatin) and Component B-2 (i.e., LAP) prepared in Example 155, or Component A-88 prepared in Example 88 (i.e. HA-cNB), Component A-144 prepared in Example 144 (i.e. HA-cNB-MA) and Component B-2 prepared in Example 155 (i.e. LAP) were taken as example s to be evaluated by CCK-8 kit. First, fibroblast HDFs were seeded in a 96-well plate with a cell density of $5 \times 10^3$ cells/well, then added the medium and cultured at 37° C./5% $CO_2$ for 24 h. Each group of test samples diluted in a cell culture medium was added to well plate in which cells were cultured, and cultured for 24 h. Then, the cell fluid in the well was aspirated and added 100 μL of the medium and 10 μL of CCK-8 solution, and the cells were further incubated for 2 h. Finally, the absorbance at 450 nm in each well was measured using a microplate reader. Cell viability is calculated as follows:

Cell Viability (%)=(The average absorbance of the experimental group/the average absorbance of the control group)×100%

Figure 4:
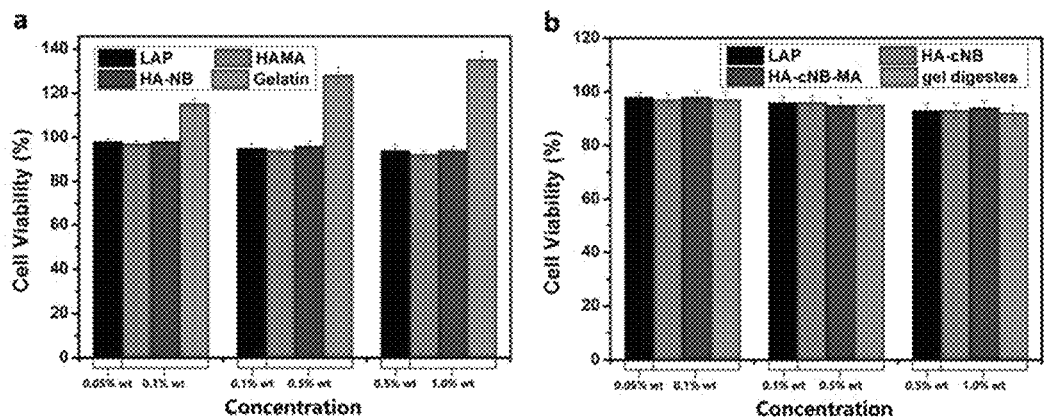
FIG. 4 is a graph of biocompatibility testing of the hydrogel (HA-NB/Gelatin/HAMA/LAP 或 HA-cNB/HA-cNB-MA/LAP).

As shown in FIG. 4, this Formula of photo-crosslinked hydrogel has good biocompatibility.

In the in vivo immune inflammatory response test, Component A-1 (i.e., HA-NB) prepared in Example 1, Component A-107 (i.e., HAMA) prepared in Example 107, Component C-4 (i.e., gelatin) and Component B-2 (i.e., LAP) prepared in Example 155, or Component A-88 prepared in Example 88 (i.e. HA-cNB), Component A-144 prepared in Example 144 (i.e. HA-cNB-MA) and Component B-2 prepared in Example 155 (i.e. LAP) were taken as examples to be implanted under the skin of the rabbit, and the inflammatory reaction of the hydrogel on the body was analyzed by tissue section staining at different time points.

The biocompatibility of other hydrogel systems compared by different materials is also different. The specific data is shown in Table 5.

TABLE 5

| Composition of hydrogel material | Survival rate (%) | Composition of hydrogel material | Survival rate (%) |
|---|---|---|---|
| Component A-1/ Component B-1 | 98 | Component A-1/ Component A-107/ Component B-3 | 96 |
| Component A-1/ Component B-3 | 95 | Component A-1/ Component A-107/ Component B-2 | 94 |
| Component A-1/ Component B-2 | 94 | Component A-1/ Component A-108/ Component B-2 | 98 |
| Component A-2/ Component B-2 | 97 | Component A-1/ Component A-109/ Component B-2 | 93 |
| Component A-8/ Component B-2 | 93 | Component A-1/ Component A-110/ Component B-2 | 97 |
| Component A-13/ Component B-2 | 94 | Component A-1/ Component A-111/ Component B-2 | 95 |
| Component A-28/ Component B-2 | 97 | Component A-1/ Component A-112/ Component B-2 | 96 |
| Component A-33/ Component B-2 | 95 | Component A-1/ Component A-113/ Component B-2 | 93 |
| Component A-37/ Component B-2 | 92 | Component A-1/ Component A-115/ Component B-2 | 93 |
| Component A-38/ Component B-2 | 98 | Component A-51/ Component A-107/ Component B-2 | 97 |
| Component A-39/ Component B-2 | 92 | Component A-52/ Component A-107/ Component B-2 | 98 |
| Component A-40/ Component B-2 | 96 | Component A-70/ Component A-107/ Component B-2 | 94 |
| Component A-41/ Component B-2 | 92 | Component A-71/ Component A-107/ Component B-2 | 93 |
| Component A-43/ Component B-2 | 98 | Component A-88/ Component A-107/ Component B-2 | 90 |
| Component A-44/ Component B-2 | 92 | Component A-89/ Component A-107/ Component B-2 | 91 |
| Component A-45/ Component B-2 | 96 | Component A-90/ Component A-107/ Component B-2 | 97 |
| Component A-46/ Component B-2 | 98 | Component A-1/ Component A-116/ Component B-1 | 95 |
| Component A-47/ Component B-2 | 93 | Component A-1/ Component A-116/ Component B-3 | 97 |
| Component A-50/ Component B-2 | 90 | Component A-1/ Component A-116/ Component B-2 | 93 |
| Component A-51/ Component B-2 | 93 | Component A-1/ Component A-117/ Component B-2 | 96 |
| Component A-52/ Component B-2 | 91 | Component A-1/ Component A-118/ Component B-2 | 98 |
| Component A-53/ Component B-2 | 95 | Component A-1/ Component A-122/ Component B-2 | 93 |
| Component A-55/ Component B-2 | 94 | Component A-1/ Component A-123/ Component B-2 | 96 |
| Component A-62/ Component B-2 | 93 | Component A-1/ Component A-124/ Component B-2 | 94 |
| Component A-65/ Component B-2 | 94 | Component A-1/ Component A-125/ Component B-2 | 90 |
| Component A-66/ Component B-2 | 93 | Component A-1/ Component A-126/ Component B-2 | 95 |
| Component A-67/ Component B-2 | 90 | Component A-1/ Component A-127/ Component B-2 | 96 |
| Component A-68/ Component B-2 | 94 | Component A-1/ Component A-128/ Component B-2 | 93 |
| Component A-69/ Component B-2 | 93 | Component A-1/ Component A-132/ Component B-2 | 97 |
| Component A-69/ Component B-2 | 99 | Component A-1/ Component A-133/ Component B-2 | 95 |
| Component A-71/ Component B-2 | 94 | Component A-1/ Component A-134/ Component B-2 | 93 |
| Component A-72/ Component B-2 | 96 | Component A-1/ Component A-135/ Component B-2 | 96 |
| Component A-74/ Component B-2 | 92 | Component A-1/ Component A-136/ Component B-2 | 94 |
| Component A-80/ Component B-2 | 98 | Component A-1/ Component A-137/ Component B-2 | 90 |
| Component A-83/ Component B-2 | 97 | Component A-1/ Component A-141/ Component B-2 | 94 |
| Component A-84/ Component B-2 | 94 | Component A-1/ Component A-142/ Component B-2 | 95 |
| Component A-85/ Component B-2 | 91 | Component A-1/ Component A-143/ Component B-2 | 93 |
| Component A-86/ Component B-2 | 94 | Component A-1/ Component A-144/ Component B-2 | 91 |
| Component A-87/ Component B-2 | 93 | Component A-1/ Component A-145/ Component B-2 | 97 |
| Component A-88/ Component B-2 | 98 | Component A-1/ Component A-146/ Component B-2 | 98 |
| Component A-89/ Component B-2 | 97 | Component A-1/ Component A-147/ Component B-2 | 94 |
| Component A-90/ Component B-2 | 91 | Component A-1/ Component A-152/ Component B-2 | 97 |
| Component A-91/ Component B-2 | 95 | Component A-1/ Component A-153/ Component B-2 | 94 |
| Component A-93/ Component B-2 | 95 | Component A-1/ Component A-154/ Component B-2 | 93 |
| Component A-98/ Component B-2 | 93 | Component A-51/ Component A-126/ Component B-2 | 97 |
| Component A-102/ Component B-2 | 95 | Component A-52/ Component A-127/ Component B-2 | 94 |
| Component A-103/ Component B-2 | 95 | Component A-71/ Component A-135/ Component B-2 | 93 |
| Component A-104/ Component B-2 | 92 | Component A-72/ Component A-136/ Component B-2 | 96 |
| Component A-105/ Component B-2 | 97 | Component A-88/ Component A-144/ Component B-2 | 98 |

TABLE 5-continued

| Composition of hydrogel material | Survival rate (%) | Composition of hydrogel material | Survival rate (%) |
|---|---|---|---|
| Component A-106/ Component B-2 | 95 | Component A-89/ Component A-145/ Component B-2 | 94 |
| Component A-1/ Component A-107/ Component C-3/ Component B-1 | 93 | Component A-90/ Component A-146/ Component B-2 | 93 |
| Component A-1/ Component A-107/ Component C-3/ Component B-3 | 95 | Component A-51/ Component A-107/ Component C-3/ Component B-2 | 97 |
| Component A-1/ Component A-107/ Component C-3/ Component B-2 | 97 | Component A-52/ Component A-107/ Component C-3/ Component B-2 | 94 |
| Component A-1/ Component A-107/ Component C-4/ Component B-2 | 95 | Component A-71/ Component A-107/ Component C-3/ Component B-2 | 92 |
| Component A-1/ Component A-107/ Component C-8/ Component B-2 | 97 | Component A-72/ Component A-107/ Component C-3/ Component B-2 | 90 |
| Component A-1/ Component A-107/ Component C-10/ Component B-2 | 98 | Component A-88/ Component A-107/ Component C-3/ Component B-2 | 91 |
| Component A-1/ Component A-107/ Component C-11/ Component B-2 | 95 | Component A-89/ Component A-107/ Component C-3/ Component B-2 | 96 |
| Component A-1/ Component A-107/ Component C-14/ Component B-2 | 97 | Component A-90/ Component A-107/ Component C-3/ Component B-2 | 92 |

The relationship between component A and component B in the hydrogel materials of the above different components is 2% wt: 0.2% wt. The relationship between component A and component B and component C was 2% wt: 0.2% wt: 2% wt.

Example 171: Photo-Crosslinked Hydrogel for Wound Closure-Skin Repair

Figure 5:
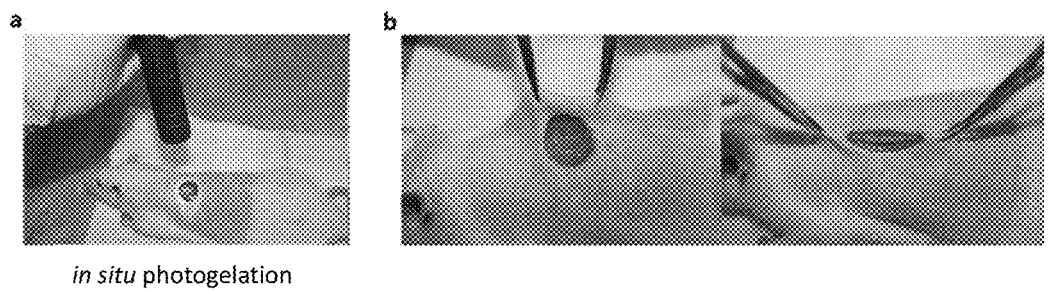
FIG. 5 is a visual representation of the effect of wound closure of the hydrogel (Component A-1/Component A-107/Component C-4/Component B-2).

In the experiment, a total skin defect wound with a diameter of 1.8 cm was constructed on the back of SD rats. Then 400 L hydrogel precursor solution (2% A-1/1% A-107/6% C-4/0.2% B-2) was filled into the wound site. Due to the good fluidity of the solution, the wound could be sufficiently filled and infiltrated by the hydrogel precursor solution. Then, under the illumination of 395 nm LED light source, the hydrogel was performed in situ in the skin defect, which closed the wound (as shown in FIG. 5). Then, the repair effects of in-situ hydrogels, preformed hydrogels and saline treatment on the back skin wounds of SD rats were compared within 7 days. The wound healing rate of in-situ hydrogels was significantly faster than the other two groups. The wound shrinkage area was the largest at 7 days, which played a good repairing effect. Preformed hydrogel materials was difficult to adequately fill the wound site. In addition, there is a lack of good organizational integration because of no seamless interface with covalent connections between organizations. And it is difficult for new cells and tissues to quickly enter the hydrogel material, so that the preformed hydrogel cannot fully play the role of the scaffold material. As a result, the repair rates and effects of pre-formed hydrogel were worse than in-situ hydrogels. The wound repair rate without hydrogel filling is the slowest, indicating that the photo-crosslinked hydrogel can promote wound repair as a cell scaffold material to.

Hydrogel systems of different materials (Component A: Component A-1~Component A-154; Component B: Component B-1~Component B-3; Component C-1~C-21) as photo-crosslinked hydrogel can also be used for wound closure and skin repair.

Figure 6:
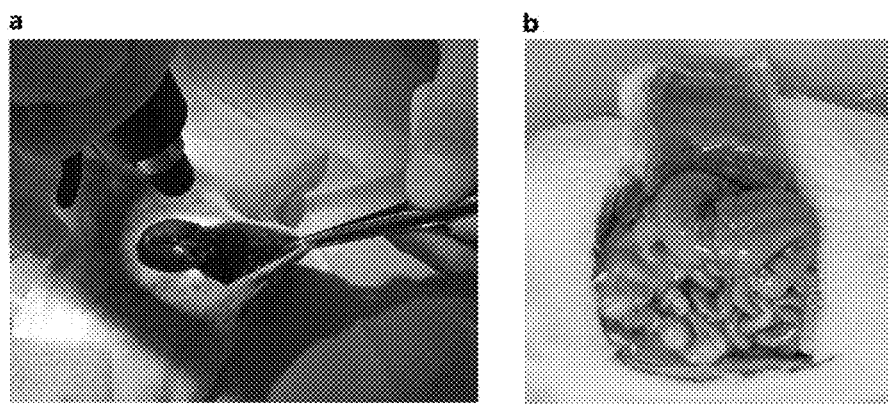
FIG. 6 is an effect view of the hydrogel as postoperative anti-adhesion (Component A-1/Component A-107/Component C-4/Component B-2).

Example 172: Photo-Crosslinked Hydrogel for Wound Closure-Postoperative Anti-Adhesion In the experiment, SD rats were used to construct an adhesion model of abdominal wall-cecum scraping. Because the cecum is the thickest, most accessible, and most abundant intestine in the abdominal cavity, the probability of abdominal adhesion is extremely high when the corresponding abdominal wall is simultaneously damaged and no measures are taken. The structural adhesion model is stable. During the surgery, the hydrogel precursor solution (2% Component A-1/1% Component A-107/6% Component C-4/0.2% component B-2) can adequately cover the cecal and abdominal wall wounds, and has sufficient residence time on the vertical tissue surface until it is lightly gelled. After giving 30 s of light, the obtained hydrogel was fixed at the wound site, and the hydrogel was not peeled off from the wound site with a certain force applied by a surgical blade. The above process from the administration of the hydrogel precursor solution to the complete gelation can be completed within 1 min (as shown in FIG. 6). After the surgery, the above SD rats were reared for 14 days in a sterile environment. After 14 days, the abdominal cavity of SD rats was opened again, and the abdominal adhesion was recorded. Among the 10 rats in the hydrogel-treated experimental group, 8 rats did not show any intestinal-abdominal wall and intestinal-intestinal adhesion after 14 days; One rat developed a moderate adhesion between the abdominal wall and the cecum; one rat developed a thin layer of adhesion between the intestine and the intestine. In addition, no residual hydrogel residue was observed in the above 9 SD rats without intestinal-abdominal adhesion, and the wound on the abdominal wall was completely healed. Severe abdominal and cecal adhesions occurred in 10 rats in the control group. Next, histological analysis of the tissue sections of the wound site in the experimental and control groups was performed by H&E staining. The injury of the cecum and abdominal wall was completely restored after 14 days in the SD rats in the experimental group, and the surface layer was re-epithelialized. In 14 days after SD rats in the control group, the smooth muscle of the cecum was completely fused with the muscle tissue of the abdominal wall, and fibroblasts and inflammatory cells were deposited at the adhesion site.

Hydrogel systems of other different materials (Component A: Component A-1 to Component A-154; Component B: Component B-1 to Component B-3; Component C-1 to C-21) belong to photo-crosslinked hydrogels, which can also be applied to wound closure-postoperative anti-adhesion.

Example 173: Photo-Crosslinked Hydrogel for Wound Closure-Oral Ulcer

In the experiment, an oral ulcer defect wound with a diameter of 1.0 cm was constructed in the oral cavity of SD rats. Then fill the wound site with 200 μL of the hydrogel precursor solution ((2% Component A-1/1% Component A-107/6% Component C-4/0.2% Component B-2). Due to the good fluidity of the solution, the wound can be sufficiently filled and infiltrated by the hydrogel precursor solution. Then, under the illumination of a 395 nm LED light source, a hydrogel was prepared in situ at the oral cavity to achieve closure of the oral wound. Next, the repair effect of the in-situ hydrogel, the pre-formed hydrogel and the SD rat oral wound treated with physiological saline alone was compared in 7 days. The wound healing rate of in-situ hydrogels was significantly faster than the other two groups. The wound shrinkage area was the largest at 7 days, which played a good repairing effect. The pre-formed hydrogel material is difficult to fully fill the wound site; in addition, there is no seamless interface with covalent connections between the tissues, and lack of good tissue integration. It is difficult for new cells and tissues to quickly enter the hydrogel material, so that it can fully play the role of the scaffold material. As a result, pre-formed hydrogel repair rates and effects are worse than in-situ hydrogels. The wound repair rate without hydrogel filling is the slowest, indicating that the photo-crosslinked hydrogel acts as a cell scaffold material to promote oral ulcer repair.

Hydrogel systems of other different materials (Component A: Component A-1 to Component A-154; Component B: Component B-1 to Component B-3; Component C-1~C-21) belong to photo-crosslinked hydrogels and can also be applied to wound closures-oral ulcers.

Example 174: Photo-Crosslinked Hydrogel Applied to Tissue Exudate Plugging-Intestinal Leakage Sealing New Zealand male white rabbits were used and divided into two groups for cecal leakage closure experiments: a: hydrogel treatment (2% Component A-1/1% Component A-107/6% Component C-4/0.2% Component B-2) group; b: untreated control group. In the experiment, a model of leakage was made in the cecum of the rabbit, and then the hydrogel precursor solution was applied to the wound. After being fully infiltrated, the light was gelled in situ, and the hydrogel adhered firmly to the defect after gelation. No additional fixing is required. Four weeks after the operation, the rabbits in the experiment were sacrificed by intravenous injection of air, and the cecum was extracted to evaluate the effect of the experimental repair. The results showed that there was no leakage of the cecum blocked with hydrogel, and severe leakage occurred in the cecum without hydrogel treatment. After several weeks of repair, the original cecal defect has been repaired by hydrogel treatment. Therefore, the hydrogel can not only effectively block the leakage, but also facilitate the repair of damaged tissue after surgery.

Hydrogel systems composed of other different materials (Component A: Component A-1 to Component A-154; Component B: Component B-1 to Component B-3; Component C-1~C-21) belong to photo-crosslinked hydrogels, and can also be applied to tissue exudate plugging-intestinal leakage plugging.

Example 175: Photo-Crosslinked Hydrogel Applied to Tissue Exudate Plugging-Surgical Suture Male New Zealand white rabbits were used and divided into three groups for surgical suture experiments: a: hydrogel treatment (2% Component A-1/1% Component A-107/6% Component C-4/0.2% Component B-2) group; b: surgical suture treatment group; c: no control group. In the experiment, a model of wound suture was made in the abdomen of the rabbit. In group a, the hydrogel precursor solution is applied to the wound, and after being fully infiltrated, the light is in situ gelled to achieve the sealing of the wound. Due to the excellent tissue adhesion of the hydrogel, the effect of tissue suturing can be achieved; group b was treated with conventional surgical sutures; group c was treated without treatment. Two weeks after the operation, the rabbits in the experiment were sacrificed by intravenous injection of air, and samples were taken to evaluate the effect of the experimental repair. The results showed that the wound treated with the hydrogel had a better suturing effect, which was almost the same as the surgical suture group, and the wounds that were not treated could not be effectively joined together. After 4 weeks of repair, the original wound defect site was hydrogel treated and the tissue was able to connect together and was significantly repaired. Therefore, the hydrogel can not only effectively suture the wound, but also facilitate the repair of the damaged tissue after surgery.

Hydrogel systems of other different materials (Component A: Component A-1 to Component A-154; Component B: Component B-1 to Component B-3; Component C-1~C-21) belong to photo-crosslinked hydrogels, and can also be applied to tissue exudate plugging-surgical sutures.

Figure 7:
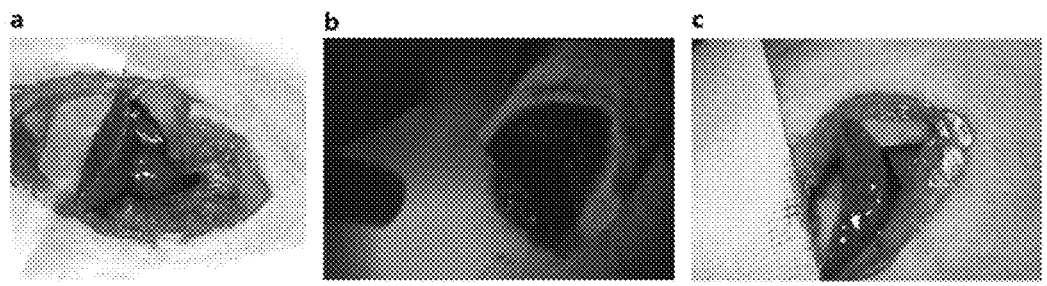
FIG. 7 is an effect view of the hydrogel as hemostasis in the liver (Component A-1/Component A-107/Component C-4/Component B-2).

Example 176: Photo-Crosslinked Hydrogel Applied to Hemostatic Material-Liver Hemostasis The SD rats were used to evaluate the hemostatic effect of the hydrogel, and the liver hemostasis experiments were divided into three groups: a: gelatin sponge group; b: hydrogel treatment (2% Component A-1/1% Component A-107/6% Component C-4/0.2% Component B-2) group; c positive control group. The rats were anesthetized by intraperitoneal injection of chloral hydrate (4% aqueous solution). The injection was measured to be 0.9 ml/100 g. After deep anesthesia, the rat's anterior chest was shaved with a shaver and the iodine was disinfected. Then cut approximately 4 cm long incision along the midline of the chest, open the chest and expose the liver. Make an approximately 2 cm incision in the left lobe of the liver. Group a was treated with gelatin sponge to stop bleeding; group b was treated with hydrogel precursor solution at the incision to cover the section, and 395 nm LED light for 2 min to form a gel to stop bleeding; The c group did not do any treatment, so that the liver incision oozing naturally coagulated, and the oozing was sucked by gauze, and the amount of bleeding and the bleeding time were recorded by the weight loss method (as shown in FIG. 7). After the end of the experiment, group a adhered to the cut gelatin sponge and left in the rat for suturing. Group b hydrogels were cross-connected in situ in the incision and the wounds were isolated, the liver was placed back into the chest, and sutured. Group c was directly sutured without treatment. After 14 days, the liver recovery of SD rats was observed. The rats were sacrificed by intraperitoneal injection of excess anesthetic chloral hydrate (4% aqueous solution, 2.7 ml/100 g). The thoracic cavity was opened along the midline of the thoracic cavity, and the liver recovery of the three groups of rats was observed and photographed. At the same time, the liver injury site was sampled, and the specimen was fixed with 4% formalin solution for 2 days. After dehydration treatment, paraffin was embedded and sliced with a microtome. The thickness of the sample was 5 μm. Finally, the specimens were subjected to H&E staining, and photographs were taken with an optical microscope. The experimental results showed that the liver of group b recovered well, the hydrogel was completely degraded, no adhesion occurred, and the liver incision grew new liver tissue. The gelatin sponge in the rats in group a was still not degraded, and the adhesion between the organs and the omentum was severe. Hepatic and omental adhesions were common in group c. H&E staining showed that the liver surface of the experimental group was smooth and round, with abundant blood vessel distribution and clear liver interface. The liver of the adhesion was found by H&E staining, and the liver interface was uneven. The liver and the omentum were stuck together, and there were deposited inflammatory cells at the interface.

Hydrogel systems of other different materials (Component A: Component A-1 to Component A-154; Component B: Component B-1 to Component B-3; Component C-1~C-21) belong to photo-crosslinked hydrogels, and can also be applied to hemostatic materials-liver hemostasis.

Example 177: Photo-Crosslinked Hydrogel Applied to Hemostatic Material-Bone Section Hemostasis Male New Zealand white rabbits were used and divided into three groups for bone section hemostasis experiments: a: hydrogel treatment (2% Component A-1/1% Component A-107/6% Component C-4/0.2% Component B-2) group; b: bone wax treatment group; c: Control group not treated. In the experiment, a bone section bleeding model was made in the rabbit femur. In group a, the hydrogel precursor solution is applied to the wound, and after being fully infiltrated, the light is in situ gelatinized to achieve effective sealing of the bone section bleeding. Due to the excellent tissue adhesion and photocuring speed of the hydrogel, a timely and effective hemostatic effect can be achieved; Group b is the treatment of bleeding wounds with conventional bone wax; Group c is not treated for bleeding wounds. After 8 weeks of surgery, the rabbits in the experiment were sacrificed by intravenous injection of air, and samples were taken to evaluate the effect of the experimental repair. The results showed that the hydrogel-treated wounds had a better hemostatic effect, which was almost the same as the bone wax group, and the wounds that were not treated had sustained bleeding. After 2 weeks of repair, the original wound hemorrhage site was treated with hydrogel treatment, and the bone wax treated wound was not repaired, mainly because the bone wax did not degrade in the body. Therefore, the hydrogel can not only effectively achieve hemostasis of the bone section, but also facilitate the repair of damaged tissue after surgery.

Hydrogel systems of other different materials (Component A: Component A-1 to Component A-154; Component B: Component B-1 to Component B-3; Component C-1~C-21) belong to photo-crosslinked hydrogels, and can also be applied to hemostasis materials-bone section hemostasis.

Example 178: Photo-Crosslinked Hydrogel Applied to Hemostatic Material-Arterial Hemostasis Male New Zealand white rabbits were used and divided into three groups for arterial hemostasis: a: hydrogel treatment (2% Component A-1/1% Component A-107/6% Component C-4/0.2% Component B-2) group; b: hemostat treatment group; c: A control group that was not treated. In the experiment, a bleeding model was made in the rabbit femoral artery. In group a, the hydrogel precursor solution is applied to the wound, and after being fully infiltrated, the light is in situ gelatinized to achieve effective sealing of the femoral artery bleeding. Due to the excellent tissue adhesion and photocuring speed of the hydrogel, a timely and effective hemostatic effect can be achieved; group b was treated with conventional hemostatic forceps to treat bleeding wounds; group c was treated without bleeding wounds. Two weeks after the operation, the rabbits in the experiment were sacrificed by intravenous injection of air, and samples were taken to evaluate the effect of the experimental repair. The results show that the wound treated with hydrogel has a better hemostatic effect, which is almost the same as that of the hemostatic forceps, and the wound that is not treated will have a continuous bleeding condition. After 2 weeks of repair, the original wound hemorrhage site was treated with hydrogel and the tissue was repaired. Therefore, the hydrogel can not only effectively achieve femoral artery hemostasis, but also facilitate repair of damaged tissue after surgery.

Hydrogel systems of other different materials (Component A: Component A-1 to Component A-154; Component B: Component B-1 to Component B-3; Component C-1~C-21) belong to photo-crosslinked hydrogels, and can also be applied to hemostatic materials-arterial hemostasis.

Example 179: Photo-Crosslinked Hydrogel Applied to Hemostatic Material-Cardiac Hemostasis New Zealand male white rabbits were used and divided into three groups for cardiac hemostasis experiments: a: hydrogel treatment (2% Component A-1/1% Component A-107/6% Component C-4/0.2% Component B-2); b: gelatin sponge treatment group; c: control group not treated. In the experiment, a bleeding model was made in the rabbit heart. In group a, the hydrogel precursor solution is applied to the wound, and after being fully infiltrated, the light is in situ gelled to achieve effective sealing of the heart bleeding. Due to the excellent tissue adhesion and photocuring speed of the hydrogel, a timely and effective hemostatic effect can be achieved; Group b is to treat bleeding wounds with a conventional gelatin sponge; Group c is not treated for bleeding wounds. Two weeks after the operation, the rabbits in the experiment were sacrificed by intravenous injection of air, and samples were taken to evaluate the effect of the experimental repair. The results show that the wound treated with hydrogel has a better hemostatic effect, and the hemostatic effect of the gelatin sponge is better than that of the wound without treatment. After 2 weeks of repair, the original wound hemorrhage site was treated with hydrogel and the tissue was repaired significantly, and the repair effect was better than gelatin sponge. Therefore, the hydrogel can not only effectively achieve cardiac hemostasis, but also facilitate repair of damaged tissue after surgery.

Hydrogel systems of other different materials (Component A: Component A-1 to Component A-154; Component B: Component B-1 to Component B-3; Component C-1~C-21) belong to photo-crosslinked hydrogels, and can also be applied to hemostatic materials-cardiac hemostasis.

Example 180: Photo-Crosslinked Hydrogel Applied to Tissue Engineering Scaffold Material-Cartilage Repair Male New Zealand white rabbits were used and divided into three groups for repair of articular cartilage: a: group of hydrogels (2% Component A-1/1% Component A-107/6% Component C-4/0.2% Component B-2) wrapped with chondrocytes, that is, a group of Gel+ chondrocytes; b: pure hydrogel (2% Component A-1/1% Component A-107/6% Component C-4/0.2% Component B-2) group, ie Gel group. c: The control group that is not processed, that is, the Control group. In the experiment, the hydrogel precursor solution can fully penetrate and fill the defect of the rabbit articular cartilage, and the glue adheres firmly to the defect after the glue is formed, and no additional fixation is needed. After 12 weeks of surgery, the rabbits in the experiment were sacrificed by intravenous injection of air, and the injured joints were extracted to evaluate the experimental repair effect. Gross photographs of rabbit articular cartilage lesions showed that after 12 weeks, the Gel+ chondrocyte group developed smooth neonatal cartilage tissue at the joint defect and was well integrated with the old cartilage tissue; The cartilage was also repaired in the Gel group, but the contour of the cartilage wound during surgery was also seen; In the Control group, the cartilage tissue was basically not repaired, and the lesion was still obvious. Next, we further evaluated the repair of cartilage in each of the above groups by H&E staining. H&E staining results showed that both the Gel+ chondrocyte group and the Gel group had new tissue formation and integrated well with the old cartilage tissue; however, the thickness of the new tissue of the Gel+ chondrocyte group was better than that of the Gel group, and the surface was flat; In the Control group, it is difficult to find obvious signs of new tissue. In addition, the components of neonatal cartilage were analyzed by Safranin-O and immunohistochemical staining. In the Gel+ chondrocyte group and the Gel group, the neonatal cartilage tissue showed a Safranin-O staining activity, and it was confirmed that the new cartilage tissue contained the glycoprotein component of normal cartilage. At the same time, the neonatal cartilage tissue of the Gel+ chondrocyte group and the Gel group showed staining activity of Formula II collagen, which proved that the cartilage tissue contained a large amount of Formula II collagen. The results of the above-mentioned Safranin-O and immunohistochemical staining demonstrated that the new cartilage tissue was hyaline cartilage when the new photo-crosslinked hydrogel material was used for cartilage repair.

Hydrogel systems of other different materials (Component A: Component A-1 to Component A-154; Component B: Component B-1 to Component B-3; Component C-1~C-21) belong to photo-crosslinked hydrogels and can also be applied to tissue engineering scaffold materials-cartilage repair.

Example 181: Photo-Crosslinked Hydrogel Applied to Tissue Engineering Scaffold Material-Bone Repair SD rats were used for skull repair experiments, and the above SD rats were randomly divided into 3 groups: a: an experimental group of hydrogel (2% Component A-1/1% Component A-107/6% Component C-4/0.2% Component B-2)+hydroxyapatite; b: hydrogel treatment (2% Component A-1/1% Component A-107/6% Component C-4/0.2% Component B-2); c: Control group without material treatment. In the experiment, 4% chloral hydrate solution (0.9 mL per gram body weight) was used for abdominal anesthesia and iodine disinfection. The scalp at the skull of the rat is then opened using a surgical blade. A complete skull defect model with a diameter of 5 mm was made symmetrically around the skull of the mouse using a dental ring drill. In the experimental group, 200 μL of the hydrogel precursor solution was filled into the SD rat skull defect to fully penetrate into the wound edge; The 395 nm LED light source (20 mW/cm$^2$) was used to illuminate it for 30 s to completely gel; the suture was used to suture the mouse's scalp. In the control group, after the SD rat skull defect model was made, the scalp was directly sutured without any other treatment. The above SD rats were kept in a sterile, 37° C. environment for 8 weeks. Then, the repair of the skull of SD rats in each group was evaluated by micro-CT scanning imaging.

The results showed that in the control group without any treatment, the skull defect of the SD rat was not substantially repaired. There is new osteogenesis at the edge of the skull defect filled with hydrogel, but the amount of new bone tissue is small, and most of the defects are not well repaired. The skull defect filled with hydrogel+hydroxyapatite was basically repaired, and a large amount of new bone tissue was formed at the defect. The histological staining of the skull was then performed by Van Gieson staining. The results showed that both the hydrogel+hydroxyapatite-treated SD rats had intact new bone tissue in the skull defect, and only a small amount of new bone tissue was formed in the skull defect treated with hydrogel. Most of the defects were found. The bone tissue at the site is still defective. In the control group, almost no new bone tissue was formed. The tissue staining results further confirmed that the hydrogel coated with hydroxyapatite has a good repair effect on bone defects.

Hydrogel systems of other different materials (Component A: Component A-1 to Component A-154; Component B: Component B-1 to Component B-3; Component C-1~C-21) belong to photo-crosslinked hydrogels and can also be applied to tissue engineering scaffold materials-bone repair.

Figure 8:
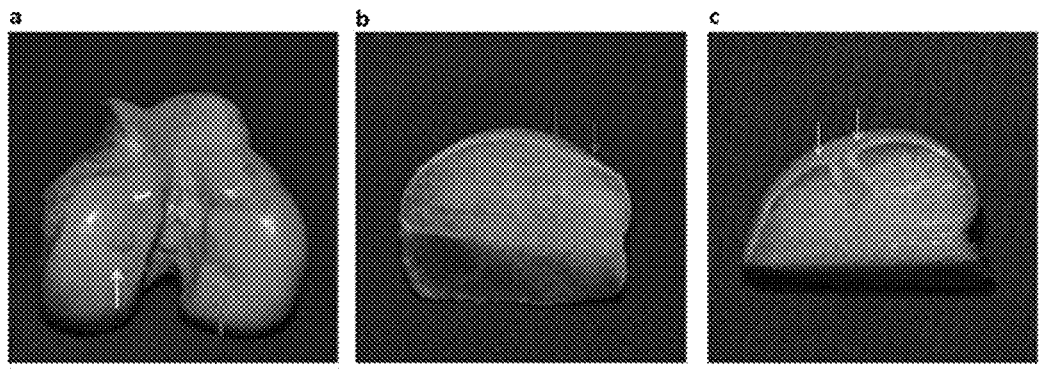
FIG. 8 is an effect view of the hydrogel as bone/cartilage tissue engineering scaffold material (Component A-1/Component A-107/Component C-4/Component B-2).

Example 182: Photo-Crosslinked Hydrogel Applied to Tissue Engineering Scaffold Material-Bone/Cartilage Composite Defect Repair Pigs were used as animal models, cartilage phase materials were hydrogels+chondrocytes, bone phase materials were hydrogels+hydroxyapatite+BMSCs, and three groups were used to repair joint bone/cartilage complex defects: a: a hydrogel group (2% Component A-1/1% Component A-107/6% Component C-4/0.2% component B-2) in which chondrocytes and BMSCs are respectively wrapped, that is, a Gel+ cell group; b: a simple hydrogel (2% Component A-1/1% Component A-107/6% Component C-4/0.2% Component B-2) group, namely the Gel group. In the experiment, the bone phase material is first filled into the bone phase defect, and the gel precursor solution is fully infiltrated. After the light is gelatinized, the hydrogel adheres firmly to the bone defect, and then the cartilage phase material is filled into the cartilage phase defect. At the same time, the hydrogel adheres firmly to the cartilage defect after the light is glued (as shown in FIG. 8). Six months after the operation, the experimental pigs were sacrificed and the injured joints were extracted to evaluate the experimental repair effect. The Gel+ cell group developed smooth neonatal cartilage tissue and bone tissue at the joint defect, and was well integrated with the old cartilage/bone tissue. At the same time, the cartilage tissue and bone tissue were well integrated. In the Gel group, there was almost no repair of the bone/cartilage tissue, and the lesion was still a clear cavity. Next, the repair of the above-mentioned groups of cartilage was further evaluated by the method of H&E staining. H&E staining results showed that the Gel+ cell group had new tissue formation and was well integrated with the old cartilage tissue; however, it was difficult to find obvious signs of new tissue in the Gel group. In addition, the components of neonatal cartilage were analyzed by Safranin-O and immunohistochemical staining. In the Gel+ cell group, the neonatal cartilage tissue showed a Safranin-O staining activity, and it was confirmed that the new cartilage tissue contained the glycoprotein component of normal cartilage. At the same time, the neonatal cartilage tissue of the Gel+ cell group showed the staining activity of Formula II collagen, which proved that the cartilage tissue contained a large amount of Formula II collagen. The results of the above-mentioned Safranin-O and immunohistochemical staining demonstrated that the new cartilage tissue was hyaline cartilage when the new photo-crosslinked hydrogel material was used for cartilage repair. The histological staining of the bone tissue sections was then performed by Van Gieson staining. The results showed that the new bone tissue was formed in the bone defect treated by the Gel+ cell group, while only a small amount of new bone tissue was formed in the bone defect in the Gel group, and the bone tissue in most of the defect was still in a defect state. The tissue staining results further confirmed that the cell-added hydrogel has a good repair effect on bone defects.

Hydrogel systems of other different materials (Component A: Component A-1 to Component A-154; Component B: Component B-1 to Component B-3; Component C-1~C-21) belong to photo-crosslinked hydrogels, and can also be applied to tissue engineering scaffold materials-bone/cartilage composite defect repair.

Figure 9:
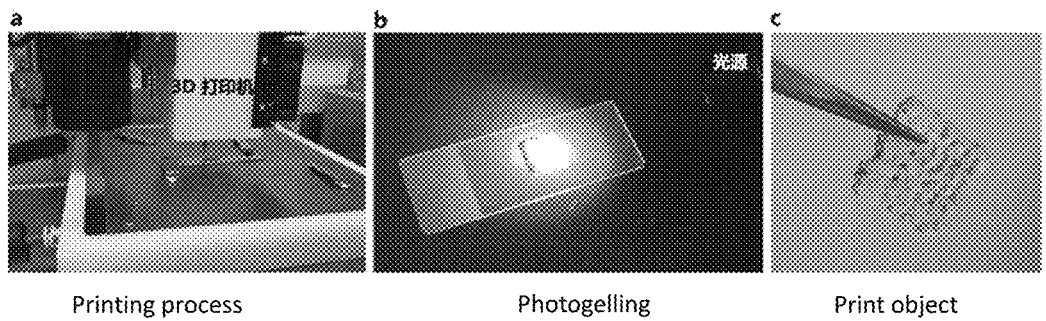
FIG. 9 is an effect view of the hydrogel as bio-ink (Component A-1/Component A-107/Component C-4/Component B-2).

Example 183: Photo-Crosslinked Hydrogel for 3D Printing (FDM) Bio-Ink 3D printing technology is a three-dimensional molding technology that has been rapidly developed in recent years and has been widely used. Current 3D printing technologies include fused deposition (FDM), photocurable molding (SLA), laser sintering (SLS), continuous liquid level manufacturing (CLIP), and the like. But the way that is suitable for cell printing is currently mainly FDM. Materials with cell printing are primarily hydrogel materials, so developing bio-ink-printable hydrogel materials for 3D printing and increasing the resolution of hydrogel material printing are fundamental issues in this area of research. Component A-1 (i.e. HA-NB) prepared by Example 1, Component A-107 (i.e. HAMA) prepared by Example 107, component c-4 (i.e. Gelatin), and component b-2 (i.e. LAP) prepared by Example 155; Component A-88 from Example 88 (i.e. HA-cNB), Component A-144 from Example 144 (i.e. HA-cNB-MA), and component b-2 from Example 155 (i.e. LAP) are taken as example s. After uniformly mixing the hydrogel precursor solution of a certain mass concentration into the low temperature printing barrel, the printing temperature is controlled at about 25° C., and the viscosity of the bio ink is adjusted by the temperature to obtain the best printing state. Then determine the appropriate print pressure and print speed for bioprinting of different structures. After printing, the hydrogel was cross-connected by light (or by printing while printing) to obtain a cell-structured hydrogel with 3D cell culture (as shown in FIG. 9).

Hydrogel systems of other different materials (Component A: Component A-1 to Component A-154; Component B: Component B-1 to Component B-3; Component C-1~C-21) belong to photo-crosslinked hydrogels and can also be applied to 3D printing (FDM) bio-inks.

Example 184: Photo-Crosslinked Hydrogel for 3D Printing (DLP) Bio-Ink

DLP (Digital Light Processing) 3D printing technology is a new Formula of photo-curing printing method developed in recent years. Compared to SLA (stereo-curing) printers, DLP has the advantages of fast printing speed and high resolution, which is unmatched by most printing methods. Currently, it has certain application prospects in the fields of dental models and jewelry design. However, the printing inks currently used in the market are limited to photocurable resins, and hydrogels have not received much attention as an emerging bio-ink, mainly because there is no hydrogel material suitable for DLP printing. The composite photo-crosslinked hydrogel material proposed by the invention is very suitable for 3D printing with its fast photocuring speed and excellent mechanical properties, and has higher printing precision. Component A-1 (i.e. HA-NB) prepared by Example 1, Component A-107 (i.e. HAMA) prepared by Example 107, component c-4 (i.e. Gelatin), and component b-2 (i.e. LAP) prepared by Example 155; Component A-88 from Example 88 (i.e. HA-cNB), Component A-144 from Example 144 (i.e. HA-cNB-MA), and component b-2 from Example 155 (i.e. LAP) are taken as example s. After uniformly mixing the hydrogel precursor solution of a certain mass concentration into the liquid tank, By controlling the intensity of the light source, the exposure time and other parameters to adjust the printing of the bio-ink to obtain the best printing state, a hydrogel with both cells and structure can be obtained, and the 3D cell culture can be studied.

Hydrogel systems of other different materials (Component A: Component A-1 to Component A-154; Component B: Component B-1 to Component B-3; Component C-1~C-21) belong to photo-crosslinked hydrogels and can also be applied to 3D printing (DLP) bio-inks.

Example 185: Photo-Crosslinked Hydrogel for Drug Wrapping and Release

Hydrogel is a cross-linking polymer network that swells in water but does not dissolve. Since the hydrogel is mostly composed of water, it has very good biocompatibility and is Componenticularly suitable for carriers of drugs and biologically active macromolecules. The drug or biologically active macromolecule encapsulated in the hydrogel material achieves a sustained release of the drug by diffusion of the molecule and degradation of the material. Take the package and release of drugs as an example: Component A-1 (i.e., HA-NB) prepared in Example 1, Component A-107 (i.e., HAMA) prepared in Example 107, component c-4 (i.e., gelatin), and component b-2 (i.e., LAP) prepared in Example 155; Component A-88 from Example 88 (i.e. HA-cNB), Component A-144 from Example 144 (i.e. HA-cNB-MA), and component b-2 from Example 155 (i.e. LAP) are taken as example s. Dissolving it in physiological saline, Formulating a certain concentration of hydrogel precursor solution, adding a certain amount of drug molecules. 200 μL of the above solution was placed in a cyclic mold to light a hydrogel, and then placed in a 24-well cell culture plate, and a certain amount of physiological saline was added for drug release experiments. The release amount of the drug in the solution was analyzed by an ultraviolet test to evaluate the release effect of the material on the drug.

Hydrogel systems of other different materials (Component A: Component A-1 to Component A-154; Component B: Component B-1 to Component B-3; Component C-1~C-21) belong to photo-crosslinked hydrogels, which can also be applied to the wrapping and release of drugs.

The above description of the example s is intended to facilitate the understanding and use of the invention by those skilled in the art. It will be apparent to those skilled in the art that various modifications can be readily made to these example s and the general principles described herein can be applied to other example s without the inventive work.

Therefore, The invention is not limited to the example s described above, and those skilled in the art should be able to make modifications and changes within the scope of the invention without deComponenting from the scope of the invention.

We claim:

1. A method of making a photo-crosslinked hydrogel material comprising:
    dissolving a component A including a photosensitive polymer derivative in a biocompatible medium to obtain a photosensitive polymer solution A;
    dissolving a component B including a photoinitiator in a biocompatible medium to obtain a photoinitiator solution B;
    obtaining a hydrogel precursor solution by homogeneously mixing solutions including the photosensitive polymer solution A and the photoinitiator solution B; and
    under an irradiation of light, performing free radical cross-linking reaction to form a hydrogel,
    wherein the photosensitive polymer derivative is selected from one or more of the following:
    (a) a photosensitive polymer derivative containing an o-nitrobenzyl phototrigger as shown in Formula A-I; and
    (b) a photosensitive polymer derivative containing both an o-nitrobenzyl phototrigger and double bond functional group as shown in Formula A-III,

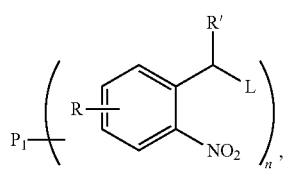

Formula A-I

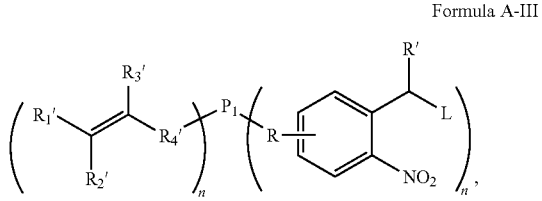

Formula A-III wherein the Formula A-1 contains an o-nitrobenzyl phototrigger represented by Formula I selected from the group consisting of Formula I-1 and Formula I-2, the Formula I-2 represents a cyclic o-nitrobenzyl phototrigger,

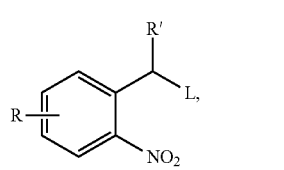

Formula I

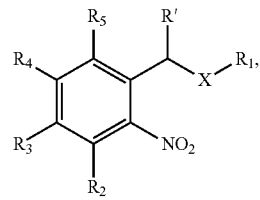

Formula I-1

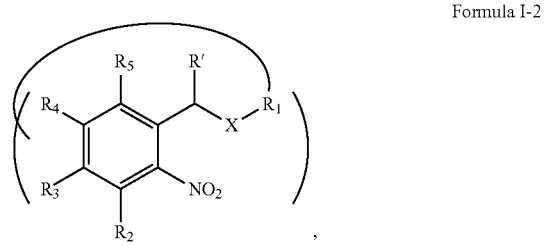

Formula I-2 where, in the Formula I-1 and the Formula I-2, when X=O, the o-nitrobenzyl phototrigger is an o-nitrobenzyl alcohol phototrigger; when X=S, the o-nitrobenzyl phototrigger is an o-nitrobenzyl sulphydryl phototrigger; and when X=N, the o-nitrobenzyl phototrigger is an o-nitrobenzyl amine phototrigger;

in the Formula A-I, Formula A-III, Formula I, Formula I-1, and Formula I-2, R' is selected from the group consisting of hydrogen atom, halogen atom, hydroxyl group, mercapto group, amine group, nitro group, cyano group, aldehyde group, ketone group, ester group, amide, phosphonic acid group, phosphonate ester group, sulfoacid group, sulfonate group, sulfone group, sulfoxide group, aryl group, heteroaryl group, alkyl group, alkylene group, modified alkyl group, and modified alkylene group;

in the Formula I-1 and Formula I-2, $R_1$ is selected from the group consisting of a hydrogen atom, an ether group, an ester group, a carbonate ester group, an amino formate ester group, a mercapto formate ester group, and a phosphonate ester group;

in the Formula I-1 and Formula I-2, $R_2$, $R_3$, $R_4$, $R_5$ are each independently selected from the group consisting of a hydrogen atom, a halogen atom, a hydroxyl group, a mercapto group, an amine group, a nitro group, a cyano group, an aldehyde group, a ketone group, a carboxyl group, an ester group, amide, a phosphonic acid group, phosphonate ester group, sulfoacid group, sulfonate group, sulfone group, sulfoxide group, aryl group, heteroaryl group, alkyl group, alkylene group, modified alkyl group, and modified alkylene group;

in the Formula I-2, X is O, S or NH, $R_1$ is connected to X and one of $R_2$, $R_3$, $R_4$ and $R_5$ to form a cyclic structure;

in the Formula A-III, $R_1'$, $R_2'$, $R_3'$ are selected from the group consisting of a hydrogen atom, an alkyl group, a modified alkyl or aryl group; $R_4'$ is selected from the group consisting of an alkyl group, an ether group, an ester group, and an amide group;

optionally, in Formula A-III, $R_1'$, $R_2'$, $R_3'$ are connected with a carbon atom to form a saturated or unsaturated alicyclic ring or alicyclic heterocyclic ring;

in the Formula A-I and the Formula A-III, n≥2, $P_1$ is independently a hydrophilic or water-soluble natural polymer or synthetic polymer;

the photoinitiator is a substance capable of generating free radicals under irradiation by light.

2. The method of claim 1, wherein the component A further comprises a polymer derivative containing double bond functional group as shown in Formula A-II:

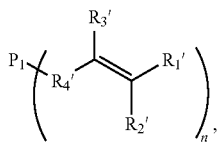

Formula A-II where, in the Formula A-II, $R'_1$, $R'_2$, $R'_3$ and are selected from hydrogen, alkyl, modified alkyl or aryl; $R'_4$ is selected from alkyl, an ether group, an ester group, an amide group;

optionally, in the Formula A-II, $R'_1$, $R'_2$, $R'_3$ are connected together with a carbon atom to form a saturated or unsaturated alicyclic ring or alicyclic heterocycle; and in Formula A-II, $n \geq 2$, $P_1$ is a hydrophilic or water-soluble natural polymer, or a hydrophilic or water-soluble synthetic polymer.

3. The method of claim 1, further comprising dissolving an auxiliary component C including another biocompatible polymer derivative in a biocompatible medium to obtain a polymer solution C, wherein the another biocompatible polymer derivative is a polymer derivative containing an amine, hydrazine, hydrazide, or hydroxylamine functional group, the solutions further include the solution C, aldehyde or ketone group produced by irradiation of the o-nitrobenzyl phototrigger in component A is capable of reacting with the amine, hydrazine, hydrazide, or hydroxylamine functional group in component C through photocoupling crosslinking, nitroso group produced by irradiation of the o-nitrobenzyl phototrigger in component A is capable of reacting with the sulphydryl group in component C through photoinduced S-nitrosylation crosslinking.

4. The method of claim 1, Wherein the alkyl group of R', $R_2$, $R_3$, $R_4$, $R_5$, $R_1'$, $R_2'$, and $R_3'$ is a saturated or unsaturated aliphatic linear or branched alkyl group having 1 to 30 carbon atoms, the alkylene group of R', $R_2$, $R_3$, $R_4$, $R_5$, $R_1'$, $R_2'$, and $R_3'$ is a saturated or unsaturated aliphatic linear chain or branched alkylene group with 1-30 carbon atoms, the modified alkyl group of R', $R_2$, $R_3$, $R_4$, $R_5$, $R_1'$, $R_2'$, and $R_3'$ has a carbon atom at least substituted by a halogen atom, —OH, —SH, —NO$_2$, —CN, —CHO, —COOH, ester, amide, aromatic, arylidene —CO—, —O—, —S—, —SO—, —SO$_2$—, amino, secondary amine, tertiary amine, quaternary ammonium salt, saturated or unsaturated single or double cyclic alkylene, or bridged aliphatic heterocyclic, the modified alkyl group of R', $R_2$, $R_3$, $R_4$, $R_4$, $R_1'$, $R_2'$, and $R_3'$ has 1~30 carbon atoms whose carbon-carbon single bond is optionally and independently replaced by a carbon-carbon double bond or a carbon-carbon triple bond, the modified alkylene group of R', $R_2$, $R_3$, $R_4$, and $R_5$ has a carbon atom least substituted by a halogen atom, —OH, —SH, —NO$_2$—CN, —CHO, —COOH, ester, amide, aromatic, arylidene, —CO—, —O—, —S—, —SO—, —SO$_2$—, amino, secondary amine, tertiary amine, quaternary ammonium salt, saturated or unsaturated single or double cyclic alkylene, or bridged aliphatic heterocyclic, and the modified alkyl group has 1~30 carbon atoms whose carbon-carbon single bond is optionally and independently replaced by a carbon-carbon double bond or a carbon-carbon triple bond, the ether group of $R_1$ and $R_4'$ is selected from the following structures:

—(CH$_2$)$_x$CH$_3$, —(CH$_2$CH$_2$O)$_x$CH$_3$, —(CH$_2$)$_x$(CH$_2$CH$_2$O)$_y$CH$_3$ and

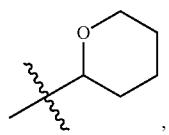

wherein x and y≥0 and are integers, the ester group R', $R_1$, $R_2$, $R_3$, $R_4$, $R_5$, $R_1'$, $R_2'$, and $R_3'$ is selected from the following structures:

—CO(CH$_2$)$_x$CH$_3$, —CO(CH$_2$CH$_2$O)$_x$CH$_3$, —CO(CH$_2$)$_x$(CH$_2$CH$_2$O)$_y$CH$_3$, wherein x and y≥0 and are integers, the carbonate group of $R_1$ is selected from the following structures:

—COO(CH$_2$)$_x$CH$_3$, —COO(CH$_2$CH$_2$O)$_x$CH$_3$, —COO(CH$_2$)$_x$(CH$_2$CH$_2$O)$_y$CH$_3$, wherein x and y≥0 and are integers, the amino formate ester group of $R_1$ is selected from the following structures:

—CONH(CH$_2$)$_x$CH$_3$, —CONH(CH$_2$CH$_2$O)$_x$CH$_3$, —CONH(CH$_2$)$_x$(CH$_2$CH$_2$O)$_y$CH$_3$, wherein x and y≥0 and are integers, the mercapto formate ester group is selected from the following structures:

—COS(CH$_2$)$_x$CH$_3$, —COS(CH$_2$CH$_2$O)$_x$CH$_3$, —COS(CH$_2$)$_x$(CH$_2$CH$_2$O)$_y$CH$_3$, wherein x and y≥0 and are integers, the phosphonate ester group is selected from the following structures:

—POOO(CH$_2$)$_x$CH$_3$, —POOO(CH$_2$CH$_2$O)$_x$CH$_3$, —POOO(CH$_2$)$_x$(CH$_2$CH$_2$O)$_y$CH$_3$, wherein x and y≥0 and are integers.

the aryl group of R', $R_1$, $R_2$, $R_3$, $R_4$, $R_5$, $R_1'$, $R_2'$, and $R_3'$ is a monocyclic or fused bicyclic ring of 5-10 atoms, the heteroaryl group of R', $R_2$, $R_3$, $R_4$, $R_5$ is a monocyclic or fused bicyclic ring containing 5 to 10 atoms, the ring contains at least one hetero atom selected from N, O, S or Si, the halogen atom is selected from F, Cl, Br or I, the alicyclic ring is a saturated or unsaturated monocyclic or polycyclic alicyclic ring of 3 to 10 atoms, and the heteroalicyclic ring is a saturated or unsaturated monocyclic or polycyclic alicyclic ring of 3 to 10 atoms, and the ring contains at least one hetero atom selected from N, O, S or Si, when the heteroalicyclic ring contains an S atom, the S atom takes the form of —S—, —SO— or —SO$_2$—; H on the alicyclic or alicyclic ring is optionally substituted by a halogen atom, a nitro group, an aryl group, an alkyl group, or a modified alkyl group.

5. The method of claim 1, wherein $P_1$ forms a linkage bond, when the photosensitive polymer derivative has the structure of the Formula A-I, $P_1$ is connected to one or more of $R_2$, $R_3$, $R_4$ and $R_5$, or connected to a saturated or unsaturated alicyclic or heteroalicyclic ring formed by $R_2$, $R_3$, $R_4$ and/or $R_5$, or connected to an aromatic ring or aromatic heterocyclic ring formed by $R_2$, $R_3$, $R_4$ and/or $R_5$ or connected to a cyclic chain formed by connecting $R_1$ with one of $R_2$, $R_3$, $R_4$ and/or $R_5$ via a linkage bond, wherein the linkage bond is represented by —O—, —S—, —NH—, -alkyl group-, —COO—, or —CONH—;

when the photosensitive polymer derivative has the structure of the Formula A-III, the linkage bond is represented by formula: A-$P_1$-B, the linkage bond has a first end and a second end, the first end is connected to one or more of $R_2$, $R_3$, $R_4$, and $R_5$, or connected to a saturated or unsaturated alicyclic or heteroalicyclic ring formed by $R_2$, $R_3$, $R_4$, and/or $R_5$, or connected to an aromatic ring or aromatic heterocyclic ring formed by $R_2$, $R_3$, $R_4$, and/or $R_5$, or connected to a cyclic chain formed by connecting $R_1$ with one of $R_2$, $R_3$, $R_4$, and $R_5$, and the second end is connected to $R_4'$;

wherein A and B are each independently selected from the group consisting of O, S, NH, alkyl group, COO, and CONH.

6. The method of claim 1, wherein the natural hydrophilic or water-soluble polymer comprises a natural polysaccharide, a protein, or a modification or degradation thereof, wherein the natural polysaccharide includes at least one selected from the group consisting of hyaluronic acid, carboxymethyl cellulose, methyl cellulose, hydroxyethyl cellulose, hydroxypropyl cellulose, alginate, dextran, agarose, heparin, chondroitin sulfate, glycol chitosan, propylene glycol chitosan, chitosan lactate, carboxymethyl chitosan, and quaternary ammonium salt of chitosan, and the protein includes at least one selected from the group consisting of a hydrophilic or water-soluble animal or plant protein, collagen, serum protein, silk fibroin protein or elastin, and a protein degradate including gelatin or polypeptide, and the hydrophilic or water-soluble synthetic polymer includes at least one selected from the group consisting of two-arm or multi-arm poly (ethylene glycol), poly (ethylene imine), dendrites, synthetic peptides, polylysine, poly (glutamic acid), poly (acrylic acid), poly (methacrylic acid), polyacrylate, poly (methacrylate), poly (acrylamide), poly (methacrylamide poly (vinyl alcohol), and poly (vinyl pyrrolidone).

7. The method of claim 1, wherein the polymer derivative is selected from the following structures:

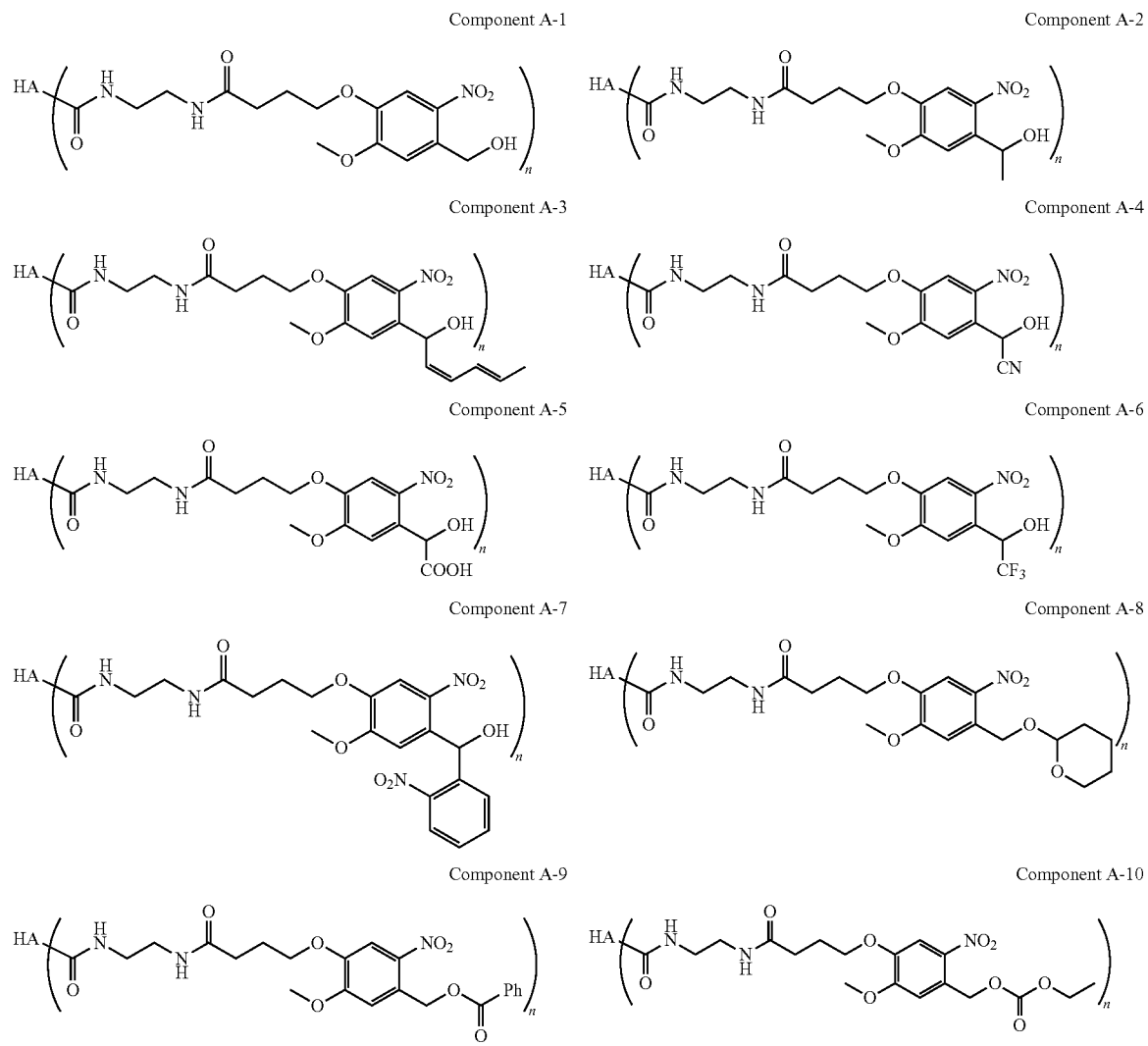

-continued
Component A-11
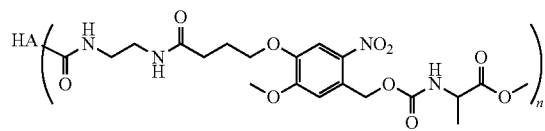
Component A-12
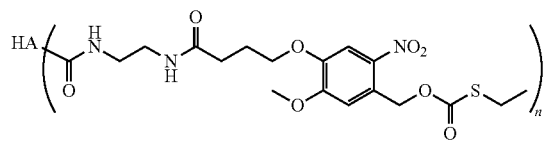
Component A-13
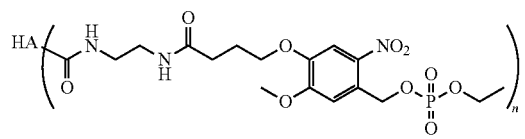
Component A-21
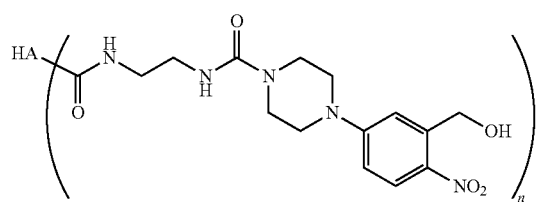
Component A-22
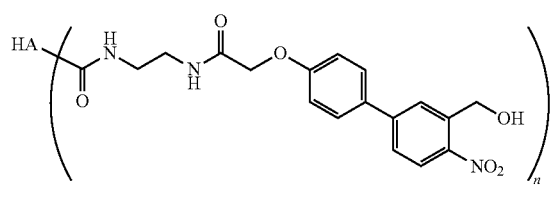
Component A-23
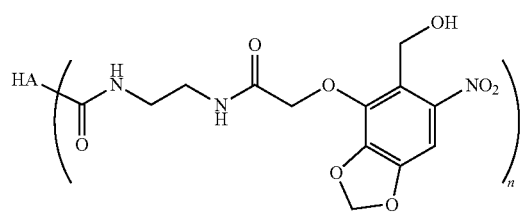
Component A-24
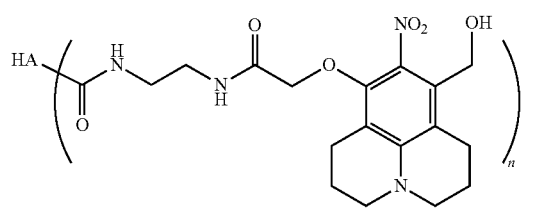
Component A-25
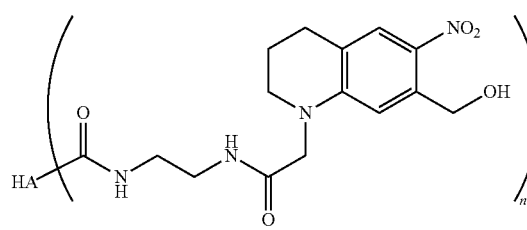
Component A-26
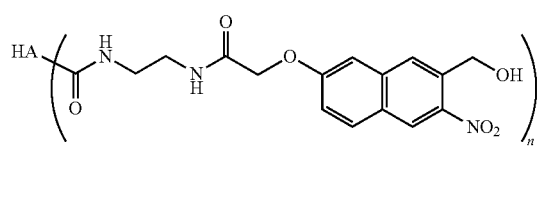
Component A-27
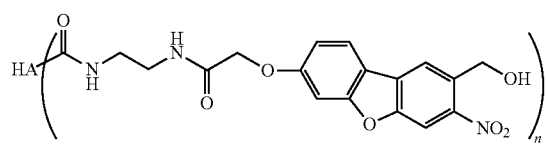
Component A-28
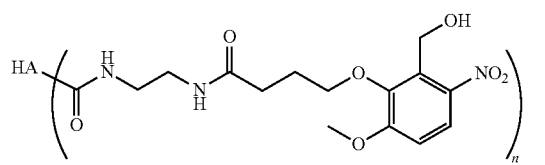
Component A-29
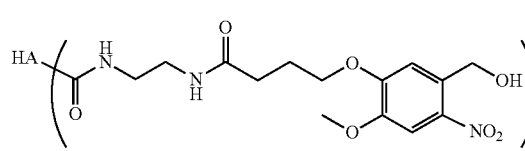
Component A-30
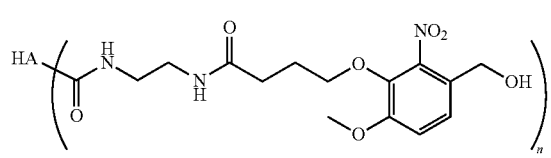
Component A-31
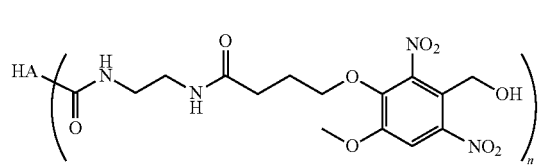

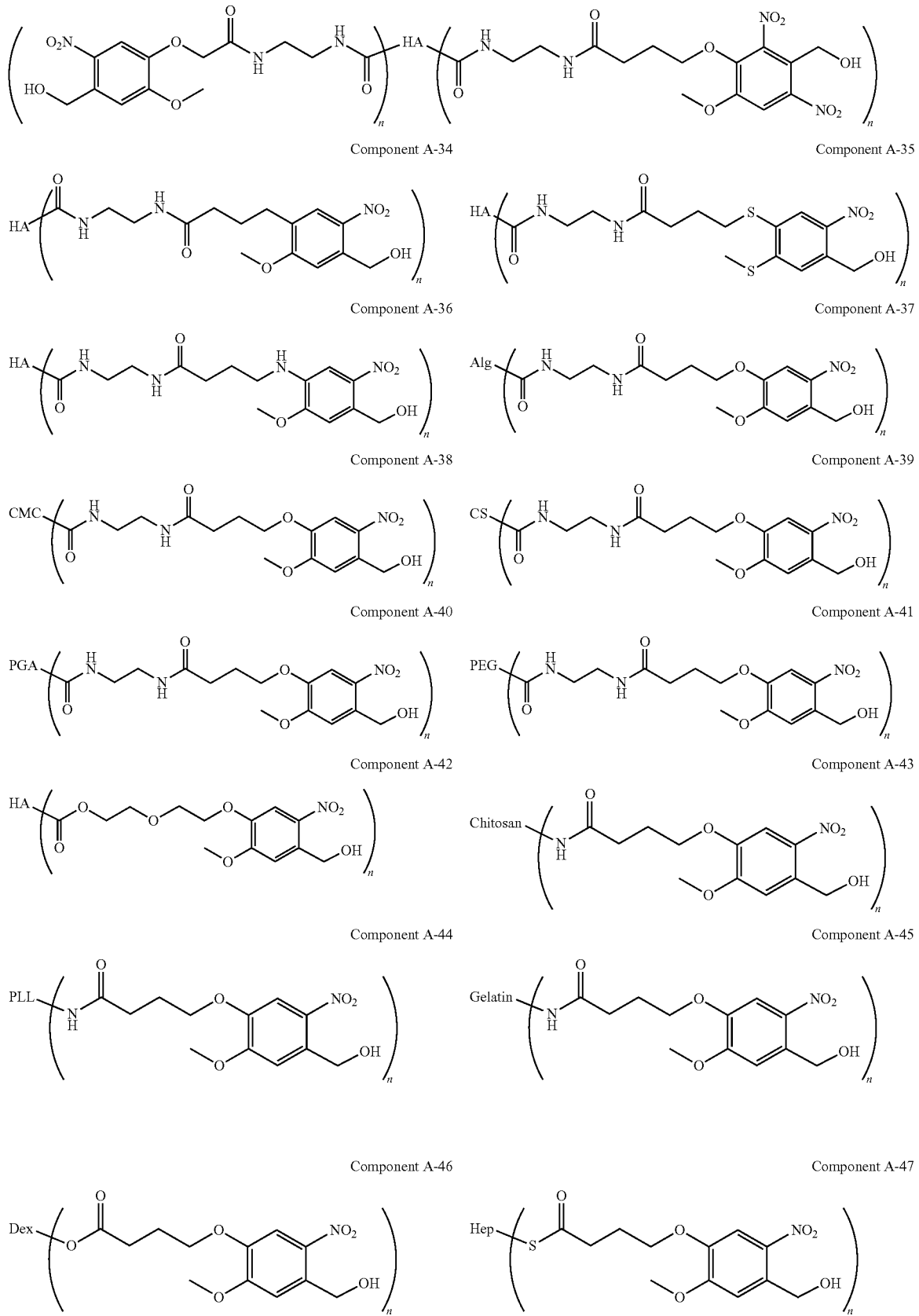

-continued
Component A-48
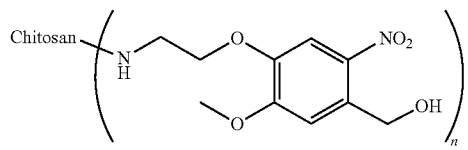
Component A-49
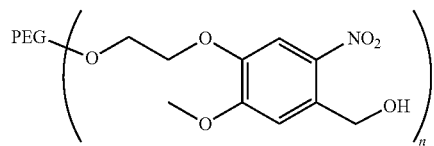
Component A-50
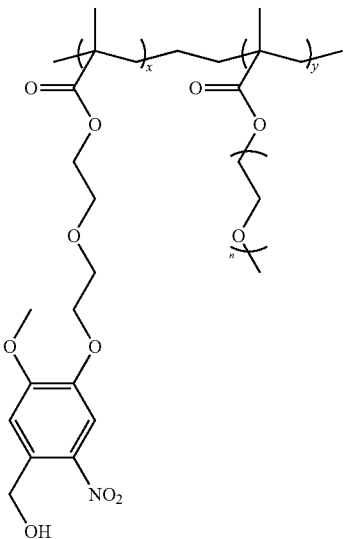
Component A-51
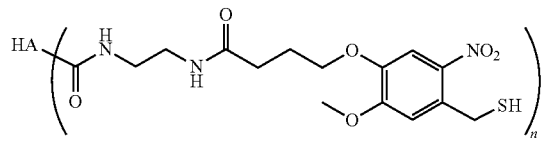
Component A-52
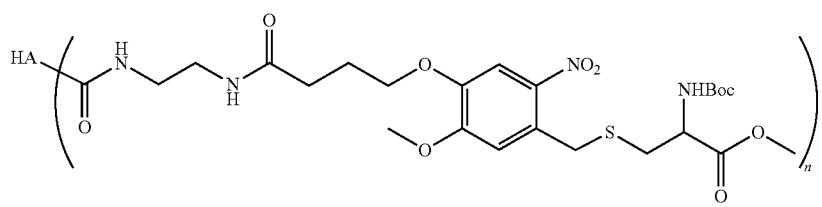
Component A-53
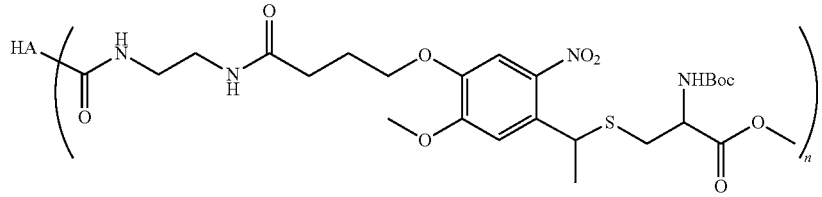
Component A-54
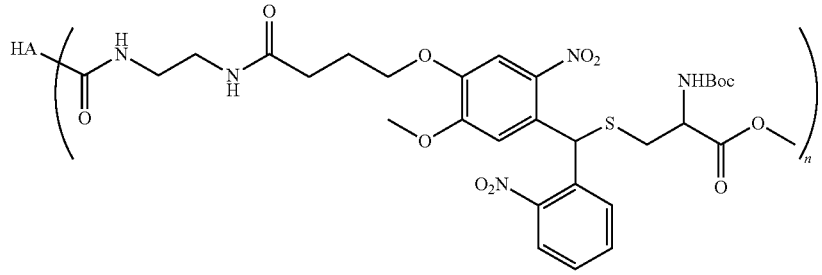
Component A-55
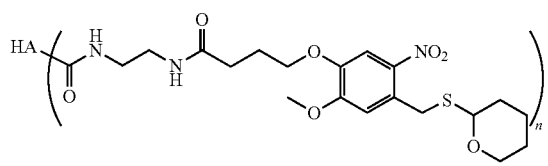
Component A-56
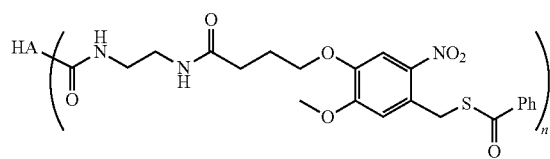

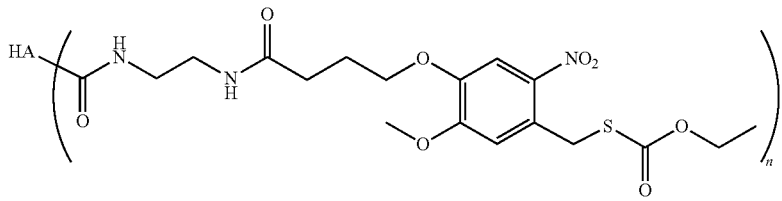
Component A-57
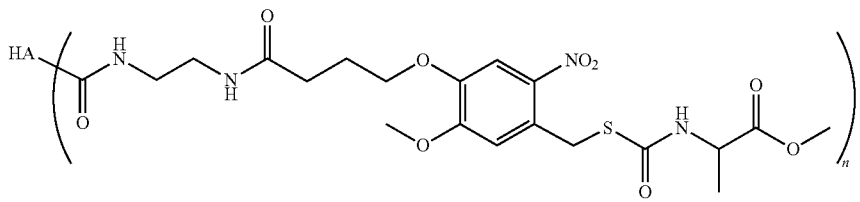
Component A-58
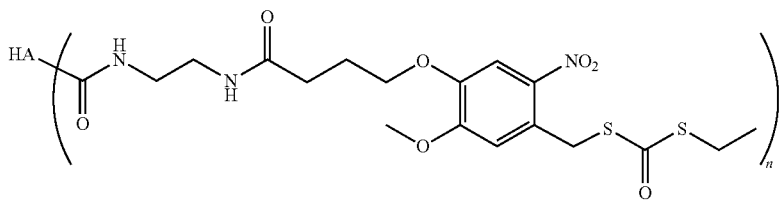
Component A-59
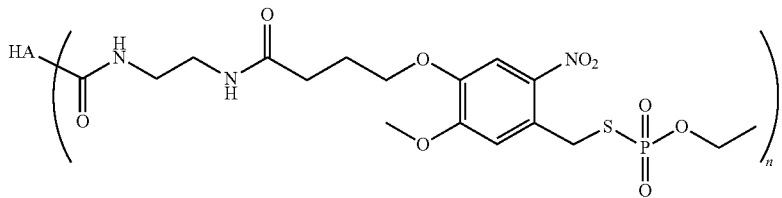
Component A-60
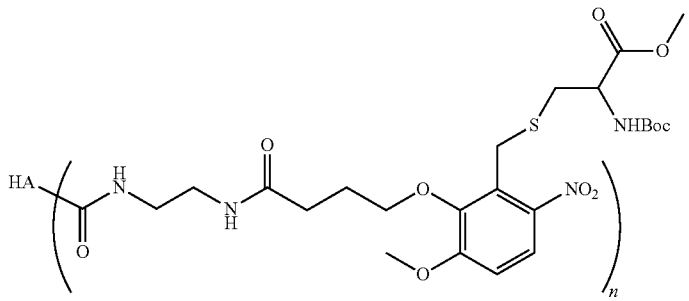
Component A-62
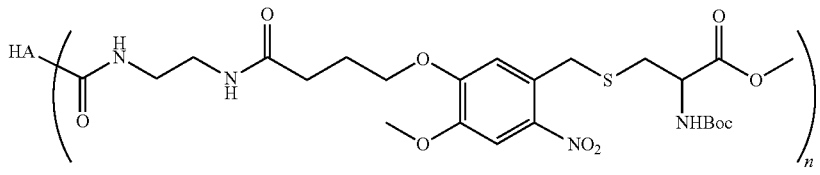
Component A-63
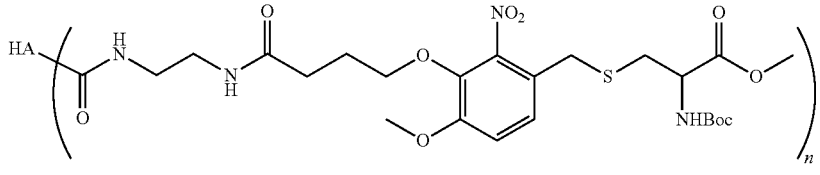
Component A-64

-continued
Component A-65
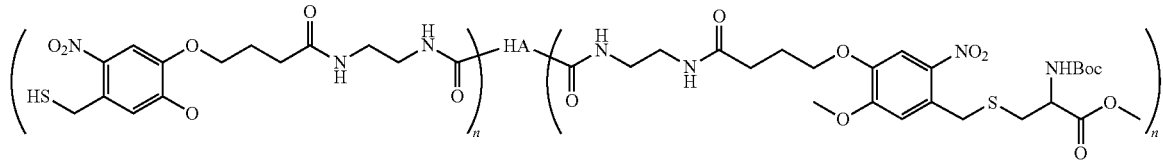
Component A-66
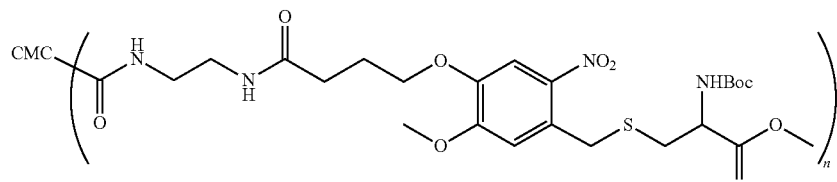
Component A-67
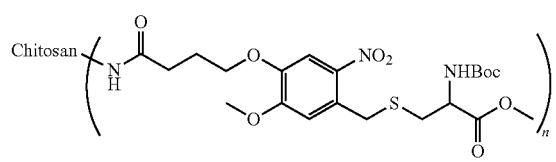
Component A-68
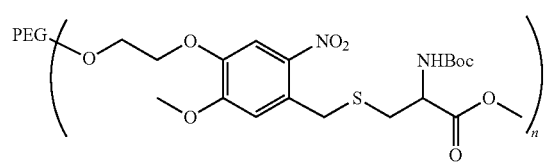
Component A-69
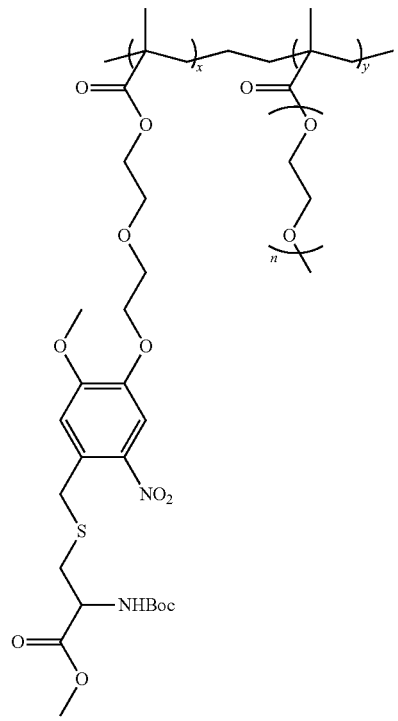
Component A-70
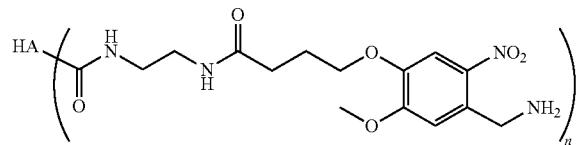
Component A-71
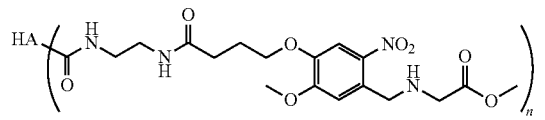
Component A-72
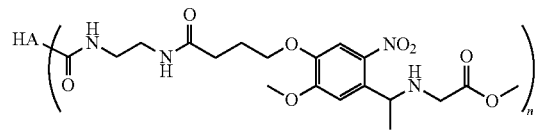

-continued
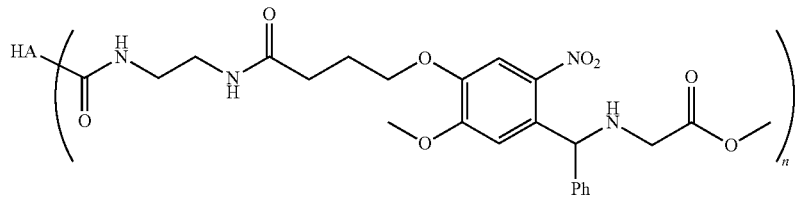
Component A-73
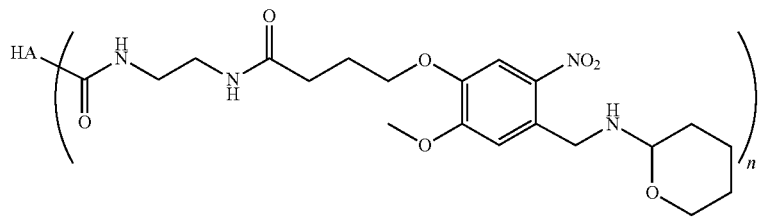
Component A-74
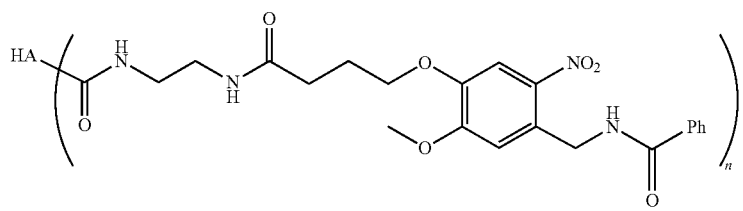
Component A-75
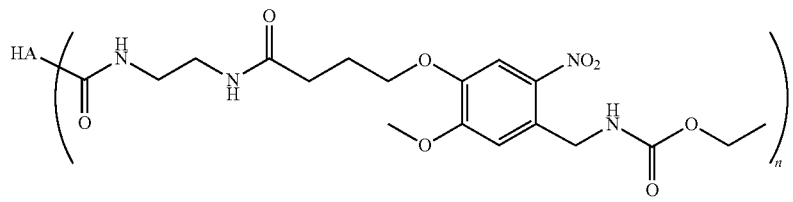
Component A-76
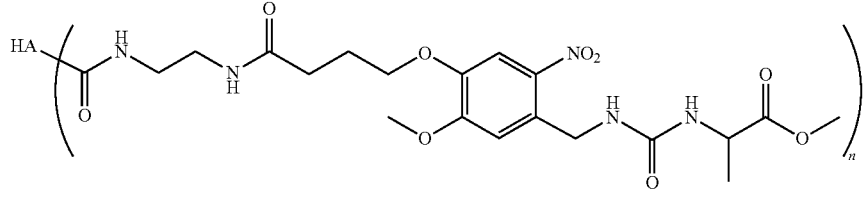
Component A-77
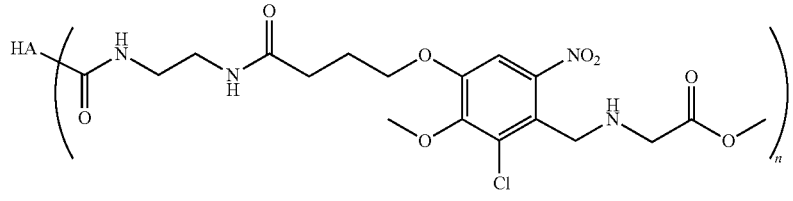
Component A-78
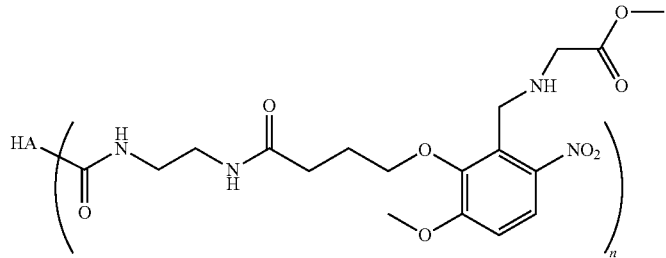
Component A-80

-continued
Component A-81
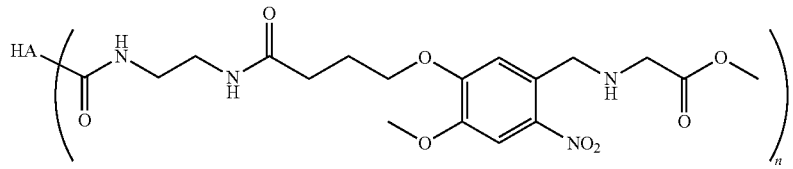
Component A-82
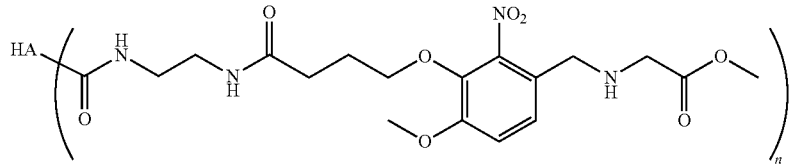
Component A-83
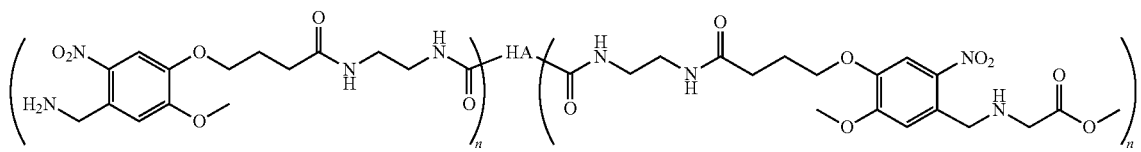
Component A-84
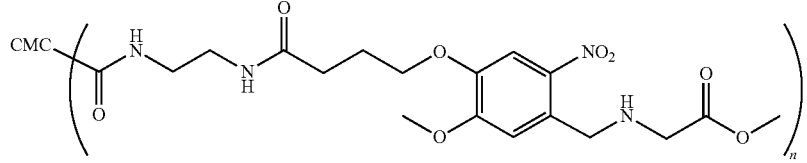
Component A-85 Component A-86
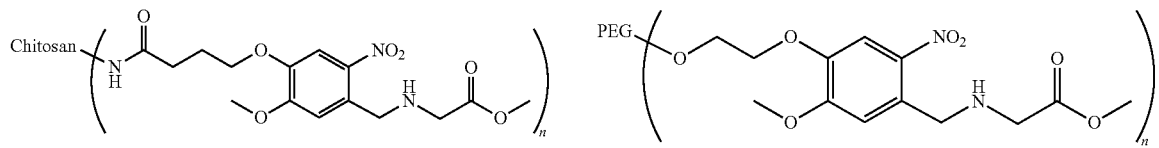
Component A-87
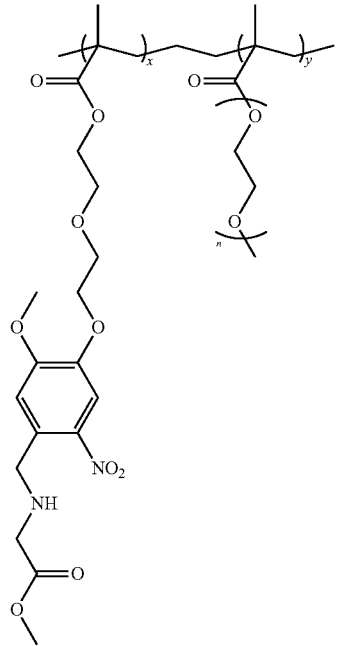
Component A-88
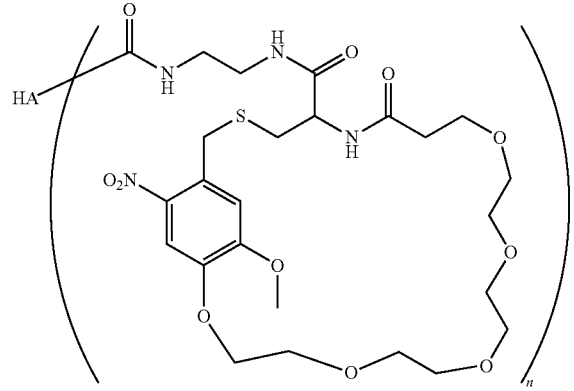

Component A-89
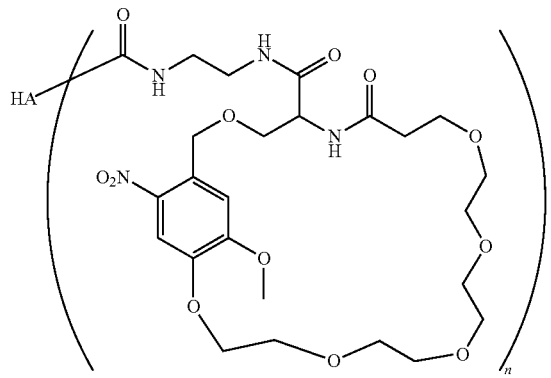
Component A-90
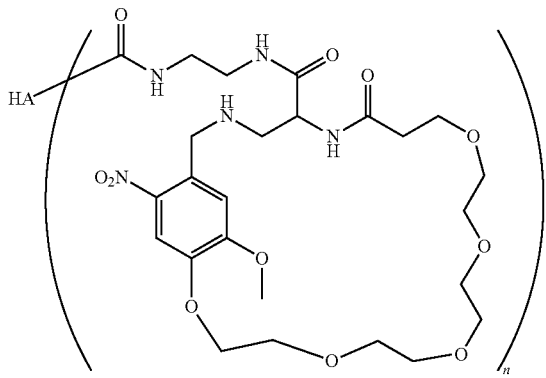
Component A-91
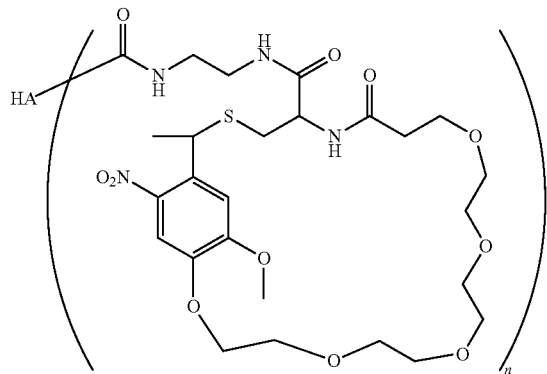
Component A-93
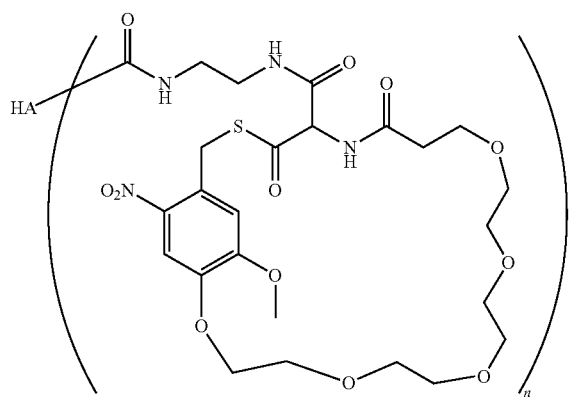
Component A-94
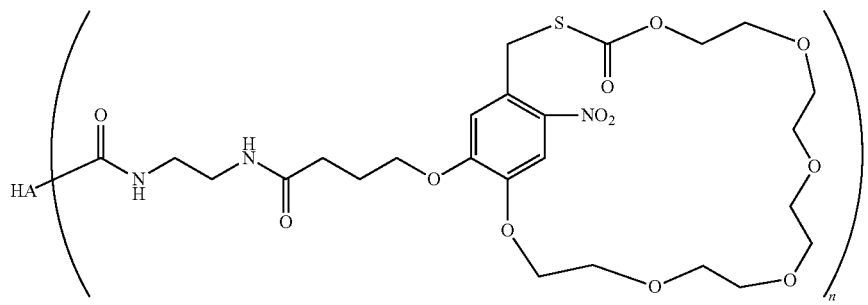

-continued
Component A-95
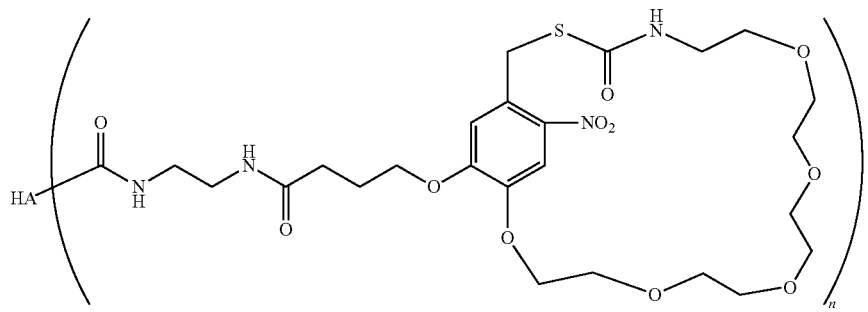
Component A-98
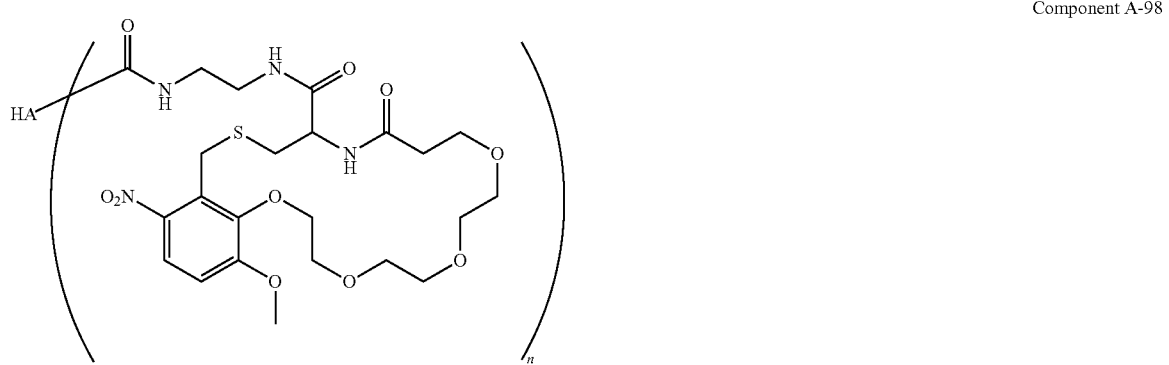
Component A-99
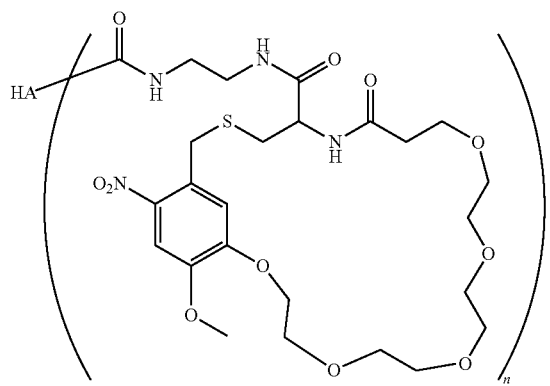
Component A-100
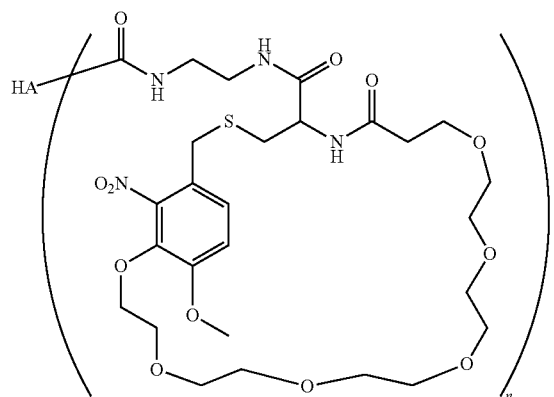
Component A-101
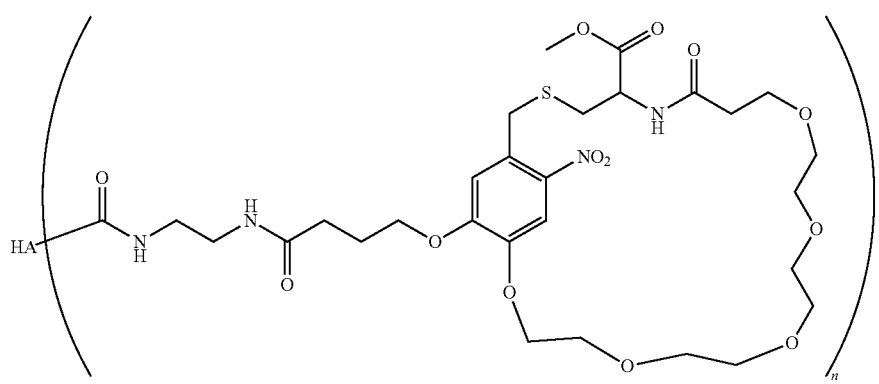

Component A-102
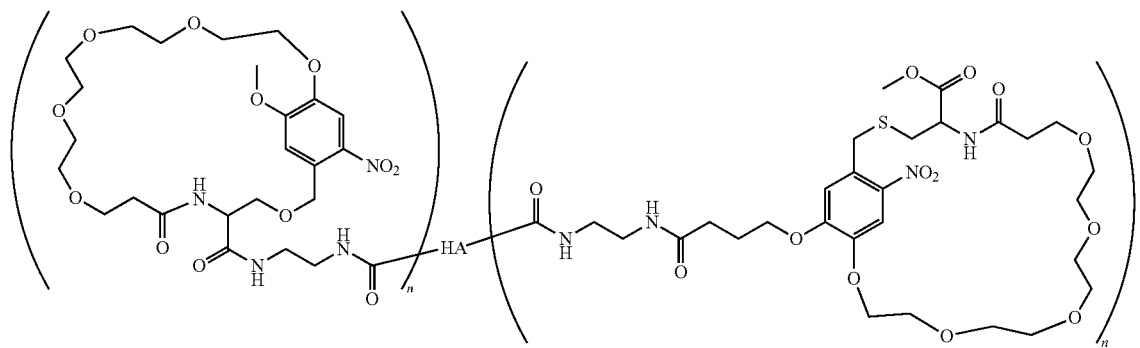
Component A-103    Component A-104
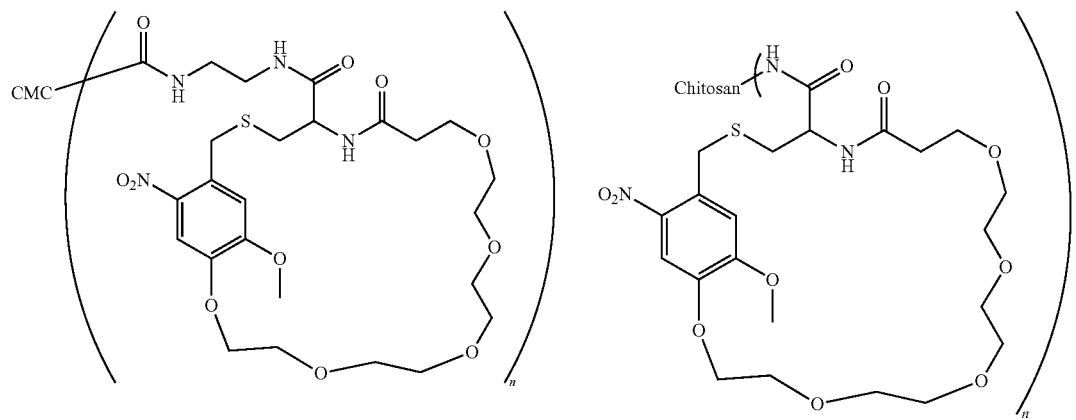
Component A-105    Component A-106
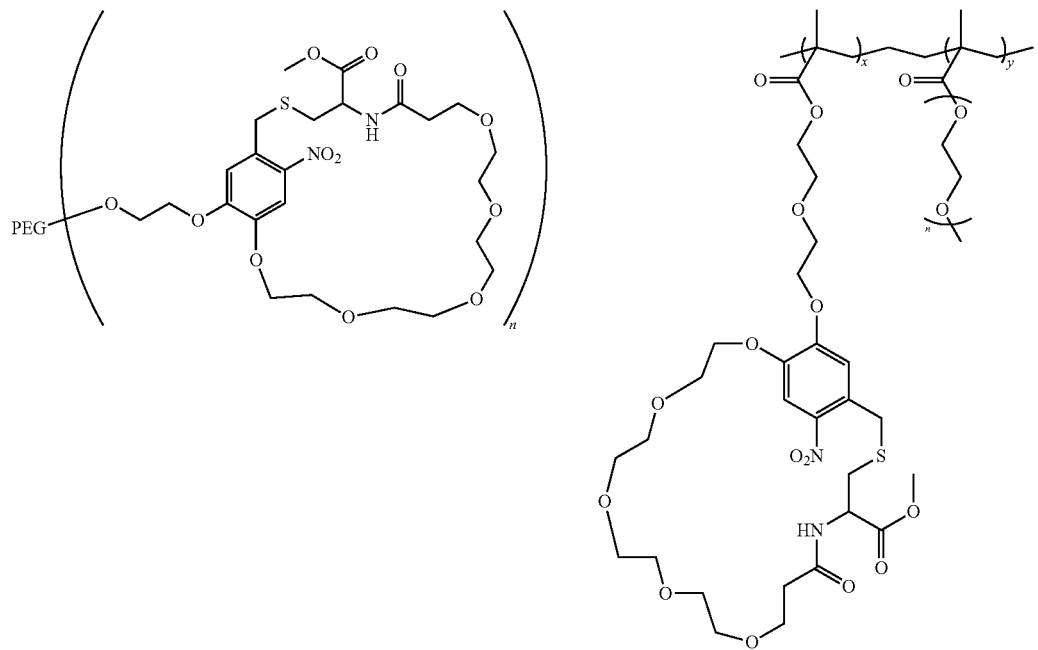

Component A-116
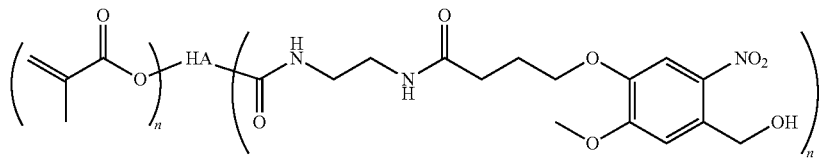
Component A-117
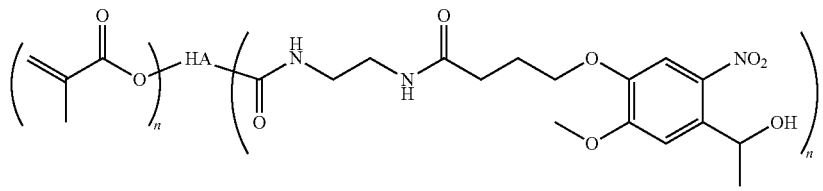
Component A-118
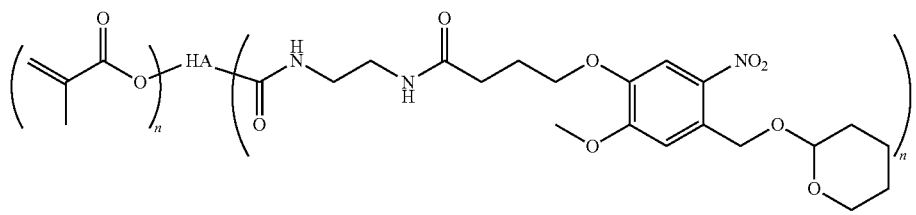
Component A-119
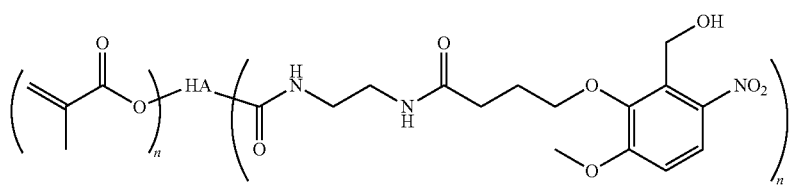
Component A-120
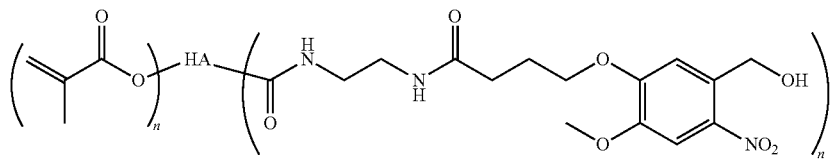
Component A-121
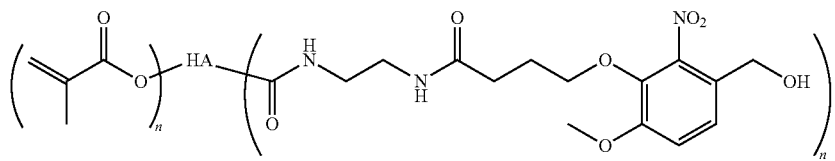
Component A-122
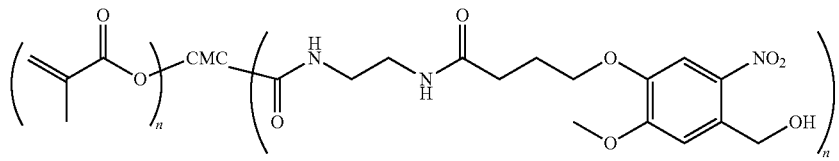
Component A-123
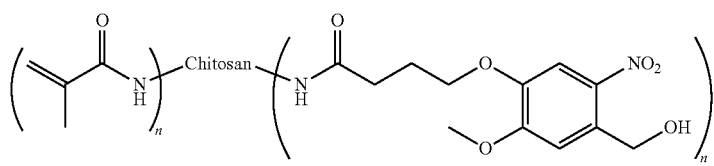

-continued
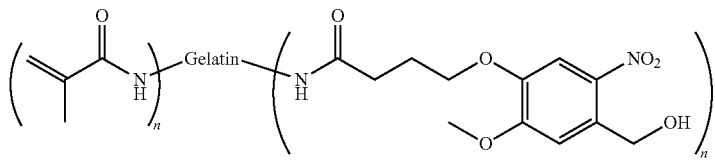
Component A-124
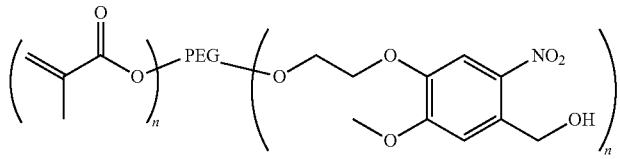
Component A-125
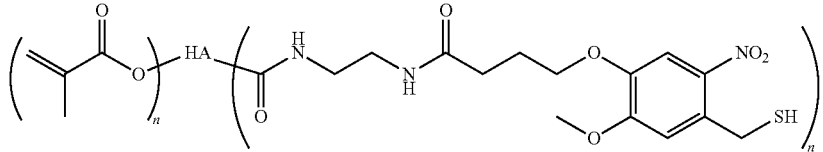
Component A-126
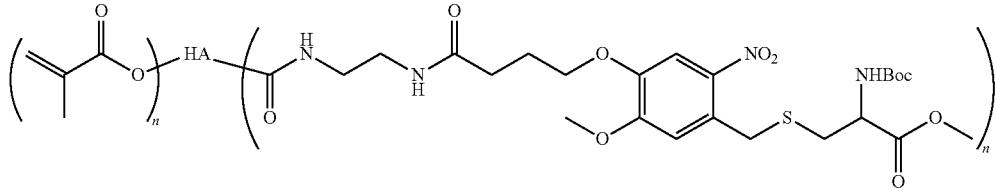
Component A-127
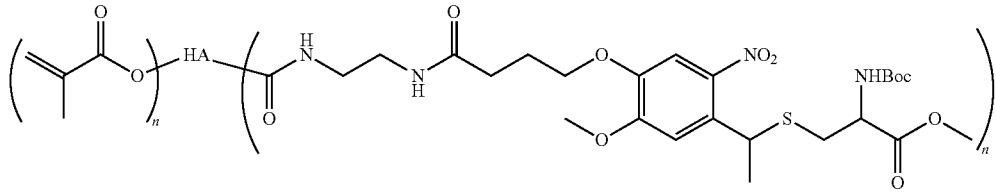
Component A-128
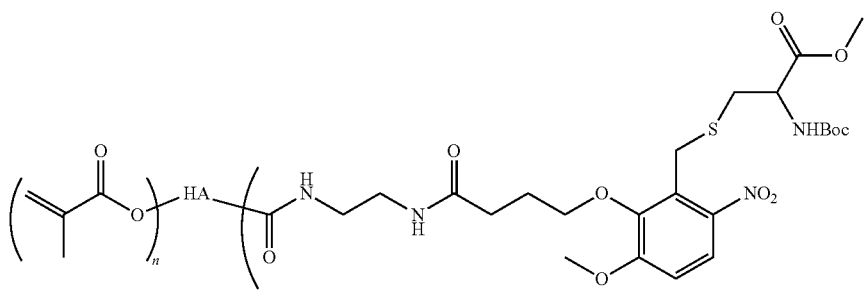
Component A-129
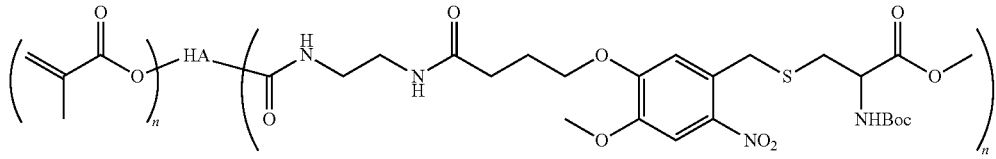
Component A-130
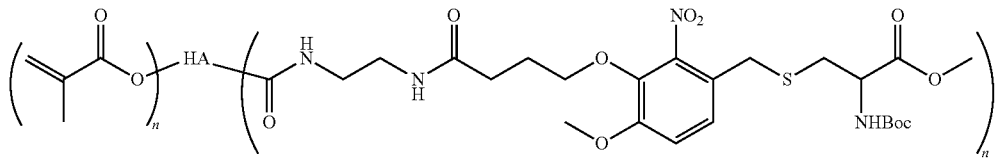
Component A-131

-continued
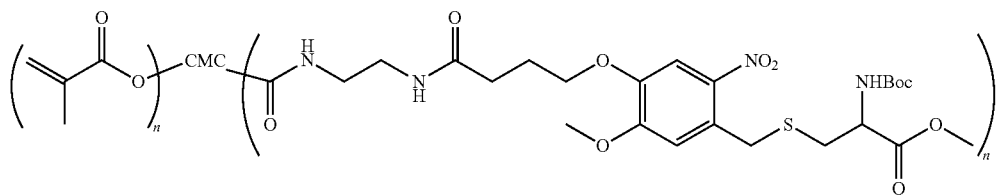
Component A-132
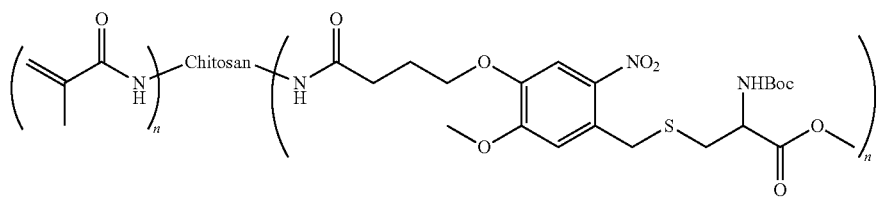
Component A-133
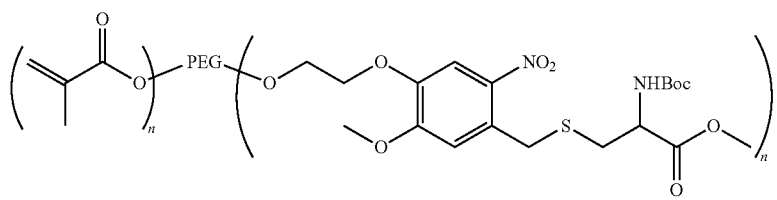
Component A-134
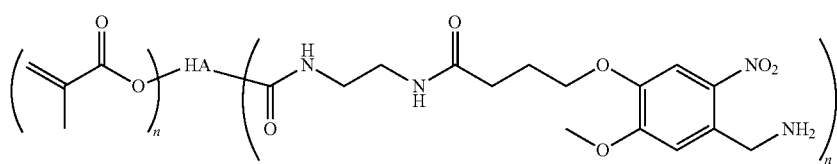
Component A-135
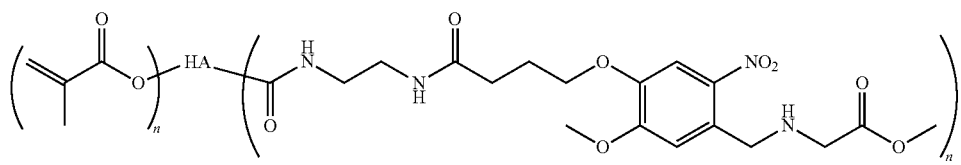
Component A-136
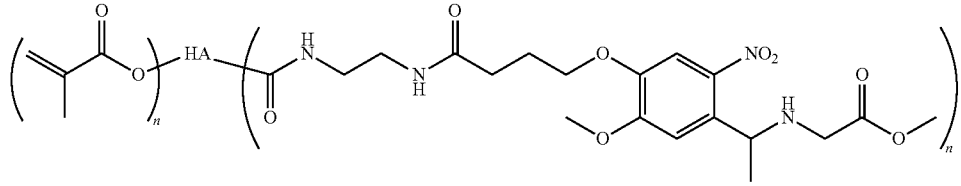
Component A-137
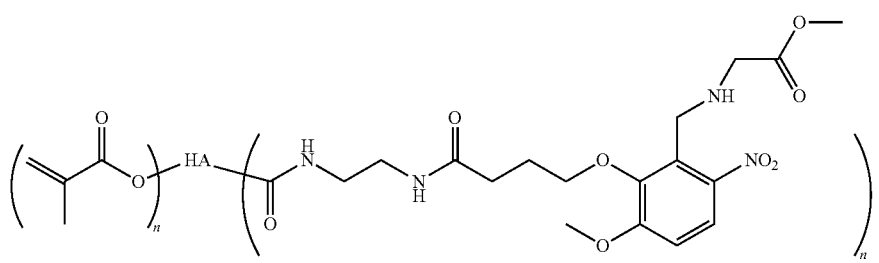
Component A-138
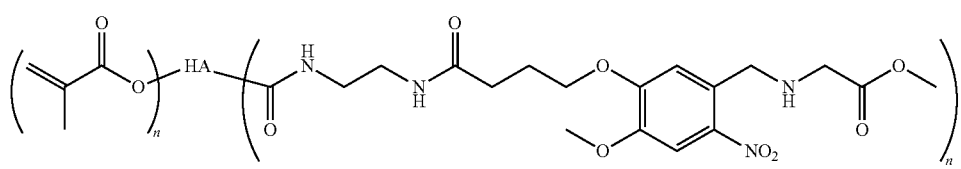
Component A-139

-continued
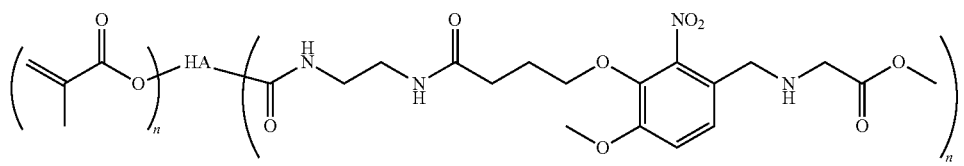
Component A-140
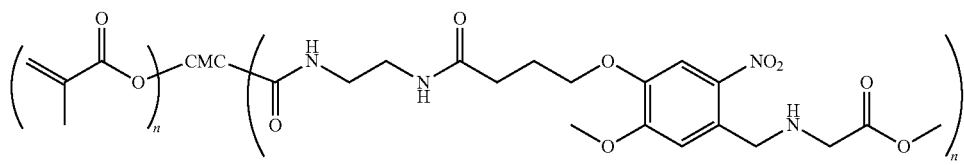
Component A-141
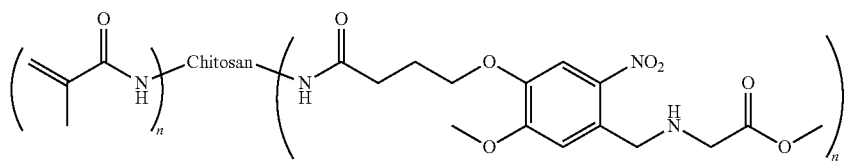
Component A-142
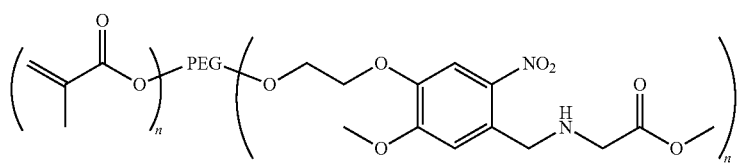
Component A-143
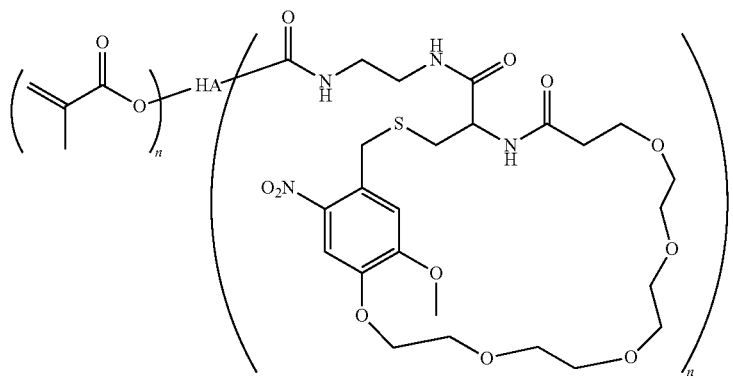
Component A-144
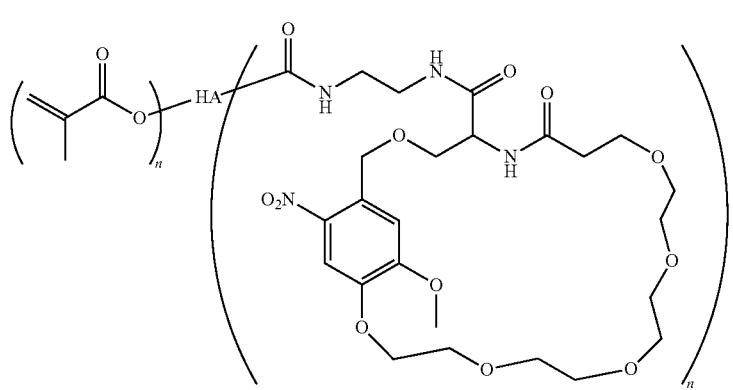
Component A-145

Component A-146
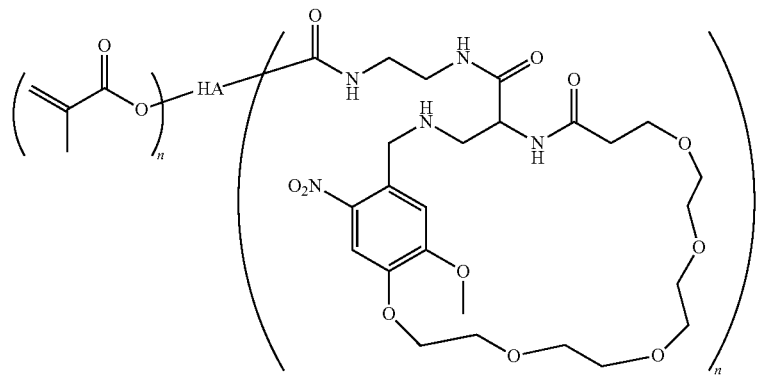
Component A-147
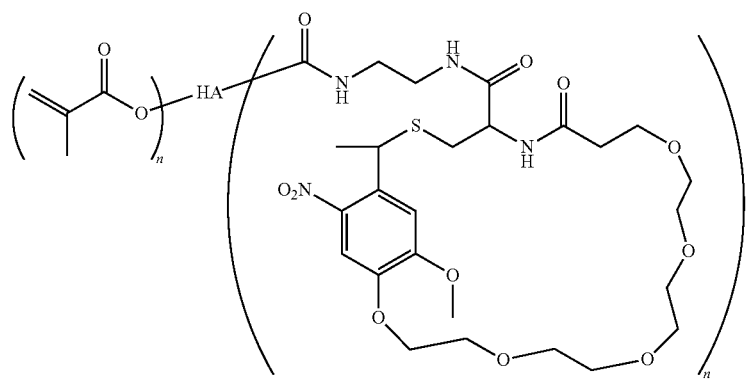
Component A-148
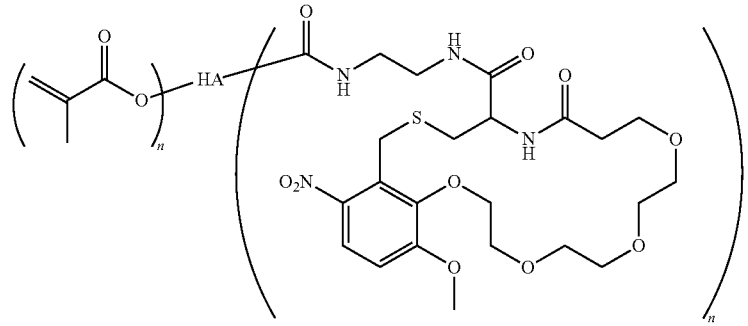
Component A-149
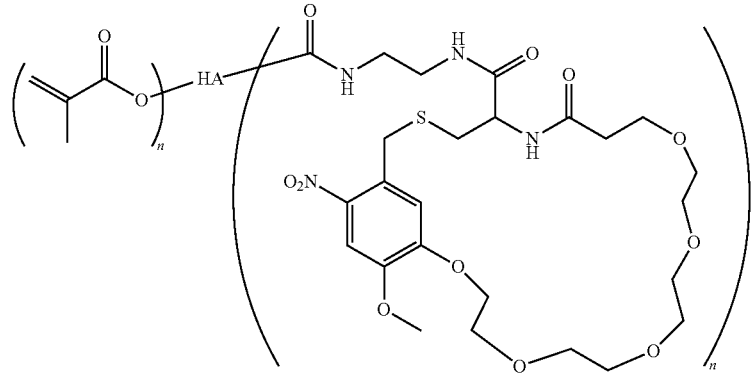

-continued
Component A-150
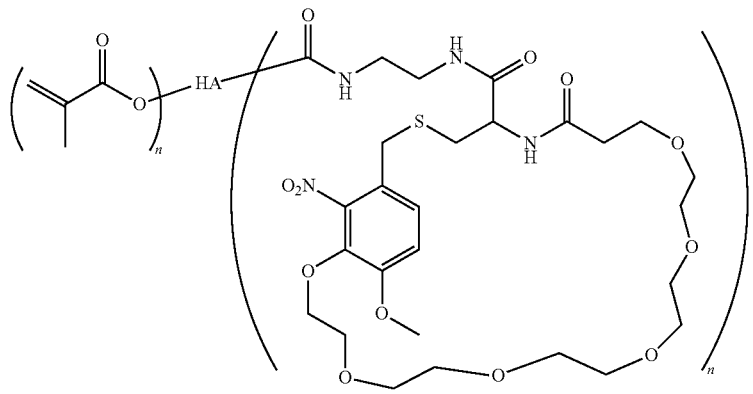
Component A-151
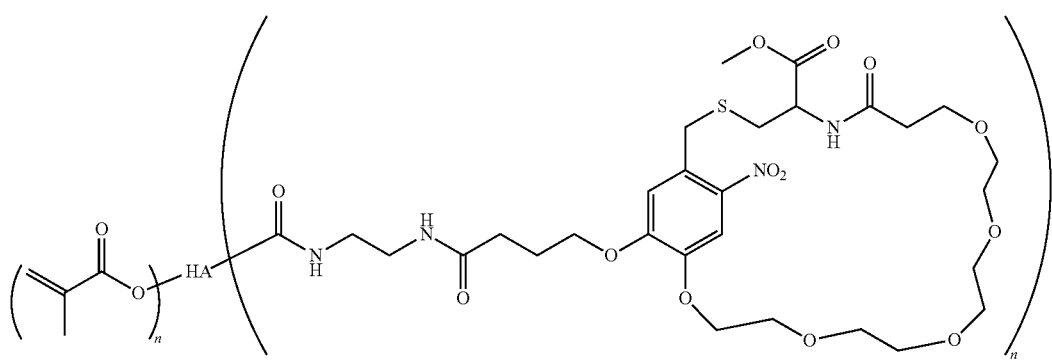
Component A-152
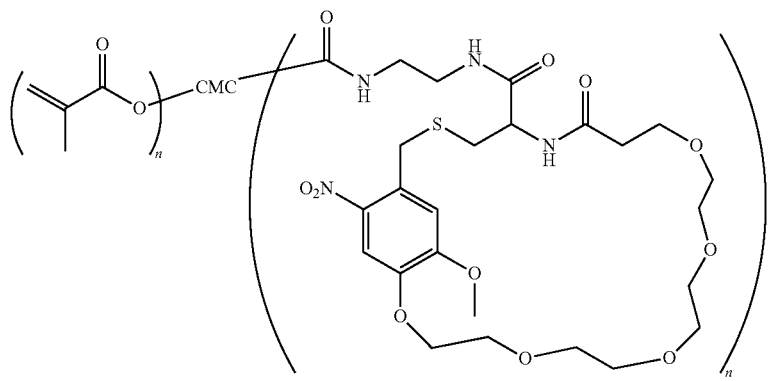
Component A-153
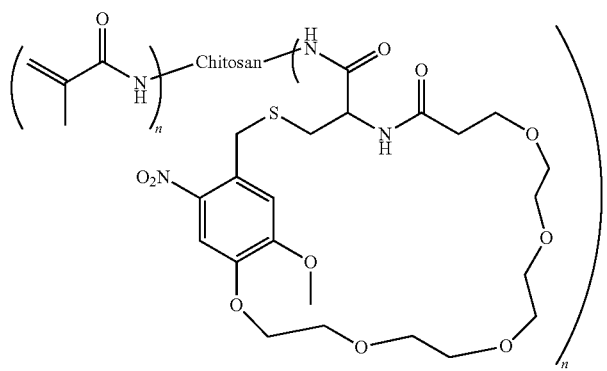

Component A-154

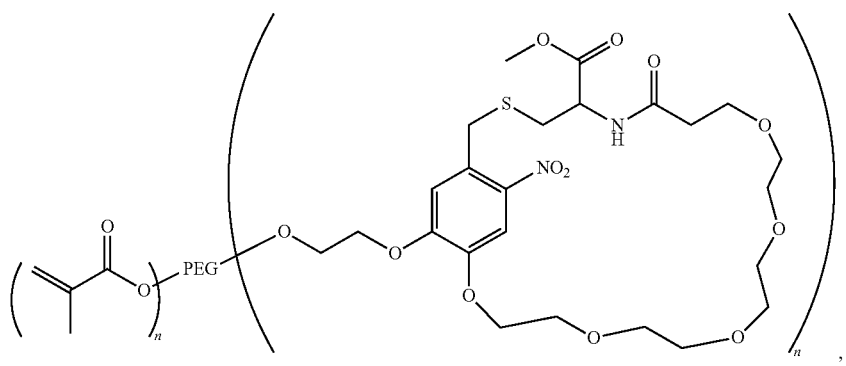

where, in Component A-1 to Component A-106 and Component A-116 to Component A-154; $n \geq 2$, HA represents hyaluronic acid; CMC represents carboxymethyl cellulose, Alg represents alginic acid, CS represents chondroitin sulfate, PGA represents polyglutamic acid, PEG represents poly ethylene-glycol, PLL represents polylysine, and Dex represents dextran; Hep represents heparin.

8. The method of claim 3, wherein
the polymer derivative containing amino, diammonium, hydrazide, and hydroxyamine group respectively have the structure of Formula C-I, Formula C-II, Formula C-III, and Formula C-IV:

Formula C-I
$$P_2 \!\!-\!\!(NH_2)_n;$$

Formula C-II
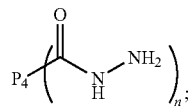

Formula C-III $$P_4 \!\!\left(\!\!\begin{array}{c}O\\\|\\C\\\end{array}\!\!\!-\!\!\!\begin{array}{c}H\\|\\N\\|\\H\end{array}\!\!\!NH_2\right)_{\!\!n};$$

Formula C-IV
$$P_5 \!\!-\!\!(O \!\!-\!\! NH_2)_n,$$

the polymer derivatives containing sulphydryl group have the structure of Formula C-V:

Formula C-V
$$P_6 \!\!-\!\!(SH)_n,$$

where, in Formula C-I, C-II, C-V, $n \geq 2$; $P_2$, $P_3$, $P_4$, $P_5$ and $P_6$ each independently are a hydrophilic or water-soluble natural polymer, or a hydrophilic or water-soluble synthetic polymer, the hydrophilic or water-soluble natural polymer includes natural polysaccharide, decoration or degradation of the natural polysaccharide, protein, or decoration, modifier or degradation of the protein, the natural polysaccharide includes hyaluronic acid, carboxymethyl cellulose, methyl cellulose, hydroxyethyl cellulose, hydroxypropyl cellulose, alginate, dextran, agarose, heparin, chondroitin sulfate, glycol chitosan, propylene glycol chitosan, chitosan lactate, carboxymethyl chitosan, or quaternary ammonium salt of chitosan, the protein includes a hydrophilic or water-soluble animal or plant protein, a collagen, a serum protein, or a silk fibroin protein and elastin, and the protein degradation include a gelatin or a polypeptide, the hydrophilic or water-soluble synthetic polymers include two-arm of multi-arm poly (ethylene glycol), poly (ethylene imine), dendrites, synthetic peptides, polylysine, poly (glutamic acid), poly (acrylic acid), poly (methacrylic acid), polyacrylate, poly (methacrylate), poly (acrylamide), poly (methacrylamide), poly (vinyl alcohol), or poly (vinyl pyrrolidone), the Formula C-I is selected from the following structure of Component C-1 to Component C-9,
the Formula C-II is selected from the following structure of Component C-10,
the Formula C-III is selected from the following structure of Component C-11 to Component C-13,
the Formula C-IV is selected from the following structure of Component C-14 to C-15,
the Formula C-V is selected from the following structure of Component C-16 to Component C-21, Component C-1

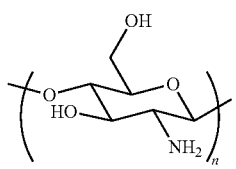

Component C-2

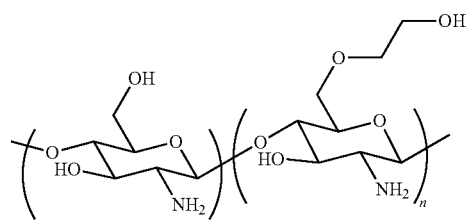

-continued
Component C-3
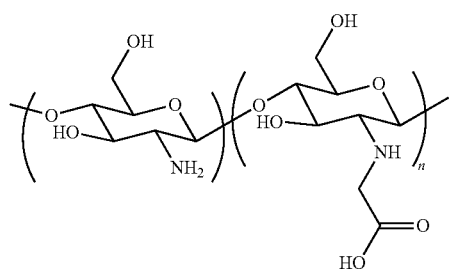
Component C-4
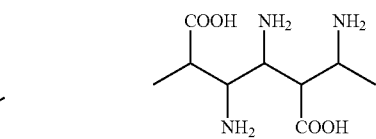
Component C-5
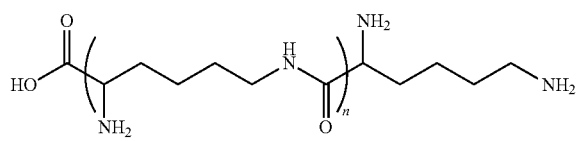
Component C-6
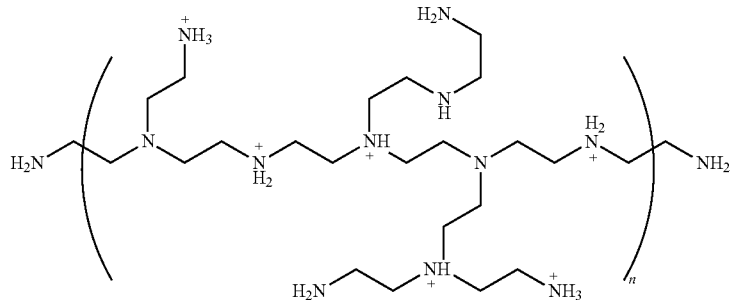
Component C-7
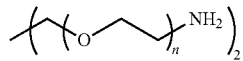
Component C-8
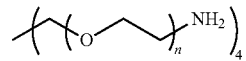
Component C-9
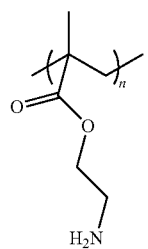
Component C-10
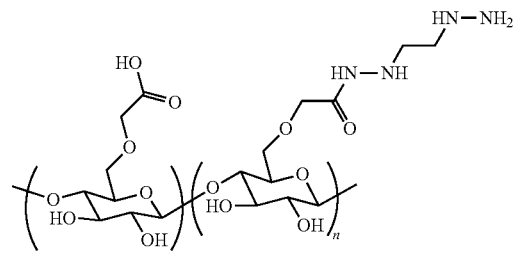
Component C11
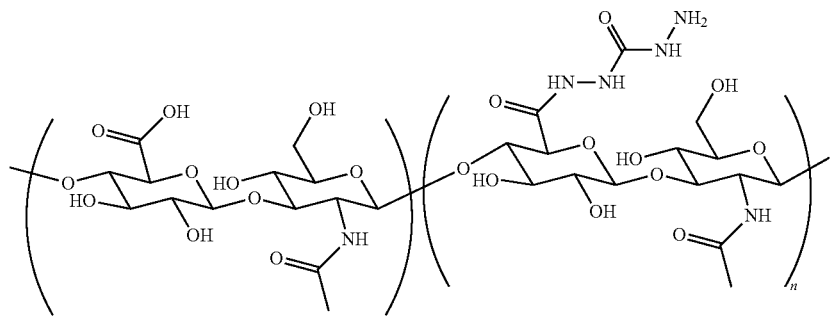

-continued
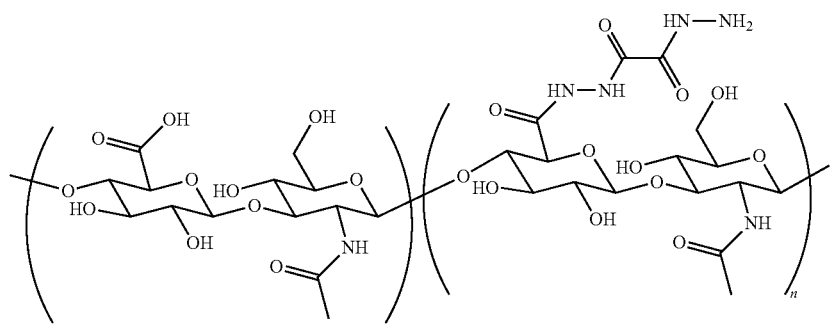
Component C-12
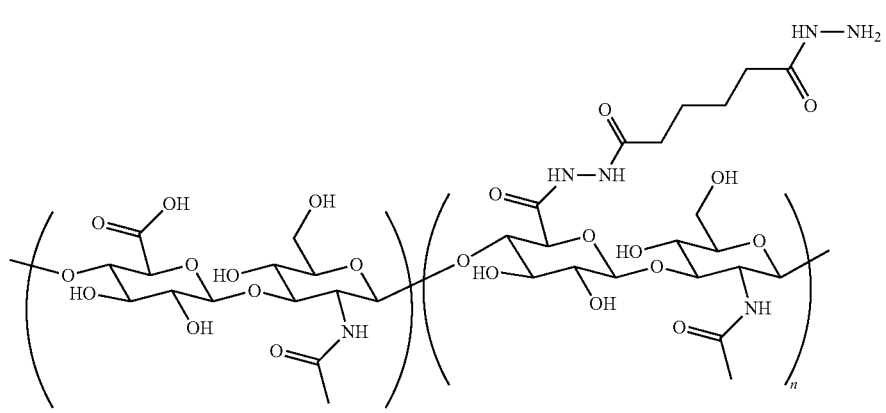
Component C-13
Component C-14
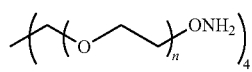
Component C-15
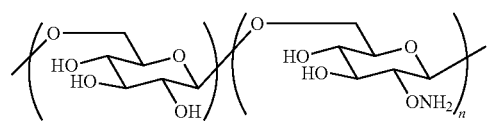
Component C-16
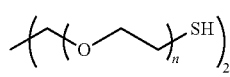
Component C-17
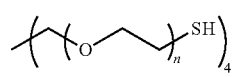
Component C-18
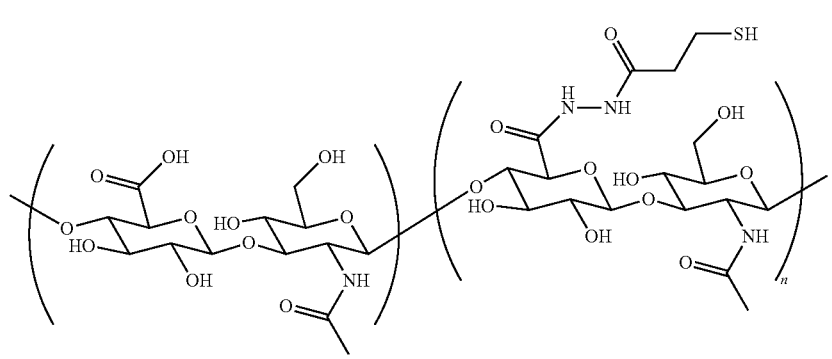

Component C-19

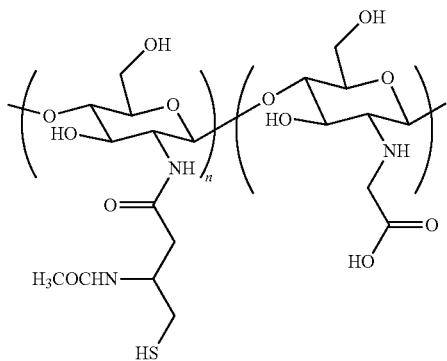

Component C-20

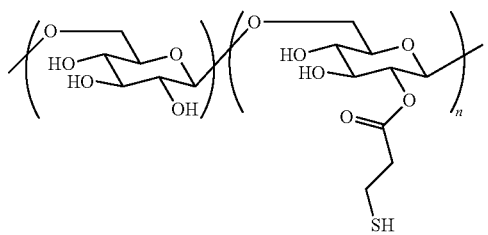

Component C-21

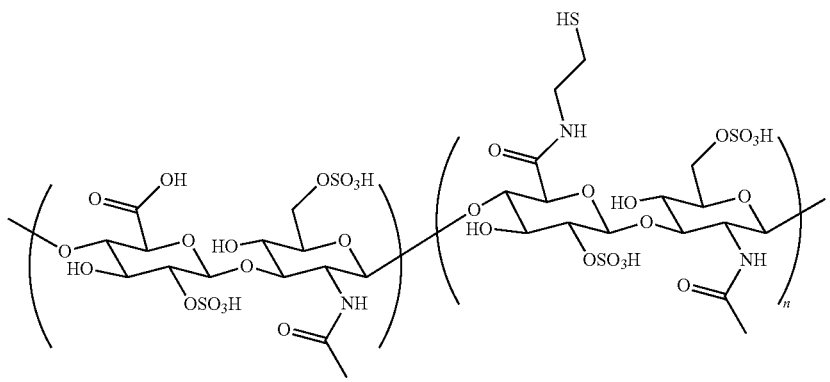

where, in Component C-1 to Component C-21, n≥2.

9. The method of claim 1, wherein, for Formula I-1 and Formula I-2, $R_2$, $R_3$, $R_4$, and $R_5$ are connected with a carbon atom to form a saturated or unsaturated alicyclic ring or alicyclic heterocycle, or form an aromatic ring or an aromatic heterocyclic ring.

10. The method of claim 1, wherein the photoinitiator is selected from Component B-1, Component B-2, Component B-3, and a derivative thereof;

Component B-1

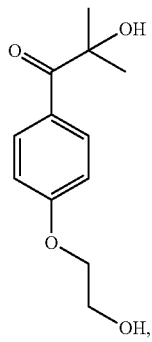

Component B-2

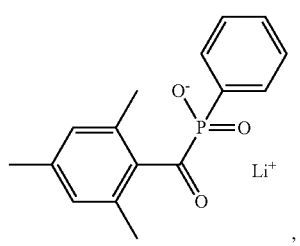

Component B-3

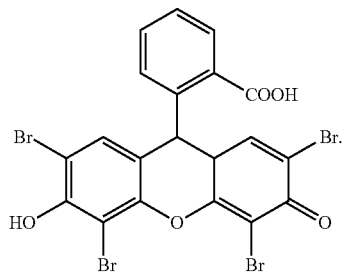

11. The method of claim 2, further comprising
dissolving an auxiliary component C including another biocompatible polymer derivative in a biocompatible medium to obtain a polymer solution C, wherein the another biocompatible polymer derivative is a polymer derivative containing an amine, hydrazine, hydrazide, or hydroxylamine functional group, the solutions further include the solution C, aldehyde or ketone group produced by irradiation of the o-nitrobenzyl phototrigger in component A is capable of reacting with the amine, hydrazine, hydrazide, or hydroxylamine functional group in component C through photocoupling crosslinking, nitroso group produced by irradiation of the o-nitrobenzyl phototrigger in component A is capable of reacting with the sulphydryl group in component C through photoinduced S-nitrosylation crosslinking.

12. The method of claim 2, wherein the polymer derivative is selected from the group consisting of Component A-107 to Component A-115;

Component A-107

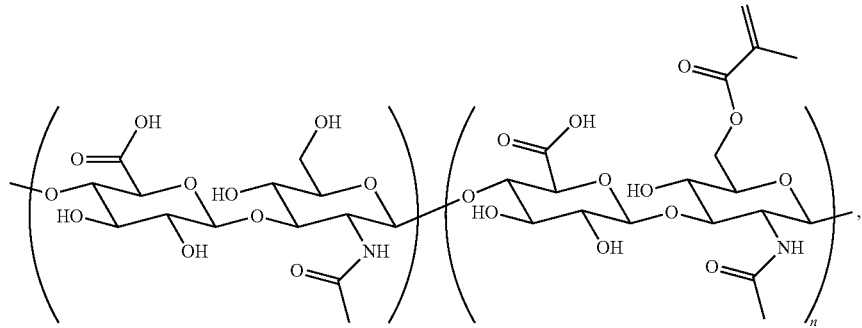

Component A-108

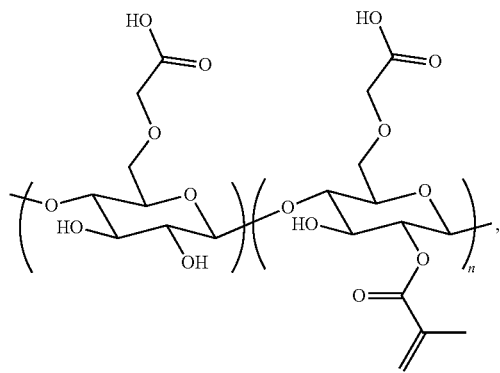

Component A-109

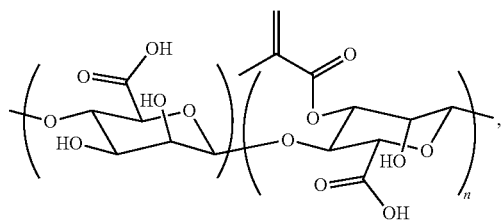

Component A-110

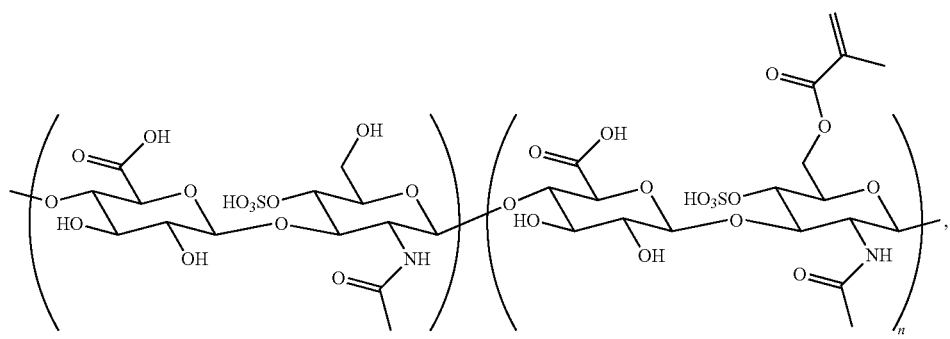

-continued

Component A-111

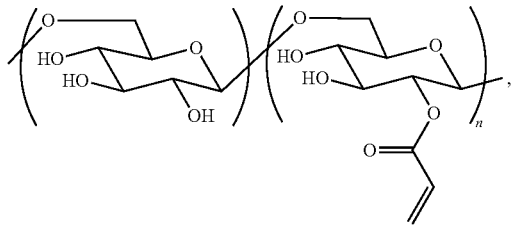

Component A-112

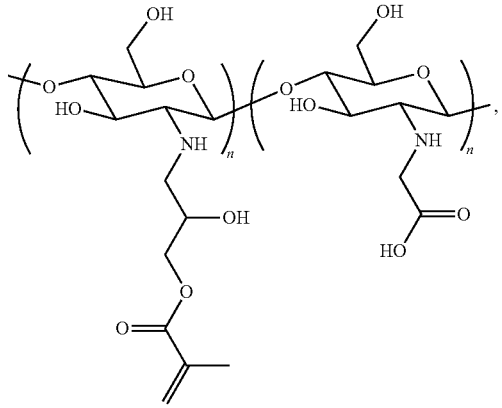

Compound A-113

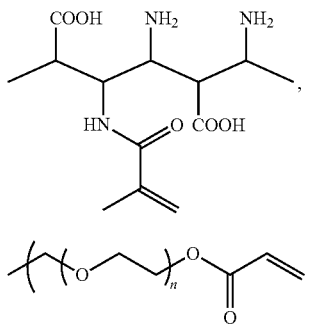

Compound A-114

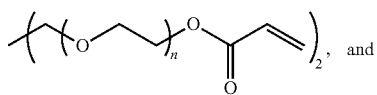, and

Compound A-115

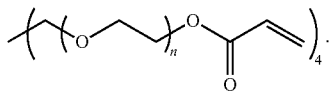.

13. The method of claim 1, wherein the photosensitive polymer derivative is the photosensitive polymer derivative containing both an o-nitrobenzyl phototrigger and double bond functional group as shown in Formula A-III.

14. The method of claim 9, wherein the aromatic ring is a monocyclic or fused bicyclic ring of 5-10 atoms,
the aromatic heterocyclic ring is a monocyclic or fused bicyclic ring containing 5 to 10 atoms,
the aromatic heterocyclic ring contains at least one hetero atom selected from the group consisting of N, O, S, and Si, and
the aromatic ring or the aromatic heterocyclic ring is optionally substituted by a halogen atom, a nitro group, an aryl group, an alkyl group, or a modified alkyl group.

* * * * *